US010722600B2

(12) United States Patent
Cadwell

(10) Patent No.: US 10,722,600 B2
(45) Date of Patent: Jul. 28, 2020

(54) METHODS AND COMPOSITIONS FOR TREATING CANCER

(71) Applicant: New York University, New York, NY (US)

(72) Inventor: Kenneth Cadwell, Forest Hills, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 15/625,934

(22) Filed: Jun. 16, 2017

(65) Prior Publication Data

US 2017/0360958 A1 Dec. 21, 2017

Related U.S. Application Data

(60) Provisional application No. 62/351,700, filed on Jun. 17, 2016, provisional application No. 62/471,443, filed on Mar. 15, 2017.

(51) Int. Cl.
*A61K 48/00* (2006.01)
*C07K 14/08* (2006.01)
*C12N 7/00* (2006.01)
*C12N 15/86* (2006.01)
*C07K 14/005* (2006.01)

(52) U.S. Cl.
CPC .......... *A61K 48/005* (2013.01); *C07K 14/005* (2013.01); *C07K 14/08* (2013.01); *C12N 7/00* (2013.01); *C12N 15/86* (2013.01); *C12N 2770/16043* (2013.01)

(58) Field of Classification Search
None
See application file for complete search history.

(56) References Cited

U.S. PATENT DOCUMENTS

| | | | |
|---|---|---|---|
| 2005/0037016 A1 | 2/2005 | Virgin |
| 2012/0276149 A1 | 11/2012 | Littman et al. |
| 2013/0149339 A1 | 6/2013 | Honda et al. |
| 2014/0187474 A1 | 7/2014 | Sonnenburg |
| 2014/0341921 A1 | 11/2014 | Honda et al. |
| 2016/0120915 A1 | 5/2016 | Blaser et al. |
| 2016/0228507 A1 | 7/2016 | Ribbeck et al. |

FOREIGN PATENT DOCUMENTS

WO 2014201037 A2 12/2014

OTHER PUBLICATIONS

Atarashi, Koji et al., "ATP drives lamina propia TH17 cell differentiation", Nature Letters (2008), vol. 455, p. 808. doi:10.1038/nature07240.

Atarashi, Koji et al., "Induction of Colonic Regulatory T Cells by Indigenous *Clostridium* Species", Science (2011), vol. 331, p. 337-341. www.sciencemag.org.

Atarashi, Koji et al., "Treg Induction by a Rationally Selected Mixture of Clostridia Strains From the Human Microbiota", Nature (2013), vol. 500, pp. 232-236 and Supplemental Material thereof.

Barnes, Michael J. and Powrie, Fiona, "Regulatory T Cells Reinforce Intestinal Homeostasis", Immunity Review (2009), vol. 31, pp. 401-411. doi:10.1016/j.immuni.2009.08.011.

Barton, Erik S. et al., "Herpesvirus latency confers symbiotic protection from bacterial infection", Nature Letters (2007), vol. 447, pp. 326-329. doi:10.1038/nature05762.

Bechara, Cherine and Sagan, Sandrine, "Cell-penetrating peptides: 20 years later, where do we stand?", FEBS Letters (2013), vol. 587, pp. 1693-1702.

Bjursell, Magnus K. et al., Functional Genomic and Metabolic Studies of the Adaptations of a Prominent Adult Human Gut Symbiont, Bacteroides thetaiotaomicron, to the Suckling Period, The Journal of Biological Chemistry (2006), vol. 281, No. 47, pp. 36269-36279. doi:101074/jbc.M606509200.

Bouskra, Djahida et al., "Lymhoid Tissue Genesis Induced by Commensals Through NOD1 Regulates Intestinal Homeostasis", Nature Letters (2008), vol. 456, p. 507-512. doi:10.1038/nature07450.

Cebra, John J., "Influences of Microbiota on Intestinal Immune System Development 1-3", Am j Clin Nutr (1999), vol. 69(suppl), pp. 1046S-1051S.

Costello, Elizabeth K. et al., "Bacterial Community Variation in Human Body Habitats Across Space and Time", Science (2009), vol. 326, No. 5960, pp. 1694-1697. doi:10.1126/science.1177486.

Curotto De Lafaille, Maria A. and Lafaille, Juan J., "Natural and Adaptive Foxp3+ Regulatory T Cells: More of the Same or a Division of Labor?", Immunity Review (2009), vol. 30, p. 626-635.

Duerkop, Breck A. and Hooper, Lora V., "Resident Viruses and Their Interactions with the Immune System", Nature Immunology (2013), vol. 14, No. 7, pp. 654-659.

Eckburg, Paul B. et al, "Diversity of the Human Intestinal Microbial Flora", Science (2005), vol. 308, pp. 1635-1638.

Gaboriau-Routhiau, Valerie et al., "The Key Role of Segmented Filamentous Bacteria in the Coordinated Maturation of Gut Helper T Cell Responses", Immunity (2009), vol. 31, pp. 677-689.

Garrett, Wendy S. et al., "Communicable Ulcerative Colitis Induced by t-bet Deficiency in the Innate Immune System", Cell (2007), vol. 131, pp. 33-45.

Grice, Elizabeth A. et al., "Topographical and Temporal Diversity of the Human Skin Microbiome", Science (2009), vol. 324, pp. 1190-1192.

Hernandez, Pedro P. et al., "Interferon-λ and Interleukin 22 Act Synergistically for the Induction of Interferon-Stimulated Genes and Control of Rotavirus Infection", Nature Immunology (2015), vol. 16, No. 7, pp. 698-707.

(Continued)

*Primary Examiner* — Nicole Kinsey White
(74) *Attorney, Agent, or Firm* — Troutman Sanders LLP

(57) ABSTRACT

The present invention relates to the use of NS1/2 region of murine norovirus MNV or a corresponding region from a member of the Caliciviridae family or a protein encoded by any one of those regions, for treating dysbiosis, immune system dysregulation and various disorders, as well as for enhancing mucosal integrity and stimulating IFN-induced genes.

11 Claims, 5 Drawing Sheets
(2 of 5 Drawing Sheet(s) Filed in Color)

Specification includes a Sequence Listing.

(56) References Cited

OTHER PUBLICATIONS

Hooper, Lora V. et al., "Interactions Between the Microbiota and the Immune System", Science (2012), vol. 336, pp. 1268-1273.
Ivanov, Ivaylo I. et al., "Induction of Intestinal Th17 Cells by Segmented Filamentous Bacteria", Cell (2009), vol. 139, pp. 485-498.
Ivanov, Ivaylo I. et al., "Specific Microbiota Direct the Differentiation of IL-17-Producing T-Helper Cells in the Mucosa of the Small Intestine", Cell Host & Microbe (2008), vol. 4, pp. 337-349.
Jones, Melissa K. et al., "Enteric Bacteria Promote Human and Mouse Norovirus Infection of B Cells", Science (2014), vol. 346, Issue 6210, pp. 755-759.
Kernbauer, Elisabeth et al., "An Enteric Virus can Replace the Beneficial Function of Commensal Bacteria", Nature (2014), vol. 516, pp. 94-98.
Lu, Li-Fan and Rudensky, Alexander, "Molecular Orchestration of Differentiation and Function of Regulatory T Cells", Genes & Development (2009), vol. 23, pp. 1270-1282.
Macpherson, Andrew J. and Harris, Nicola L., "Interactions Between Commensal Intestinal Bacteria and the Immune System", Nature Immunology (2004), vol. 4, pp. 478-485.
Mahowald, Michael A. et al., "Characterizing a Model Human Gut Microbiota Composed of Members of its Two Dominant Bacterial Phyla", PNAS (2009), vol. 106, pp. 5859-5864.
Maslowski, Kendle M. et al., "Regulation of Inflammatory Responses by Gut Microbiota and Chemoattractant Receptor GPR43", Nature (2009), vol. 461, pp. 1282-1286. doi:10.1038/nature08530.
Maynard, Craig L. et al., "Regulatory T Cells Expressing Interleukin 10 Develop from Foxp3+ and Foxp3− Precursor Cells in the Absence of Interleukin 10", Nature Immunology (2007), vol. 8, No. 9, pp. 931-941.
Nice, Timothy J. et al., "A Single-Amino-Acid Change in Murine Norovirus NS1/2 is Sufficient for Colonic Tropism and Persistence", Journal of Virology (2013), vol. 87, No. 1, pp. 327-334.
Osborne, Lisa C. et al., "Virus-helminth Co-infection Reveals a Microbiota-independent Mechanism of Immuno-modulation", Science (2014), vol. 345, (6196), pp. 578-582.
Pool-Zobel, Beatrice L. and Sauer, Julia, "Overvie of Experimental Data on Reduction of Colorectal Cancer Risk by Inulin-Type Fructans1-4", The Journal of Nutrition (2007), pp. 2580S-2584S.
Qin, Junjie et al., "A Human Gut Microbial Gene Catalogue Established by Metagenomic Sequencing", Nature (2010), vol. 464, pp. 59-65. doi:10.1038/nature08821.
Rapoport, Georges and Klier, Andre, "Gene Expression Using Bacillus", Current Opinion in Biotechnology (1990), vol. 1: pp. 21-27.
Reyes, Alejandro et al., "Viruses in the Faecal Microbiota of Monozygotic Twins and Their Mothers", Nature (2010), vol. 466, pp. 334-338. doi:10.1038/nature09199.
Roldao, Antonio et al., "Virus-like Particles in Vaccine Development", Expert Ref. Vaccines (2010), vol. 9, No. 10, pp. 1149-1176.
Round, June L. and Mazmanian, Sarkis K., "The Gut Microbiota Shapes Intestinal Immune Responses During Health and Disease", Nature Reviews Immunology (2009), vol. 9, No. 5, pp. 313-323.
Rubtsov, Yuri P. et al., "Regulatory T Cell-Derived Interleukin-10 Limits Inflammation at environmental Interfaces", Immunity (2008), vol. 28, pp. 546-558.
Sakaguchi, Shimon et al., "Regulatory T Cells and Immune Tolerance", Cell (2008), vol. 133, pp. 775-787.
Salzman, Nita H. et al., "Enteric Defensins are Essential Regulators of Intestinal Microbial Ecology", Nature Immunology (2010), vol. 11, No. 1, pp. 76-83. doi:10.1038/ni.1825.
Sanos, Stephanie L. et al., "RORγt and Commensal Microflora are Required for the Differentiation of Mucosal Interleukin 22-producing NKp46+ Cells", Nature Immunology (2009), vol. 10, No. 1, pp. 83-91. doi:10.1038/ni.1684.
Shoji-Kawata, Sanae et al., "Identification of a Candidate Therapeutic Autophagy-Inducing Peptide", Nature (2013), vol. 494, pp. 201-206. doi:10.1038/nature11866.
Sosnovtsev, Stanislav V. et al., "Cleavage Map and Proteolytic Processing of the Murine Norovirus Nonstructural Polyprotein in Infected Cells", Journal of Virology (2006), vol. 80, No. 16, pp. 7816-7831. doi:10.1128/JVI.00532-06.
Strong, David W. et al., "Protruding Domain of Capsid Protein is Necessary and Sufficient to Determine Murine Norovirus Replication and Pathogenesis In Vivo", Journal of Virology (2012), vol. 86, No. 6, pp. 2950-2958.
Thepaut, Marion et al., "Protective Role of Murine Norovirus Against Pseudomonas Aeruginosa Acute Pneumonia", Veterinary Research (2015), vol. 46, No. 91, pp. 1-7. doi:10.1186/s13567-015-0239-3.
Tomov, Vesselin T et al., "Persistent Enteric Murine Norovirus Infection is Associated With Functionally Suboptimal Virus-Specific CD8 T Cell Responses", Journal of Virology (2013), vol. 87, No. 12, pp. 7015-7031.
Virgin, Herbert W., "The virome in Mammalian Physiology and Disease", Cell (2014), pp. 142-150. http://dx.doi.org/10.1016/j.cell.2014.02.032.
Wikoff, William R. et al., "Metabolomics Analysis Reveals Large Effects of Gut Microflora on Mammalian Blood Metabolites", PNAS (2009), vol. 106, No. 1, pp. 3698-3703.
Yun, Yeonhee et al., "Nanoparticles for Oral Delivery: Targeted Nanoparticles With Peptidic Ligands for Oral Protein Delivery", Adv. Drug deliv Rev. (2013), vol. 65, No. 6, pp. 822-832.
Dabbagh, K. et al., "IL-4 Induces Mucin Gene Expression and Goblet Cell Metaplasia In Vitro and In Vivo" The Journal of Immunology (1999) vol. 162, No. 10, pp. 6233-6237.
Hunter, M.M. et al., "In Vitro-Derived Alternatively Activated Macrophages Reduce Colonic Inflammation in Mice" Gastroenterology (2010) vol. 138, No. 4, pp. 1395-1405.
Jackson, J.A. et al., "Review Series on Helminths, Immune Modulation and the Hygiene Hypothesis: Immunity Against Helminths and Immunological Phenomena in Modern Human Populations: Coevolutionary Legacies?" British Society for Immunology (2008) vol. 126, pp. 18-27.
Khan, W.I. et al., "Stat6 Dependent Goblet Cell Hyperplasia During Intestinal Nematode Infection" Parasite Immunology (2001) vol. 23, No. 1, pp. 39-42.
Loke, P. et al., "Alternative Activation is an Innate Response to Injury that Requires CD4+ T Cells to be Sustained During Chronic Infection" The Journal of Immunology (2007) vol. 179, No. 6, pp. 3926-3936.
Loke, P. et al., "PD-L1 and PD-L2 are Differentially Regulated by Th1 and Th2 Cells" PNAS (2003) vol. 100, No. 9, pp. 5336-5341.
Ramanan, D. et al., "Bacterial Sensor Nod2 Prevents Inflammation of the Small Intestine by Restricting the Expansion of the Commensal Bacteroides Vulgatus" Immunity (2014) vol. 41, pp. 311-324.
Ramanan, D. et al., "Helminth Infection Promotes Colonization Resistance Via Type 2 Immunity" Science (2016) vol. 352, Issue 6285, pp. 608-612.
Yutin, N. "A Genomic Update on Clostridial Phylogeny: Gram-Negative Spore-Formers and Other Misplaced Clostridia" Environ. Microbiol. (2013) vol. 15, No. 10, pp. 2631-2641.
Ziegler, T. et al., "A Novel Regulatory Macrophage Induced by a Helminth Molecule Instructs IL-10 in CD4+ T Cells and Protects Against Mucosal Inflammation" The Journal of Immunology (2015) vol. 194, pp. 1555-1564.
International Search Report and Written Opinion issued by the International Searching Authority in International Patent Application No. PCT/US2017/037978, dated Nov. 3, 2017, 19 pages total.
Cadwell, K., "Expanding the Role of the Virome: Commensalism in the Gut" (2015) vol. 89, No. 4, pp. 1951-1953.
Katayama, K. et al., "Plasmid-Based Human Norovirus Reverse Genetics System Produces Reporter-Tagged Progeny Virus Containing Infectious Genomic RNA" Proceedings National Academy of Sciences PNAS (2014) vol. 111, No. 38, pp. E4043-E4052.
Baker, E.S., "Characterization of the NS1-2 and NS4 Proteins of Murine Nororvirus" (2012) University of Otago, 4 pages total.
Communication (International Preliminary Report on Patenetability) issued by the International Patent Application No. PCT/US2017/037978, dated Dec. 18, 2018, 8 pages total.

(56) References Cited

OTHER PUBLICATIONS

Lee, S. et al., "A Secreted Viral Nonstructural Protein Determines Intestinal Norovirus Pathogenesis" Cell Host & Medicine (2019) vol. 25, pp. 845-857.

CW3.NS1CR6 = CW3 with the NS1/2 region of CR6

CR6.NS1CW3 = CR6 with the NS1/2 region of CW3

METHODS AND COMPOSITIONS FOR TREATING CANCER

CROSS-REFERENCE TO RELATED APPLICATIONS

This application claims the benefit of U.S. Provisional Patent Application No. 62/351,700, filed Jun. 17, 2016 and U.S. Provisional Patent Application No. 62/471,443, filed Mar. 15, 2017, each of which are incorporated by reference in their entirety.

STATEMENT REGARDING FEDERALLY SPONSORED RESEARCH

This invention was made with government support under Grant No. DK093668 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 16, 2017, is named 243735_000183_SL.txt and is 316,267 bytes in size.

FIELD OF THE INVENTION

The present invention, in some aspects, relates to the use of NS1/2 region of murine norovirus MNV or a corresponding region from another member of the Caliciviridae family or a protein encoded by any one of those regions, for treating dysbiosis, immune system dysregulation and various disorders, including diseases caused by an antibiotic exposure, infections, inflammatory disorders, metabolic disorders, aging-associated disorders, gastrointestinal disorders, conditions that affect a mucosal barrier, cancer, as well as for enhancing mucosal integrity and stimulating IFN-induced genes.

BACKGROUND

Multiple species of commensal microorganisms are harbored in the gastrointestinal (GI) tract of mammals, where they influence the development of the mucosal immune system leading to enhancement of protective functions of the mucous membranes and enabling the host to mount robust immune responses against pathogenic microbes invading the body, while staying non-responsive to dietary antigens and harmless microbes (Hooper et al., 2012, Science, 336:1268-73). Abnormality in the regulation of cross-talk between commensal bacteria and the immune system (GI dysbiosis) may lead to inflammatory and gastrointestinal conditions such as inflammatory bowel disease (IBD) ulcerative colitis, or Crohn's disease (U.S. Patent Appl. Pub. No. 20140341921 and references cited therein).

In addition to diverse populations of commensal bacterial species, the mammalian intestinal tract also hosts a broad variety of viruses that comprise the host's microvirome (Reyes et al., Nature 466, 334-338, (2010); Virgin, Cell 157, 142-150 (2014)).[3,4]. The coding potential of the enteric virome is predicted to be immense, because it includes viruses that infect host cells, endogenous retroviruses, and viruses that infect the various microbial inhabitants of the gastrointestinal tract, such as bacteria, archaea, and fungi. Recent studies indicate that the most abundant members of the enteric virome, bacteriophages that infect commensal bacteria, are diverse and likely to have a substantial impact on the host (Duerkop B A, Hooper L V. 2013. Nat. Immunol. 14:654-659).

SUMMARY OF THE INVENTION

There is a great need in the art to identify new approaches to treating dysbiosis in the gastrointestinal (GI) tract and treating GI and inflammatory disorders. The present disclosure addresses this and other needs by providing methods based on the use of NS1/2 region of murine norovirus MNV (e.g., of MNV strain CR6) or a corresponding region from a member of the Caliciviridae family, or a protein encoded by any one of those regions.

It is believed that animal viruses in the gut not only are pathogens that infect host cells and cause gastroenteritis but also are symbiotic modulators of host physiology. Members of the viral component of the intestinal microbiota could include pathogens such as noroviruses that continue to persist after disease is resolved[5], Anelloviridae and Circoviridae family members that are ubiquitously detected in healthy individuals[6-8], and uncharacterized viruses that display little sequence identity with known viruses[9-11].

Immune stimulation by viruses induces antibacterial defense mechanisms (Barton et al., Nature 447, 326-329 (2007)), suggesting that tonic signaling by viruses or virus-derived molecules could augment microbiota-driven colonization resistance. For example, enteric infection with murine norovirus (MNV) limits colonic inflammation after *Citrobacter rodentium* infection (Kernbauer et al., Nature 516, 94-98 (2014)), and reovirus infection of the small intestines of neonatal mice induces production of interleukin-22 (IL-22), a cytokine that induces expression of Reg3g by intestinal epithelial cells (Hernandez et al., Nat. Immunol. 16, 698-707 (2015)). However, specific viral-derived ligands that drive antibacterial defenses have not been identified, and thus, it remains unclear whether such ligands can enhance immune-mediated colonization resistance.

Murine norovirus (MNV) is a positive-strand RNA virus of the Caliciviridae family that is endemic in mouse facilities[13]. MNV displays tropism for myeloid cells and can establish persistent infection without causing obvious disease in immunocompetent mice[13,14]. Persistent infection by the MNV strain CR6 (MNV.CR6) induces intestinal pathologies in mice deficient in the inflammatory bowel disease (IBD) gene Atg16L115. MNV is easily detectable in the gastrointestinal tract and it has been used as a model to understand the biology of human noroviruses because of its ability to be propagated in cell culture and infect mice. MNV and human noroviruses may also share a dependence on B cells and commensal bacteria for efficient replication (Jones et al., 2014. Science 346:755-759). However, rather than inducing an acute vomiting and diarrheal disease like human noroviruses, MNV frequently establishes persistent infection in immunocompetent mice without causing obvious disease.

In one aspect, the disclosure provides a method for treating dysbiosis and/or consequences thereof in a subject in need thereof, said method comprising administering to said subject a therapeutically effective amount of NS1/2 genomic region of murine norovirus MNV or a corresponding region from a member of the Caliciviridae family, or a protein encoded by any one of those regions. In one embodiment, said dysbiosis is in at least one organ system (e.g., gastrointestinal (GI) system, skin and/or respiratory system). In one embodiment, said dysbiosis has been caused by an antibiotic exposure. In one embodiment, said dysbiosis has been caused by an infection with a pathogen (e.g., viruses, bacteria, eukaryotic parasites).

In another aspect, the disclosure provides a method for treating a disease caused by an antibiotic exposure in a subject in need thereof, said method comprising administering to said subject a therapeutically effective amount of NS1/2 genomic region of murine norovirus MNV or a corresponding region from a member of the Caliciviridae family or a protein encoded by any one of those regions.

In a further aspect, the disclosure provides a method for treating an immune system dysregulation in a subject in need thereof, said method comprising administering to said subject a therapeutically effective amount of NS1/2 genomic region of murine norovirus MNV or a corresponding region from a member of the Caliciviridae family or a protein encoded by any one of those regions.

In another aspect, the disclosure provides a method for treating an infection or an inflammatory disorder in a subject in need thereof, said method comprising administering to said subject a therapeutically effective amount of NS1/2 genomic region of murine norovirus MNV or a corresponding region from a member of the Caliciviridae family, or a protein encoded by any one of those regions. Non-limiting examples of disorders treatable by this method include, e.g., inflammatory bowel disease (IBD), ulcerative colitis, Crohn's disease, irritable bowel syndrome (IBS), sprue, autoimmune arthritis, rheumatoid arthritis, Type I diabetes, multiple sclerosis (MS), amyotrophic lateral sclerosis (ALS), osteoarthritis, juvenile chronic arthritis, Lyme arthritis, psoriatic arthritis, reactive arthritis, spondyloarthropathy, systemic lupus erythematosus (SLE), insulin dependent diabetes mellitus, thyroiditis, asthma, psoriasis, dermatitis scleroderma, atopic dermatitis, graft versus host disease, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlejn purpurea, microscopic vasculitis of the kidneys, chronic active hepatitis, uveitis, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, polyglandular deficiency type I syndrome and polyglandular deficiency type II syndrome, Schmidt's syndrome, adult (acute) respiratory distress syndrome, alopecia, alopecia areata, seronegative arthopathy, arthropathy, Reiter's disease, psoriatic arthropathy, chlamydia, yersinia and salmonella associated arthropathy, spondy-loarhopathy, atheromatous disease/arteriosclerosis, allergic colitis, atopic allergy, food allergies such as peanut allergy, tree nut allergy, egg allergy, milk allergy, soy allergy, wheat allergy, seafood allergy, shellfish allergy, or sesame seed allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, idiopathic pulmonary fibrosis, chronic eosinophilic pneumonia, lymphocytic infiltrative lung disease, postinfectious interstitial lung disease, gouty arthritis, autoimmune hepatitis, type-1 autoimmune hepatitis, type-2 autoimmune hepatitis, autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, discoid lupus, erythematosus, male infertility idiopathic or NOS, sperm autoimmunity, multiple sclerosis, insulin dependent diabetes mellitus, sympathetic ophthalmia, pulmonary hypertension secondary to connective tissue disease, Goodpasture's syndrome, pulmonary manifestation of polyarteritis nodosa, acute rheumatio fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, allergic rhinitis, anaphylaxis, pet allergies, latex allergies, drug allergies, allergic rhinoconjuctivitis, eosinophilic esophagitis, hypereosinophilic syndrome, eosinophilic gastroenteritis cutaneous lupus erythematosus, eosinophilic esophagitis, hypereosinophilic syndrome, and eosinophilic gastroenteritis, diarrhea, colon cancer, cystic fibrosis, celiac disease, Type 2 diabetes, autism-related immunopathologies, and common variable immuno-deficiency (CVID).

In yet another aspect, the disclosure provides a method for treating a metabolic disorder in a subject in need thereof, said method comprising administering to said subject a therapeutically effective amount of NS1/2 genomic region of murine norovirus MNV or a corresponding region from a member of the Caliciviridae family or a protein encoded by any one of those regions.

In a further aspect, the disclosure provides a method for treating aging in a subject in need thereof, said method comprising administering to said subject a therapeutically effective amount of NS1/2 genomic region of murine norovirus MNV or a corresponding region from a member of the Caliciviridae family or a protein encoded by any one of those regions.

In another aspect, the disclosure provides a method for treating a gastrointestinal disorder in a subject in need thereof, said method comprising administering to said subject a therapeutically effective amount of NS1/2 genomic region of murine norovirus MNV or a corresponding region from a member of the Caliciviridae family, or a protein encoded by any one of those regions. Non-limiting examples of gastrointestinal disorders treatable by this method include, e.g., inflammatory bowel disease (IBD), ulcerative colitis, Crohn's disease, irritable bowel syndrome (IBS), infectious gastroenteritis, non-infectious gastroenteritis, food allergy, gastrointestinal graft versus host disease, small intestinal cancer, colon cancer, pouchitis, intestinal failure, short bowel syndrome, and antibiotics-associated diarrhea (e.g., antibiotic-associated diarrhea is caused by *Clostridium difficile* or vancomycin-resistant Enterococcus (VRE)).

In a further aspect, the disclosure provides a method for treating a condition that affects a mucosal barrier in a subject in need thereof, said method comprising administering to said subject a therapeutically effective amount of NS1/2 genomic region of murine norovirus MNV or a corresponding region from a member of the Caliciviridae family, or a protein encoded by any one of those regions. In one embodiment, the condition is an infectious or non-infectious pneumonia.

In yet another aspect, the disclosure provides a method for treating a cancer and/or enhancing the effectiveness of an anti-cancer therapy in a subject in need thereof, said method comprising administering to said subject a therapeutically effective amount of NS1/2 genomic region of murine norovirus MNV or a corresponding region from a member of the Caliciviridae family, or a protein encoded by any one of those regions.

In a related aspect, the disclosure provides a method for improving a cancer immunotherapy in a subject in need thereof, said method comprising administering to said subject a therapeutically effective amount of NS1/2 genomic region of murine norovirus MNV or a corresponding region from a member of the Caliciviridae family, or a protein encoded by any one of those regions.

In a further aspect, the disclosure provides a method for enhancing mucosal integrity in a subject in need thereof, said method comprising administering to said subject a therapeutically effective amount of NS1/2 genomic region of murine norovirus MNV or a corresponding region from a member of the Caliciviridae family or a protein encoded by any one of those regions.

In another aspect, the disclosure provides a method for stimulating IFN-induced genes (e.g., ISG15, Apol9a, PKR, MX1, OAS1, etc.) in a subject in need thereof, said method comprising administering to said subject a therapeutically effective amount of NS1/2 genomic region of murine norovirus MNV or a corresponding region from a member of the Caliciviridae family or a protein encoded by any one of those regions.

In one embodiment of any of the above methods of the disclosure, the NS1/2 genomic region of murine norovirus MNV comprises (or consists, or consists essentially of) a nucleotide sequence encoded by a DNA sequence selected from the group consisting of SEQ ID NO: 1, SEQ ID NO: 11, SEQ ID NO: 13, SEQ ID NO: 15, SEQ ID NO: 17, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, and any functional fragment or derivative thereof. In one embodiment, the NS1/2 genomic region of murine norovirus MNV comprises (or consists, or consists essentially of) a nucleotide sequence encoded by the DNA sequence SEQ ID NO: 1, SEQ ID NO: 11, or SEQ ID NO: 108 or any functional fragment or derivative thereof. In one embodiment, a functional fragment of the NS1/2 genomic region of murine norovirus MNV comprises (or consists, or consists essentially of) a nucleotide sequence encoded by the DNA sequence SEQ ID NO: 5 or SEQ ID NO: 115. In one embodiment, a derivative of the NS1/2 genomic region of murine norovirus MNV comprises (or consists, or consists essentially of) a nucleotide sequence encoded by a DNA sequence having at least 90% identity (at least 95% identity, at least 98% identity, at least 99% identity) to SEQ ID NO: 1, SEQ ID NO: 11, SEQ ID NO: 108, SEQ ID NO: 5, or SEQ ID NO: 115. In one embodiment, a protein encoded by the NS1/2 region of murine norovirus MNV comprises (or consists, or consists essentially of) an amino acid sequence selected from the group consisting of SEQ ID NO: 4, SEQ ID NO: 12, SEQ ID NO: 14, SEQ ID NO: 16, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33. SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and any functional fragment or derivative thereof (e.g., with or without the signal sequence). In one embodiment, a protein encoded by the NS1/2 region of murine norovirus MNV comprises (or consists, or consists essentially of) the amino acid sequence SEQ ID NO: 4, SEQ ID NO: 12, or SEQ ID NO: 109 or any functional fragment or derivative thereof (e.g., with or without the signal sequence). In one embodiment, a functional fragment of a protein encoded by the NS1/2 region of murine norovirus MNV comprises (or consists, or consists essentially of) the amino acid sequence SEQ ID NO: 6 or SEQ ID NO: 116. In one embodiment, a derivative of a protein encoded by the NS1/2 genomic region of murine norovirus MNV comprises (or consists, or consists essentially of) the amino acid sequence having at least 90% identity (at least 95% identity, at least 98% identity, at least 99% identity) to SEQ ID NO: 4, SEQ ID NO: 12, SEQ ID NO: 109, SEQ ID NO: 6, or SEQ ID NO: 116.

In one embodiment of any of the above methods of the disclosure, the corresponding region from a member of the Caliciviridae family is from a human calicivirus.

In one embodiment of any of the above methods of the disclosure, the NS1/2 genomic region of murine norovirus MNV or the corresponding region from a member of the Caliciviridae family, is administered in a vector comprising said region or encoding a protein encoded by said region. In one embodiment, the vector is a viral vector. Non-limiting examples of useful viral vectors include, e.g., adenoviral vectors, adeno-associated virus (AAV) vectors, norovirus vectors, retroviral vectors, lentiviral vectors, and herpesviral vectors (e.g., cytomegalovirus vectors).

In one embodiment of any of the above methods of the disclosure, the NS1/2 genomic region of murine norovirus MNV or the corresponding region from a member of the Caliciviridae family, or a protein encoded by any one of those regions is contained within a recombinant murine norovirus MNV, engineered to infect human cells (e.g., B cells, T cells, natural killer (NK) cells, natural killer T (NKT)

cells, innate lymphoid cells (ILCs), dendritic cells, monocytes, macrophages, and/or epithelial cells [e.g., Tuft cells]). In one embodiment, the recombinant murine norovirus MNV, engineered to infect human cells comprises one or more amino acid changes in the major capsid protein VP1 and/or in the minor capsid protein VP2. In one embodiment, VP1 of MNV comprises (or consists, or consists essentially of) the amino acid sequence SEQ ID NO: 8. In one embodiment, VP2 of MNV comprises (or consists, or consists essentially of) the amino acid sequence SEQ ID NO: 10.

In one embodiment of any of the above methods of the disclosure, the NS1/2 genomic region of murine norovirus MNV or the corresponding region from a member of the Caliciviridae family, or a protein encoded by any one of those regions is administered in a nanoparticle or a liposomal particle or a virion-like particle.

In one embodiment of any of the above methods of the disclosure, the NS1/2 region of murine norovirus MNV or the corresponding region from a member of the Caliciviridae family, or a protein encoded of any of those regions is co-administered with a cell-penetrating peptide (CPP).

In one embodiment of any of the above methods of the disclosure, the NS1/2 genomic region of murine norovirus MNV or the corresponding region from a member of the Caliciviridae family, or a protein encoded by any one of those regions is administered in a recombinant bacteriophage.

In one embodiment of any of the above methods of the disclosure, the NS1/2 region of murine norovirus MNV or the corresponding region from a member of the Caliciviridae family is administered as naked RNA. In one embodiment, said naked RNA comprises one or more modified bases.

In one embodiment of any of the above methods of the disclosure, the NS1/2 region of murine norovirus MNV or the corresponding region from a member of the Caliciviridae family, or a protein encoded by any one of those regions is administered in a bacterial or fungal (e.g., yeast) host cell. Non-limiting examples of the forms in which said bacterial host cell can be administered include, e.g., live bacterial cells, conditionally lethal bacterial cells, inactivated bacterial cells, killed bacterial cells, and spores. In one embodiment, said bacterial host cell is administered together with (i) a carrier and/or buffering agent and/or (ii) one or more prebiotic agents which enhance growth or activity of said bacteria.

In one embodiment of any of the above methods of the disclosure, the administration is to a mucosal surface and/or cells compromising affected tissue.

In one embodiment of any of the above methods of the disclosure, the method comprises administering to the subject one or more additional compounds (e.g., immunosuppressives, immunostimulatory compounds, biologicals, probiotics, prebiotics, cytokines [e.g., IFN or IL-22]).

In one embodiment of any of the above methods of the disclosure, the subject is human.

In a separate aspect, the disclosure provides a recombinant vector comprising NS1/2 genomic region of murine norovirus MNV or a corresponding region from a member of the Caliciviridae family (e.g., a human calicivirus) or encoding a protein encoded by said region. In one embodiment, the vector is a viral vector. Non-limiting examples of useful viral vectors include adenoviral vectors, adeno-associated virus (AAV) vectors, norovirus vectors, retroviral vectors, lentiviral vectors, and herpesviral vectors (e.g., cytomegalovirus vectors). In one embodiment, the vector comprises the NS1/2 genomic region of murine norovirus MNV which comprises (or consists, or consists of) a nucleotide sequence encoded by a DNA sequence selected from the group consisting of SEQ ID NO: 1, SEQ ID NO: 11, SEQ ID NO: 13, SEQ ID NO: 15, SEQ ID NO: 17, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, and any functional fragment or derivative thereof. In one embodiment, the NS1/2 genomic region of murine norovirus MNV comprises (or consists, or consists of) a nucleotide sequence encoded by the DNA sequence of SEQ ID NO: 1, SEQ ID NO: 11, or SEQ ID NO: 108 or any functional fragment or derivative thereof. In one embodiment, a functional fragment of the NS1/2 genomic region of murine norovirus MNV comprises (or consists, or consists of) a nucleotide sequence encoded by the DNA sequence SEQ ID NO: 5 or SEQ ID NO: 115. In one embodiment, a derivative of the NS1/2 genomic region of murine norovirus MNV comprises (or consists, or consists essentially of) a nucleotide sequence encoded by a DNA sequence having at least 90% identity (at least 95% identity, at least 98% identity, at least 99% identity) to SEQ ID NO: 1, SEQ ID NO: 11, SEQ ID NO: 108, SEQ ID NO: 5, or SEQ ID NO: 115.

In a related aspect, the disclosure provides pharmaceutical compositions comprising any of the above vectors.

In another aspect, the disclosure provides a recombinant murine norovirus MNV comprising NS1/2 genomic region of murine norovirus MNV or a corresponding region from a member of the Caliciviridae family (e.g., a human calicivirus), or a protein encoded by any one of those regions, wherein said recombinant norovirus is engineered to infect human cells (e.g., B cells, T cells, natural killer (NK) cells, natural killer T (NKT) cells, innate lymphoid cells (ILCs), dendritic cells, monocytes, macrophages, and/or epithelial cells [e.g., Tuft cells]). In one embodiment, the NS1/2 genomic region of murine norovirus MNV comprises (or consists, or consists essentially of) a nucleotide sequence encoded by a DNA sequence selected from the group consisting of SEQ ID NO: 1, SEQ ID NO: 11, SEQ ID NO: 13, SEQ ID NO: 15, SEQ ID NO: 17, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, and any functional fragment or derivative thereof. In one embodiment, the NS1/2 genomic region of murine norovirus MNV comprises (or consists, or consists essentially of) a nucleotide sequence encoded by the DNA sequence SEQ ID NO: 1, SEQ ID NO: 11, or SEQ ID NO: 108 or any functional fragment or derivative thereof. In one embodiment, a functional fragment of the NS1/2 genomic region of murine norovirus MNV comprises (or consists, or consists essentially of) a nucleotide sequence encoded by the DNA sequence SEQ ID NO: 5 or SEQ ID NO: 115. In one embodiment, a derivative of the NS1/2 genomic region of murine norovirus MNV comprises (or consists, or consists essentially of) a nucleotide sequence encoded by a DNA sequence having at least 90% identity (at least 95% identity, at least 98% identity, at least 99% identity) to SEQ ID NO: 1, SEQ ID NO: 11, SEQ ID NO: 108, SEQ ID NO: 5, or SEQ ID NO: 115. In one embodiment, a protein encoded by the NS1/2 region of murine norovirus MNV comprises (or consists, or consists essentially of) an amino acid sequence selected from the group consisting of SEQ ID NO: 4, SEQ ID NO: 12, SEQ ID NO: 14, SEQ ID NO: 16, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33. SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and any functional fragment or derivative thereof (e.g., with or without the signal sequence). In one embodiment, a protein encoded by the NS1/2 region of murine norovirus MNV comprises (or consists, or consists essentially of) the amino acid sequence SEQ ID NO: 4, SEQ ID NO: 12, or SEQ ID NO: 109 or any functional fragment or derivative thereof (e.g., with or without the signal sequence). In one embodiment, a protein encoded by the NS1/2 region of murine norovirus MNV comprises (or consists, or consists essentially of) the amino acid sequence SEQ ID NO: 6 or SEQ ID NO: 116. In one embodiment, a derivative of a protein encoded by the NS1/2 genomic region of murine norovirus MNV comprises (or consists, or consists essentially of) the amino acid sequence having at least 90% identity (at least 95% identity, at least 98% identity, at least 99% identity) to SEQ ID NO: 4, SEQ ID NO: 12, SEQ ID NO: 109, SEQ ID NO: 6, or SEQ ID NO: 116. In one embodiment, the recombinant murine norovirus comprises one or more amino acid changes in the major capsid protein VP1 and/or in the minor capsid protein VP2. In one embodiment, VP1 of MNV comprises (or consists, or consists essentially of) the amino acid sequence SEQ ID NO: 8. In one embodiment, VP2 of MNV comprises (or consists, or consists essentially of) the amino acid sequence SEQ ID NO: 10.

In a related aspect, the disclosure provides pharmaceutical compositions comprising any of the above recombinant viruses.

In another aspect, the disclosure provides a particle comprising NS1/2 genomic region of murine norovirus MNV or a corresponding region from a member of the Caliciviridae family (e.g., human calicivirus), or a protein encoded by any one of those regions. In one embodiment, the particle is a nanoparticle or a liposomal particle or a virion-like particle. In one embodiment, the NS1/2 genomic region of murine norovirus MNV comprises (or consists, or consists essentially of) a nucleotide sequence encoded by a DNA sequence selected from the group consisting of SEQ ID NO: 1, SEQ ID NO: 11, SEQ ID NO: 13, SEQ ID NO: 15, SEQ ID NO: 17, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, and any functional fragment or derivative thereof. In one embodiment, the NS1/2 genomic region of murine norovirus MNV comprises (or consists, or consists essentially of) a nucleotide sequence encoded by the DNA sequence SEQ ID NO: 1, SEQ ID NO: 11, or SEQ ID NO: 108 or any functional fragment or derivative thereof. In one embodiment, a functional fragment of the NS1/2 genomic region of murine norovirus MNV comprises (or consists, or consists essentially of) a nucleotide sequence encoded by the DNA sequence SEQ ID NO: 5 or SEQ ID NO: 115. In one embodiment, a derivative of the NS1/2 genomic region of murine norovirus MNV comprises (or consists, or consists essentially of) a nucleotide sequence encoded by a DNA sequence having at least 90% identity (at least 95% identity, at least 98% identity, at least 99% identity) to SEQ ID NO: 1, SEQ ID NO: 11, SEQ ID NO: 108, SEQ ID NO: 5, or SEQ ID NO: 115. In one embodiment, a protein encoded by the NS1/2 region of murine norovirus MNV comprises (or consists, or consists essentially of) an amino acid sequence selected from the group consisting of SEQ ID NO: 4, SEQ ID NO: 12, SEQ ID NO: 14, SEQ ID NO: 16, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33. SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and any functional fragment or derivative thereof (e.g., with or without the signal sequence). In one embodiment, a protein encoded by the NS1/2 region of murine norovirus MNV CR6 comprises (or consists, or consists essentially of) the amino acid sequence SEQ ID NO: 4, SEQ ID NO: 12, or SEQ ID NO: 109 or any functional fragment or derivative thereof (e.g., with or without the signal sequence). In one embodiment, a protein encoded by the NS1/2 region of murine norovirus MNV comprises (or consists, or consists essentially of) the amino acid sequence SEQ ID NO: 6 or SEQ ID NO: 116. In one embodiment, a derivative of a protein encoded by the NS1/2 genomic region of murine norovirus MNV comprises (or consists, or consists essentially of) the amino acid sequence having at least 90% identity (at least 95% identity, at least 98% identity, at least 99% identity) to SEQ ID NO: 4, SEQ ID NO: 12, SEQ ID NO: 109, SEQ ID NO: 6, or SEQ ID NO: 116.

In a related aspect, the disclosure provides pharmaceutical compositions comprising any of the above particles.

In a further aspect, the disclosure provides a composition comprising (i) NS1/2 genomic region of murine norovirus MNV or a corresponding region from a member of the Caliciviridae family (e.g., a human calicivirus), or a protein encoded by any one of those regions, and (ii) a cell-penetrating peptide (CPP). In one embodiment, the NS1/2 genomic region of murine norovirus MNV or a corresponding region from a member of the Caliciviridae family is in the form of naked RNA. In one embodiment, said naked RNA comprises one or more modified bases. In one embodiment, the NS1/2 region of murine norovirus MNV comprises (or consists, or consists essentially of) a nucleotide sequence encoded by a DNA sequence selected from the group consisting of SEQ ID NO: 1, SEQ ID NO: 11, SEQ ID NO: 13, SEQ ID NO: 15, SEQ ID NO: 17, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, and any functional fragment or derivative thereof. In one embodiment, the NS1/2 genomic region of murine norovirus MNV comprises (or consists, or consists essentially of) a nucleotide sequence encoded by the DNA sequence SEQ ID NO: 1, SEQ ID NO: 11, or SEQ ID NO: 108 or any functional fragment or derivative thereof. In one embodiment, any functional fragment of the NS1/2 genomic region of murine norovirus MNV comprises (or consists, or consists essentially of) a nucleotide sequence encoded by the DNA sequence SEQ ID NO: 5 or SEQ ID NO: 115. In one embodiment, a derivative of the NS1/2 genomic region of murine norovirus MNV comprises (or consists, or consists essentially of) a nucleotide sequence encoded by a DNA sequence having at least 90% identity (at least 95% identity, at least 98% identity, at least 99% identity) to SEQ ID NO: 1, SEQ ID NO: 11, SEQ ID NO: 108, SEQ ID NO: 5, or SEQ ID NO: 115. In one embodiment, a protein encoded by the NS1/2 region of murine norovirus MNV comprises (or consists, or consists essentially of) an amino acid sequence selected from the group consisting of SEQ ID NO: 4, SEQ ID NO: 12, SEQ ID NO: 14, SEQ ID NO: 16, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33. SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and any functional fragment or derivative thereof (e.g., with or without the signal sequence). In one embodiment, a protein encoded by the NS1/2 region of murine norovirus MNV comprises (or consists, or consists essentially of) the amino acid sequence SEQ ID NO: 4, SEQ ID NO: 12, or SEQ ID NO: 109 or any functional fragment or derivative thereof (e.g., with or without the signal sequence). In one embodiment, a protein encoded by the NS1/2 region of murine norovirus MNV comprises (or consists, or consists essentially of) the amino acid sequence SEQ ID NO: 6 or SEQ ID NO: 116. In one embodiment, a derivative of a protein encoded by the NS1/2 genomic region of murine norovirus MNV comprises (or consists, or consists essentially of) the amino acid sequence having at least 90% identity (at least 95% identity, at least 98% identity, at least 99% identity) to SEQ ID NO: 4, SEQ ID NO: 12, SEQ ID NO: 109, SEQ ID NO: 6, or SEQ ID NO: 116.

In another aspect, the disclosure provides a recombinant bacteriophage comprising NS1/2 genomic region of murine norovirus MNV or a corresponding region from a member of the Caliciviridae family (e.g., a human calicivirus), or a protein encoded by any one of those regions. In one embodiment, the NS1/2 region of murine norovirus MNV comprises (or consists, or consists essentially of) a nucleotide sequence encoded by a DNA sequence selected from the group consisting of SEQ ID NO: 1, SEQ ID NO: 11, SEQ ID NO: 13, SEQ ID NO: 15, SEQ ID NO: 17, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, and any functional fragment or derivative thereof. In one embodiment, the NS1/2 genomic region of murine norovirus MNV comprises (or consists, or consists essentially of) a nucleotide sequence encoded by the DNA sequence SEQ ID NO: 1, SEQ ID NO: 11, or SEQ ID NO: 108 or any functional fragment or derivative thereof. In one embodiment, a functional fragment of the NS1/2 genomic region of murine norovirus MNV comprises (or consists, or consists essentially of) a nucleotide sequence encoded by the DNA sequence SEQ ID NO: 5 or SEQ ID NO: 115. In one embodiment, a derivative of the NS1/2 genomic region of murine norovirus MNV comprises (or consists, or consists essentially of) a nucleotide sequence encoded by a DNA sequence having at least 90% identity (at least 95% identity, at least 98% identity, at least 99% identity) to SEQ ID NO: 1, SEQ ID NO: 11, SEQ ID NO: 108, SEQ ID NO: 5, or SEQ ID NO: 115. In one embodiment, a protein encoded by the NS1/2 region of murine norovirus MNV comprises (or consists, or consists essentially of) an amino acid sequence selected from the group consisting of SEQ ID NO: 4, SEQ ID NO: 12, SEQ ID NO: 14, SEQ ID NO: 16, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33. SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and any functional fragment or derivative thereof (e.g., with or without the signal sequence). In one embodiment, a protein encoded by the NS1/2 region of murine norovirus MNV comprises (or consists, or consists essentially of) the amino acid sequence SEQ ID NO: 4, SEQ ID NO: 12, or SEQ ID NO: 109 or any functional fragment or derivative thereof (e.g., with or without the signal sequence). In one embodiment, a protein encoded by the NS1/2 region of murine norovirus MNV comprises (or consists, or consists essentially of) the amino acid sequence SEQ ID NO: 6 or SEQ ID NO: 116. In one embodiment, a derivative of a protein encoded by the NS1/2 genomic region of murine norovirus MNV comprises (or consists, or consists essentially of) the amino acid sequence having at least 90% identity (at least 95% identity, at least 98% identity, at least 99% identity) to SEQ ID NO: 4, SEQ ID NO: 12, SEQ ID NO: 109, SEQ ID NO: 6, or SEQ ID NO: 116.

In a related aspect, the disclosure provides pharmaceutical compositions comprising any of the above bacteriophages.

In a further aspect, the disclosure provides a recombinant bacterial or fungal (e.g., yeast) cell comprising NS1/2 genomic region of murine norovirus MNV or a corresponding region from a member of the Caliciviridae family (e.g., a human calicivirus), or a protein encoded by any one of those regions. In one embodiment, the NS1/2 region of murine norovirus MNV comprises (or consists, or consists essentially of) a nucleotide sequence encoded by a DNA sequence selected from the group consisting of SEQ ID NO: 1, SEQ ID NO: 11, SEQ ID NO: 13, SEQ ID NO: 15, SEQ ID NO: 17, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, and any functional fragment or derivative thereof. In one embodiment, the NS1/2 genomic region of murine norovirus MNV comprises (or consists, or consists essentially of) a nucleotide sequence encoded by the DNA sequence SEQ ID NO: 1, SEQ ID NO: 11, or SEQ ID NO: 108 or any functional fragment or derivative thereof. In one embodiment, a functional fragment of the NS1/2 genomic region of murine norovirus MNV comprises (or consists, or consists essentially of) a nucleotide sequence encoded by the DNA sequence SEQ ID NO: 5 or SEQ ID NO: 115. In one embodiment, a derivative of the NS1/2 genomic region of murine norovirus MNV comprises (or consists, or consists essentially of) a nucleotide sequence encoded by a DNA sequence having at least 90% identity (at least 95% identity, at least 98% identity, at least 99% identity) to SEQ ID NO: 1, SEQ ID NO: 11, SEQ ID NO: 108, SEQ ID NO: 5, or SEQ ID NO: 115. In one embodiment, a protein encoded by the NS1/2 region of murine norovirus MNV comprises (or consists, or consists essentially of) an amino acid sequence selected from the group consisting of SEQ ID NO: 4, SEQ ID NO: 12, SEQ ID NO: 14, SEQ ID NO: 16, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33. SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and any functional fragment or derivative thereof (e.g., with or without the signal sequence). In one embodiment, a protein encoded by the NS1/2 region of murine norovirus MNV comprises (or consists, or consists essentially of) the amino acid sequence SEQ ID NO: 4, SEQ ID NO: 12, or SEQ ID NO: 109 or any functional fragment or derivative thereof (e.g., with or without the signal sequence). In one embodiment, a protein encoded by the NS1/2 region of murine norovirus MNV comprises (or consists, or consists essentially of) the amino acid sequence SEQ ID NO: 6 or SEQ ID NO: 116. In one embodiment, a derivative of a protein encoded by the NS1/2 genomic region of murine norovirus MNV comprises (or consists, or consists essentially of) the amino acid sequence having at least 90% identity (at least 95% identity, at least 98% identity, at least 99% identity) to SEQ ID NO: 4, SEQ ID NO: 12, SEQ ID NO: 109, SEQ ID NO: 6, or SEQ ID NO: 116.

In a related aspect, the disclosure provides pharmaceutical compositions comprising any of the above recombinant bacterial or fungal (e.g., yeast) cells. Non-limiting examples of forms in which bacterial cells can be present in such pharmaceutical compositions include, e.g., live bacterial cells, conditionally lethal bacterial cells, inactivated bacterial cells, killed bacterial cells, and spores.

Any of the compositions of the disclosure can be formulated for various routes of administration (e.g., oral, topical, rectal, mucosal, sublingual, nasal, intravenous, subcutaneous, by inhalation, or via naso/oro-gastric gavage).

Also provided herein are methods comprising administering to a subject having dysbiosis an engineered (e.g., recombinant or synthetic) nucleic acid comprising (or consisting, or consisting essentially of) a nucleotide sequence that is at least 90% identical to the nucleotide sequence of SEQ ID NO: 1. In some aspects, the methods comprise administering to a subject having dysbiosis an engineered (e.g., recombinant or synthetic) nucleic acid comprising (or consisting, or consisting essentially of) a nucleotide sequence that is at least 90% identical to the nucleotide sequence of SEQ ID NO: 11. In some aspects, the methods comprise administering to a subject having dysbiosis an engineered (e.g., recombinant or synthetic) nucleic acid comprising (or consisting, or consisting essentially of) a nucleotide sequence that is at least 90% identical to the nucleotide sequence of SEQ ID NO: 108. In some aspects, the methods comprise administering to a subject having dysbiosis an engineered (e.g., recombinant or synthetic) nucleic acid comprising (or consisting, or consisting essentially of) a nucleotide sequence that is at least 90% identical to the nucleotide sequence of SEQ ID NO: 5. In some aspects, the methods comprise administering to a subject having dysbiosis an engineered (e.g., recombinant or synthetic) nucleic acid comprising (or consisting, or consisting essentially of) a nucleotide sequence that is at least 90% identical to the nucleotide sequence of SEQ ID NO: 115.

Also provided herein are methods comprising administering to a subject having a gastrointestinal disorder an engineered (e.g., recombinant or synthetic) nucleic acid comprising (or consisting, or consisting essentially of) a nucleotide sequence that is at least 90% identical to the nucleotide sequence of SEQ ID NO: 1. In some aspects, the methods comprise administering to a subject having a gastrointestinal disorder an engineered (e.g., recombinant or synthetic) nucleic acid comprising (or consisting, or consisting essentially of) a nucleotide sequence that is at least 90% identical to the nucleotide sequence of SEQ ID NO: 11. In some aspects, the methods comprise administering to a subject having a gastrointestinal disorder an engineered (e.g., recombinant or synthetic) nucleic acid comprising (or consisting, or consisting essentially of) a nucleotide sequence that is at least 90% identical to the nucleotide sequence of SEQ ID NO: 108. In some aspects, the methods comprise administering to a subject having a gastrointestinal disorder an engineered (e.g., recombinant or synthetic) nucleic acid comprising (or consisting, or consisting essentially of) a nucleotide sequence that is at least 90% identical to the nucleotide sequence of SEQ ID NO: 5. In some aspects, the methods comprise administering to a subject having a gastrointestinal disorder an engineered (e.g., recombinant or synthetic) nucleic acid comprising (or consisting, or consisting essentially of) a nucleotide sequence that is at least 90% identical to the nucleotide sequence of SEQ ID NO: 115.

In some aspects, the gastrointestinal disorder is an inflammatory bowel disease. The inflammatory bowel disease may be, for example, irritable bowel syndrome, ulcerative colitis or Crohn's disease.

In some aspects, the engineered nucleic acid comprises (or consists, or consists essentially of) a nucleotide sequence that is at least 95% identical to the nucleotide sequence of SEQ ID NO: 1, SEQ ID NO: 11, SEQ ID NO: 108, SEQ ID NO: 5, or SEQ ID NO: 115. In some aspects, the engineered nucleic acid comprises (or consists, or consists essentially of) a nucleotide sequence that is at least 98% identical to the nucleotide sequence of SEQ ID NO: 1, SEQ ID NO: 11, SEQ ID NO: 108, SEQ ID NO: 5, or SEQ ID NO: 115. In some aspects, the engineered nucleic acid comprises (or consists, or consists essentially of) a nucleotide sequence that is at least 99% identical to the nucleotide sequence of SEQ ID NO: 1, SEQ ID NO: 11, SEQ ID NO: 108, SEQ ID NO: 5, or SEQ ID NO: 115. In some aspects, the engineered nucleic acid comprises (or consists, or consists essentially of) a nucleotide sequence that is identical to the nucleotide sequence of SEQ ID NO: 1, SEQ ID NO: 11, SEQ ID NO: 108, SEQ ID NO: 5, or SEQ ID NO: 115.

In some aspects, the subject has been or is being treated for a pathogenic infection. The pathogenic infection may be, for example, a bacterial infection, a viral infection or a parasitic infection.

In some aspects, the subject has been exposed to or is being exposed to (e.g., is receiving, is consuming, or is being treated with) an antibiotic.

In some aspects, the engineered nucleic acid is operably linked to an inducible promoter. For example, an inducible promoter may be activated (is responsive) in the presence of an antibiotic.

In some aspects, the engineered nucleic acid is a component of (e.g. is cloned into) a eukaryotic viral vector. The eukaryotic viral vector may be an adenoviral vector, an adeno-associated virus (AAV) vector, a norovirus vector, a retroviral vector, a lentiviral vectors, or a herpes viral vector.

In some aspects, the engineered nucleic acid is a component of a murine norovirus vector modified to infect human cells. For example, the human cells may be B cells, T cells, natural killer (NK) cells, natural killer T (NKT) cells, innate lymphoid cells (ILCs), dendritic cells, monocytes, macrophages, epithelial cells, or a combination of any two or more of the foregoing cells.

In some aspects, the engineered nucleic acid is engineered deoxyribonucleic acid (DNA). In some aspects, the engineered nucleic acid is engineered ribonucleic acid (RNA).

In some aspects, the engineered nucleic acid is administered orally, nasally, topically, intravenously, intrathecally, subcutaneously, or sublingually.

Also provided herein are methods, comprising administering to a subject who has a gastrointestinal disorder and has been exposed to or is being exposed to (e.g., is receiving, is consuming, or is being treated with) an antibiotic a eukaryotic viral vector comprising (or consisting, or consisting essentially of) a nucleotide sequence that is at least 90% identical to the nucleotide sequence of SEQ ID NO: 1. In some aspects, the methods comprise administering to a subject who has a gastrointestinal disorder and has been exposed to or is being exposed to (e.g., is receiving, is consuming, or is being treated with) an antibiotic a eukaryotic viral vector comprising (or consisting, or consisting essentially of) a nucleotide sequence that is at least 90% identical to the nucleotide sequence of SEQ ID NO: 11. In some aspects, the methods comprise administering to a subject who has a gastrointestinal disorder and has been exposed to or is being exposed to (e.g., is receiving, is consuming, or is being treated with) an antibiotic a eukaryotic viral vector comprising (or consisting, or consisting essentially of) a nucleotide sequence that is at least 90% identical to the nucleotide sequence of SEQ ID NO: 108. In some aspects, the methods comprise administering to a subject who has a gastrointestinal disorder and has been exposed to or is being exposed to (e.g., is receiving, is consuming, or is being treated with) an antibiotic a eukaryotic viral vector comprising (or consisting, or consisting essentially of) a nucleotide sequence that is at least 90% identical to the nucleotide sequence of SEQ ID NO: 5. In some aspects, the methods comprise administering to a subject who has a gastrointestinal disorder and has been exposed to or is being exposed to (e.g., is receiving, is consuming, or is being treated with) an antibiotic a eukaryotic viral vector comprising (or consisting, or consisting essentially of) a nucleotide sequence that is at least 90% identical to the nucleotide sequence of SEQ ID NO: 115.

Also provided herein are methods comprising administering to a subject having dysbiosis, an engineered (e.g., recombinant or synthetic) nucleic acid comprising (or consisting, or consisting essentially of) a nucleotide sequence encoding an amino acid sequence that is at least 90% identical to the amino acid sequence of SEQ ID NO: 4. In some aspects, the methods comprise administering to a subject having dysbiosis, an engineered (e.g., recombinant or synthetic) nucleic acid comprising (or consisting, or consisting essentially of) a nucleotide sequence encoding an amino acid sequence that is at least 90% identical to the amino acid sequence of SEQ ID NO: 12. In some aspects, the methods comprise administering to a subject having dysbiosis an engineered (e.g., recombinant or synthetic) nucleic acid comprising (or consisting, or consisting essentially of) a nucleotide sequence encoding an amino acid sequence that is at least 90% identical to the nucleotide sequence of SEQ ID NO: 109. In some aspects, the methods comprise administering to a subject having dysbiosis an engineered (e.g., recombinant or synthetic) nucleic acid comprising (or consisting, or consisting essentially of) a nucleotide sequence encoding an amino acid sequence that is at least 90% identical to the nucleotide sequence of SEQ ID NO: 6. In some aspects, the methods comprise administering to a subject having dysbiosis an engineered (e.g., recombinant or synthetic) nucleic acid comprising (or consisting, or consisting essentially of) a nucleotide sequence encoding an amino acid sequence that is at least 90% identical to the nucleotide sequence of SEQ ID NO: 116.

Also provided herein are methods, comprising administering to a subject having a gastrointestinal disorder, an engineered (e.g., recombinant or synthetic) nucleic acid comprising (or consisting, or consisting essentially of) a nucleotide sequence encoding an amino acid sequence that is at least 90% identical to the amino acid sequence of SEQ ID NO: 4. In some aspects, the methods comprise administering to a subject having a gastrointestinal disorder, an engineered (e.g., recombinant or synthetic) nucleic acid comprising (or consisting, or consisting essentially of) a nucleotide sequence encoding an amino acid sequence that is at least 90% identical to the amino acid sequence of SEQ ID NO: 12. In some aspects, the methods comprise administering to a subject having a gastrointestinal disorder an engineered (e.g., recombinant or synthetic) nucleic acid comprising (or consisting, or consisting essentially of) a nucleotide sequence encoding an amino acid sequence that is at least 90% identical to the nucleotide sequence of SEQ ID NO: 109. In some aspects, the methods comprise administering to a subject having a gastrointestinal disorder an engineered (e.g., recombinant or synthetic) nucleic acid comprising (or consisting, or consisting essentially of) a nucleotide sequence encoding an amino acid sequence that is at least 90% identical to the nucleotide sequence of SEQ ID NO: 6. In some aspects, the methods comprise administering to a subject having a gastrointestinal disorder an engineered (e.g., recombinant or synthetic) nucleic acid comprising (or consisting, or consisting essentially of) a nucleotide sequence encoding an amino acid sequence that is at least 90% identical to the nucleotide sequence of SEQ ID NO: 116.

In some aspects, the gastrointestinal disorder is an inflammatory bowel disease. The inflammatory bowel disease may be, for example, irritable bowel syndrome, ulcerative colitis or Crohn's disease.

In some aspects, the engineered nucleic acid encodes an amino acid sequence that is at least 95% identical to the amino acid sequence of SEQ ID NO: 4, SEQ ID NO: 12, SEQ ID NO: 109, SEQ ID NO: 6, or SEQ ID NO: 116. In some aspects, the engineered nucleic acid encodes an amino acid sequence that is at least 98% identical to the amino acid sequence of SEQ ID NO: 4, SEQ ID NO: 12, SEQ ID NO: 109, SEQ ID NO: 6, or SEQ ID NO: 116. In some aspects, the engineered nucleic acid encodes an amino acid sequence that is at least 99% identical to the amino acid sequence of SEQ ID NO: 4, SEQ ID NO: 12, SEQ ID NO: 109, SEQ ID NO: 6, or SEQ ID NO: 116. In some aspects, the engineered nucleic acid encodes an amino acid sequence that is identical to the amino acid sequence of SEQ ID NO: 4, SEQ ID NO: 12, SEQ ID NO: 109, SEQ ID NO: 6, or SEQ ID NO: 116.

In some aspects, the subject has been or is being treated for a pathogenic infection. The pathogenic infection may be, for example, a bacterial infection, a viral infection or a parasitic infection.

In some aspects, the subject has been exposed to or is being exposed to (e.g., is receiving, is consuming, or is being treated with) an antibiotic.

In some aspects, the engineered nucleic acid is operably linked to an inducible promoter. For example, an inducible promoter may be activated in the presence of an antibiotic.

In some aspects, the engineered nucleic acid is a component of a eukaryotic viral vector. The eukaryotic viral vector may be an adenoviral vector, an adeno-associated virus (AAV) vector, a norovirus vector, a retroviral vector, a lentiviral vectors, or a herpes viral vector.

In some aspects, the engineered nucleic acid is a component of a murine norovirus vector modified to infect human cells. For example, the human cells may be B cells, T cells, natural killer (NK) cells, natural killer T (NKT) cells, innate lymphoid cells (ILCs), dendritic cells, monocytes, macrophages, epithelial cells, or a combination of any two or more of the foregoing cells.

In some aspects, the engineered nucleic acid is engineered deoxyribonucleic acid (DNA). In some aspects, the engineered nucleic acid is engineered ribonucleic acid (RNA).

In some aspects, the engineered nucleic acid is administered orally, nasally, topically, intravenously, intrathecally, subcutaneously, or sublingually.

Also provided herein are methods, comprising administering to a subject who has a gastrointestinal disorder and has been exposed to or is being exposed to (e.g., is receiving, is consuming, or is being treated with) an antibiotic a eukaryotic viral vector encoding an amino acid sequence that is at least 90% identical to the amino acid sequence of SEQ ID NO: 4. In some aspects, the methods comprise administering to a subject who has a gastrointestinal disorder and has been exposed to or is being exposed to (e.g., is receiving, is consuming, or is being treated with) an antibiotic a eukaryotic viral vector encoding an amino acid sequence that is at least 90% identical to the amino acid sequence of SEQ ID NO: 12. In some aspects, the methods comprise administering to a subject who has been exposed to or is being exposed to (e.g., is receiving, is consuming, or is being treated with) an antibiotic a eukaryotic viral vector encoding an amino acid sequence that is at least 90% identical to the amino acid sequence of SEQ ID NO: 109. In some aspects, the methods comprise administering to a subject who has been exposed to or is being exposed to (e.g., is receiving, is consuming, or is being treated with) an antibiotic a eukaryotic viral vector encoding an amino acid sequence that is at least 90% identical to the amino acid sequence of SEQ ID NO: 6. In some aspects, the methods comprise administering to a subject who has been exposed to or is being exposed to (e.g., is receiving, is consuming, or is being treated with) an antibiotic a eukaryotic viral vector encoding an amino acid sequence that is at least 90% identical to the amino acid sequence of SEQ ID NO: 116.

Also provided herein are methods comprising administering to a subject having a dysbiosis, such as a gastrointestinal disorder, an engineered (e.g., recombinant or synthetic) polypeptide comprising (or consisting, or consisting essentially of) an amino acid sequence that is at least 90% identical to the amino acid sequence of SEQ ID NO: 4. In some aspects, the methods comprise administering to a subject having a dysbiosis, such as a gastrointestinal disorder, an engineered (e.g., recombinant or synthetic) polypeptide comprising (or consisting, or consisting essentially of) an amino acid sequence that is at least 90% identical to the amino acid sequence of SEQ ID NO: 12. In some aspects, the methods comprise administering to a subject having a dysbiosis, such as a gastrointestinal disorder, an engineered (e.g., recombinant or synthetic) polypeptide comprising (or consisting, or consisting essentially of) an amino acid sequence that is at least 90% identical to the nucleotide sequence of SEQ ID NO: 109. In some aspects, the methods comprise administering to a subject having a dysbiosis, such as a gastrointestinal disorder, an engineered (e.g., recombinant or synthetic) polypeptide comprising (or consisting, or consisting essentially of) an amino acid sequence that is at least 90% identical to the nucleotide sequence of SEQ ID NO: 6. In some aspects, the methods comprise administering to a subject having a dysbiosis, such as a gastrointestinal disorder, an engineered (e.g., recombinant or synthetic) polypeptide comprising (or consisting, or consisting essentially of) an amino acid sequence that is at least 90% identical to the nucleotide sequence of SEQ ID NO: 116.

In some aspects, the gastrointestinal disorder is an inflammatory bowel disease may be, for example, irritable bowel syndrome, ulcerative colitis or Crohn's disease.

In some aspects, the polypeptide comprises (or consists, or consists essentially of) an amino acid sequence that is at least 95% identical to the amino acid sequence of SEQ ID NO: 4, SEQ ID NO: 12, SEQ ID NO: 109, SEQ ID NO: 6, or SEQ ID NO: 116. In some aspects, the polypeptide comprises (or consists, or consists essentially of) an amino acid sequence that is at least 98% identical to the amino acid sequence of SEQ ID NO: 4, SEQ ID NO: 12, SEQ ID NO: 109, SEQ ID NO: 6, or SEQ ID NO: 116. In some aspects, the polypeptide comprises (or consists, or consists essentially of) an amino acid sequence that is identical to the amino acid sequence of SEQ ID NO: 4, SEQ ID NO: 12, SEQ ID NO: 109, SEQ ID NO: 6, or SEQ ID NO: 116.

In some aspects, the subject has been or is being treated for a pathogenic infection. The pathogenic infection may be, for example, a bacterial infection, a viral infection or a parasitic infection.

In some aspects, the subject has been exposed to or is being exposed to (e.g., is receiving, is consuming, or is being treated with) an antibiotic.

In some aspects, the polypeptide is administered orally, nasally, topically, intravenously, intrathecally, subcutaneously, or sublingually.

Also provided herein are methods, comprising administering to a subject who has a gastrointestinal disorder and has been exposed to or is being exposed to (e.g., is receiving, is consuming, or is being treated with) an antibiotic a polypeptide comprising (or consisting, or consisting essentially of) an amino acid sequence that is at least 90% identical to the amino acid sequence of SEQ ID NO: 4. In some aspects, the methods comprise administering to a subject who has a gastrointestinal disorder and has been exposed to or is being exposed to (e.g., is receiving, is consuming, or is being treated with) an antibiotic a polypeptide comprising (or consisting, or consisting essentially of) an amino acid sequence that is at least 90% identical to the amino acid sequence of SEQ ID NO: 12. In some aspects, the methods comprise administering to a subject who has a gastrointestinal disorder and has been exposed to or is being exposed to (e.g., is receiving, is consuming, or is being treated with) an antibiotic a polypeptide comprising (or consisting, or consisting essentially of) an amino acid sequence that is at least 90% identical to the amino acid sequence of SEQ ID NO: 109. In some aspects, the methods comprise administering to a subject who has a gastrointestinal disorder and has been exposed to or is being exposed to (e.g., is receiving, is consuming, or is being treated with) an antibiotic a polypeptide comprising (or consisting, or consisting essentially of) an amino acid sequence that is at least 90% identical to the amino acid sequence of SEQ ID NO: 6. In some aspects, the methods comprise administering to a subject who has a gastrointestinal disorder and has been exposed to or is being exposed to (e.g., is receiving, is consuming, or is being treated with) an antibiotic a polypeptide comprising (or consisting, or consisting essentially of) an amino acid sequence that is at least 90% identical to the amino acid sequence of SEQ ID NO: 116.

These and other aspects of the present invention will be apparent to those of ordinary skill in the art in the following description, claims and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A is a graph showing that MNV CR6 strain restores survival of antibiotics-treated mice and germ-free mice following treatment with dextran sodium sulfate (DSS), a chemical that is otherwise lethal when administered to mice lacking bacteria. In contrast, infection by the MNV CW3 strain provides little or no protection from DSS-mediated injury. FIG. 2B is a graph showing MNV CR6 in which the VP1 region (capsid) is swapped with the VP1 region of CW3 still protects from DSS-mediated injury, while MNV CW3 in which the VP1 region (capsid) is swapped with the VP1 region of CR6 does not gain protection from DSS-mediated injury. FIG. 2C is a graph showing that MNV CW3 in which the NS1 region is swapped with the NS1 region of CR6 gains protection from DSS-mediated injury, while MNV CR6 in which the NS1 region is swapped with the NS1 region of CW3 loses protection from DSS-mediated injury.

DETAILED DESCRIPTION OF THE INVENTION

Figure 1:
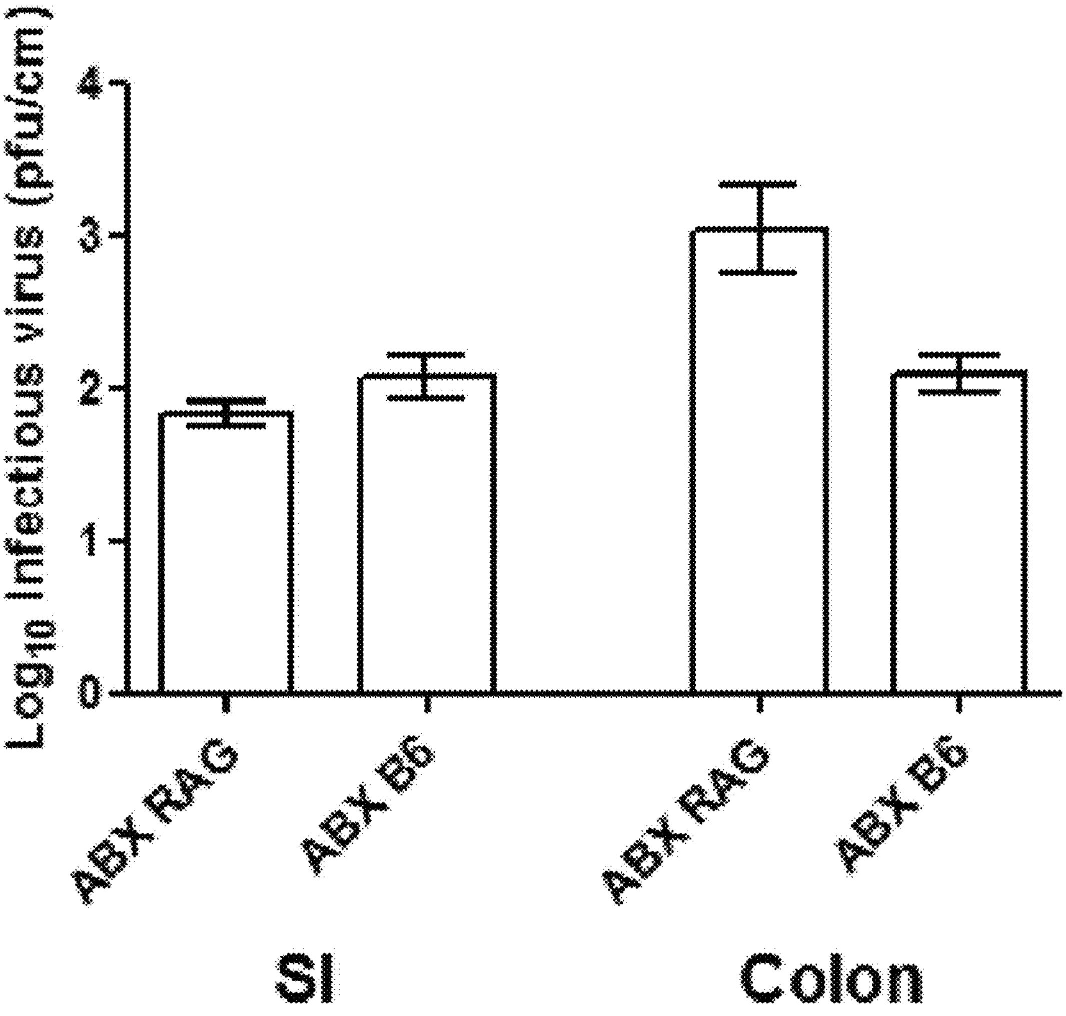
FIG. 1 is a graph showing viral titer in antibiotics (ABX) treated Rag−/− mice. No decrease in MNV is observed by plaque assay in small intestine (SI) or colon in Rag−/− compared with wild-type B6 mice, indicating that B cells (and T cells) are not necessary to support persistent viral replication in this setting.

The present invention is based on unexpected experimental data demonstrating that the MNV CR6 strain, and particularly the NS1/2 region, restores survival of antibiotics-treated mice and germ-free mice following treatment with dextran sodium sulfate (DSS), a chemical that is otherwise lethal when administered to mice lacking bacteria.

Definitions

Unless defined otherwise, technical and scientific terms used herein have the same meaning as commonly understood by one of ordinary skill in the art to which this invention belongs.

The term "NS1/2 genomic region" encompasses both RNA and DNA molecules. In one embodiment, the NS1/2 genomic region of murine norovirus MNV comprises or is encoded by a nucleotide sequence comprising a sequence selected from the group consisting of SEQ ID NO: 1, SEQ ID NO: 11, SEQ ID NO: 13, SEQ ID NO: 15, SEQ ID NO: 17, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, and any functional fragment (i.e., smaller portions of any of the above sequences that possess a therapeutic activity with respect to any of the conditions recited herein) thereof. In one embodiment, the NS1/2 genomic region of murine norovirus MNV comprises or is encoded by the nucleotide sequence comprising SEQ ID NO: 1, SEQ ID NO: 11, or SEQ ID NO: 108 or any functional fragment or derivative thereof. In one embodiment, a functional fragment of the NS1/2 genomic region of murine norovirus MNV comprises or is encoded by the nucleotide sequence comprising SEQ ID NO: 5 or SEQ ID NO: 115. In certain embodiments, the functional fragment can be a product of enzyme cleavage, e.g., a product of caspase 3 cleavage. (see, e.g., Sosnovtsev et al., *J Virol.* 2006 80(16):7816-31, incorporated herein by reference in its entirety). In certain embodiments, a derivative (see, e.g., Nice et al., *J Virol.* 2013 January; 87(1):327-34) of the NS1/2 genomic region of murine norovirus MNV comprises a nucleotide sequence encoded by a DNA sequence having at least 90% identity (at least 95% identity, at least 98% identity, at least 99% identity) to SEQ ID NO: 1, SEQ ID NO: 11, SEQ ID NO: 108, SEQ ID NO: 5, or SEQ ID NO: 115.

In some aspects, a NS1/2 genomic region useful in the methods of the invention comprises a nucleotide sequence having at least 80% (e.g., at least 85%, at least 90%, at least 95%, at least 96%, at least 97%, at least 98%, at least 99%) identity to the nucleotide sequence selected from the group consisting of SEQ ID NO: 1, SEQ ID NO: 11, SEQ ID NO: 13, SEQ ID NO: 15, SEQ ID NO: 17, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 5, and SEQ ID NO: 115. In some embodiments, a NS1/2 genomic region comprises a nucleotide sequence having at least 80% (e.g., at least 85%, at least 90%, at least 95%, at least 96%, at least 97%, at least 98%, at least 99%) identity to the nucleotide sequence of SEQ ID NO: 1. In some embodiments, a NS1/2 genomic region comprises a nucleotide sequence having at least 80% (e.g., at least 85%, at least 90%, at least 95%, at least 96%, at least 97%, at least 98%, at least 99%) identity to the nucleotide sequence of SEQ ID NO: 11. In some embodiments, a NS1/2 genomic region comprises a nucleotide sequence having at least 80% identity to the nucleotide sequence of SEQ ID NO: 108. In some embodiment, a NS1/2 genomic region comprises a nucleotide sequence having at least 80% identity (e.g., at least 85%, at least 90%, at least 95%, at least 96%, at least 97%, at least 98%, at least 99%) to the nucleotide sequence of SEQ ID NO: 5. In some embodiment, a NS1/2 genomic region comprises a nucleotide sequence having at least 80% identity (e.g., at least 85%, at least 90%, at least 95%, at least 96%, at least 97%, at least 98%, at least 99%) to the nucleotide sequence of SEQ ID NO: 115.

In some embodiments, a NS1/2 genomic region comprises a nucleotide sequence having at least 85% identity to the nucleotide sequence of SEQ ID NO: 1, SEQ ID NO: 11, SEQ ID NO: 108, SEQ ID NO: 5, or SEQ ID NO: 115. In some embodiments, a NS1/2 genomic region comprises a nucleotide sequence having at least 90% identity to the nucleotide sequence of SEQ ID NO: 1, SEQ ID NO: 11, SEQ ID NO: 108, SEQ ID NO: 5, or SEQ ID NO: 115. In some embodiments, a NS1/2 genomic region comprises a nucleotide sequence having at least 95% identity to the nucleotide sequence of SEQ ID NO: 1, SEQ ID NO: 11, SEQ ID NO: 108, SEQ ID NO: 5, or SEQ ID NO: 115. In some embodiments, a NS1/2 genomic region comprises a nucleotide sequence having at least 96% identity to the nucleotide sequence of SEQ ID NO: 1, SEQ ID NO: 11, SEQ ID NO: 108, SEQ ID NO: 5, or SEQ ID NO: 115. In some embodiments, a NS1/2 genomic region comprises a nucleotide sequence having at least 97% identity to the nucleotide sequence of SEQ ID NO: 1, SEQ ID NO: 11, SEQ ID NO: 108, SEQ ID NO: 5, or SEQ ID NO: 115. In some embodiments, a NS1/2 genomic region comprises a nucleotide sequence having at least 98% identity to the nucleotide sequence of SEQ ID NO: 1, SEQ ID NO: 11, SEQ ID NO: 108, SEQ ID NO: 5, or SEQ ID NO: 115. In some embodiments, a NS1/2 genomic region comprises a nucleotide sequence having at least 99% identity to the nucleotide sequence of SEQ ID NO: 1, SEQ ID NO: 11, SEQ ID NO: 108, SEQ ID NO: 5, or SEQ ID NO: 115.

The percentages of nucleotide or amino acid sequence identity provided herein relate to any method for calculating identity known in the art. Calculation of the percent identity of two sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). The comparison of sequences and determination of percent identity between two sequences can be accomplished using a mathematical algorithm, such as, e.g., the GCG (Genetics Computer Group, Program Manual for the GCG Package, Version 7, Madison, Wis.) pileup program, BLAST, Gapped BLAST, FASTA, etc.

In one embodiment, a protein encoded by the NS1/2 region of murine norovirus MNV comprises an amino acid sequence selected from the group consisting of SEQ ID NO: 4, SEQ ID NO: 12, SEQ ID NO: 14, SEQ ID NO: 16, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33. SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, and any functional fragment or derivative thereof (e.g., with or without the signal sequence). In one embodiment, a protein encoded by the NS1/2 region of murine norovirus MNV comprises the amino acid sequence SEQ ID NO: 4, SEQ ID NO: 12, or SEQ ID NO: 109 or any functional fragment or derivative thereof (e.g., with or without the signal sequence). In one embodiment, a functional fragment of a protein encoded by the NS1/2 region of murine norovirus MNV comprises the amino acid sequence SEQ ID NO: 6 or SEQ ID NO: 116. In one embodiment, a derivative of a protein encoded by the NS1/2 genomic region of murine norovirus MNV comprises the amino acid sequence having at least 90% identity (at least 95% identity, at least 98% identity, at least 99% identity) to SEQ ID NO: 4, SEQ ID NO: 12, SEQ ID NO: 109, SEQ ID NO: 6, or SEQ ID NO: 116.

In some embodiments, a protein useful in the methods of the invention can be encoded by a NS1/2 region comprises an amino acid sequence having at least 80% (e.g., at least 85%, at least 90%, at least 95%, at least 96%, at least 97%, at least 98%, at least 99%) identity to the amino acid sequence selected from the group consisting of SEQ ID NO: 4, SEQ ID NO: 12, SEQ ID NO: 14, SEQ ID NO: 16, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33. SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 6 and SEQ ID NO: 116. In some embodiments, a protein encoded by the NS1/2 region comprises an amino acid sequence having at least 80% (e.g., at least 85%, at least 90%, at least 95%, at least 96%, at least 97%, at least 98%, at least 99%) identity to the amino acid sequence of SEQ ID NO: 4, SEQ ID NO: 12, or SEQ ID NO: 109. In some embodiments, a protein encoded by the NS1/2 region comprises an amino acid sequence having at least 80% (e.g., at least 85%, at least 90%, at least 95%, at least 96%, at least 97%, at least 98%, at least 99%) identity to the amino acid sequence of SEQ ID NO: 6 or SEQ ID NO: 116.

In some embodiments, a protein encoded by a NS1/2 genomic region comprises an amino acid sequence having at least 85% identity to the amino acid sequence of SEQ ID NO: 4, SEQ ID NO: 12, SEQ ID NO: 109, SEQ ID NO: 6 or SEQ ID NO: 116. In some embodiments, a protein encoded by a NS1/2 genomic region comprises an amino acid sequence having at least 90% identity to the amino acid sequence of SEQ ID NO: 4, SEQ ID NO: 12, SEQ ID NO: 109, SEQ ID NO: 6 or SEQ ID NO: 116. In some embodiments, a protein encoded by a NS1/2 genomic region comprises an amino acid sequence having at least 95% identity to the amino acid sequence of SEQ ID NO: 4, SEQ ID NO: 12, SEQ ID NO: 109, SEQ ID NO: 6 or SEQ ID NO: 116. In some embodiments, a protein encoded by a NS1/2 genomic region comprises an amino acid sequence having at least 96% identity to the amino acid sequence of SEQ ID NO: 4, SEQ ID NO: 12, SEQ ID NO: 109, SEQ ID NO: 6 or SEQ ID NO: 116. In some embodiments, a protein encoded by a NS1/2 genomic region comprises an amino acid sequence having at least 97% identity to the amino acid sequence of SEQ ID NO: 4, SEQ ID NO: 12, SEQ ID NO: 109, SEQ ID NO: 6 or SEQ ID NO: 116. In some embodiments, a protein encoded by a NS1/2 genomic region comprises an amino acid sequence having at least 98% identity to the amino acid sequence of SEQ ID NO: 4, SEQ ID NO: 12, SEQ ID NO: 109, SEQ ID NO: 6 or SEQ ID NO: 116. In some embodiments, a protein encoded by a NS1/2 genomic region comprises an amino acid sequence having at least 99% identity to the amino acid sequence of SEQ ID NO: 4, SEQ ID NO: 12, SEQ ID NO: 109, SEQ ID NO: 6 or SEQ ID NO: 116.

The terms "intestinal microbiota", "gut flora", and "gastrointestinal (GI) microbiota" are used interchangeably to refer to microorganisms (e.g., bacteria, fungi, unicellular parasites) and viruses (e.g., phages and eukaryotic viruses) in the digestive tract.

Specific changes in GI microbiota discussed herein can be detected using various methods, including without limitation quantitative PCR or high-throughput sequencing methods which detect over- and under-represented genes in the total bacterial population (e.g., 454-sequencing for community analysis; screening of microbial 16S ribosomal RNAs (16S rRNA), etc.), or transcriptomic or proteomic studies that identify lost or gained microbial transcripts or proteins within total bacterial populations. See, e.g., U.S. Patent Publication No. 2010/0074872; Eckburg et al., Science, 2005, 308:1635-8; Costello et al., Science, 2009, 326:1694-7; Grice et al., Science, 2009, 324:1190-2; Li et al., Nature, 2010, 464: 59-65; Bjursell et al., Journal of Biological Chemistry, 2006, 281:36269-36279; Mahowald et al., PNAS, 2009, 14:5859-5864; Wikoff et al., PNAS, 2009, 10:3698-3703.

As used herein, the term "dysbiosis" refers to a microbial imbalance on or inside the body. Dysbiosis can result from, e.g., antibiotic exposure as well as other causes, e.g., infections with pathogens including viruses, bacteria and eukaryotic parasites. The term "consequences of dysbiosis" refers to various disorders associates with dysbiosis. For example, dysbiosis in the GI tract has been reported to be associated with a wide variety of illnesses, such as, e.g., irritable bowel syndrome (IBS), inflammatory bowel disease (IBD), chronic fatigue syndrome, obesity, rheumatoid arthritis, ankylosing spondylitis, bacterial vaginosis, colitis, small intestinal cancer, colorectal cancer, metabolic syndrome, cardiovascular disease, Crohn's disease, infectious gastroenteritis, non-infectious gastroenteritis, food allergy, Celiac disease, gastrointestinal graft versus host disease, pouchitis, intestinal failure, short bowel syndrome, antibiotics-associated diarrhea, etc.

As used herein, the term “16S rRNA sequencing” refers to the sequencing of 16S ribosomal RNA (rRNA) gene sequences by using primers such as universal primers and/or species-specific primers to identify the bacteria present in a sample. 16S rRNA genes contain both highly conserved sites and hypervariable regions that can provide species-specific signature sequences useful for identification of bacteria. Such universal primers are well known in the art.

As used herein, the term “probiotic” refers to a substantially pure bacteria (i.e., a single isolate, of, e.g., live bacterial cells, conditionally lethal bacterial cells, inactivated bacterial cells, killed bacterial cells, spores, recombinant carrier strains), or a mixture of desired bacteria, bacteria components or bacterial extract, or bacterially-derived products (natural or synthetic bacterially-derived products such as, e.g., bacterial antigens or metabolic products) and may also include any additional components that can be administered to a mammal. Such compositions are also referred to herein as a “bacterial inoculant.”

As used herein, the term “prebiotic” refers to an agent that increases the number and/or activity of one or more desired bacteria, enhancing their growth. Non-limiting examples of prebiotics useful in the methods of the present disclosure include fructooligosaccharides (e.g., oligofructose, inulin, inulin-type fructans), galactooligosaccharides, human milk oligosaccharides (HMO), Lacto-N-neotetraose, D-Tagatose, xylo-oligosaccharides (XOS), arabinoxylan-oligosaccharides (AXOS), N-acetylglucosamine, N-acetylgalactosamine, glucose, other five- and six-carbon sugars (such as arabinose, maltose, lactose, sucrose, cellobiose, etc.), amino acids, alcohols, resistant starch (RS), and mixtures thereof. See, e.g., Ramirez-Farias et al., Br J Nutr (2008) 4:1-10; Pool-Zobel and Sauer, J Nutr (2007), 137:2580S-2584S.

The terms “treat” or “treatment” of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein, the term “therapeutically effective amount” refers to the amount of a compound, vector, virus, bacteriophage, particle, or bacterial inoculant that, when administered to a subject for treating (e.g., preventing or ameliorating) a state, disorder or condition, is sufficient to effect such treatment. The “therapeutically effective amount” will vary depending, e.g., on the compound, vector, virus, bacteriophage, particle, or bacteria administered as well as the disease and physical conditions and responsiveness of the subject to be treated.

As used herein, the phrase “pharmaceutically acceptable” refers to molecular entities and compositions that are generally regarded as physiologically tolerable.

As used herein, the term “combination” of a compound, vector, virus, bacteriophage, particle, or bacterial inoculant and at least a second pharmaceutically active ingredient means at least two, but any desired combination of compounds can be delivered simultaneously or sequentially (e.g., within a 24 hour period).

The terms “patient”, “individual”, “subject”, and “animal” are used interchangeably herein and refer to mammals, including, without limitation, human and veterinary animals (e.g., cats, dogs, cows, horses, sheep, pigs, etc.) and experimental animal models. In a preferred embodiment, the subject is a human.

As used herein, the term “stimulate” when used in connection with growth and/or activity of bacteria encompasses the term “enhance”.

The term “carrier” refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in “Remington’s Pharmaceutical Sciences” by E. W. Martin.

The term “about” or “approximately” means within a statistically meaningful range of a value. Such a range can be within an order of magnitude, preferably within 50%, more preferably within 20%, still more preferably within 10%, and even more preferably within 5% of a given value or range. The allowable variation encompassed by the term “about” or “approximately” depends on the particular system under study, and can be readily appreciated by one of ordinary skill in the art.

The terms “a,” “an,” and “the” do not denote a limitation of quantity, but rather denote the presence of “at least one” of the referenced item.

The practice of the present disclosure employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J. Additional techniques are explained, e.g., in U.S. Pat. No. 7,912,698 and U.S. Patent Appl. Pub. Nos. 2011/0202322 and 2011/0307437.

Methods

In one aspect, the disclosure provides a method for treating dysbiosis in the gastrointestinal tract of a subject (e.g., human) in need thereof, said method comprising administering to said subject a therapeutically effective amount of NS1/2 region of murine norovirus MNV or a corresponding region from a member of the Caliciviridae family (e.g., from a human calicivirus), or a protein encoded by any one of those regions.

In another aspect, the disclosure provides a method for treating an infection or an inflammatory disorder in a subject (e.g., human) in need thereof, said method comprising administering to said subject a therapeutically effective amount of NS1/2 region of murine norovirus MNV or a corresponding region from a member of the Caliciviridae family (e.g., from a human calicivirus), or a protein encoded by any one of those regions. Non-limiting examples of encompassed disorders include, e.g., inflammatory bowel disease (IBD), ulcerative colitis, Crohn's disease, irritable bowel syndrome (IBS), sprue, autoimmune arthritis, rheumatoid arthritis, Type I diabetes, multiple sclerosis (MS), amyotrophic lateral sclerosis (ALS), osteoarthritis, juvenile chronic arthritis, Lyme arthritis, psoriatic arthritis, reactive arthritis, spondyloarthropathy, systemic lupus erythematosus (SLE), insulin dependent diabetes mellitus, thyroiditis, asthma, psoriasis, dermatitis scleroderma, atopic dermatitis, graft versus host disease, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlejn purpurea, microscopic vasculitis of the kidneys, chronic active hepatitis, uveitis, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, polyglandular deficiency type I syndrome and polyglandular deficiency type II syndrome, Schmidt's syndrome, adult (e.g., acute) respiratory distress syndrome, alopecia, alopecia areata, seronegative arthopathy, arthropathy, Reiter's disease, psoriatic arthropathy, chlamydia, yersinia and salmonella associated arthropathy, spondyloarhopathy, atheromatous disease/arteriosclerosis, allergic colitis, atopic allergy, food allergies such as peanut allergy, tree nut allergy, egg allergy, milk allergy, soy allergy, wheat allergy, seafood allergy, shellfish allergy, or sesame seed allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (e.g., common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, idiopathic pulmonary fibrosis, chronic eosinophilic pneumonia, lymphocytic infiltrative lung disease, postinfectious interstitial lung disease, gouty arthritis, autoimmune hepatitis, type-1 autoimmune hepatitis (e.g., classical autoimmune or lupoid hepatitis), type-2 autoimmune hepatitis (e.g., anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, discoid lupus, erythematosus, male infertility idiopathic or NOS, sperm autoimmunity, multiple sclerosis (all subtypes), insulin dependent diabetes mellitus, sympathetic ophthalmia, pulmonary hypertension secondary to connective tissue disease, Goodpasture's syndrome, pulmonary manifestation of polyarteritis nodosa, acute rheumatio fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, allergic rhinitis (e.g., pollen allergies), anaphylaxis, pet allergies, latex allergies, drug allergies, allergic rhinoconjuctivitis, eosinophilic esophagitis, hypereosinophilic syndrome, eosinophilic gastroenteritis cutaneous lupus erythematosus, eosinophilic esophagitis, hypereosinophilic syndrome, and eosinophilic gastroenteritis, diarrhea, colon cancer, cystic fibrosis, celiac disease, Type 2 diabetes, autism-related immunopathologies, and common variable immuno-deficiency (CVID).

In another aspect, the disclosure provides a method for treating a gastrointestinal (GI) disorder in a subject (e.g., human) in need thereof, said method comprising administering to said subject a therapeutically effective amount of NS1/2 region of murine norovirus MNV or a corresponding region from a member of the Caliciviridae family (e.g., from a human calicivirus), or a protein encoded by any one of those regions. Non-limiting examples of encompassed GI disorders include, e.g., inflammatory bowel disease (IBD), ulcerative colitis, Crohn's disease, irritable bowel syndrome (IBS), infectious gastroenteritis, non-infectious gastroenteritis, food allergy, gastrointestinal graft versus host disease, small intestinal cancer, colon cancer, pouchitis, intestinal failure, short bowel syndrome, and antibiotics-associated diarrhea (e.g., antibiotic-associated diarrhea caused by *Clostridium difficile* or vancomycin-resistant *Enterococcus* (VRE) [e.g., *Enterococcus faecium* or *Enterococcus faecalis*]).

In a further aspect, the disclosure provides a method for treating a condition that affects a mucosal barrier in a subject (e.g., human) in need thereof, said method comprising administering to said subject a therapeutically effective amount of NS1/2 region of murine norovirus MNV or a corresponding region from a member of the Caliciviridae family (e.g., from a human calicivirus), or a protein encoded by any one of those regions. Non-limiting examples of the encompassed conditions include infectious and non-infectious pneumonia.

In yet another aspect, the disclosure provides a method for treating a cancer and/or enhancing the effectiveness of an anti-cancer therapy in a subject (e.g., human) in need thereof, said method comprising administering to said subject a therapeutically effective amount of NS1/2 region of murine norovirus MNV or a corresponding region from a member of the Caliciviridae family (e.g., from a human calicivirus), or a protein encoded by any one of those regions. In a related aspect, the disclosure provides a method for improving cancer immunotherapy in a subject (e.g., human) in need thereof, said method comprising administering to said subject a therapeutically effective amount of NS1/2 region of murine norovirus MNV or a corresponding region from a member of the Caliciviridae family (e.g., from a human calicivirus), or a protein encoded by any one of those regions.

In any of the methods of the disclosure, the administration can be performed to a mucosal surface and/or cells compromising affected tissue.

In one embodiment of any of the above methods of the disclosure, the NS1/2 region of murine norovirus MNV comprises or is encoded by a nucleotide sequence comprising a sequence selected from the group consisting of SEQ ID NO: 1, SEQ ID NO: 11, SEQ ID NO: 13, SEQ ID NO: 15, SEQ ID NO: 17, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, and SEQ ID NO: 108 or any functional fragment or derivative thereof. In one embodiment, the NS1/2 genomic region of murine norovirus MNV comprises or is encoded by a nucleotide sequence comprising SEQ ID NO: 1, SEQ ID NO: 11, or SEQ ID NO: 108 or any functional fragment or derivative thereof. In one embodiment, a functional fragment of the NS1/2 genomic region of murine norovirus MNV comprises a nucleotide sequence encoded by the DNA sequence SEQ ID NO: 5 or SEQ ID NO: 115. In one embodiment, a derivative of the NS1/2 genomic region of murine norovirus MNV comprises a nucleotide sequence encoded by a DNA sequence having at least 90% identity (at least 95% identity, at least 98% identity, at least 99% identity) to SEQ ID NO: 1, SEQ ID NO: 11, SEQ ID NO: 108, SEQ ID NO: 5, or SEQ ID NO: 115. In one embodiment, a protein encoded by this NS1/2 region of murine norovirus MNV comprises an amino acid sequence selected from the group consisting of SEQ ID NO: 4, SEQ ID NO: 12, SEQ ID NO: 14, SEQ ID NO: 16, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33. SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, and SEQ ID NO: 109 or any functional fragment or derivative thereof. In one embodiment, a protein encoded by the NS1/2 region of murine norovirus MNV CR6 comprises the amino acid sequence of SEQ ID NO: 4, SEQ ID NO: 12, or SEQ ID NO: 109 or any functional fragment or derivative thereof (e.g., with or without the signal sequence). In one embodiment, a functional fragment of a protein encoded by the NS1/2 region of murine norovirus MNV comprises the amino acid sequence SEQ ID NO: 6 or SEQ ID NO: 116. In one embodiment, a derivative of a protein encoded by the NS1/2 genomic region of murine norovirus MNV comprises the amino acid sequence having at least 90% identity (at least 95% identity, at least 98% identity, at least 99% identity) to SEQ ID NO: 4, SEQ ID NO: 12, SEQ ID NO: 109, SEQ ID NO: 6, or SEQ ID NO: 116.

It is contemplated that when used to treat various diseases, the compositions and methods of the present disclosure can be utilized with other therapeutic methods and/or agents suitable for the same or similar diseases. Such other therapeutic methods and/or agents can be co-administered (simultaneously or sequentially) to generate additive or synergistic effects. Suitable therapeutically effective dosages for each agent may be lowered due to the additive action or synergy.

In one embodiment of any of the above methods of the disclosure, the method further comprises administering to the subject one or more additional compounds selected from the group consisting of immuno-suppressives, biologicals, probiotics, prebiotics, and cytokines (e.g., IFN or IL-22).

For treatment of inflammatory disorders, the methods of the disclosure can be combined with other therapies that block inflammation (e.g., via blockage of IL1, INFα/β, IL6, TNF, IL23, etc.). The methods of the disclosure can be also combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 41BB, OX40, etc.). The methods of the disclosure can be also combined with other treatments that possess the ability to modulate NKT function or stability, including but not limited to CD1d, CD1d-fusion proteins, CD1d dimers or larger polymers of CD1d either unloaded or loaded with antigens, CD1d-chimeric antigen receptors (CD1d-CAR), or any other of the five known CD1 isomers existing in humans (CD1a, CD1b, CD1c, CD1e).

In any of the methods of the disclosure, NS1/2 region of murine norovirus MNV or a corresponding region from a member of the Caliciviridae family (e.g., a human calicivirus), or a protein encoded by any one of those regions can be delivered in any form which achieves successful delivery to a mucosal surface and/or cells compromising affected tissue. Non-limiting examples of useful delivery forms are provided in the section below.

Compositions

In conjunction with the above-identified methods of the invention, the invention provides various compositions.

In one embodiment, the disclosure provides recombinant vectors comprising NS1/2 region of murine norovirus MNV or a corresponding region from a member of the Caliciviridae family (e.g., a human calicivirus) or encoding a protein encoded by said region. Non-limiting examples of useful vectors include viral vectors such as, e.g., adenoviral vectors, retroviral vectors, lentiviral vectors, and herpesviral vectors (e.g., cytomegalovirus vectors). The disclosure also provides pharmaceutical compositions comprising the vectors of the disclosure.

In a separate embodiment, the disclosure provides a recombinant murine norovirus MNV comprising NS1/2 region of murine norovirus MNV or a corresponding region from a member of the Caliciviridae family (e.g., a human calicivirus), or a protein encoded by any one of those regions, and engineered (e.g., by (i) mutating the major (VP1) and/or minor (VP2) capsid proteins to enable binding to human cells; (ii) making hybrid and/or chimeric viruses between MNV (e.g., MNV CR6 or MNV-SKI) and a virus capable of infecting human cells (e.g., a human calicivirus such as, e.g., norovirus or sapovirus); and/or (iii) passaging MNV (e.g., MNV CR6 or MNV-SKI) continuously in human cell lines (e.g., 293T, HeLa, Caco-2, BJAB, HL-60, THP-1, A549, HMEC-1, MCF-7, U937, HT-29, Jurkat)) to infect human cells (e.g., B cells, T cells, natural killer (NK) cells, natural killer T (NKT) cells, innate lymphoid cells (ILCs), dendritic cells, monocytes, macrophages, or epithelial cells [e.g., Tuft cells]).

The disclosure also provides pharmaceutical compositions comprising the recombinant viruses of the disclosure.

In a further embodiment, the disclosure provides particles comprising NS1/2 region of murine norovirus MNV or a corresponding region from a member of the Caliciviridae family (e.g., a human calicivirus), or a protein encoded by any one of those regions. Non-limiting examples of useful particles include, e.g., nanoparticles (see, e.g., Yun et al., Adv Drug Deliv Rev. 2013; 65(6): 822-832), liposomal particles, and virion-like particles (see, e.g, Roldao et al., Expert Rev Vaccines 2010 October; 9(10):1149-1176). Also provided are pharmaceutical compositions comprising the particles of the disclosure.

In another embodiment, the disclosure provides compositions comprising (i) NS1/2 genomic region of murine norovirus MNV or a corresponding region from a member of the Caliciviridae family (e.g., a human calicivirus), or a protein encoded by any one of those regions and (ii) a cell-penetrating peptide (CPP).

In yet another embodiment, the disclosure provides recombinant bacteriophages comprising NS1/2 region of murine norovirus MNV or a corresponding region from a member of the Caliciviridae family (e.g., a human calicivirus), or a protein encoded by any one of those regions, as well as pharmaceutical compositions comprising such bacteriophages.

In a further embodiment, the disclosure provides recombinant bacterial or fungal (e.g., yeast) cells comprising NS1/2 region of murine norovirus MNV or a corresponding region from a member of the Caliciviridae family (e.g., a human calicivirus), or a protein encoded by any one of those regions, as well as pharmaceutical compositions comprising such recombinant bacterial or fungal (e.g. yeast) cells. Bacterial cells can be present in the pharmaceutical compositions, e.g., in the form of live bacterial cells, conditionally lethal bacterial cells, inactivated bacterial cells, killed bacterial cells, or spores.

In one embodiment of any of the above compositions of the disclosure, the NS1/2 region of murine norovirus MNV in the compositions of the disclosure comprises or is encoded by a nucleotide sequence comprising a sequence selected from the group consisting of SEQ ID NO: 1, SEQ ID NO: 11, SEQ ID NO: 13, SEQ ID NO: 15, SEQ ID NO: 17, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, and SEQ ID NO: 108 or any functional fragment or derivative thereof. In one embodiment, the NS1/2 genomic region of murine norovirus MNV comprises or is encoded by a nucleotide sequence comprising SEQ ID NO: 1, SEQ ID NO: 11, or SEQ ID NO: 108 or any functional fragment or derivative thereof. In one embodiment, a functional fragment of the NS1/2 genomic region of murine norovirus MNV comprises a nucleotide sequence encoded by the DNA sequence SEQ ID NO: 5 or SEQ ID NO: 115. In one embodiment, a derivative of the NS1/2 genomic region of murine norovirus MNV comprises a nucleotide sequence encoded by a DNA sequence having at least 90% identity (at least 95% identity, at least 98% identity, at least 99% identity) to SEQ ID NO: 1, SEQ ID NO: 11, SEQ ID NO: 108, SEQ ID NO: 5, or SEQ ID NO: 115. In one embodiment, a protein encoded by this NS1/2 region of murine norovirus MNV comprises an amino acid sequence selected from the group consisting of SEQ ID NO: 4, SEQ ID NO: 12, SEQ ID NO: 14, SEQ ID NO: 16, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33. SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, and SEQ ID NO: 109 or any functional fragment or derivative thereof. In one embodiment, a protein encoded by the NS1/2 region of murine norovirus MNV comprises the amino acid sequence SEQ ID NO: 4, SEQ ID NO: 12, or SEQ ID NO: 109 or any functional fragment or derivative—thereof (e.g., with or without the signal sequence). In one embodiment, a functional fragment of a protein encoded by the NS1/2 region of murine norovirus MNV comprises the amino acid sequence SEQ ID NO: 6 or SEQ ID NO: 116. In one embodiment, a derivative of a protein encoded by the NS1/2 genomic region of murine norovirus MNV comprises the amino acid sequence having at least 90% identity (at least 95% identity, at least 98% identity, at least 99% identity) to SEQ ID NO: 4, SEQ ID NO: 12, SEQ ID NO: 109, SEQ ID NO: 6, or SEQ ID NO: 116.

As specified above, in some embodiments of the present disclosure, NS1/2 region of murine norovirus MNV or a corresponding region from a member of the Caliciviridae family, may be expressed by genetically engineered non-invasive and non-pathogenic bacteria (e.g., non-commensal and/or non-colonizing bacteria), yeast, and/or other non-invasive, non-pathogenic, genetically tractable, easily manipulated microorganisms, and viruses, which include those that infect eukaryotic cells or bacterial cells. The microorganisms may comprise one or more nucleic acid constructs in which the nucleic acid encoding the cytokine is under control of appropriate regulatory sequences for expression (promoter, terminator, and/or enhancer). Vectors also normally contain marker genes and other sequences as appropriate.

The expression nucleic acid constructs comprising a sequence for NS1/2 region of murine norovirus MNV or a corresponding sequence from a member of the Caliciviridae family, wherein the coding sequence is under the control of a promoter for expression in a non-invasive and/or non-pathogenic microorganism, is provided as a further aspect of the present disclosure. The promoter employed in accordance with the described vector can be, e.g., constitutive or inducible. The expression nucleic acid constructs encoding NS1/2 region of murine norovirus MNV or a corresponding sequence from a member of the Caliciviridae family, can comprise a secretory signal sequence. Non-limiting examples of suitable secretory signal sequences include any of those with activity in *Bacillus, Clostridium* and/or *Lactobacillus*, such as, e.g., α-amylase secretion leader of *Bacillus amyloliquefaciens* or the secretion leader of the Staphylokinase enzyme secreted by some strains of Staphylococcus, which is known to function in both Gram-positive and Gram-negative hosts (see "Gene Expression Using *Bacillus*", Rapoport (1990) *Current Opinion in Biotechnology* 1:21-27), or leader sequences from numerous other *Bacillus* enzymes or S-layer proteins (see pp 341-344 of Harwood and Cutting, "Molecular Biological Methods for *Bacillus*", John Wiley & Co. 1990). To generate a recombinant microorganism for use in the present disclosure, nucleic acid is introduced into a host cell.

The compositions of the disclosure can further comprise (i) a carrier and/or buffering agent and/or (ii) one or more prebiotic agents which enhance growth or activity of one or more bacteria present in the composition. The precise nature of the carrier or other material may depend on the route of administration. For intravenous, cutaneous or subcutaneous injection, or injection at the site of an affliction, a parenterally acceptable aqueous solution may be employed which is pyrogen-free and has suitable pH, isotonicity and stability. Those of relevant skill in the art are well able to prepare suitable solutions. Preservatives, stabilizers, buffers, antioxidants and/or other additives may be included, as required.

The compositions of the disclosure can be formulated for various routes of administration, including, e.g., oral, topical, rectal, mucosal, sublingual, nasal, intravenous, subcutaneous, and via naso/oro-gastric gavage.

Administration and Delivery

Potential methods of delivering NS1/2 include, without limitation, (1) expressing NS1/2 in a heterologous viral delivery system/vector, such as, e.g., adenoviral, retroviral, herpesviral (e.g., cytomegalovirus), or lentiviral delivery systems/vectors; (2) engineering MNV or a corresponding member of the Caliciviridae family to infect human cells (e.g., by (i) mutating the major (VP1) and/or minor (VP2) capsid proteins to enable binding to human cells; (ii) making hybrid and/or chimeric viruses between MNV (e.g., MNV CR6 or MNV-SKI) and a virus capable of infecting human cells (e.g., a human calicivirus such as, e.g., norovirus or sapovirus); and/or (iii) passaging MNV (e.g., MNV CR6 or MNV-SKI) continuously in human cell lines (e.g., 293T, HeLa, Caco-2, BJAB, HL-60, THP-1, A549, HMEC-1, MCF-7, U937, HT-29, Jurkat) to infect human cells (e.g., B cells, T cells, natural killer (NK) cells, natural killer T (NKT) cells, innate lymphoid cells (ILCs), dendritic cells, monocytes, macrophages, or epithelial cells [e.g., Tuft cells]); (3) engineering a human calicivirus or other enteric viruses to be avirulent (e.g., by mutating the capsid protein VP1 and/or by serial passaging in cell lines) while maximizing or improving NS1/2 activity (e.g., by overexpression, codon optimization, enhanced transcription and/or translation, increasing activity of an activator and/or decreasing activity of an inhibitor), and (4) delivering NS1/2 using non-viral delivery systems such as, e.g., nanoparticles, liposomal particles, virion-like particles, bacteriophages, cell-penetrating peptides (CPPs) or bacteria. For a description of nanoparticles formulated for targeted delivery in the gastrointestinal tract, see, e.g., Yun et al., Adv Drug Deliv Rev. 2013; 65(6): 822-832 (e.g., mucoadhesive nanoparticles, negatively charged carboxylate- or sulfate-modified particles, etc.). For a description of virion-like particles suitable for use in the invention, see, e.g., Roldao et al., Expert Rev Vaccines 2010 October; 9(10):1149-1176. For a description of cell-penetrating peptides (CPPs) useful in the invention, see, e.g., Shoji-Kawata et al., Nature 2013; 494(7436):201-6 and Bechara et al., FEBS Lett. 2013; 587(12):1693-702.

Administration of the compounds, organisms and compositions in the methods of the disclosure can be accomplished by any method known in the art. Non-limiting examples of useful routes of delivery include oral, topical, rectal, mucosal, sublingual, nasal, intravenous, subcutaneous, and via naso/oro-gastric gavage. The active agent may be systemic after administration or may be localized by the use of regional administration, intramural administration, or use of an implant that acts to retain the active dose at the site of implantation. The active agent, vector, virus, bacteriophage, particle, or a bacterial inoculant can be mixed with a carrier and (for easier delivery to the digestive tract) applied to liquid or solid food, or feed or to drinking water. The carrier material should be non-toxic to the virus/bacteriophage/bacteria and the subject/patient. Non-limiting examples of formulations useful in the methods of the present disclosure include oral capsules and saline suspensions for use in feeding tubes, transmission via nasogastric tube, or enema. If live virus, bacteriophage or bacteria are used, the carrier should preferably contain an ingredient that promotes viability of the virus/bacteriophage/bacteria during storage. The formulation can include added ingredients to improve palatability, improve shelf-life, impart nutritional benefits, and the like. If a reproducible and measured dose is desired, the formulation can be administered by a rumen cannula. In certain embodiments, the formulation used in the methods of the disclosure further comprises a buffering agent. Examples of useful buffering agents include saline, sodium bicarbonate, milk, yogurt, infant formula, and other dairy products.

The useful dosages of the compounds and formulations of the disclosure will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. The bacteria-containing formulation may also comprise one or more prebiotics which promote growth and/or immunomodulatory activity of the bacteria in the formulation. While it is possible to use a compound, vector, virus, bacteriophage, particle, or a bacterial inoculant of the present disclosure for therapy as is, it may be preferable to administer it in a pharmaceutical formulation, e.g., in admixture with a suitable pharmaceutical excipient, diluent or carrier selected with regard to the intended route of administration and standard pharmaceutical practice. The excipient, diluent and/or carrier must be "acceptable" in the sense of being compatible with the other ingredients of the formulation and not deleterious to the recipient thereof. Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice. Although there are no physical limitations to delivery of the formulations of the present disclosure, oral delivery is preferred for delivery to the digestive tract because of its ease and convenience, and because oral formulations readily accommodate additional mixtures, such as milk, yogurt, and infant formula.

Oral delivery may also include the use of nanoparticles that can be targeted, e.g., to the GI tract of the subject, such as those described in Yun et al., Adv Drug Deliv Rev. 2013, 65(6):822-832 (e.g., mucoadhesive nanoparticles, negatively charged carboxylate- or sulfate-modified particles, etc.). Non-limiting examples of other methods of targeting delivery of compositions to the GI tract are discussed in U.S. Pat. Appl. Pub. No. 2013/0149339 and references cited therein (e.g., pH sensitive compositions [such as, e.g., enteric polymers which release their contents when the pH becomes alkaline after the enteric polymers pass through the stomach], compositions for delaying the release [e.g., compositions which use hydrogel as a shell or a material which coats the active substance with, e.g., in vivo degradable polymers, gradually hydrolyzable polymers, gradually water-soluble polymers, and/or enzyme degradable polymers], bioadhesive compositions which specifically adhere to the colonic mucosal membrane, compositions into which a protease inhibitor is incorporated, a carrier system being specifically decomposed by an enzyme present in the colon).

For oral administration, the active ingredient(s) can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and nonaqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Depletion of commensal bacteria following antibiotic treatment is a health hazard in humans, as evidenced by antibiotic-associated diarrhea. MNV can replace many of the beneficial functions of gastrointestinal microbiota (e.g., protection from intestinal injury), providing substantial protection in antibiotic-treated mice in two models of intestinal damage, administration of dextran sodium sulfate (DSS) in drinking water and oral infection by *Citrobacter rodentium* (Gram-negative bacterium related to *Escherichia coli*) (Kernbauer et al., 2014. Nature 516:94-98). Specifically, the MNV CR6 strain restores survival of antibiotics-treated mice and germ-free mice following treatment with dextran sodium sulfate (DSS), a chemical that is otherwise lethal when administered to mice lacking bacteria. The effect of MNV was dependent on type I interferon (IFN-I), which is a conserved response to viruses. In contrast, infection by the MNV CW3 strain provides little or no protection from DSS-mediated injury (Kernbauer et al., Nature. 2014; 516 (7529):94-98). The Examples described below provide data showing, unexpectedly, that the NS1/2 region of MNV is sufficient to confer a survival benefit on hosts having an intestinal injury and that the NS1/2 region of MNV has a role in mediating the inflammatory (e.g., cytokine) response.

Example 1

Compared with MNV CR6, MNV CW3 has been shown to be more virulent and less capable of establishing persistent infection in conventional mice. These functional differences between these two strains have been attributed to amino acid sequence differences in the capsid protein VP1 and the poorly characterized protein NS1/2 (also referred to as N-term) (Nice et al., J Virol. 2013; 87(1):327-334; Strong et al., J Virol. 2012; 86(6):2950-2958; Tomov et al., J Virol. 2013; 87(12):7015-7031).

Figure 2A:
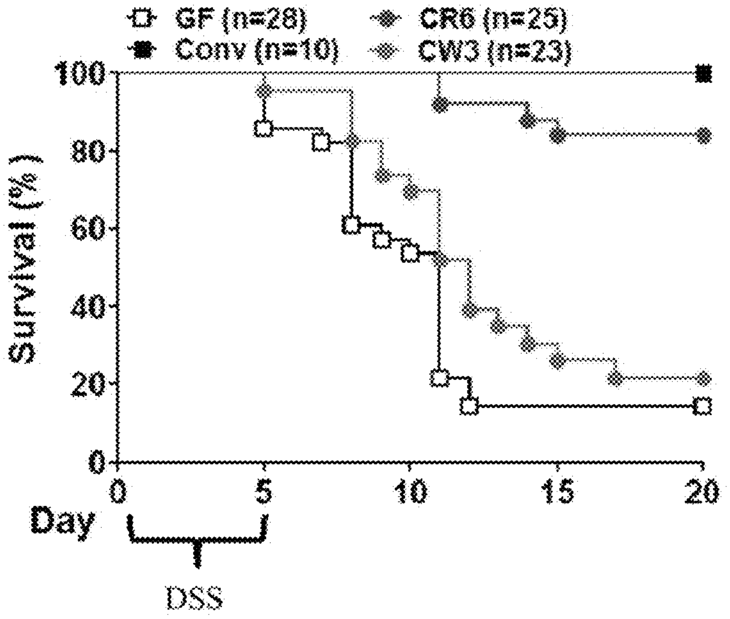
FIG. 2A-2C.

To identify the genomic region of MNV CR6 that accounts for its ability to protect against intestinal injury, germ-free mice were infected with chimeric viruses that have specific regions of CR6 and CW3 swapped with one another. Germ-free C57BL/6 mice (bred onsite in a gnotobiotics facility) were removed from gnotobiotic isolators and kept on antibiotics (1 g/L ampicillin, 500 mg/L vancomycin, 1 g/L neomycin sulfate, and 1 g/L metronidazole) throughout the study to maintain sterility. They were inoculated with $1\times10^6$ plaque forming units of the chimeric viruses described below. As controls, germ-free mice were also inoculated with the parental strain of MNV CR6 and CW3 (the infectious viruses were generated from a plasmid that was transfected into 293T cells; plasmids were provided by Skip Virgin from Washington University School of Medicine, see, e.g., Nice et al., J Virol. 2013; 87(1):327-34 and Kernbauer et al., Nature 2014; 516(7529):94-98) or left uninfected (FIG. 2A). Conventional C57BL/6 mice (bred from parents obtained from Jackson Laboratories), which were not treated with antibiotics, were also included. The generation of these viruses from a plasmid-based system has previously been described (Kernbauer et al., Nature 2014; 516(7529):94-98). Mice received 3% DSS (TdB Consultancy AB (Uppsala, Sweden)) in their drinking water on day 10 post-infection. On day 5 post-DSS treatment, the DSS-containing water was replaced with untreated water, and mice were monitored for survival.

Figure 2B:
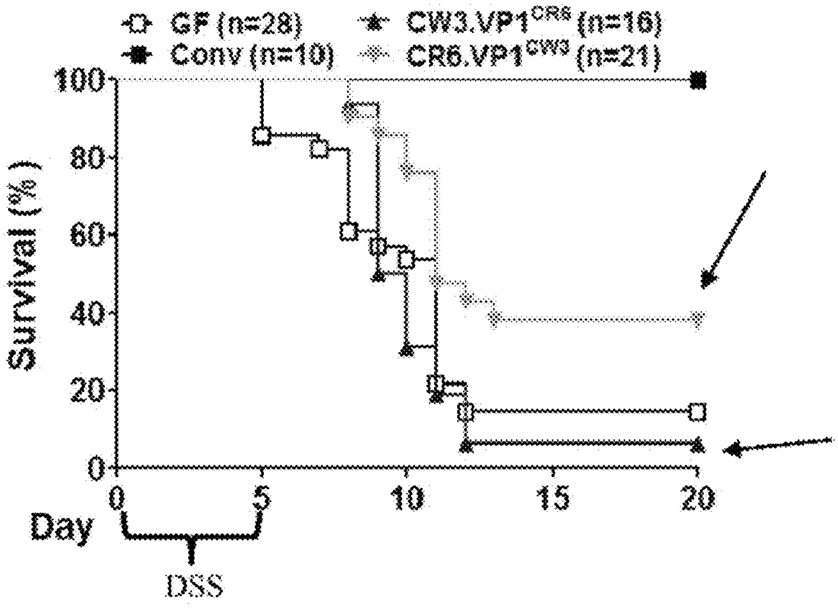
Figure 2C:
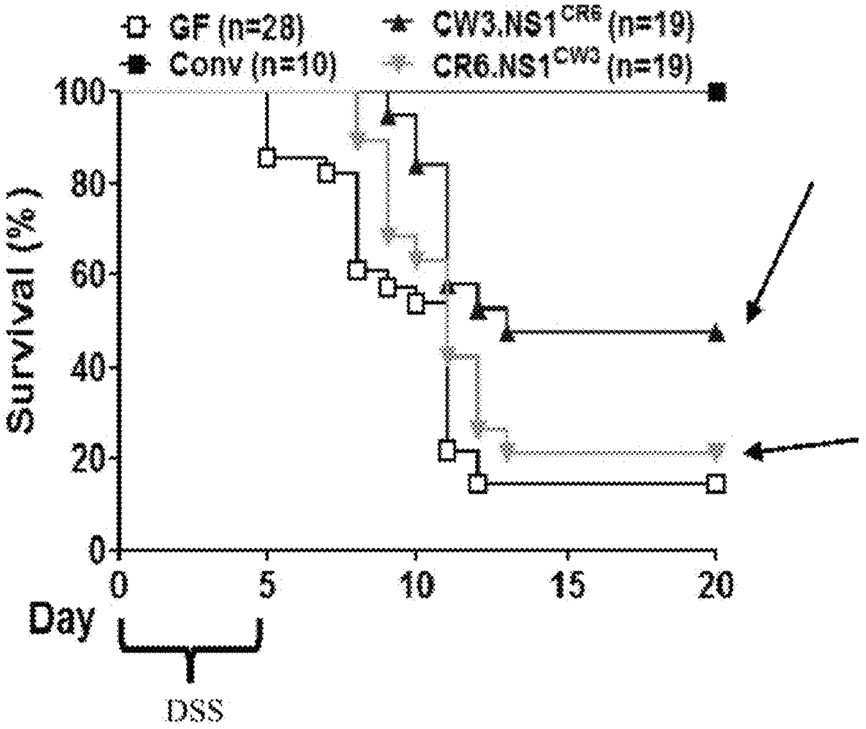
Figure 3A:
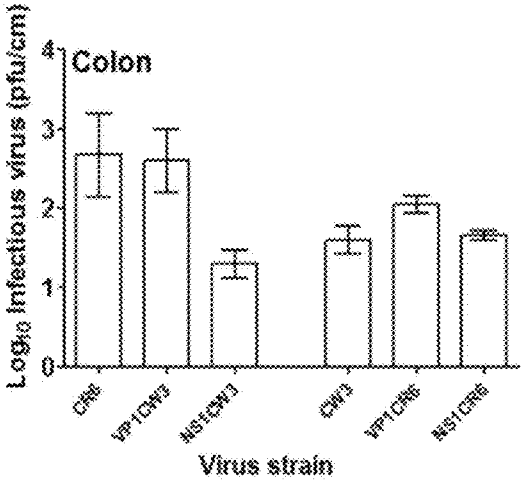
FIGS. 3A-3C are graphs showing viral burden for the chimeric viruses from FIG. 2C. The two chimeras in which the NS1 are swapped display similar replication. Therefore, the NS1 from CR6 is not making the virus better at replicating. Also, CR6 generally replicates better than CW3 and all the other chimeras. This may explain why none of the chimeras protect as well.
Figure 3B:
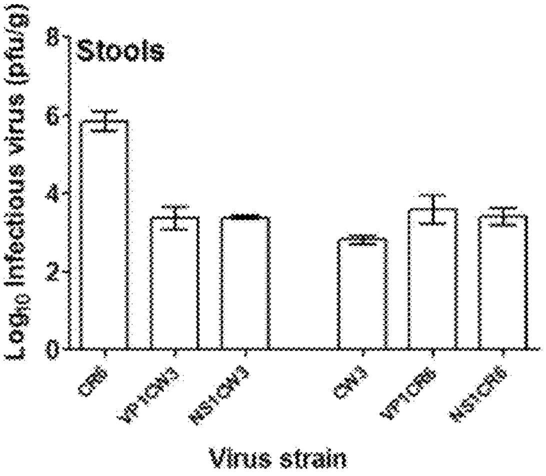
Figure 3C:
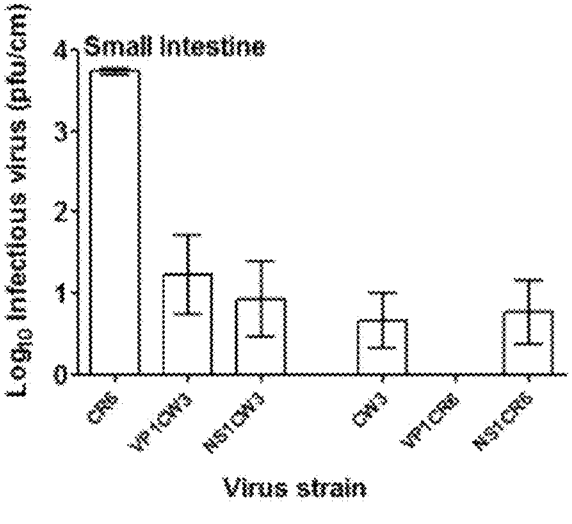

Mice infected by MNV CR6 with the CW3 VP1 region (CR6-CW3 VP1 (SEQ ID NO: 113)) have an increase in the rate of survival following DSS treatment compared with uninfected mice, while mice infected by MNV CW3 with the CR6 VP1 region (CW3-CR6 VP1 (SEQ ID NO: 114)) do not (FIG. 2B). In contrast, when MNV CR6 was combined with the CW3 NS1/2 region (CR6-CW3 NS1/2 (SEQ ID NO: 111)), the chimeric virus lost its ability to improve the survival rate (FIG. 2C). When MNV CW3 was combined with the CR6 NS1/2 region (CW3-CR6 NS1/2 (SEQ ID NO: 112)), the chimeric virus gained the ability to increase the rate of survival over uninfected mice (FIG. 2C). Therefore, the NS1/2 region from MNV CR6 is sufficient to confer a beneficial property to a strain that is otherwise not capable of improving survival following intestinal injury. CW3 and CW3-CR6 NS1/2 display the same amount of replication in germ-free mice (FIG. 3). Thus, increased replication cannot account for the improved survival of DSS-treated mice mediated by the CR6 NS1/2 region.

These findings indicate that NS1/2 region of MNV CR6 mediates the beneficial properties of this virus during intestinal injury. The NS1/2 region or a corresponding region from a member of the Caliciviridae family (e.g., a human calicivirus and/or MNV-SKI as described in Kernbauer et al., Nature. 2014; 516(7529):94-98) may also have beneficial properties during intestinal injury. For example, as shown herein, NS1/2 has a role in production of cytokines, such as production of pro-inflammatory cytokines IFNβ, IL-6, TNFα, and IL-1α. Production of pro-inflammatory cytokines assessed was less when the NS1/2 region was administered than when CW3 was given. This provides a basis for a method of reducing pro-inflammatory cytokines in a subject in need thereof, such as an individual suffering from a condition that affects a mucosal barrier. Delivery or expression of NS1/2 may be therefore used to treat a variety of conditions that affect mucosal barriers including infectious and inflammatory diseases such as, e.g., enteric infections, dysbiosis and inflammatory bowel disease. As extra-intestinal effects of MNV infection have been observed (e.g., improved survival of conventional mice following intranasal inoculation with *Pseudomonas aeruginosa*, Thepaut et al., Vet Res. 2015; 46:91), patients with non-intestinal diseases may also benefit from this application. Potential methods of delivering NS1/2 include: (1) expressing NS1/2 in a heterologous viral delivery system/vector, such as, e.g., adenoviral, retroviral, herpesviral (e.g., cytomegalovirus), or lentiviral delivery systems/vectors; (2) engineering MNV CR6 to infect human cells (e.g., B cells, T cells, natural killer (NK) cells, natural killer T (NKT) cells, innate lymphoid cells (ILCs), dendritic cells, monocytes, macrophages, or epithelial cells [e.g., Tuft cells]), e.g., by (i) mutating the major (VP1) and/or minor (VP2) capsid proteins to enable binding to human cells; (ii) making hybrid and/or chimeric viruses between MNV CR6 and a virus capable of infecting human cells (e.g., a human calicivirus such as, e.g., norovirus or sapovirus); and/or (iii) passaging MNV CR6 continuously in human cell lines (e.g., 293T, HeLa, Caco-2, BJAB, HL-60, THP-1, A549, HMEC-1, MCF-7, U937, HT-29, Jurkat); (3) engineering a human calicivirus or other enteric viruses to be avirulent (e.g., by mutating the capsid protein VP1 and/or by serial passaging in cell lines) while maximizing or improving NS1/2 activity (e.g., by overexpression, codon optimization, enhanced transcription and/or translation, increasing activity of an activator and/or decreasing activity of an inhibitor); (4) delivering MNV CR6 NS1/2 using non-viral delivery systems such as, e.g., nanoparticles, liposomal particles, plasmids, cell-penetrating peptides (CPPs), or bacteria.

FIG. 1 is a graph showing viral titer in antibiotics (ABX) treated Rag−/− mice. No decrease in MNV is observed by plaque assay in small intestine (SI) or colon in Rag−/− compared with wild-type B6 mice, indicating that B cells (and T cells) are not necessary to support persistent viral replication in this setting.

Example 2

Figure 4:
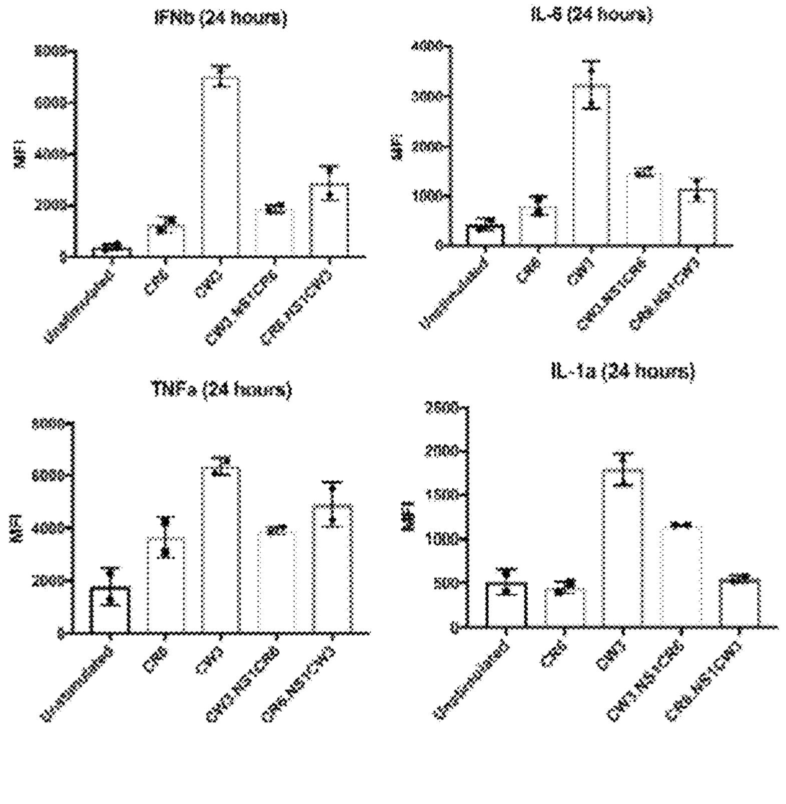
FIG. 4 are graphs showing cytokine production, in particular IFNβ, IL-6, TNFα, and IL-1α, 24 hours post infection with MNV CR6 (SEQ ID NO: 2), MNV CW3 (SEQ ID NO: 3), and CW3 with the NS1/2 region of CR6 (CW3.NS1CR6/NS1CR6; SEQ ID NO: 112), and CR6 with the NS1/2 region of CW3 (CR6.NS1CW3/NS1CW3 SEQ ID NO: 111). CW3 induces increased cytokine production while CR6 does not initiate appreciable cytokine production. Replacing NS1/2 of CW3 (SEQ ID NO: 110) with that of CR6 (SEQ ID NO: 1) is sufficient to decrease the cytokine response, while replacing NS1/2 of CR6 with CW3 leads to modest increases in cytokine release.

The effect of MNV CR6 (SEQ ID NO: 2), MNV CW3 (SEQ ID NO: 3), and CW3 with the NS1/2 region of CR6 (CW3.NS1CR6; SEQ ID NO: 112), and CR6 with the NS1/2 region of CW3 (SEQ ID NO: 111) on cytokine production was examined. A multiplex bead array in immortalized bone marrow derived macrophages (iBMDMs) were studied 24 hours post infection with the MNV. As shown in FIG. 4, CW3 induces increased production of pro-inflammatory cytokines IFNβ, IL-6, TNFα, and IL-1α, 24 hours post infection as compared with production of these cytokines induced by CR6. Replacing NS1/2 of CW3 with that of CR6 was sufficient to decrease the cytokine response, which is consistent with the role of NS1/2 in cytokine responses. Replacement of CR6 NS1/2 with CW3, however, only partially led to the production of cytokines. That the amount of IFNβ produced during CR6 infection is low, surprisingly suggests a mechanism by which the virus evades or suppresses the response.

For the assays, plasmids containing the genomes were transfected into HEK 293T cells to generate the infectious viruses, which were amplified on RAW 264.7 cells to make sufficient amount of viruses for the experiments. iBMDM cells were seeded in a 24 well tray with $2\times10^5$ cells/well. In each experiment, each virus was infected in duplicate (Unstimulated+4 viruses=10 total wells) at a multiplicity of infection (MOI) of 1. The plates were then placed to rock (e.g., 5 RPM on a Boekel Rocker II plate rocker) at room temperature for an hour. The virus was then aspirated off and 500 μl of media was added to each well. The plate was then left in the incubator for 24 hours. The next day, each well was separated into two eppendorf tubes (1 for plaque assay+1 for bead kit) and frozen down until ready for analysis using the Legendplex Mouse Inflammation Panel (13-plex) kit following the manufacturer's protocol. A BD LSR II flow cytometer and Flojo software for analyses was used. Data was graphed as mean fluorescent intensity (MFI).

Notes on the Sequence Listing:

| SEQ ID NO. | Description |
|---|---|
| 1 | NS1/2 genomic region from MNV CR6 |
| 2 | Murine norovirus GV/CR6/2005/USA, complete genome (gi\|156186707\|gb\|EU004676.1) |
| 3 | Murine norovirus 1 clone CW3, complete genome (gi\|116490118\|gb\|EF014462.1) |
| 4 | Protein sequence encoded by NS1/2 genomic region of MNV CR6 (SEQ ID NO: 1) |
| 5 | Fragment of NS1/2 genomic region of MNV CR6 |
| 6 | Protein sequence encoded by fragment of NS1/2 genomic region of MNV CR6 (SEQ ID NO: 5) |
| 7 | VP1 nucleic acid sequence of MNV CR6 |
| 8 | VP1 amino acid sequence of MNV CR6 |
| 9 | VP2 nucleic acid sequence of MNV CR6 |

-continued

| SEQ ID NO. | Description |
|---|---|
| 10 | VP2 amino acid sequence of MNV CR6 |
| 11 | NS1/2 genomic region of MNV CR6 |
| 12 | NS1/2 protein sequence encoded by NS1/2 genomic region of MNV CR6 (SEQ ID NO: 11) |
| 13 | NS1/2 nucleic acid sequence (6-1028) from Genbank Accession No. JQ237823.1 There is a base substitution at position 512 (G→C) as compared to SEQ ID NO: 11 that does not lead to a change at the amino acid level. |
| 14 | Protein encoded by NS1/2 nucleic acid sequence (6-1028) from Genbank Accession No. JQ237823.1 (SEQ ID NO: 13) |
| 15 | NS1/2 nucleic acid sequence of MNV CR6 which is the same as Genbank Accession No. EU004676.1. Contains the substitution at position 512 and an additional substitution at position 697 (C→T) as compared to SEQ ID NO: 11. The second substitution changes the amino acid sequence. |
| 16 | Protein encoded by NS1/2 nucleic acid sequence of MNV CR6 which is the same as Genbank Accession No. EU004676.1 (SEQ ID NO: 15) |
| 17 | NS1/2 nucleic acid sequence of the MNV CR6 strain including the first 5 non-coding nucleotides (1-1028) |
| 18 | Polyprotein precursor nucleic acid sequence of the MNV CR6 strain |
| 19 | Polyprotein precursor amino acid sequence of the MNV CR6 strain |
| 20 | NS1/2 nucleic acid sequence of MNV isolate O1 (KF113527.1) (6-1028) |
| 21 | NS1/2 amino acid sequence of MNV isolate O1 (KF113527.1) (6-1028) |
| 22 | NS1/2 nucleic acid sequence of MNV strain MuNoVIT1(KR349276.1). There is a degenerate “R” nucleotide in this sequence. (6-1028). |
| 23 | NS1/2 amino acid sequence of MNV strain MuNoVIT1(KR349276.1) (6-1028) |
| 24 | NS1/2 nucleic acid sequence of MNV strain Guangzhou/K162/09/CHN (HQ317203.1) |
| 25 | NS1/2 amino acid sequence of MNV strain Guangzhou/K162/09/CHN (HQ317203.1) |
| 26 | NS1/2 nucleic acid sequence of MNV strain BJ 10-2062 (KM458057.1) |
| 27 | NS1/2 amino acid sequence of MNV strain BJ 10-2062 (KM458057.1) |
| 28 | NS1/2 nucleic acid sequence of MNV strain MT30-2 (AB601769.1) |
| 29 | NS1/2 amino acid sequence of MNV strain MT30-2 (AB601769.1) |
| 30 | NS1/2 nucleic acid sequence of MNV strain NIH-D220 (JF320653.1) |
| 31 | NS1/2 amino acid sequence of MNV strain NIH-D220 (JF320653.1) |
| 32 | NS1/2 nucleic acid sequence of MNV strain NIH-A114 (JF320652.1) |
| 33 | NS1/2 amino acid sequence of MNV strain NIH-A114 (JF320652.1) |
| 34 | NS1/2 nucleic acid sequence of MNV strain NIH-4431 (JF320651.1) |
| 35 | NS1/2 amino acid sequence of MNV strain NIH-4431 (JF320651.1) |
| 36 | NS1/2 nucleic acid sequence of MNV strain NIH-4428 (JF320650.1) |
| 37 | NS1/2 amino acid sequence of MNV strain NIH-4428 (JF320650.1) |
| 38 | NS1/2 nucleic acid sequence of MNV strain NIH-4421 (JF320649.1) |
| 39 | NS1/2 amino acid sequence of MNV strain NIH-4421 (JF320649.1) |
| 40 | NS1/2 nucleic acid sequence of MNV strain NIH-2750 (JF320648.1) |
| 41 | NS1/2 amino acid sequence of MNV strain NIH-2750 (JF320648.1) |
| 42 | NS1/2 nucleic acid sequence of MNV strain NIH-2747 (JF320647.1) |
| 43 | NS1/2 amino acid sequence of MNV strain NIH-2747 (JF320647.1) |

-continued

| SEQ ID NO. | Description |
|---|---|
| 44 | NS1/2 nucleic acid sequence of MNV strain NIH-2411 (JF320646.1) |
| 45 | NS1/2 amino acid sequence of MNV strain NIH-2411 (JF320646.1) |
| 46 | NS1/2 nucleic acid sequence of MNV strain NIH-2410 (JF320645.1) |
| 47 | NS1/2 amino acid sequence of MNV strain NIH-2410 (JF320645.1) |
| 48 | NS1/2 nucleic acid sequence of MNV strain NIH-2409 (JF320644.1) |
| 49 | NS1/2 amino acid sequence of MNV strain NIH-2409 (JF320644.1) |
| 50 | NS1/2 nucleic acid sequence of MNV strain S7-PP3 (AB435515.1) |
| 51 | NS1/2 amino acid sequence of MNV strain S7-PP3 (AB435515.1) |
| 52 | NS1/2 nucleic acid sequence of MNV 3 strain K4 (FJ446720.1) |
| 53 | NS1/2 amino acid sequence of MNV 3 strain K4 (FJ446720.1) |
| 54 | NS1/2 nucleic acid sequence of MNV 4 strain S18 (FJ446719.1) |
| 55 | NS1/2 amino acid sequence of MNV 4 strain S18 (FJ446719.1) |
| 56 | NS1/2 nucleic acid sequence of MNV 1 (AY228235.2) |
| 57 | NS1/2 amino acid sequence of MNV 1 (AY228235.2) |
| 58 | NS1/2 nucleic acid sequence of MNV 1 strain CW3 (EF014462.1) |
| 59 | NS1/2 amino acid sequence of MNV 1 strain CW3 (EF014462.1) |
| 60 | NS1/2 nucleic acid sequence of MNV strain Berlin (DQ911368.1) |
| 61 | NS1/2 amino acid sequence of MNV strain Berlin (DQ911368.1) |
| 62 | NS1/2 nucleic acid sequence of MNV strain KHU-1 (JX048594.1) |
| 63 | NS1/2 amino acid sequence of MNV strain KHU-1 (JX048594.1) |
| 64 | NS1/2 nucleic acid sequence of MNV CR18 (EU004683.1) |
| 65 | NS1/2 amino acid sequence of MNV CR18 (EU004683.1) |
| 66 | NS1/2 nucleic acid sequence of MNV CR17 (EU004682.1) |
| 67 | NS1/2 amino acid sequence of MNV CR18 (EU004683.1) |
| 68 | NS1/2 nucleic acid sequence of MNV CR15 (EU004681.1) |
| 69 | NS1/2 amino acid sequence of MNV CR15 (EU004681.1) |
| 70 | NS1/2 nucleic acid sequence of MNV CR13 (EU004680.1) |
| 71 | NS1/2 amino acid sequence of MNV CR13 (EU004680.1) |
| 72 | NS1/2 nucleic acid sequence of MNV CR11 (EU004679.1) |
| 73 | NS1/2 amino acid sequence of MNV CR11 (EU004679.1) |
| 74 | NS1/2 nucleic acid sequence of MNV CR10 (EU004678.1) |
| 75 | NS1/2 amino acid sequence of MNV CR10 (EU004678.1) |
| 76 | NS1/2 nucleic acid sequence of MNV CR7 (EU004677.1) |
| 77 | NS1/2 amino acid sequence of MNV CR7 (EU004677.1) |
| 78 | NS1/2 nucleic acid sequence of MNV CR5 (EU004675.1) |
| 79 | NS1/2 amino acid sequence of MNV CR5 (EU004675.1) |
| 80 | NS1/2 nucleic acid sequence of MNV CR4 (EU004674.1) |
| 81 | NS1/2 amino acid sequence of MNV CR4 (EU004674.1) |
| 82 | NS1/2 nucleic acid sequence of MNV CR3 (EU004673.1) |
| 83 | NS1/2 amino acid sequence of MNV CR3 (EU004673.1) |
| 84 | NS1/2 nucleic acid sequence of MNV CR1 (EU004672.1) |
| 85 | NS1/2 amino acid sequence of MNV CR3 (EU004673.1) |
| 86 | NS1/2 nucleic acid sequence of MNV WU26 (EU004671.1) |
| 87 | NS1/2 amino acid sequence of MNV WU26 (EU004671.1) |
| 88 | NS1/2 nucleic acid sequence of MNV WU25 (EU004670.1) |
| 89 | NS1/2 amino acid sequence of MNV WU25 (EU004670.1) |
| 90 | NS1/2 nucleic acid sequence of MNV WU24 (EU004669.1) |
| 91 | NS1/2 amino acid sequence of MNV WU24 (EU004669.1) |
| 92 | NS1/2 nucleic acid sequence of MNV WU23 (EU004668.1) |
| 93 | NS1/2 amino acid sequence of MNV WU23 (EU004668.1) |
| 94 | NS1/2 nucleic acid sequence of MNV WU22 (EU004667.1) |
| 95 | NS1/2 amino acid sequence of MNV WU22 (EU004667.1) |

-continued

| SEQ ID NO. | Description |
|---|---|
| 96 | NS1/2 nucleic acid sequence of MNV WU21 (EU004666.1) |
| 97 | NS1/2 amino acid sequence of MNV WU21 (EU004666.1) |
| 98 | NS1/2 nucleic acid sequence of MNV WU20 (EU004665.1) |
| 99 | NS1/2 amino acid sequence of MNV WU20 (EU004665.1) |
| 100 | NS1/2 nucleic acid sequence of MNV WU12 (EU004664.1) |
| 101 | NS1/2 amino acid sequence of MNV WU12 (EU004664.1) |
| 102 | NS1/2 nucleic acid sequence of MNV WU11 (EU004663.1) |
| 103 | NS1/2 amino acid sequence of MNV WU11 (EU004663.1) |
| 104 | NS1/2 nucleic acid sequence of MNV strain Berlin 06 (EF531291.1) |
| 105 | NS1/2 amino acid sequence of MNV strain Berlin 06 (EF531291.1) |
| 106 | NS1/2 nucleic acid sequence of MNV strain Berlin 05 (EF531290.1) |
| 107 | NS1/2 amino acid sequence of MNV strain Berlin 05 (EF531290.1) |
| 108 | NS1/2 genomic region of MNV strain CR6 |
| 109 | Protein encoded by NS1/2 genomic region of MNV strain CR6 (SEQ ID NO: 108) |
| 110 | NS1/2 genomic region of MNV strain CW3 |
| 111 | Nucleic acid sequence for NS1CW3 chimera |
| 112 | Nucleic acid sequence for NS1CR6 chimera |
| 113 | Nucleic acid sequence for CR6 - VP1$^{CW3}$ chimera (CR6 virus with the VP1 region of CW3) |
| 114 | Nucleic acid sequence for CW3 - VP1$^{CR6}$ chimera (CW3 virus with the VP1 region of CR6) |
| 115 | Fragment of NS1/2 genomic region of MNV CR6 |
| 116 | Protein sequence encoded by fragment of NS1/2 genomic region of MNV CR6 (SEQ ID NO: 115) |

REFERENCES

1. Kernbauer, E., Ding, Y. and Cadwell, K. An enteric virus can replace the beneficial function of commensal bacteria. Nature. 2014; 516(7529):94-98. 4257755
2. Nice, T. J., Strong, D. W., McCune, B. T., Pohl, C. S. and Virgin, H. W. A single-amino-acid change in murine norovirus NS1/2 is sufficient for colonic tropism and persistence. J Virol. 2013; 87(1):327-334. 3536416
3. Strong, D. W., Thackray, L. B., Smith, T. J. and Virgin, H. W. Protruding domain of capsid protein is necessary and sufficient to determine murine norovirus replication and pathogenesis in vivo. Journal of virology. 2012; 86(6): 2950-2958. 3302348
4. Tomov, V. T., Osborne, L. C., Dolfi, D. V., Sonnenberg, G. F., Monticelli, L. A., Mansfield, K., Virgin, H. W., Artis, D. and Wherry, E. J. Persistent enteric murine norovirus infection is associated with functionally suboptimal virus-specific CD8 T cell responses. J Virol. 2013; 87(12):7015-7031. 3676130
5. Thepaut, M., Grandjean, T., Hober, D., Lobert, P. E., Bortolotti, P., Faure, K., Dessein, R., Kipnis, E. and Guery, B. Protective role of murine norovirus against *Pseudomonas aeruginosa* acute pneumonia. Vet Res. 2015; 46:91. PMC4558952

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A method for treating a subject, wherein the subject has cancer and/or is receiving a therapy for cancer, the method comprising administering to said subject a therapeutically effective amount of the NS1/2 genomic region of murine norovirus (MNV) comprising a nucleotide sequence encoded by the DNA sequence of SEQ ID NO: 1 or a corresponding region from a member of the Caliciviridae family or a protein encoded by any one of those regions.

2. The method of claim 1, wherein the subject has a small intestinal cancer or colon cancer.

3. The method of claim 1, comprising administering a region corresponding to the NS1/2 genomic region of murine norovirus (MNV) from a human calicivirus.

4. The method of claim 1, wherein the NS1/2 genomic region of murine norovirus (MNV) or the corresponding region from a member of the Caliciviridae family is administered in a vector.

5. The method of claim 1, wherein the NS1/2 genomic region of murine norovirus (MNV) or the corresponding region from a member of the Caliciviridae family or a protein encoded by any one of those regions is administered within a recombinant murine norovirus (MNV) engineered to infect human cells.

6. The method of claim 1, wherein the NS1/2 genomic region of murine norovinis (MNV) or the corresponding region from a member of the Caliciviridae family or a protein encoded by any one of those regions is administered in a nanoparticle, a liposomal particle, a virion-like particle, or a recombinant bacteriophage.

7. The method of claim 1, wherein the NS1/2 genomic region of murine norovirus (MNV) or the corresponding region from a member of the Caliciviridae family is administered as naked RNA, optionally with one or more modified bases.

8. The method of claim 1, wherein the NS1/2 region of murine norovirus (MNV) or the corresponding region from a member of the Caliciviridae family or a protein encoded by any one of those regions is administered in a bacterial or fungal host cell, optionally, selected from live bacterial cells, conditionally lethal bacterial cells, inactivated bacterial cells, killed bacterial cells, and spores.

9. The method of claim 1, wherein administration is to a mucosal surface.

10. The method of claim 1, wherein the subject is human.

11. A method for enhancing the effectiveness of an anti-cancer therapy in a subject in need thereof, the method comprising administering to said subject a therapeutically effective amount of the NS1/2 genomic region of murine norovirus (MNV) comprising a nucleotide sequence encoded by the DNA sequence of SEQ ID NO: 1 or a corresponding region from a member of the Caliciviridae family or a protein encoded by any one of those regions.

* * * * *

SEQUENCE LISTING

```
<160> NUMBER OF SEQ ID NOS: 116

<210> SEQ ID NO 1
<211> LENGTH: 1023
<212> TYPE: DNA
<213> ORGANISM: Murine norovirus

<400> SEQUENCE: 1

gtgaaatgag gatggcaacg ccatcttctg cgtcctctgt gcgcaacaca gagaaacgca      60

aaaataaaaa ggcttcatct aaggctagtg tctcctttgg agcacctagc ttactctctt     120

cggagagtga agatgaagtt aattacatga cccctcctga gcaggaagct cagcccggcg     180

ccctcgcggc cctccatgcg gacgggccgc atgccgggct ccctgtgacc cgaagtgatg     240

cacgcgtgct gatcttcaat gattgggagg agaggaagag gtccgagccg tggctacggc     300

tggacatgtc tgacaaggct atcttccgcc gctaccccca cctgcggcct aaggaagata     360

aagccgatgc gccctcccat gcggaggacg ccatggatgc aagggagccc ataattgggt     420

ccattcttga gcaggatgat cataagttct accattactc tgtctacatt ggtaacggcc     480

aggtgatggg cgtcaacaat cccggcgccg cggtttgcca ggctgtgatt gatgtggaga     540

agctccacct gtggtggagg ccagtgtggg agccccgtca acccctcgac ccggctgagt     600

tgaggaagtg cgttggcatg accgttccct atgtggcgac caccgtcaat tgctaccagg     660

tctgctgctg gattgttggg attaaggaca cctggccgaa gagggcgaag atctctaggg     720

attcgccctt ctacagtcct gtccaggact ggaacatcga cccccaggat cctttcatcc     780
```

cttccaagct caggatggtt tctgatggca tcttggtggc tcttgcaacg gtgattggtc 840
ggccgatcaa gaacctgctg gcatctgtga agcctctcaa catccttaac atcgtgttga 900
gctgtgactg gactttctcg ggcattgtca acgccctgat tctccttgct gaactcttcg 960
acatcttctg gacccccct gatgttacca attggatgat ctccatcttt ggagagtggc 1020
agg 1023

<210> SEQ ID NO 2
<211> LENGTH: 7383
<212> TYPE: DNA
<213> ORGANISM: Murine norovirus

<400> SEQUENCE: 2
gtgaaatgag gatggcaacg ccatcttctg cgtcctctgt gcgcaacaca gagaaacgca 60
aaaataaaaa ggcttcatct aaggctagtg tctcctttgg agcacctagc ttactctctt 120
cggagagtga agatgaagtt aattacatga cccctcctga gcaggaagct cagcccggcg 180
ccctcgcggc cctccatgcg gacgggccgc atgccgggct ccctgtgacc cgaagtgatg 240
cacgcgtgct gatcttcaat gattgggagg agaggaagag gtccgagccg tggctacggc 300
tggacatgtc tgacaaggct atcttccgcc gctaccccca cctgcggcct aaggaagata 360
aagccgatgc gccctcccat gcggaggacg ccatggatgc aagggagccc ataattgggt 420
ccattcttga gcaggatgat cataagttct accattactc tgtctacatt ggtaacggcc 480
aggtgatggg cgtcaacaat cccggcgccg ccgtttgcca ggctgtgatt gatgtggaga 540
agctccacct gtggtggagg ccagtgtggg agccccgtca acccctcgac ccggctgagt 600
tgaggaagtg cgttggcatg accgttccct atgtggcgac caccgtcaat tgctaccagg 660
tctgctgctg gattgttggg attaaggaca cctggctgaa gagggcgaag atctctaggg 720
attcgccctt ctacagtcct gtccaggact ggaacatcga cccccaggat cctttcatcc 780
cttccaagct caggatggtt tctgatggca tcttggtggc tcttgcaacg gtgattggtc 840
ggccgatcaa gaacctgctg gcatctgtga agcctctcaa catccttaac atcgtgttga 900
gctgtgactg gactttctcg ggcattgtca acgccctgat tctccttgct gaactcttcg 960
acatcttctg gacccccct gatgttacca attggatgat ctccatcttt ggagagtggc 1020
aggctgaggg tccctttgac ctcgccctgg atgtcgtgcc cactcttctt ggtgggattg 1080
gcatggcatt tggcctgaca tctgagacca ttgggcgtaa gctcgcctcc accaactcgg 1140
ccctcaaggc cgcccaggag atgggaaagt ttgcaattga ggtcttcaag caaatcatgg 1200
catggatttg gccctccgaa gaccctgttc ctgccctgct ctccaacatg gagcaagctg 1260
tcatcaagaa tgagtgccaa cttgagaatc aactcacggc catgctgcgg gatcgcaacg 1320
ctggagctga gttcctgaaa gcacttgatg aagaagagca ggaggtccgc aagattgctg 1380
ccaagtgcgg gaactctgcc accacgggca cgaccaacgc tctgctagct aggatcagca 1440
tggcgcgcgc agccttcgag aaggcccgcg ctgagcagac atctcgggtt cgacccgtcg 1500
tgatcatggt ctctggcagg cccgggatcg ggaaaacttg tttttgccag aacctggcaa 1560
agaggattgc tgcctccctt ggggatgaga cctcagtcgg catcataccg cgtgccgatg 1620
tggaccactg ggacgcctac aagggcgcca gagttgttct ttgggacgac tttggcatgg 1680
acaatgtggt gaaggatgca ctgcggctgc agatgctcgc tgacacctgc cccgtcacgc 1740
tcaactgtga cagaattgag aacaagggaa agatgtttga ctctcaagtc atcatcatca 1800
ctaccaatca gcaaacccca gtacccctgg actatgttaa cttggaggca gtttgccgcc 1860

-continued

```
gcatagactt cttggtttat gctgagagcc ctgtggttga cgccgctcga gccagatcac   1920
ccggcgacgt gaccgccgtc aaggccgcca tgaggccaga ctacagccat atcaatttta   1980
ttctggcacc gcagggtggc tttgatcggc agggcaacac cccctacggc aagggcgtca   2040
ctaagatcat tggcgccacc gcgctctgcg caagggcagt cgcccttgtc cacgagcgcc   2100
atgatgactt cggcctccaa agcaagacct atgactttga tgctggtaaa gtgactgcct   2160
tcaaggctat ggcagctgat gctggaatcc cctggtacaa gatggcagcg attggctgta   2220
aggccatgag ctgcacctgt gtggaggaag ccatgaactt gctcaaggac tatgaggtgg   2280
ccccgtgcca ggtggtctac aatggagcca cctacaatgt cagctgcatc aagggtgctc   2340
ccatggtcga gagggtcaag gagcccgagc tacccaaaac actagtcaat tgtgttagga   2400
ggatcaagga ggctcgcctc cgctgctact gcagaatggc cacagatgtc atcacctcca   2460
tcctgcaggc ggctgggaca gctttctcca tctaccatca gattgagaag aaaactcggc   2520
cctccttcta ctgggaccac ggttacacct accgagacgg cccgggtgcc ttcgatctct   2580
ttgaggatga caacgacgga tggtaccact ctgaaggcaa gaaaggcagg aacaagagag   2640
gccgtgggcg gcccggagtt ttcaagtccc gtgggctcac ggacgaggaa tatgatgaat   2700
tcaagaaacg ccgcgagtcc aagggcggca agtactccat tgatgattac ctcgctgacc   2760
gtgagcgaga agaggagctc caggagcgtg atgaagagga ggccatcttt ggggacggtt   2820
ttggtctgaa ggccacacgc cgttcccgta aagcggagag ggccaagctt agcctagtct   2880
cgggggggtga catccgcgcc cgaagaccaa ttgactggaa tgtggtcggc ccctcttggg   2940
ctgacgatga ccgccaggtc gactatggtg agaagatcaa ctttgaggct ccagtctcaa   3000
tctggacccg tgttgtgcaa tttggcacgg ggtggggctt ctgggtcagc ggccacgtct   3060
tcatcactgc caagcatgtg gccccaccca agggcacaga ggtgtttggg cgcaagcctg   3120
gagacttcac cgtcacttcc agtggagact tcctaaaata tcattttacc aatgctgtta   3180
ggcctgacat ccccgccatg gtcttggaaa acggctgcca ggagggcgtc gtcgcctcag   3240
tcctcgtcaa gagggcctcc ggtgagatgc tcgctttggc agtcaggatg ggctcgcaag   3300
ctgccatcaa gatcggcagc gctgtggtgc acgggcagac cggtatgctc ttaaccggtt   3360
ccaatgctaa ggcccaagat ctcgggacca tcccgggtga ttgtggttgc ccctatgtct   3420
acaagaaggg gaacacctgg gtggtgattg gagtgcacgt ggcggccacc aggtctggta   3480
acacagttat cgccgccacc catggagagc ccacacttga ggccctggag tttcagggtc   3540
cccccatgct ccctcgccct tctggcacct atgcaggcct tcctatcgcc gactacggcg   3600
acgccccccc tttgagcacc aagaccatgt tctggcgcac ctcaccagag aagcttcctc   3660
ctggagcttg ggagcctgcc tacctcggct ctaaggacga gagagtcgac gggccttctc   3720
tgcagcaggt tatgcgggat cagcttaaac cctattcaga gtcacgcggc ttgctgcccc   3780
ctcaggagat cttggacgcg gtttgtgatg ccatcgagaa ccgccttgag aacacccttg   3840
agccacaaaa gccctggacg ttcaagaagg cctgtgagag cctggataag aacaccagca   3900
gtgggtaccc ctaccataag cagaaaagca aggattggac agggaccgcc ttcgtcggtg   3960
agcttggtga ccaggccacc catgccaaca acatgtatga gatgggcaag tccatgcggc   4020
ccgtctacac agctgccctc aaggatgagc tagtcaagcc agataagatc tacaagaaga   4080
taaagaagag gctcctttgg ggttctgacc tcggcaccat gatccgtgcc gcccgtgctt   4140
ttggcccctt ttgtgaagct ttgaaggaga cttgcatttt taatcccatc agagtgggca   4200
```

-continued

```
tgtcaatgaa tgaggatgga cccttcatct tcgcgaggca tgccaatttc aggtaccaca   4260
tggatgcaga ctataccaga tgggactcca cccagcaaag ggccattctg aagcgcgctg   4320
gtgatatcat ggtgcgcctc tcccctgagc cagagctggc tcgggtggtg atggatgatc   4380
tcttggcccc ttcattgcta gatgtcggcg actacaagat cgtcgtcgag gagggactcc   4440
cgtctggttg cccttgcacc acacagctaa atagtatggc ccattggatt ttgaccctct   4500
gcgcgatggt ggaggtgacc cggattgacc ctgacatcgt gatgcaagag tctgaatttt   4560
ccttctatgg tgatgatgag gtggtctcaa ccaaccttga attggacatg accaagtaca   4620
ccatggccct gaagcggtat ggtcttctcc cgacgcgtgc ggacaaggag gagggacccc   4680
tggagcgccg tcagacgctg cagggcatct ccttcttgcg ccgtgcgata atcggtgatc   4740
agtttggctg gtatggccgt cttgaccgtg ccagcattga ccgtcagctt ctttggacta   4800
aaggacccaa ccatcagaat ccctttgaga ctctcccagg acatgctcag agaccctccc   4860
aattgatggc cctgctcggt gaggctgcca tgcatggtga aaagtattac aggactgtgg   4920
cttcccgggt ctccaaggag gccgcccata gtgggataga aatggtggtc ccacgccacc   4980
gatctgttct gcgctgggtg cgctttggaa caatggatgc tgagaccccg caggaacgct   5040
cagcagtctt tgtgaatgag gatgagtgat ggcgcagcgc caaaagccaa cggctctgaa   5100
gccagcggcc aagatcttgt tcctaccgcc gttgaacagg ccgtccccat tcagcccgtg   5160
gctggtgcgg ctcttgccgc ccccgccgcc gggcaaatca accaaattga cccctggatc   5220
ttccaaaatt ttgtccaatg ccccccttggt gagttttcca tttcgcctcg aaacacccca   5280
ggtgaaatac tctttgattt ggccctcggg ccagggctca accccctacct tgcccacctc   5340
tcagccatgt acaccggctg ggttgggaac atggaggttc agctggtcct cgccggcaat   5400
gcctttactg ctggcaaggt ggttgttgcc cttgtaccac cctatttccc caaagggtca   5460
ctcaccaccg cccagatcac atgcttccca cacgtcatgt gtgatgtgcg taccctggag   5520
cccattcaat tgcctcttct tgacgtgcgt cgagttcttt ggcatgctac ccaggatcag   5580
gaggaatcta tgcgcctggt ctgcatgctg tacacgccac tccgcacaaa cagcccgggt   5640
gatgagtctt ttgtggtctc tggccgcctt ctttctaagc cggcacctga tttcaacttt   5700
gtatacctga ccccccctat cgagagaact atttaccgga tggttgactt gcccgtgttg   5760
cagccgcggc tgtgcacgca cgctcgttgg ccggccccgg tctatggcct cttggtagac   5820
ccatccctcc catccaatcc ccagtggcag aatggtagag tgcaagttga tgggactctt   5880
cttggtacaa cgcctgtgtc tggttcatgg gtttcctgct ttgcagctga ggctgcctac   5940
gagttccaag ctgggactgg tgaggtggtg accttcacca tgattgagca ggacggatcc   6000
gcctatgtcc ccggtgacag ggcggccccc cttgggtacc ccgacttctc tgggcaactg   6060
gagatcgagg tgcagactga gaccaccaaa acaggcgaca agctcagggt gaccaccttc   6120
gagatgatcc ttggccccac caccaacgtg gaccaggccc cctaccaggg cagagcgtac   6180
gcgagcttaa cagctgcagc ctcgcttgac ctggtggatg ggagagttag ggcggtccca   6240
cgctccatct attctttcca ggatgagctc ccagagtata atgatggtct tttggttccc   6300
cttgccccac ccctaggccc ctttcttcct ggtgaggttt tgttgaggtt tcgtacctac   6360
atgcgccagc ttgacaccgc tgacgccgca gcgcagccga tcgactgtgc cttgccccag   6420
gagtttatct cctggtttgc aagcaacaac ttcacggtcc agtcggacgc gctcctggtt   6480
aggtaccgga ataccttgac tggccagctc ctgtttgagg ctaagcttta tagtgaaggc   6540
tacattgctg tgtcttactc agggtctggc cccctcactt tccccactga cggcttcttt   6600
```

gaggttgtca gctgggtccc ccgcctcttt caattggcct ccgtgggaag cttggtaaca 6660
ggccgaacac tcaaacaata atggctggcg cactctttgg tgcgattgga ggtggcctga 6720
tgggcataat tggcaattcc atctcaacag tccagaatct tcaggcaaat aaacaattgg 6780
ctgcacagca atttggctat aattcctctc tgcttgcaac gcaaattcag gcccagaagg 6840
atctcacact gatggggcag cagttcaacc agcagctcca agccaactct ttcaagcatg 6900
accttgagat gcttggcgcc caggtgcaag cccaggcgca ggcccaggag aacgctatca 6960
acatcaggtc ggcgcagctc caggccgcag gcttttcaaa gtccgacgcc attcgcttgg 7020
cctcggggca gcaaccgacg agggccgttg actggtctgg gacgcggtat tacgccgcta 7080
accagccggt tacgggcttc tcgggtggct tcaccccaag ttacactcca ggtaggcaaa 7140
tggcagtccg ccctgtggac acatcccctc taccggtctc gggtggacgc atgccgtccc 7200
ttcgtggagg ttcctggtct ccgcgtgatt acacgccgca gacccaaggc acctacacga 7260
acgggcggtt tgtgtccttc ccaaagatcg ggagtagcag ggcataggtt ggaagagaaa 7320
cctttctgtg aaaatgattt ctgcttactg ctcttttctt ttggtagtat ttagatgcat 7380
ttt 7383

<210> SEQ ID NO 3
<211> LENGTH: 7382
<212> TYPE: DNA
<213> ORGANISM: Murine norovirus

<400> SEQUENCE: 3
gtgaaatgag gatggcaacg ccatcttctg cgccctctgt gcgcaacaca gagaaacgca 60
aaaacaagaa ggcttcgtct aaagctagtg tctcctttgg agcacctagc cccctctctt 120
cggagagcga agacgaaatt aattacatga cccctcctga gcaggaagct cagcccggcg 180
cccttgcggc ccttcatgcg gaagggccgc ttgccgggct ccccgtgacg cgtagtgatg 240
cacgcgtgct gatcttcaat gagtgggagg agaggaagaa gtctgatccg tggctacggc 300
tggacatgtc tgataaggct atcttccgcc gttacccccca tctgcggcct aaggaggata 360
ggcctgacgc gccctcccat gcggaggacg ctatggatgc caaggagcct gtgatcggct 420
ctatcttgga gcaggatgat cacaagtttt accattactc tgtctacatc ggtggcggcc 480
ttgtgatggg ggtcaacaac cccagtgctg cggtctgcca ggcaacgatt gatgtggaga 540
agctacacct ctggtggcgg cctgtctggg agccccgcca tcccccttgac tcggctgagt 600 tgaggaagtg cgtgggcatg actgtcccct acgtggccac caccgtcaac tgttatcagg 660
tctgctgctg gattgttggc atcaaggaca cctggctgaa gagggcgaag atctctagag 720
atctgccctt ctacagcccc gtccaggact ggaacgtcga cccccaggag cccttcattc 780
catccaagct caggatggtc tcggatggca tcctggtggc cttgtcggca gtgattggcc 840
ggccaattaa gaacctactg gcctcagtta agccgctcaa cattctcaac atcgtgctga 900
gctgtgattg gacctttttcg ggcattgtca atgccctgat cttgcttgct gagctctttg 960
acatcttttg gacccccccct gatgtgacca actggatgat ctctatcttc ggggaatggc 1020
aggccgaagg gcccttcgac cttgctcttg acatggtgcc caccctgttg ggcgggatcg 1080
ggatggcttt tggcctcacc tctgagacca tcgggcgcaa gctcgcttcc accaactcgg 1140
ctctcaaggc cgcccaagag atgggcaagt tcgccataga ggtcttcaag caaattatgg 1200
cctggatctg gccctctgag gacccagtgc cagccctctt atccaacatg gagcaggcca 1260

-continued

```
tcattaagaa tgagtgtcaa ctggagaacc aactcacggc catgttgcgg gatcgcaacg   1320
caggggctga attcctaagg tcccttgatg aggaggagca ggaagtccgc aagatcgcag   1380
ctaagtgcgg caactcggcc accactggaa ccaccaacgc tctgctggcc aggatcagca   1440
tggcccgcgc ggcctttgag aaagctcgcg ctgaacagac ctcccgagtc cgccctgtgg   1500
tgatcatggt ctcaggcagg cccgggatcg ggaaaacctg cttttgccaa aacctagcca   1560
agaggattgc tgcgtccctg ggtgatgaga cctctgttgg catcatacca cgcgctgatg   1620
tcgaccactg ggatgcttac aagggagcca gagtggttct ctgggatgat ttcggcatgg   1680
acaacgtggt gaaggatgca ctgaggcttc agatgcttgc cgacacgtgc ccagtgacac   1740
tcaattgtga caggattgag aacaagggaa agatgtttga ctctcaggtc attatcatca   1800
ccacaaatca acaaaccccc gtgcccctgg actatgtcaa cctggaggcg gtctgccgcc   1860
gcatagattt cctggtttat gctgagagcc ctgttgttga tgatgctcgg gccagagccc   1920
ctggcgatgt gaatgcagtg aaagctgcca tgaggcccga ttacagccac atcaatttca   1980
tcttggcacc gcagggcggc tttgaccgtc agggaaacac cccctacggt aagggcgtca   2040
ccaagatcat tggcgccact gctctttgcg cgagagcggt tgctcttgtc catgagcgcc   2100
atgatgattt cggcctccag aacaaggtct atgactttga tgccggcaag gtcaccgcct   2160
tcaaagccat ggcggctgac gccggcattc catggtacaa aatggcagct attgggtgca   2220
aagcaatggg gtgcacctgt gtagaggagg ccatgcattt acttaaggat tatgaggtgg   2280
ctccctgtca ggtgatctac aatggtgcca cctataatgt gagctgcatc aagggtgccc   2340
caatggttga aaaggtcaag gagcctgaat tgcccaaaac acttgtcaac tgtgtcagaa   2400
ggataaagga ggcccgcctc cgctgctact gtaggatggc tgctgacgtc atcacgtcca   2460
ttctgcaggc ggccggcacg gccttctcta tttaccacca gattgagaag aggtctagac   2520
catcctttta ttgggatcat ggatacacct accgtgacgg acctggatcc tttgacatct   2580
ttgaggatga cgatgatggg tggtaccact ctgagggaaa gaagggcaag aacaagaagg   2640
gccgggggcg acccggagtc ttcagaaccc gtgggctcac ggatgaggag tacgatgaat   2700
tcaagaagcg ccgcgagtct agggggcggca agtactccat tgatgattac ctcgctgacc   2760
gcgagcgaga agaagaactc ctggagcggg acgaggagga ggctatcttc ggggatggct   2820
tcgggttgaa ggccacccgc cgttcccgca aggcagagag agccaaactg ggcctggttt   2880
ctggtggcga catccgcgcc cgcaagccga tcgactggaa tgtggttggc ccctcctggg   2940
ctgacgatga ccgccaggtc gactacggcg agaagatcaa ctttgaggcc ccagtctcca   3000
tctggtcccg tgttgtgcag ttcggcacgg ggtggggctt ttgggtgagc ggccacgtct   3060
tcatcaccgc caagcatgtg gcgccccccca agggcacgga gatctttggg cgcaagcccg   3120
gggacttcac tgtcacttcc agcggggact tcttgaagta ctacttcacc agcgccgtca   3180
ggcctgacat tcccgccatg gtcctggaga atgggtgcca ggagggcgtc gtcgcctcgg   3240
tccttgtcaa gagagcctcc ggcgagatgc ttgccctggc tgtcaggatg ggttcacagg   3300
ccgccatcaa gattggtagt gccgttgtgc atgggcaaac tggcatgctc ctgactggct   3360
ctaatgccaa ggcccaggac ctcgggacca tcccgggcga ctgtggctgt ccctatgttt   3420
ataagaaggg taacacctgg gttgtgattg ggtgcacgt ggcggccact aggtctggta   3480
acacagtcat tgccgccact cacggagaac ccacacttga ggctctggag ttccagggac   3540
cccccatgct tccccgcccc tcaggcacct atgcaggcct ccccatcgcc gattacggcg   3600
acgctccccc cttgagcacc aagaccatgt tctggcgtac ctcgccagag aagcttcccc   3660
```

-continued

```
ctggggcttg ggagccagcc tatctcggct ctaaagatga gagggtggac ggtccttccc   3720
ttcagcaggt catgcgagat cagcttaagc cctattcaga accacgcggt ctgcttcccc   3780
ctcaagaaat ccttgatgca gtctgcgatg ccattgagaa ccgccttgag aacacccttg   3840
aaccacagaa gccctggaca tttaagaagg cttgtgagag cttggacaag aacaccagta   3900
gcgggtatcc ctatcacaag cagaagagca aggactggac ggggagcgct tttattggcg   3960
atcttggtga ccaggccacc cacgccaaca acatgtatga gatgggtaaa tccatgcgac   4020
ccatttatac agctgccctc aaggatgaac tggttaagcc agacaagatc tacgggaaga   4080
taaagaagag gcttctctgg ggctctgacc ttggcaccat gattcgcgct gcccgtgctt   4140
ttggcccttt ctgtgatgct ctgaaagaaa cctgcatttt caaccccatc agagtgggca   4200
tgtcgatgaa cgaagatggc cccttcatct tcgcaagaca cgccaatttc aggtaccaca   4260
tggatgctga ctataccagg tgggactcca cccaacagag agccatccta aagcgcgctg   4320
gcgacatcat ggtgcgcctc tcccctgagc cagacttggc tcgggttgtc atggatgatc   4380
tcctggcccc ctcgctgttg gacgtcggcg actataagat cgttgtcgag gaggggctcc   4440
catccggctg cccttgcacc acacagctga atagtttggc tcactggatt ttgacccttt   4500
gtgcaatggt tgaggtaacc cgagttgacc ctgacattgt gatgcaagaa tctgagttct   4560
ccttctatgg tgatgacgag gtggtttcga ccaacctcga gttggatatg gttaagtaca   4620
ccatggcttt gaggcggtac ggtctcctcc cgactcgcgc ggacaaggag gagggacctc   4680
tggagcgtcg ccagacgctg cagggcatct ccttcctgcg ccgtgcgata gttggtgacc   4740
agtttgggtg gtacggtcgt cttgatcgtg ccagcatcga ccgccagctc ctctggacta   4800
aaggacctaa ccaccagaac ccctttgaga ctctccctgg acatgctcag agaccctccc   4860
aactaatggc cctgctcggt gaggctgcca tgcatggtga aaagtattac aggactgtgg   4920
cttcccgtgt ctccaaggag gccgcccaaa gtgggataga aatggtagtc ccacgccacc   4980
gatctgttct gcgctgggtg cgctttggaa caatggatgc tgagaccccg caggaacgct   5040
cagcagtctt tgtgaatgag gatgagtgat ggcgcagcgc caaaagccaa tggctctgag   5100
gccagcggcc aggatcttgt tcctgccgcc gttgaacagg ccgtccccat tcaacccgtg   5160
gctggcgcgg ctcttgccgc ccccgccgcc gggcaaatta accaaattga cccctggatc   5220
ttccaaaatt ttgtccagtg ccccctt ggt gagttttcca tttcgcctcg aaacacccca   5280
ggtgaaatac tgtttgattt ggccctcggg ccagggctta acccctacct tgcccacctc   5340
tcagccatgt acaccggctg ggttgggaac atggaggttc agctggtcct cgccggcaat   5400
gcctttactg ctggcaaggt ggttgttgcc cttgtaccac cctattttcc caaggggtca   5460
ctcaccactg cccagatcac atgcttccca catgtcatgt gtgatgtgcg caccctggag   5520
cccattcaac tccctcttct tgatgtgcgt cgagtccttt ggcatgctac ccaggatcaa   5580
gaggaatcta tgcgcctggt ttgcatgctg tacacgccac tccgcacaaa cagcccgggt   5640
gatgagtctt ttgtggtctc tggccgcctt ctttctaagc cggcggctga tttcaatttt   5700
gtctacctaa ctccccccat agagagaacc atctaccgga tggtcgactt gcccgtgata   5760
cagccgcggc tgtgcacgca cgcacgttgg cctgccccgg tctatggtct cttggtggac   5820
ccatccctcc cctcaaatcc ccagtggcag aatggaaggg tgcacgttga tgggaccctg   5880
cttggtacca ccccaatctc cggttcatgg gtgtcctgct ttgcggcgga ggctgcctat   5940
aagttccaat cgggcaccgg tgaggtggcg acattcaccc tgattgagca ggatggatct   6000
```

gcctacgtcc ccggtgacag ggcagcacca ctcggttacc ccgatttctc tgggcaactg 6060
gagatcgagg tccagaccga gaccaccaag actggagaca agctcaaggt caccactttt 6120
gagatgattc ttggcccaac gaccaacgcg gaccaggccc cctaccaggg cagggtgttc 6180
gccagcgtca ctgctgcggc ctctcttgac ttggtggatg gcagggttcg tgcggtccca 6240
agatccatct acggttttca ggacaccatc cctgaataca acgatgggct actggttccc 6300
cttgcccccc caattggtcc ctttctcccc ggcgaggtcc tcctgaggtt ccggacctac 6360
atgcgtcaga tcgacaccgc tgacgccgca gcagaggcga tagactgtgc actcccccag 6420
gagtttgtct cctggttcgc gtctaacgcg ttcaccgtgc agtccgaggc cctgctcctt 6480
agatacagga acaccctgac tgggcaactg ctgttcgagt gcaagctcta caacgaaggt 6540
tacatcgcct tgtcttattc cggctcagga cccctcacct tcccgaccga tggcatcttt 6600
gaggtcgtca gttgggttcc tcgcctttac caattggcct ctgtgggaag tttggcaaca 6660
ggccgaatgc tcaaacaata atggctggtg ctctttttgg agcgattgga ggtggcctga 6720
tgggcataat tggcaattcc atctcaaatg ttcaaaacct tcaggcaaac aaacaattgg 6780
cagctcagca atttggttat aattcttccc tgcttgcaac gcaaattcaa gcccagaagg 6840
atctcactct gatggggcag caattcaacc agcagctcca aaccaactct ttcaagcacg 6900
acttggaaat gcttggcgct caggtgcaag cccaggcgca ggcccaggag aacgccatca 6960
atatcaaaac ggcgcagctc caggccgcag gcttttcaaa gacggatgcc gcacgccttg 7020
ccttggggca gcagcccacg agggccgtgg attggtctgg gacgcggtac tacaccgcta 7080
accagccagt cacgggcttc tcgggtggct ttaccccaac ctacactcca ggtaggcaag 7140
tgacatcccg ccctgtggac acatcccctc taccgatctc gggtggacgc ttgccctccc 7200
ttcgtggagg ttcctggtcc ccgcgcgacc atacgccggc gactcaaggc acctacacga 7260
acggacggtt cgtgtctctc cctaagatcg ggagtagcag ggcataggtt ggaagagaaa 7320
ccttttgtga aaatgatttc tgcttactgc tttcttttct ttgtggtagt tagatgcatt 7380
tt 7382

<210> SEQ ID NO 4
<211> LENGTH: 339
<212> TYPE: PRT
<213> ORGANISM: Murine norovirus

<400> SEQUENCE: 4

Met Arg Met Ala Thr Pro Ser Ser Ala Ser Ser Val Arg Asn Thr Glu
1 5 10 15

Lys Arg Lys Asn Lys Lys Ala Ser Ser Lys Ala Ser Val Ser Phe Gly
20 25 30

Ala Pro Ser Leu Leu Ser Ser Glu Ser Glu Asp Glu Val Asn Tyr Met
35 40 45

Thr Pro Pro Glu Gln Glu Ala Gln Pro Gly Ala Leu Ala Ala Leu His
50 55 60

Ala Asp Gly Pro His Ala Gly Leu Pro Val Thr Arg Ser Asp Ala Arg
65 70 75 80

Val Leu Ile Phe Asn Asp Trp Glu Glu Arg Lys Arg Ser Glu Pro Trp
85 90 95

Leu Arg Leu Asp Met Ser Asp Lys Ala Ile Phe Arg Arg Tyr Pro His
100 105 110

Leu Arg Pro Lys Glu Asp Lys Ala Asp Ala Pro Ser His Ala Glu Asp
115 120 125

```
Ala Met Asp Ala Arg Glu Pro Ile Ile Gly Ser Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Pro Lys Arg Ala Lys Ile Ser Arg Asp Ser
225                 230                 235                 240

Pro Phe Tyr Ser Pro Val Gln Asp Trp Asn Ile Asp Pro Gln Asp Pro
                245                 250                 255

Phe Ile Pro Ser Lys Leu Arg Met Val Ser Asp Gly Ile Leu Val Ala
            260                 265                 270

Leu Ala Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln


<210> SEQ ID NO 5
<211> LENGTH: 346
<212> TYPE: DNA
<213> ORGANISM: Murine norovirus

<400> SEQUENCE: 5

atgaggatgg caacgccatc ttctgcgtcc tctgtgcgca acacagagaa acgcaaaaat      60

aaaaaggctt catctaaggc tagtgtctcc tttggagcac ctagcttact ctcttcggag     120

agtgaagatg aagttaatta catgacccct cctgagcagg aagctcagcc cggcgccctc     180

gcggccctcc atgcggacgg gccgcatgcc gggctccctg tgacccgaag tgatgcacgc     240

gtgctgatct tcaatgattg ggaggagagg aagaggtccg agccgtggct acggctggac     300

atgtctgaca aggctatctt ccgccgctac ccccacctgc ggccta                    346


<210> SEQ ID NO 6
<211> LENGTH: 115
<212> TYPE: PRT
<213> ORGANISM: Murine norovirus

<400> SEQUENCE: 6

Met Arg Met Ala Thr Pro Ser Ser Ala Ser Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Val Asn Tyr Met
        35                  40                  45
```

```
Thr Pro Pro Glu Gln Glu Ala Gln Pro Gly Ala Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Asp Trp Glu Glu Arg Lys Arg Ser Glu Pro Trp
                85                  90                  95

Leu Arg Leu Asp Met Ser Asp Lys Ala Ile Phe Arg Arg Tyr Pro His
            100                 105                 110

Leu Arg Pro
        115


<210> SEQ ID NO 7
<211> LENGTH: 1626
<212> TYPE: DNA
<213> ORGANISM: Murine norovirus

<400> SEQUENCE: 7

atgaggatga gtgatggcgc agcgccaaaa gccaacggct ctgaagccag cggccaagat      60

cttgttccta ccgccgttga acaggccgtc cccattcagc ccgtggctgg tgcggctctt     120

gccgcccccg ccgccgggca aatcaaccaa attgacccct ggatcttcca aaattttgtc     180

caatgccccc ttggtgagtt ttccatttcg cctcgaaaca ccccaggtga aatactcttt     240

gatttggccc tcgggccagg gctcaacccc taccttgccc acctctcagc catgtacacc     300

ggctgggttg ggaacatgga ggttcagctg gtcctcgccg gcaatgcctt tactgctggc     360

aaggtggttg ttgcccttgt accaccctat ttccccaaag ggtcactcac caccgcccag     420

atcacatgct tcccacacgt catgtgtgat gtgcgtaccc tggagcccat tcaattgcct     480

cttcttgacg tgcgtcgagt tctttggcat gctacccagg atcaggagga atctatgcgc     540

ctggtctgca tgctgtacac gccactccgc acaaacagcc cgggtgatga gtcttttgtg     600

gtctctggcc gccttctttc taagccggca cctgatttca actttgtata cctgaccccc     660

cctatcgaga gaactattta ccggatggtt gacttgcccg tgttgcagcc gcggctgtgc     720

acgcacgctc gttggccggc cccggtctat ggcctcttgg tagacccatc cctcccatcc     780

aatccccagt ggcagaatgg tagagtgcaa gttgatggga ctcttcttgg tacaacgcct     840

gtgtctggtt catgggtttc ctgctttgca gctgaggctg cctacgagtt ccaagctggg     900

actggtgagg tggtgacctt caccatgatt gagcaggacg gatccgccta tgtccccggt     960

gacagggcgg ccccccttgg gtaccccgac ttctctgggc aactggagat cgaggtgcag    1020

actgagacca ccaaaacagg cgacaagctc agggtgacca ccttcgagat gatccttggc    1080

cccaccacca acgtggacca ggccccctac cagggcagag cgtacgcgag cttaacagct    1140

gcagcctcgc ttgacctggt ggatgggaga gttagggcgg tcccacgctc catctattct    1200

ttccaggatg agctcccaga gtataatgat ggtgttttgg ttccccttgc cccacccccta   1260

ggcccctttc ttcctggtga ggttttgttg aggtttcgta cctacatgcg ccagcttgac    1320

accgctgacg ccgcagcgca gccgatcgac tgtgccttgc cccaggagtt tatctcctgg    1380

tttgcaagca acaacttcac ggtccagtcg gacgcgctcc tggttaggta ccggaatacc    1440

ttgactggcc agctcctgtt tgaggctaag ctttatagtg aaggctacat tgctgtgtct    1500

tactcagggt ctggcccccct cactttcccc actgacggct tctttgaggt tgtcagctgg   1560

gtcccccgcc tctttcaatt ggcctccgtg ggaagcttgg taacaggccg aacactcaaa    1620

caataa                                                              1626
```

<210> SEQ ID NO 8
<211> LENGTH: 541
<212> TYPE: PRT
<213> ORGANISM: Murine norovirus

<400> SEQUENCE: 8

```
Met Arg Met Ser Asp Gly Ala Ala Pro Lys Ala Asn Gly Ser Glu Ala
1               5                   10                  15

Ser Gly Gln Asp Leu Val Pro Thr Ala Val Glu Gln Ala Val Pro Ile
            20                  25                  30

Gln Pro Val Ala Gly Ala Ala Leu Ala Ala Pro Ala Ala Gly Gln Ile
        35                  40                  45

Asn Gln Ile Asp Pro Trp Ile Phe Gln Asn Phe Val Gln Cys Pro Leu
    50                  55                  60

Gly Glu Phe Ser Ile Ser Pro Arg Asn Thr Pro Gly Glu Ile Leu Phe
65                  70                  75                  80

Asp Leu Ala Leu Gly Pro Gly Leu Asn Pro Tyr Leu Ala His Leu Ser
                85                  90                  95

Ala Met Tyr Thr Gly Trp Val Gly Asn Met Glu Val Gln Leu Val Leu
            100                 105                 110

Ala Gly Asn Ala Phe Thr Ala Gly Lys Val Val Val Ala Leu Val Pro
        115                 120                 125

Pro Tyr Phe Pro Lys Gly Ser Leu Thr Thr Ala Gln Ile Thr Cys Phe
    130                 135                 140

Pro His Val Met Cys Asp Val Arg Thr Leu Glu Pro Ile Gln Leu Pro
145                 150                 155                 160

Leu Leu Asp Val Arg Arg Val Leu Trp His Ala Thr Gln Asp Gln Glu
                165                 170                 175

Glu Ser Met Arg Leu Val Cys Met Leu Tyr Thr Pro Leu Arg Thr Asn
            180                 185                 190

Ser Pro Gly Asp Glu Ser Phe Val Val Ser Gly Arg Leu Leu Ser Lys
        195                 200                 205

Pro Ala Pro Asp Phe Asn Phe Val Tyr Leu Thr Pro Pro Ile Glu Arg
    210                 215                 220

Thr Ile Tyr Arg Met Val Asp Leu Pro Val Leu Gln Pro Arg Leu Cys
225                 230                 235                 240

Thr His Ala Arg Trp Pro Ala Pro Val Tyr Gly Leu Leu Val Asp Pro
                245                 250                 255

Ser Leu Pro Ser Asn Pro Gln Trp Gln Asn Gly Arg Val Gln Val Asp
            260                 265                 270

Gly Thr Leu Leu Gly Thr Thr Pro Val Ser Gly Ser Trp Val Ser Cys
        275                 280                 285

Phe Ala Ala Glu Ala Ala Tyr Glu Phe Gln Ala Gly Thr Gly Glu Val
    290                 295                 300

Val Thr Phe Thr Met Ile Glu Gln Asp Gly Ser Ala Tyr Val Pro Gly
305                 310                 315                 320

Asp Arg Ala Ala Pro Leu Gly Tyr Pro Asp Phe Ser Gly Gln Leu Glu
                325                 330                 335

Ile Glu Val Gln Thr Glu Thr Thr Lys Thr Gly Asp Lys Leu Arg Val
            340                 345                 350

Thr Thr Phe Glu Met Ile Leu Gly Pro Thr Thr Asn Val Asp Gln Ala
        355                 360                 365

Pro Tyr Gln Gly Arg Ala Tyr Ala Ser Leu Thr Ala Ala Ala Ser Leu
    370                 375                 380
```

-continued

Asp Leu Val Asp Gly Arg Val Arg Ala Val Pro Arg Ser Ile Tyr Ser
385                 390                 395                 400

Phe Gln Asp Glu Leu Pro Glu Tyr Asn Asp Gly Val Leu Val Pro Leu
                405                 410                 415

Ala Pro Pro Leu Gly Pro Phe Leu Pro Gly Glu Val Leu Leu Arg Phe
            420                 425                 430

Arg Thr Tyr Met Arg Gln Leu Asp Thr Ala Asp Ala Ala Ala Gln Pro
        435                 440                 445

Ile Asp Cys Ala Leu Pro Gln Glu Phe Ile Ser Trp Phe Ala Ser Asn
    450                 455                 460

Asn Phe Thr Val Gln Ser Asp Ala Leu Leu Val Arg Tyr Arg Asn Thr
465                 470                 475                 480

Leu Thr Gly Gln Leu Leu Phe Glu Ala Lys Leu Tyr Ser Glu Gly Tyr
                485                 490                 495

Ile Ala Val Ser Tyr Ser Gly Ser Gly Pro Leu Thr Phe Pro Thr Asp
            500                 505                 510

Gly Phe Phe Glu Val Val Ser Trp Val Pro Arg Leu Phe Gln Leu Ala
        515                 520                 525

Ser Val Gly Ser Leu Val Thr Gly Arg Thr Leu Lys Gln
    530                 535                 540

<210> SEQ ID NO 9
<211> LENGTH: 626
<212> TYPE: DNA
<213> ORGANISM: Murine norovirus

<400> SEQUENCE: 9
atggctggcg cactctttgg tgcgattgga ggtggcctga tgggcataat tggcaattcc      60
atctcaacag tccagaatct tcaggcaaat aaacaattgg ctgcacagca atttggctat     120
aattcctctc tgcttgcaac gcaaattcag gcccagaagg atctcacact gatggggcag     180
cagttcaacc agcagctcca agccaactct ttcaagcatg accttgagat gcttggcgcc     240
caggtgcaag cccaggcgca ggcccaggag aacgctatca acatcaggtc gcgcagctcc     300
aggccgcagg cttttcaaag tccgacgcca ttcgcttggc ctcggggcag caaccgacga     360
gggccgttga ctggtctggg acgcggtatt acgccgctaa ccagccggtt acgggcttct     420
cgggtggctt caccccaagt tacactccag gtaggcaaat ggcagtccgc cctgtggaca     480
catcccctct accggtctcg ggtggacgca tgccgtccct tcgtggaggt tcctggtctc     540
cgcgtgatta cacgccgcag acccaaggca cctacacgaa cgggcggttt gtgtccttcc     600
caaagatcgg gagtagcagg gcatag                                          626

<210> SEQ ID NO 10
<211> LENGTH: 208
<212> TYPE: PRT
<213> ORGANISM: Murine norovirus

<400> SEQUENCE: 10

Met Ala Gly Ala Leu Phe Gly Ala Ile Gly Gly Gly Leu Met Gly Ile
1               5                   10                  15

Ile Gly Asn Ser Ile Ser Thr Val Gln Asn Leu Gln Ala Asn Lys Gln
            20                  25                  30

Leu Ala Ala Gln Gln Phe Gly Tyr Asn Ser Ser Leu Leu Ala Thr Gln
        35                  40                  45

Ile Gln Ala Gln Lys Asp Leu Thr Leu Met Gly Gln Gln Phe Asn Gln

```
    50                  55                  60

Gln Leu Gln Ala Asn Ser Phe Lys His Asp Leu Glu Met Leu Gly Ala
65                  70                  75                  80

Gln Val Gln Ala Gln Ala Gln Ala Gln Glu Asn Ala Ile Asn Ile Arg
                85                  90                  95

Ser Ala Gln Leu Gln Ala Ala Gly Phe Ser Lys Ser Asp Ala Ile Arg
            100                 105                 110

Leu Ala Ser Gly Gln Gln Pro Thr Arg Ala Val Asp Trp Ser Gly Thr
        115                 120                 125

Arg Tyr Tyr Ala Ala Asn Gln Pro Val Thr Gly Phe Ser Gly Gly Phe
    130                 135                 140

Thr Pro Ser Tyr Thr Pro Gly Arg Gln Met Ala Val Arg Pro Val Asp
145                 150                 155                 160

Thr Ser Pro Leu Pro Val Ser Gly Gly Arg Met Pro Ser Leu Arg Gly
                165                 170                 175

Gly Ser Trp Ser Pro Arg Asp Tyr Thr Pro Gln Thr Gln Gly Thr Tyr
            180                 185                 190

Thr Asn Gly Arg Phe Val Ser Phe Pro Lys Ile Gly Ser Ser Arg Ala
        195                 200                 205
```

<210> SEQ ID NO 11
<211> LENGTH: 1023
<212> TYPE: DNA
<213> ORGANISM: Murine norovirus

<400> SEQUENCE: 11

```
atgaggatgg caacgccatc ttctgcgtcc tctgtgcgca acacagagaa acgcaaaaat     60

aaaaaggctt catctaaggc tagtgtctcc tttggagcac ctagcttact ctcttcggag    120

agtgaagatg aagttaatta catgacccct cctgagcagg aagctcagcc cggcgccctc    180

gcggccctcc atgcggacgg gccgcatgcc gggctccctg tgacccgaag tgatgcacgc    240

gtgctgatct tcaatgattg ggaggagagg aagaggtccg agccgtggct acggctggac    300

atgtctgaca aggctatctt ccgccgctac ccccacctgc ggcctaagga agataaagcc    360

gatgcgccct cccatgcgga ggacgccatg gatgcaaggg agcccataat tgggtccatt    420

cttgagcagg atgatcataa gttctaccat tactctgtct acattggtaa cggccaggtg    480

atgggcgtca acaatcccgg cgccgcggtt tgccaggctg tgattgatgt ggagaagctc    540

cacctgtggt ggaggccagt gtgggagccc cgtcaacccc tcgacccggc tgagttgagg    600

aagtgcgttg gcatgaccgt tccctatgtg gcgaccaccg tcaattgcta ccaggtctgc    660

tgctggattg ttgggattaa ggacacctgg ccgaagaggg cgaagatctc tagggattcg    720

cccttctaca gtcctgtcca ggactggaac atcgaccccc aggatccttt catcccttcc    780

aagctcagga tggtttctga tggcatcttg gtggctcttg caacggtgat tggtcggccg    840

atcaagaacc tgctggcatc tgtgaagcct ctcaacatcc ttaacatcgt gttgagctgt    900

gactggactt tctcgggcat tgtcaacgcc ctgattctcc ttgctgaact cttcgacatc    960

ttctggaccc cccctgatgt taccaattgg atgatctcca tctttggaga gtggcaggct   1020

gag                                                                 1023
```

<210> SEQ ID NO 12
<211> LENGTH: 341
<212> TYPE: PRT
<213> ORGANISM: Murine norovirus

```
<400> SEQUENCE: 12

Met Arg Met Ala Thr Pro Ser Ser Ala Ser Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Val Asn Tyr Met
        35                  40                  45

Thr Pro Pro Glu Gln Glu Ala Gln Pro Gly Ala Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Asp Trp Glu Glu Arg Lys Arg Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Ala Asp Ala Pro Ser His Ala Glu Asp
        115                 120                 125

Ala Met Asp Ala Arg Glu Pro Ile Ile Gly Ser Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Pro Lys Arg Ala Lys Ile Ser Arg Asp Ser
225                 230                 235                 240

Pro Phe Tyr Ser Pro Val Gln Asp Trp Asn Ile Asp Pro Gln Asp Pro
                245                 250                 255

Phe Ile Pro Ser Lys Leu Arg Met Val Ser Asp Gly Ile Leu Val Ala
            260                 265                 270

Leu Ala Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340


<210> SEQ ID NO 13
<211> LENGTH: 1023
<212> TYPE: DNA
<213> ORGANISM: Murine norovirus

<400> SEQUENCE: 13

atgaggatgg caacgccatc ttctgcgtcc tctgtgcgca acacagagaa acgcaaaaat      60

aaaaaggctt catctaaggc tagtgtctcc tttggagcac ctagcttact ctcttcggag     120
```

agtgaagatg aagttaatta catgacccct cctgagcagg aagctcagcc cggcgccctc 180
gcggccctcc atgcggacgg gccgcatgcc gggctccctg tgacccgaag tgatgcacgc 240
gtgctgatct tcaatgattg ggaggagagg aagaggtccg agccgtggct acggctggac 300
atgtctgaca aggctatctt ccgccgctac ccccacctgc ggcctaagga agataaagcc 360
gatgcgccct cccatgcgga ggacgccatg gatgcaaggg agcccataat tgggtccatt 420
cttgagcagg atgatcataa gttctaccat tactctgtct acattggtaa cggccaggtg 480
atgggcgtca acaatcccgg cgccgcggtt tgccaggctg tgattgatgt ggagaagctc 540
cacctgtggt ggaggccagt gtgggagccc cgtcaacccc tcgacccggc tgagttgagg 600
aagtgcgttg gcatgaccgt tccctatgtg gcgaccaccg tcaattgcta ccaggtctgc 660
tgctggattg ttgggattaa ggacacctgg ccgaagaggg cgaagatctc tagggattcg 720
cccttctaca gtcctgtcca ggactggaac atcgaccccc aggatccttt catcccttcc 780
aagctcagga tggtttctga tggcatcttg gtggctcttg caacggtgat tggtcggccg 840
atcaagaacc tgctggcatc tgtgaagcct ctcaacatcc ttaacatcgt gttgagctgt 900
gactggactt tctcgggcat tgtcaacgcc ctgattctcc ttgctgaact cttcgacatc 960
ttctggaccc cccctgatgt taccaattgg atgatctcca tctttggaga gtggcaggct 1020
gag 1023

<210> SEQ ID NO 14
<211> LENGTH: 341
<212> TYPE: PRT
<213> ORGANISM: Murine norovirus

<400> SEQUENCE: 14

Met Arg Met Ala Thr Pro Ser Ser Ala Ser Ser Val Arg Asn Thr Glu
1 5 10 15

Lys Arg Lys Asn Lys Lys Ala Ser Ser Lys Ala Ser Val Ser Phe Gly
20 25 30

Ala Pro Ser Leu Leu Ser Ser Glu Ser Glu Asp Glu Val Asn Tyr Met
35 40 45

Thr Pro Pro Glu Gln Glu Ala Gln Pro Gly Ala Leu Ala Ala Leu His
50 55 60

Ala Asp Gly Pro His Ala Gly Leu Pro Val Thr Arg Ser Asp Ala Arg
65 70 75 80

Val Leu Ile Phe Asn Asp Trp Glu Glu Arg Lys Arg Ser Glu Pro Trp
85 90 95

Leu Arg Leu Asp Met Ser Asp Lys Ala Ile Phe Arg Arg Tyr Pro His
100 105 110

Leu Arg Pro Lys Glu Asp Lys Ala Asp Ala Pro Ser His Ala Glu Asp
115 120 125

Ala Met Asp Ala Arg Glu Pro Ile Ile Gly Ser Ile Leu Glu Gln Asp
130 135 140

Asp His Lys Phe Tyr His Tyr Ser Val Tyr Ile Gly Asn Gly Gln Val
145 150 155 160

Met Gly Val Asn Asn Pro Gly Ala Ala Val Cys Gln Ala Val Ile Asp
165 170 175

Val Glu Lys Leu His Leu Trp Trp Arg Pro Val Trp Glu Pro Arg Gln
180 185 190

Pro Leu Asp Pro Ala Glu Leu Arg Lys Cys Val Gly Met Thr Val Pro
195 200 205

Tyr Val Ala Thr Thr Val Asn Cys Tyr Gln Val Cys Cys Trp Ile Val
    210                 215                 220

Gly Ile Lys Asp Thr Trp Pro Lys Arg Ala Lys Ile Ser Arg Asp Ser
225                 230                 235                 240

Pro Phe Tyr Ser Pro Val Gln Asp Trp Asn Ile Asp Pro Gln Asp Pro
                245                 250                 255

Phe Ile Pro Ser Lys Leu Arg Met Val Ser Asp Gly Ile Leu Val Ala
            260                 265                 270

Leu Ala Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340

<210> SEQ ID NO 15
<211> LENGTH: 1023
<212> TYPE: DNA
<213> ORGANISM: Murine norovirus

<400> SEQUENCE: 15
atgaggatgg caacgccatc ttctgcgtcc tctgtgcgca acacagagaa acgcaaaaat 60
aaaaaggctt catctaaggc tagtgtctcc tttggagcac ctagcttact ctcttcggag 120
agtgaagatg aagttaatta catgacccct cctgagcagg aagctcagcc cggcgccctc 180
gcggccctcc atgcggacgg gccgcatgcc gggctccctg tgacccgaag tgatgcacgc 240
gtgctgatct tcaatgattg ggaggagagg aagaggtccg agccgtggct acggctggac 300
atgtctgaca aggctatctt ccgccgctac ccccacctgc ggcctaagga agataaagcc 360
gatgcgccct cccatgcgga ggacgccatg gatgcaaggg agcccataat tgggtccatt 420
cttgagcagg atgatcataa gttctaccat tactctgtct acattggtaa cggccaggtg 480
atgggcgtca acaatcccgg cgccgccgtt tgccaggctg tgattgatgt ggagaagctc 540
cacctgtggt ggaggccagt gtgggagccc cgtcaacccc tcgacccggc tgagttgagg 600
aagtgcgttg gcatgaccgt tccctatgtg gcgaccaccg tcaattgcta ccaggtctgc 660
tgctggattg ttgggattaa ggacacctgg ctgaagaggg cgaagatctc tagggattcg 720
cccttctaca gtcctgtcca ggactggaac atcgaccccc aggatccttt catcccttcc 780
aagctcagga tggtttctga tggcatcttg gtggctcttg caacggtgat tggtcggccg 840
atcaagaacc tgctggcatc tgtgaagcct ctcaacatcc ttaacatcgt gttgagctgt 900
gactggactt tctcgggcat tgtcaacgcc ctgattctcc ttgctgaact cttcgacatc 960
ttctggaccc cccctgatgt taccaattgg atgatctcca tctttggaga gtggcaggct 1020
gag 1023

<210> SEQ ID NO 16
<211> LENGTH: 341
<212> TYPE: PRT
<213> ORGANISM: Murine norovirus

<400> SEQUENCE: 16

-continued

```
Met Arg Met Ala Thr Pro Ser Ser Ala Ser Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Val Asn Tyr Met
        35                  40                  45

Thr Pro Pro Glu Gln Glu Ala Gln Pro Gly Ala Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Asp Trp Glu Glu Arg Lys Arg Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Ala Asp Ala Pro Ser His Ala Glu Asp
        115                 120                 125

Ala Met Asp Ala Arg Glu Pro Ile Ile Gly Ser Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Ile Asp Pro Gln Asp Pro
                245                 250                 255

Phe Ile Pro Ser Lys Leu Arg Met Val Ser Asp Gly Ile Leu Val Ala
            260                 265                 270

Leu Ala Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

```
<210> SEQ ID NO 17
<211> LENGTH: 1028
<212> TYPE: DNA
<213> ORGANISM: Murine norovirus

<400> SEQUENCE: 17

gtgaaatgag gatggcaacg ccatcttctg cgtcctctgt gcgcaacaca gagaaacgca      60

aaaataaaaa ggcttcatct aaggctagtg tctcctttgg agcacctagc ttactctctt     120
```

-continued

```
cggagagtga agatgaagtt aattacatga cccctcctga gcaggaagct cagcccggcg    180

ccctcgcggc cctccatgcg gacgggccgc atgccgggct ccctgtgacc cgaagtgatg    240

cacgcgtgct gatcttcaat gattgggagg agaggaagag gtccgagccg tggctacggc    300

tggacatgtc tgacaaggct atcttccgcc gctacccccca cctgcggcct aaggaagata    360

aagccgatgc gccctcccat gcggaggacg ccatggatgc aagggagccc ataattgggt    420

ccattcttga gcaggatgat cataagttct accattactc tgtctacatt ggtaacggcc    480

aggtgatggg cgtcaacaat cccggcgccg cggtttgcca ggctgtgatt gatgtggaga    540

agctccacct gtggtggagg ccagtgtggg agccccgtca acccctcgac ccggctgagt    600

tgaggaagtg cgttggcatg accgttccct atgtggcgac caccgtcaat tgctaccagg    660

tctgctgctg gattgttggg attaaggaca cctggccgaa gagggcgaag atctctaggg    720

attcgccctt ctacagtcct gtccaggact ggaacatcga cccccaggat cctttcatcc    780

cttccaagct caggatggtt tctgatggca tcttggtggc tcttgcaacg gtgattggtc    840

ggccgatcaa gaacctgctg gcatctgtga agcctctcaa catccttaac atcgtgttga    900

gctgtgactg gactttctcg ggcattgtca acgccctgat tctccttgct gaactcttcg    960

acatcttctg gacccccccct gatgttacca attggatgat ctccatcttt ggagagtggc   1020

aggctgag                                                             1028
```

<210> SEQ ID NO 18
<211> LENGTH: 5061
<212> TYPE: DNA
<213> ORGANISM: Murine norovirus

<400> SEQUENCE: 18

```
atgaggatgg caacgccatc ttctgcgtcc tctgtgcgca acacagagaa acgcaaaaat     60

aaaaaggctt catctaaggc tagtgtctcc tttggagcac ctagcttact ctcttcggag    120

agtgaagatg aagttaatta catgacccct cctgagcagg aagctcagcc cggcgccctc    180

gcggccctcc atgcggacgg gccgcatgcc gggctccctg tgacccgaag tgatgcacgc    240

gtgctgatct tcaatgattg ggaggagagg aagaggtccg agccgtggct acggctggac    300

atgtctgaca aggctatctt ccgccgctac cccccacctgc ggcctaagga agataaagcc    360

gatgcgccct cccatgcgga ggacgccatg gatgcaaggg agcccataat tgggtccatt    420

cttgagcagg atgatcataa gttctaccat tactctgtct acattggtaa cggccaggtg    480

atgggcgtca acaatcccgg cgccgcggtt tgccaggctg tgattgatgt ggagaagctc    540

cacctgtggt ggaggccagt gtgggagccc cgtcaacccc tcgacccggc tgagttgagg    600

aagtgcgttg gcatgaccgt tccctatgtg gcgaccaccg tcaattgcta ccaggtctgc    660

tgctggattg ttgggattaa ggacacctgg ccgaagaggg cgaagatctc tagggattcg    720

cccttctaca gtcctgtcca ggactggaac atcgaccccc aggatccttt catcccttcc    780

aagctcagga tggtttctga tggcatcttg gtggctcttg caacggtgat tggtcggccg    840

atcaagaacc tgctggcatc tgtgaagcct ctcaacatcc ttaacatcgt gttgagctgt    900

gactggactt tctcgggcat tgtcaacgcc ctgattctcc ttgctgaact cttcgacatc    960

ttctggaccc cccctgatgt taccaattgg atgatctcca tctttggaga gtggcaggct   1020

gagggtccct ttgacctcgc cctggatgtc gtgcccactc ttcttggtgg gattggcatg   1080

gcatttggcc tgacatctga gaccattggg cgtaagctcg cctccaccaa ctcggccctc   1140

aaggccgccc aggagatggg aaagtttgca attgaggtct tcaagcaaat catggcatgg   1200
```

-continued

```
atttggccct ccgaagaccc tgttcctgcc ctgctctcca acatggagca agctgtcatc   1260
aagaatgagt gccaacttga gaatcaactc acggccatgc tgcgggatcg caacgctgga   1320
gctgagttcc tgaaagcact tgatgaagaa gagcaggagg tccgcaagat tgctgccaag   1380
tgcgggaact ctgccaccac gggcacgacc aacgctctgc tagctaggat cagcatggcg   1440
cgcgcagcct tcgagaaggc ccgcgctgag cagacatctc gggttcgacc cgtcgtgatc   1500
atggtctctg gcaggcccgg gatcgggaaa acttgttttt gccagaacct ggcaaagagg   1560
attgctgcct cccttgggga tgagacctca gtcggcatca taccgcgtgc cgatgtggac   1620
cactgggacg cctacaaggg cgccagagtt gttctttggg acgactttgg catggacaat   1680
gtggtgaagg atgcactgcg gctgcagatg ctcgctgaca cctgccccgt cacgctcaac   1740
tgtgacagaa ttgagaacaa gggaaagatg tttgactctc aagtcatcat catcactacc   1800
aatcagcaaa ccccagtacc cctggactat gttaacttgg aggcagtttg ccgccgcata   1860
gacttcttgg tttatgctga gagccctgtg gttgacgccg ctcgagccag atcacccggc   1920
gacgtgaccg ccgtcaaggc cgccatgagg ccagactaca gccatatcaa ttttattctg   1980
gcaccgcagg gtggctttga tcggcagggc aacaccccct acggcaaggg cgtcactaag   2040
atcattggcg ccaccgcgct ctgcgcaagg gcagtcgccc ttgtccacga gcgccatgat   2100
gacttcggcc tccaaagcaa gacctatgac tttgatgctg gtaaagtgac tgccttcaag   2160
gctatggcag ctgatgctgg aatcccctgg tacaagatgg cagcgattgg ctgtaaggcc   2220
atgagctgca cctgtgtgga ggaagccatg aacttgctca agggctatga ggtggccccg   2280
tgccaggtgg tctacaatgg agccacctac aatgtcagct gcatcaaggg tgctcccatg   2340
gtcgagaggg tcaaggagcc cgagctaccc aaaacactag tcaattgtgt taggaggatc   2400
aaggaggctc gcctccgctg ctactgcaga atggccacag atgtcatcac ctccatcctg   2460
caggcggctg ggacagcttt ctccatctac catcagattg agaagaaaac tcggccctcc   2520
ttctactggg accacggtta cacctaccga gacggcccgg gtgccttcga tctctttgag   2580
gatgacaacg acggatggta ccactctgaa ggcaagaaag gcaggaacaa gagaggccgt   2640
gggcggcccg gagttttcaa gtcccgtggg ctcacggacg aggaatatga tgaattcaag   2700
aaacgccgcg agtccaaggg cggcaagtac tccattgatg attacctcgc tgaccgtgag   2760
cgagaagagg agctccagga gcgtgatgaa gaggaggcca tctttgggga cggttttggt   2820
ctgaaggcca cacgccgttc ccgtaaagcg gagagggcca agcttagcct agtctcgggg   2880
ggtgacatcc gcgcccgaag accaattgac tggaatgtgg tcggcccctc ttgggctgac   2940
gatgaccgcc aggtcgacta tggtgagaag atcaactttg aggctccagt ctcaatctgg   3000
acccgtgttg tgcaatttgg cacggggtgg ggcttctggg tcagcggcca cgtcttcatc   3060
actgccaagc atgtggcccc acccaagggc acagaggtgt ttgggcgcaa gcctggagac   3120
ttcaccgtca cttccagtgg agacttccta aaatatcatt ttaccaatgc tgttaggcct   3180
gacatccccg ccatggtctt ggaaaacggc tgccaggagg gcgtcgtcgc ctcagtcctc   3240
gtcaagaggg cctccggtga gatgctcgct ttggcagtca ggatgggctc gcaagctgcc   3300
atcaagatcg gcagcgctgt ggtgcacggg cagaccggta tgctcttaac cggttccaat   3360
gctaaggccc aagatctcgg gaccatcccg ggtgattgtg gttgccccta tgtctacaag   3420
aaggggaaca cctgggtggt gattggagtg cacgtggcgg ccaccaggtc tggtaacaca   3480
gttatcgccg ccacccatgg agagcccaca cttgaggccc tggagtttca gggtcccccc   3540
```

```
atgctccctc gcccttctgg cacctatgca ggccttccta tcgccgacta cggcgacgcc   3600

ccccctttga gcaccaagac catgttctgg cgcacctcac cagagaagct tcctcctgga   3660

gcttgggagc ctgcctacct cggctctaag gacgagagag tcgacgggcc ttctctgcag   3720

caggttatgc gggatcagct taaaccctat tcagagtcac gcggcttgct gccccctcag   3780

gagatcttgg acgcggtttg tgatgccatc gagaaccgcc ttgagaacac ccttgagcca   3840

caaaagccct ggacgttcaa gaaggcctgt gagagcctgg ataagaacac cagcagtggg   3900

taccccctacc ataagcagaa aagcaaggat tggacaggga ccgccttcgt cggtgagctt   3960

ggtgaccagg ccacccatgc caacaacatg tatgagatgg gcaagtccat gcggcccgtc   4020

tacacagctg ccctcaagga tgagctagtc aagccagata agatctacaa gaagataaag   4080

aagaggctcc tttggggttc tgacctcggc accatgatcc gtgccgcccg tgcttttggc   4140

cccttttgtg aagctttgaa ggagacttgc atttttaatc ccatcagagt gggcatgtca   4200

atgaatgagg atggaccctt catcttcgcg aggcatgcca atttcaggta ccacatggat   4260

gcagactata ccagatggga ctccacccag caaagggcca ttctgaagcg cgctggtgat   4320

atcatggtgc gcctctcccc tgagccagag ctggctcggg tggtgatgga tgatctcttg   4380

gccccttcat tgctagatgt cggcgactac aagatcgtcg tcgaggaggg actcccgtct   4440

ggttgccctt gcaccacaca gctaaatagt atggcccatt ggattttgac cctctgcgcg   4500

atggtggagg tgacccggat tgaccctgac atcgtgatgc aagagtctga attttccttc   4560

tatggtgatg atgaggtggt ctcaaccaac cttgaattgg acatgaccaa gtacaccatg   4620

gccctgaagc ggtatggtct tctcccgacg cgtgcggaca aggaggaggg acccctggag   4680

cgccgtcaga cgctgcaggg catctccttc ttgcgccgtg cgataatcgg tgatcagttt   4740

ggctggtatg gccgtcttga ccgtgccagc attgaccgtc agcttctttg gactaaagga   4800

cccaaccatc agaatccctt tgagactctc ccaggacatg ctcagagacc ctcccaattg   4860

atggccctgc tcggtgaggc tgccatgcat ggtgaaaagt attacaggac tgtggcttcc   4920

cgggtctcca aggaggccgc ccatagtggg atagaaatgg tggtcccacg ccaccgatct   4980

gttctgcgct gggtgcgctt tggaacaatg gatgctgaga ccccgcagga acgctcagca   5040

gtctttgtga atgaggatga g                                               5061
```

<210> SEQ ID NO 19
<211> LENGTH: 1687
<212> TYPE: PRT
<213> ORGANISM: Murine norovirus

<400> SEQUENCE: 19

```
Met Arg Met Ala Thr Pro Ser Ser Ala Ser Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Val Asn Tyr Met
        35                  40                  45

Thr Pro Pro Glu Gln Glu Ala Gln Pro Gly Ala Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Asp Trp Glu Glu Arg Lys Arg Ser Glu Pro Trp
                85                  90                  95

Leu Arg Leu Asp Met Ser Asp Lys Ala Ile Phe Arg Arg Tyr Pro His
```

-continued

```
            100                 105                 110

Leu Arg Pro Lys Glu Asp Lys Ala Asp Ala Pro Ser His Ala Glu Asp
        115                 120                 125

Ala Met Asp Ala Arg Glu Pro Ile Ile Gly Ser Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Pro Lys Arg Ala Lys Ile Ser Arg Asp Ser
225                 230                 235                 240

Pro Phe Tyr Ser Pro Val Gln Asp Trp Asn Ile Asp Pro Gln Asp Pro
                245                 250                 255

Phe Ile Pro Ser Lys Leu Arg Met Val Ser Asp Gly Ile Leu Val Ala
            260                 265                 270

Leu Ala Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu Gly Pro Phe Asp Leu Ala Leu Asp Val Val Pro
            340                 345                 350

Thr Leu Leu Gly Gly Ile Gly Met Ala Phe Gly Leu Thr Ser Glu Thr
        355                 360                 365

Ile Gly Arg Lys Leu Ala Ser Thr Asn Ser Ala Leu Lys Ala Ala Gln
    370                 375                 380

Glu Met Gly Lys Phe Ala Ile Glu Val Phe Lys Gln Ile Met Ala Trp
385                 390                 395                 400

Ile Trp Pro Ser Glu Asp Pro Val Pro Ala Leu Leu Ser Asn Met Glu
                405                 410                 415

Gln Ala Val Ile Lys Asn Glu Cys Gln Leu Glu Asn Gln Leu Thr Ala
            420                 425                 430

Met Leu Arg Asp Arg Asn Ala Gly Ala Glu Phe Leu Lys Ala Leu Asp
        435                 440                 445

Glu Glu Glu Gln Glu Val Arg Lys Ile Ala Ala Lys Cys Gly Asn Ser
    450                 455                 460

Ala Thr Thr Gly Thr Thr Asn Ala Leu Leu Ala Arg Ile Ser Met Ala
465                 470                 475                 480

Arg Ala Ala Phe Glu Lys Ala Arg Ala Glu Gln Thr Ser Arg Val Arg
                485                 490                 495

Pro Val Val Ile Met Val Ser Gly Arg Pro Gly Ile Gly Lys Thr Cys
            500                 505                 510

Phe Cys Gln Asn Leu Ala Lys Arg Ile Ala Ala Ser Leu Gly Asp Glu
        515                 520                 525
```

-continued

```
Thr Ser Val Gly Ile Ile Pro Arg Ala Asp Val Asp His Trp Asp Ala
    530                 535                 540

Tyr Lys Gly Ala Arg Val Val Leu Trp Asp Asp Phe Gly Met Asp Asn
545                 550                 555                 560

Val Val Lys Asp Ala Leu Arg Leu Gln Met Leu Ala Asp Thr Cys Pro
                565                 570                 575

Val Thr Leu Asn Cys Asp Arg Ile Glu Asn Lys Gly Lys Met Phe Asp
            580                 585                 590

Ser Gln Val Ile Ile Ile Thr Thr Asn Gln Gln Thr Pro Val Pro Leu
        595                 600                 605

Asp Tyr Val Asn Leu Glu Ala Val Cys Arg Arg Ile Asp Phe Leu Val
    610                 615                 620

Tyr Ala Glu Ser Pro Val Val Asp Ala Ala Arg Ala Arg Ser Pro Gly
625                 630                 635                 640

Asp Val Thr Ala Val Lys Ala Ala Met Arg Pro Asp Tyr Ser His Ile
                645                 650                 655

Asn Phe Ile Leu Ala Pro Gln Gly Gly Phe Asp Arg Gln Gly Asn Thr
            660                 665                 670

Pro Tyr Gly Lys Gly Val Thr Lys Ile Ile Gly Ala Thr Ala Leu Cys
        675                 680                 685

Ala Arg Ala Val Ala Leu Val His Glu Arg His Asp Asp Phe Gly Leu
    690                 695                 700

Gln Ser Lys Thr Tyr Asp Phe Asp Ala Gly Lys Val Thr Ala Phe Lys
705                 710                 715                 720

Ala Met Ala Ala Asp Ala Gly Ile Pro Trp Tyr Lys Met Ala Ala Ile
                725                 730                 735

Gly Cys Lys Ala Met Ser Cys Thr Cys Val Glu Glu Ala Met Asn Leu
            740                 745                 750

Leu Lys Gly Tyr Glu Val Ala Pro Cys Gln Val Val Tyr Asn Gly Ala
        755                 760                 765

Thr Tyr Asn Val Ser Cys Ile Lys Gly Ala Pro Met Val Glu Arg Val
    770                 775                 780

Lys Glu Pro Glu Leu Pro Lys Thr Leu Val Asn Cys Val Arg Arg Ile
785                 790                 795                 800

Lys Glu Ala Arg Leu Arg Cys Tyr Cys Arg Met Ala Thr Asp Val Ile
                805                 810                 815

Thr Ser Ile Leu Gln Ala Ala Gly Thr Ala Phe Ser Ile Tyr His Gln
            820                 825                 830

Ile Glu Lys Lys Thr Arg Pro Ser Phe Tyr Trp Asp His Gly Tyr Thr
        835                 840                 845

Tyr Arg Asp Gly Pro Gly Ala Phe Asp Leu Phe Glu Asp Asp Asn Asp
    850                 855                 860

Gly Trp Tyr His Ser Glu Gly Lys Lys Gly Arg Asn Lys Arg Gly Arg
865                 870                 875                 880

Gly Arg Pro Gly Val Phe Lys Ser Arg Gly Leu Thr Asp Glu Glu Tyr
                885                 890                 895

Asp Glu Phe Lys Lys Arg Arg Glu Ser Lys Gly Gly Lys Tyr Ser Ile
            900                 905                 910

Asp Asp Tyr Leu Ala Asp Arg Glu Arg Glu Glu Glu Leu Gln Glu Arg
        915                 920                 925

Asp Glu Glu Glu Ala Ile Phe Gly Asp Gly Phe Gly Leu Lys Ala Thr
    930                 935                 940
```

-continued

```
Arg Arg Ser Arg Lys Ala Glu Arg Ala Lys Leu Ser Leu Val Ser Gly
945                 950                 955                 960

Gly Asp Ile Arg Ala Arg Arg Pro Ile Asp Trp Asn Val Val Gly Pro
                965                 970                 975

Ser Trp Ala Asp Asp Asp Arg Gln Val Asp Tyr Gly Glu Lys Ile Asn
            980                 985                 990

Phe Glu Ala Pro Val Ser Ile Trp  Thr Arg Val Val Gln  Phe Gly Thr
        995                 1000                 1005

Gly Trp  Gly Phe Trp Val Ser  Gly His Val Phe Ile  Thr Ala Lys
    1010                 1015                 1020

His Val  Ala Pro Pro Lys Gly  Thr Glu Val Phe Gly  Arg Lys Pro
    1025                 1030                 1035

Gly Asp  Phe Thr Val Thr Ser  Ser Gly Asp Phe Leu  Lys Tyr His
    1040                 1045                 1050

Phe Thr  Asn Ala Val Arg Pro  Asp Ile Pro Ala Met  Val Leu Glu
    1055                 1060                 1065

Asn Gly  Cys Gln Glu Gly Val  Val Ala Ser Val Leu  Val Lys Arg
    1070                 1075                 1080

Ala Ser  Gly Glu Met Leu Ala  Leu Ala Val Arg Met  Gly Ser Gln
    1085                 1090                 1095

Ala Ala  Ile Lys Ile Gly Ser  Ala Val Val His Gly  Gln Thr Gly
    1100                 1105                 1110

Met Leu  Leu Thr Gly Ser Asn  Ala Lys Ala Gln Asp  Leu Gly Thr
    1115                 1120                 1125

Ile Pro  Gly Asp Cys Gly Cys  Pro Tyr Val Tyr Lys  Lys Gly Asn
    1130                 1135                 1140

Thr Trp  Val Val Ile Gly Val  His Val Ala Ala Thr  Arg Ser Gly
    1145                 1150                 1155

Asn Thr  Val Ile Ala Ala Thr  His Gly Glu Pro Thr  Leu Glu Ala
    1160                 1165                 1170

Leu Glu  Phe Gln Gly Pro Pro  Met Leu Pro Arg Pro  Ser Gly Thr
    1175                 1180                 1185

Tyr Ala  Gly Leu Pro Ile Ala  Asp Tyr Gly Asp Ala  Pro Pro Leu
    1190                 1195                 1200

Ser Thr  Lys Thr Met Phe Trp  Arg Thr Ser Pro Glu  Lys Leu Pro
    1205                 1210                 1215

Pro Gly  Ala Trp Glu Pro Ala  Tyr Leu Gly Ser Lys  Asp Glu Arg
    1220                 1225                 1230

Val Asp  Gly Pro Ser Leu Gln  Gln Val Met Arg Asp  Gln Leu Lys
    1235                 1240                 1245

Pro Tyr  Ser Glu Ser Arg Gly  Leu Leu Pro Pro Gln  Glu Ile Leu
    1250                 1255                 1260

Asp Ala  Val Cys Asp Ala Ile  Glu Asn Arg Leu Glu  Asn Thr Leu
    1265                 1270                 1275

Glu Pro  Gln Lys Pro Trp Thr  Phe Lys Lys Ala Cys  Glu Ser Leu
    1280                 1285                 1290

Asp Lys  Asn Thr Ser Ser Gly  Tyr Pro Tyr His Lys  Gln Lys Ser
    1295                 1300                 1305

Lys Asp  Trp Thr Gly Thr Ala  Phe Val Gly Glu Leu  Gly Asp Gln
    1310                 1315                 1320

Ala Thr  His Ala Asn Asn Met  Tyr Glu Met Gly Lys  Ser Met Arg
    1325                 1330                 1335

Pro Val  Tyr Thr Ala Ala Leu  Lys Asp Glu Leu Val  Lys Pro Asp
```

-continued

```
    1340                1345                1350

Lys Ile  Tyr Lys Lys Ile Lys  Lys Arg Leu Leu Trp  Gly Ser Asp
    1355                1360                1365

Leu Gly  Thr Met Ile Arg Ala  Ala Arg Ala Phe Gly  Pro Phe Cys
    1370                1375                1380

Glu Ala  Leu Lys Glu Thr Cys  Ile Phe Asn Pro Ile  Arg Val Gly
    1385                1390                1395

Met Ser  Met Asn Glu Asp Gly  Pro Phe Ile Phe Ala  Arg His Ala
    1400                1405                1410

Asn Phe  Arg Tyr His Met Asp  Ala Asp Tyr Thr Arg  Trp Asp Ser
    1415                1420                1425

Thr Gln  Gln Arg Ala Ile Leu  Lys Arg Ala Gly Asp  Ile Met Val
    1430                1435                1440

Arg Leu  Ser Pro Glu Pro Glu  Leu Ala Arg Val Val  Met Asp Asp
    1445                1450                1455

Leu Leu  Ala Pro Ser Leu Leu  Asp Val Gly Asp Tyr  Lys Ile Val
    1460                1465                1470

Val Glu  Glu Gly Leu Pro Ser  Gly Cys Pro Cys Thr  Thr Gln Leu
    1475                1480                1485

Asn Ser  Met Ala His Trp Ile  Leu Thr Leu Cys Ala  Met Val Glu
    1490                1495                1500

Val Thr  Arg Ile Asp Pro Asp  Ile Val Met Gln Glu  Ser Glu Phe
    1505                1510                1515

Ser Phe  Tyr Gly Asp Asp Glu  Val Val Ser Thr Asn  Leu Glu Leu
    1520                1525                1530

Asp Met  Thr Lys Tyr Thr Met  Ala Leu Lys Arg Tyr  Gly Leu Leu
    1535                1540                1545

Pro Thr  Arg Ala Asp Lys Glu  Glu Gly Pro Leu Glu  Arg Arg Gln
    1550                1555                1560

Thr Leu  Gln Gly Ile Ser Phe  Leu Arg Arg Ala Ile  Ile Gly Asp
    1565                1570                1575

Gln Phe  Gly Trp Tyr Gly Arg  Leu Asp Arg Ala Ser  Ile Asp Arg
    1580                1585                1590

Gln Leu  Leu Trp Thr Lys Gly  Pro Asn His Gln Asn  Pro Phe Glu
    1595                1600                1605

Thr Leu  Pro Gly His Ala Gln  Arg Pro Ser Gln Leu  Met Ala Leu
    1610                1615                1620

Leu Gly  Glu Ala Ala Met His  Gly Glu Lys Tyr Tyr  Arg Thr Val
    1625                1630                1635

Ala Ser  Arg Val Ser Lys Glu  Ala Ala His Ser Gly  Ile Glu Met
    1640                1645                1650

Val Val  Pro Arg His Arg Ser  Val Leu Arg Trp Val  Arg Phe Gly
    1655                1660                1665

Thr Met  Asp Ala Glu Thr Pro  Gln Glu Arg Ser Ala  Val Phe Val
    1670                1675                1680

Asn Glu  Asp Glu
    1685
```

<210> SEQ ID NO 20
<211> LENGTH: 1023
<212> TYPE: DNA
<213> ORGANISM: Murine norovirus

<400> SEQUENCE: 20

-continued

```
atgaggatgg caacgccatc ttctgcgccc tctgtgcgca acacagagaa acgcaaaaac      60
aaaaagactt catctaaagc tagcgtctcc tttggagcgc ctagccctct ctcttcggag     120
agtgaagatg aagtcaacta catgacccct cctgagcagg aagctcagcc cggcacgctt     180
gcggcccttc atgccgacgg gccgcacgcc gggctccccg tgacacgaag cgatgcacgc     240
gtgctgatct tcaatgagtg ggaggagagg aagaagtctg agccgtggct acggctggac     300
atgtctgaca aggccatctt ccgtcgcttt ccccacctgc gacctaagga agacaggcct     360
gacgcgccct cccacgcgga ggacgccatg gatgcaaagg agcctgtcgt gggaaccatc     420
cttgagcaag atgaccataa gttctaccac tattctgtct acatcggcaa tggccaggtg     480
atgggcgtca ataaccctgg cgccgctgtc tgccaagccg tgattgatgt ggagaaactc     540
catctgtggt ggaggccagt ctgggagccc cgccagcccc tcgacccggc cgagttgagg     600
aagtgtgttg gcatgaccgt accctatgtg gcgaccactg tcaattgcta ccaggtctgt     660
tgttggattg tagggatcga ggacacttgg ctgaagcggg cgaagatctc tagagaatcg     720
cccttctaca gccctgttca ggattggagc gttgatcccc gggaaccctt cattccgtct     780
aaactcagga tggtgtcaga cggcatcctg gtggctctct caacagtgat tggtcggccg     840
atcaagaact tgttggcatc tgtgaagcca cttaacatcc tcaacattgt gttgaactgt     900
gactggacct tttcgggcat agtcaacgcc ctgattctcc ttgctgagct ctttgatgtt     960
ttctggactc cccctgatgt caccaactgg atgatctcca tcttcggaga gtggcaggcc    1020
gag                                                                  1023
```

<210> SEQ ID NO 21
<211> LENGTH: 341
<212> TYPE: PRT
<213> ORGANISM: Murine norovirus

<400> SEQUENCE: 21

```
Met Arg Met Ala Thr Pro Ser Ser Ala Pro Ser Val Arg Asn Thr Glu
1               5                   10                  15

Lys Arg Lys Asn Lys Lys Thr Ser Ser Lys Ala Ser Val Ser Phe Gly
            20                  25                  30

Ala Pro Ser Pro Leu Ser Ser Glu Ser Glu Asp Glu Val Asn Tyr Met
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Phe Pro His
            100                 105                 110

Leu Arg Pro Lys Glu Asp Arg Pro Asp Ala Pro Ser His Ala Glu Asp
        115                 120                 125

Ala Met Asp Ala Lys Glu Pro Val Val Gly Thr Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190
```

```
Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Glu Asp Thr Trp Leu Lys Arg Ala Lys Ile Ser Arg Glu Ser
225                 230                 235                 240

Pro Phe Tyr Ser Pro Val Gln Asp Trp Ser Val Asp Pro Arg Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Asn Cys Asp Trp Thr Phe
    290                 295                 300

Ser Gly Ile Val Asn Ala Leu Ile Leu Leu Ala Glu Leu Phe Asp Val
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 22
<211> LENGTH: 1023
<212> TYPE: DNA
<213> ORGANISM: Murine norovirus

<400> SEQUENCE: 22

```
atgaggatgg caacgccatc ttctgcgtcc tctgtgcgca acacrgagaa acgcaaaaac      60

aaaaaggctt catctaaggc tagcgtctcc tttggagcac ctagccttct ctcttcggag     120

agtgaagatg aagttaacta tatgacccct cccgagcagg aagctcagcc cggcacgctt     180

gcggcccttc atgctgatgg gccgcacgcc gggctccccg taacgcgaag tgatgcacgc     240

gtgctgatct tcaatgagtg ggaggagagg aaaaagtctg agccgtggct acggctagac     300

atgtctgaca aggctatctt ccgtcgcttc ccccacctgc gacctaagga ggataagcct     360

gatgcgccct cccacgcgga ggacgctatg gatgcaaaag agcctgttgt gggaaccatt     420

cttgagcagg atgaccataa gttctaccac tactctgtct acatcggcaa cggccaggtg     480

atgggtgtca acaaccccgg cgccgccgtc tgccaggctg tgattgacgt ggagaagctc     540

catctgtggt ggagaccagt ctgggagccc tgccagcccc tcgacccggc tgagttgagg     600

aagtgcgtcg gcatgaccgt gccctatgta gcaactactg tcaactgcta ccaggtctgc     660

tgctggattg ttggaatcaa ggacacttgg ctgaagcggg cgaagatctc tagaaattcg     720

cccttctaca gccctgttca ggattggaat gttgaccccc aggagccttt catcccgtcc     780

aagcttagga tggtgtctga cggcatcctg gtggccctct caacggtgat tggtcggccg     840

atcaagaacc tgttggcatc tgtgaagcca ctcaacattc ttaacatcgt gttgagctgt     900

gattggactt tctcgggcat agtcaacgcc ctgatcctcc ttgctgagct ctttgatatc     960

ttctggacac cccctgatgt caccaactgg atgatctcca tttttgggga gtggcaggcc    1020

gag                                                                  1023
```

<210> SEQ ID NO 23
<211> LENGTH: 341
<212> TYPE: PRT

<213> ORGANISM: Murine norovirus

<400> SEQUENCE: 23

```
Met Arg Met Ala Thr Pro Ser Ser Ala Ser Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Val Asn Tyr Met
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Phe Pro His
            100                 105                 110

Leu Arg Pro Lys Glu Asp Lys Pro Asp Ala Pro Ser His Ala Glu Asp
        115                 120                 125

Ala Met Asp Ala Lys Glu Pro Val Val Gly Thr Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Cys Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asn Ser
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 24
<211> LENGTH: 1023
<212> TYPE: DNA
<213> ORGANISM: Murine norovirus

<400> SEQUENCE: 24

```
atgaggatgg caacgccatc ttctgcgccc tctgtgcgta acacagagaa acgcaaaaac      60
```

-continued

```
aaaaaggctt catctaaagc tagtgtctcc ttcggagcac ctagccttct ctcttcggag    120

agtgaagatg aagtcaatta tgcgacccct cctgagcagg aagctcagcc cggcaccctc    180

gcggccctcc atgctgacgg gccgcatgcc gggctccccg tgacccgaag tgatgcacgc    240

gtgctgatct tcaatgagtg ggaggagagg aagaagtctg agccgtggct acggctggac    300

atgtctgaca aggccatctt ccgtcgcttt ccccatctgc gacctcagga agatagggct    360

gatgcgcccc cccatgcaga aggcgctatg gatgcaaggg agcccgtggt ggggtctatc    420

cttgagcagg atgatcacaa attctaccac tactctgtct acatcggcaa cggtatggtg    480

atgggtgtca acaatcctgg tgccgccatc tgccaggccg tgattgatgt ggagaagctc    540

cacctgtggt ggagaccagt ttgggagccc cgacagcccc ttgacccggc tgagttgagg    600

aagtgcgttg gtatgactgt tccctacgtg gcaaccaccg tcaactgcta tcaggtttgc    660

tgctggattg ttgggatcaa ggacacctgg ctgaggaggg cgaagatctc tagagactcg    720

cccttctaca gccctgttca agactggaac attgatcccc aggagccctt cattccgtcc    780

aagcttagga tggtctcaga cgggatactg gtggccctgt caacggtgat tggtcggccg    840

atcaagaacc tgttggcatc agtgaagccg ctcaacattc ttaacattgt gttgggttgt    900

gattggactt tctcgggcat agtcaacgcc ctgatccttc ttgccgagct ctttgacatc    960

ttttggaccc cccccgatgt taccaactgg atgatctcca tttttggaga gtggcaggct   1020

gag                                                                 1023


<210> SEQ ID NO 25
<211> LENGTH: 341
<212> TYPE: PRT
<213> ORGANISM: Murine norovirus

<400> SEQUENCE: 25

Met Arg Met Ala Thr Pro Ser Ser Ala Pro Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Val Asn Tyr Ala
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Phe Pro His
            100                 105                 110

Leu Arg Pro Gln Glu Asp Arg Ala Asp Ala Pro Pro His Ala Glu Gly
        115                 120                 125

Ala Met Asp Ala Arg Glu Pro Val Val Gly Ser Ile Leu Glu Gln Asp
    130                 135                 140

Asp His Lys Phe Tyr His Tyr Ser Val Tyr Ile Gly Asn Gly Met Val
145                 150                 155                 160

Met Gly Val Asn Asn Pro Gly Ala Ala Ile Cys Gln Ala Val Ile Asp
                165                 170                 175

Val Glu Lys Leu His Leu Trp Trp Arg Pro Val Trp Glu Pro Arg Gln
            180                 185                 190
```

-continued

```
Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Arg Arg Ala Lys Ile Ser Arg Asp Ser
225                 230                 235                 240

Pro Phe Tyr Ser Pro Val Gln Asp Trp Asn Ile Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Gly Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 26
<211> LENGTH: 1023
<212> TYPE: DNA
<213> ORGANISM: Murine norovirus

<400> SEQUENCE: 26

```
atgaggatgg caacgccatc ttctgcgtcc tctgtgcgca acacagagaa acgcaaaaac      60

aaaaaggctt cgtctaaggc tagcgtctcc tttggagcac ctagccttct ctcttcggag     120

agcgaagacg aagttaacta catgacccct cctgagcagg aagctcagcc cggcgccctc     180

gcggccctcc atgcagaagg gccgcttgcc gggctccccg tgacgcgtag tgatgcacgc     240

gtgctgatct tcaatgagtg ggaggagagg aagaagtctg agccgtggct acggctggac     300

atgtctgata aggctatctt ccgccgctac cctcatctgc ggcctaagga agacaagcct     360

gacgcgccct ctcatgcgga ggacgccatg gatgccaggg agccggtgat cggttccatc     420

ttggagcagg atgaccataa gttctaccac tactccgttt atatcggcaa cggccaggtg     480

atgggtgtta acaaccccgg cgccgccgtc tgccaagctg tgattgatgt ggagaagctc     540

cacctgtggt ggaggccagt ctgggagccc cgccagcccc tcgacccggc tgagttgagg     600

aagtgtgttg gcatgaccgt tccctatgtg gcaaccactg tcaactgcta ccaagtctgc     660

tgttggattg ttgggatcaa ggacacctgg ctgaagaggg cgaagatctc gagggacttg     720

cctttctata gccccgtcca agactggaac attgatcccc aggaaccctt tatcccctcc     780

aagctcagga tggtctctga tggcatcctg gtggctctct caacggtgat tggtcggccg     840

atcaaaaacc ttctggcatc tgtgaagccg ctcaacatcc tcaacatcgt gttgagctgt     900

gattggactt tttccggaat agtcaatgcc ctgatccttc ttgctgagct ctttgatatc     960

ttctggaccc cccccgatgt taccaactgg atgatttcta tcttcgggga gtggcaggcc    1020

gag                                                                  1023
```

<210> SEQ ID NO 27
<211> LENGTH: 341
<212> TYPE: PRT
<213> ORGANISM: Murine norovirus

<400> SEQUENCE: 27

Met Arg Met Ala Thr Pro Ser Ser Ala Ser Ser Val Arg Asn Thr Glu
1 5 10 15

Lys Arg Lys Asn Lys Lys Ala Ser Ser Lys Ala Ser Val Ser Phe Gly
20 25 30

Ala Pro Ser Leu Leu Ser Ser Glu Ser Glu Asp Glu Val Asn Tyr Met
35 40 45

Thr Pro Pro Glu Gln Glu Ala Gln Pro Gly Ala Leu Ala Ala Leu His
50 55 60

Ala Glu Gly Pro Leu Ala Gly Leu Pro Val Thr Arg Ser Asp Ala Arg
65 70 75 80

Val Leu Ile Phe Asn Glu Trp Glu Glu Arg Lys Lys Ser Glu Pro Trp
85 90 95

Leu Arg Leu Asp Met Ser Asp Lys Ala Ile Phe Arg Arg Tyr Pro His
100 105 110

Leu Arg Pro Lys Glu Asp Lys Pro Asp Ala Pro Ser His Ala Glu Asp
115 120 125

Ala Met Asp Ala Arg Glu Pro Val Ile Gly Ser Ile Leu Glu Gln Asp
130 135 140

Asp His Lys Phe Tyr His Tyr Ser Val Tyr Ile Gly Asn Gly Gln Val
145 150 155 160

Met Gly Val Asn Asn Pro Gly Ala Ala Val Cys Gln Ala Val Ile Asp
165 170 175

Val Glu Lys Leu His Leu Trp Trp Arg Pro Val Trp Glu Pro Arg Gln
180 185 190

Pro Leu Asp Pro Ala Glu Leu Arg Lys Cys Val Gly Met Thr Val Pro
195 200 205

Tyr Val Ala Thr Thr Val Asn Cys Tyr Gln Val Cys Cys Trp Ile Val
210 215 220

Gly Ile Lys Asp Thr Trp Leu Lys Arg Ala Lys Ile Ser Arg Asp Leu
225 230 235 240

Pro Phe Tyr Ser Pro Val Gln Asp Trp Asn Ile Asp Pro Gln Glu Pro
245 250 255

Phe Ile Pro Ser Lys Leu Arg Met Val Ser Asp Gly Ile Leu Val Ala
260 265 270

Leu Ser Thr Val Ile Gly Arg Pro Ile Lys Asn Leu Leu Ala Ser Val
275 280 285

Lys Pro Leu Asn Ile Leu Asn Ile Val Leu Ser Cys Asp Trp Thr Phe
290 295 300

Ser Gly Ile Val Asn Ala Leu Ile Leu Leu Ala Glu Leu Phe Asp Ile
305 310 315 320

Phe Trp Thr Pro Pro Asp Val Thr Asn Trp Met Ile Ser Ile Phe Gly
325 330 335

Glu Trp Gln Ala Glu
340

<210> SEQ ID NO 28
<211> LENGTH: 1023
<212> TYPE: DNA
<213> ORGANISM: Murine norovirus

<400> SEQUENCE: 28
atgaggatgg caacgccatc ttctgcgtcc tctgtgcgca acacagagaa acgcaaaaac 60

-continued

```
aaaaagactt catctaaagc tagtgtctcc tttggagcac ctagccttct ctcttcggag    120

agtgaagatg aatttaatta catgacccct cctgagcagg aagctcagcc cggcaccctt    180

gcggccctcc atgccgatgg gccgcatgcc gggctccccg tgacccgaag tgatgcacgc    240

gtgctgatct tcaatgagtg ggaggagagg aagaagtccg aaccgtggct acggttggac    300

atgtctgaca aggccatctt ccgtcgctat ccccacctgc gacccaagga agataaggct    360

gacgcaccct cccatgcgga ggatgccatg gatgcaagag agcctgtggt gggatccatc    420

cttgagcagg atgaccacaa gttctaccac tactctgtct acatcggcaa cggccaggtg    480

atgggggtca acaaccccgg cgccgccgtt tgccaggctg tgattgatgt ggagaaactt    540

cacctgtggt ggaggccagt ctgggagccc cgccaacccc tcgacccggc tgagttgagg    600

aagtgcgttg gcatgactgt cccttacgtg gcaactactg tcaactgcta ccaagtttgc    660

tgctggattg ttgggatcaa ggatacttgg ctgaagaggg cgaaggtctc tagggactcg    720

cctttctaca gccctgtcca ggattggaac atcgatcccc aggagccttt catcccctcc    780

aaactcagga tggtttctga tggcatcttg gtggctctct caacggtgat tggtcggccg    840

atcaagaacc tgctggcatc tgtgaagccg ctcaacattc tcaacatcgt gttgagctgt    900

gattggactt tctcgggcat agtcaacgcc ctgattctcc ttgctgagct ctttgacatc    960

ttttggaccc ctcctgatgt caccaactgg atgatctcca tctttggaga gtggcaggct   1020

gaa                                                                 1023
```

<210> SEQ ID NO 29
<211> LENGTH: 341
<212> TYPE: PRT
<213> ORGANISM: Murine norovirus

<400> SEQUENCE: 29

```
Met Arg Met Ala Thr Pro Ser Ser Ala Ser Ser Val Arg Asn Thr Glu
1               5                   10                  15

Lys Arg Lys Asn Lys Lys Thr Ser Ser Lys Ala Ser Val Ser Phe Gly
            20                  25                  30

Ala Pro Ser Leu Leu Ser Ser Glu Ser Glu Asp Glu Phe Asn Tyr Met
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Ala Asp Ala Pro Ser His Ala Glu Asp
        115                 120                 125

Ala Met Asp Ala Arg Glu Pro Val Val Gly Ser Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
```

-continued

```
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Val Ser Arg Asp Ser
225                 230                 235                 240

Pro Phe Tyr Ser Pro Val Gln Asp Trp Asn Ile Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 30
<211> LENGTH: 1023
<212> TYPE: DNA
<213> ORGANISM: Murine norovirus

<400> SEQUENCE: 30

```
atgaggatgg caacgccatc ttctgcgtcc tctgtgcgca acacagagaa acgcaaaaat     60

aagaagactt catctaagct tagcgtctcc tttggagcgc ctggctcact ctcttcggag    120

agcgaagatg aagttaatta catgacccct cctgagcagg aagctcagcc cggcaccctc    180

gcggcccttc atgcagatgg gccgcacgcc gggctccctg tgacccgaag tgatgcacgc    240

gtgctgattt tcaatgattg ggaggagagg aagaagtccg agccgtggct tcggctggac    300

atgtctgaca aggccatctt ccgccgcttt ccccatctgc ggcccaagga agacaaggcc    360

gacgcaccct cccacgcgga ggatgccatg gatgcaaggg agcctgtggt ggggtccatc    420

cttgagcagg acgaccacaa gttctaccac tactctgtct acattggtaa cggccaggtg    480

atgggcgtta acaaccctgg tgccgccgtc tgccaggccg tgattgacgt ggagaagctc    540

catttgtggt ggaggccggt ctgggaaccc cgccaacccc tcgacccggc tgagttgagg    600

aagtgcgttg gtatgactgt cccttatgtg gcaaccactg tcaactgtta tcaggtctgc    660

tgctggattg ttggtatcaa agatacctgg ctgaagaggg cgaagatctc cagggactcg    720

cccttctaca gccccgttca ggactggaat gttgaccccc aggagccctt tatcccctcc    780

aagctcagga tggtctccga cggtgtcctg gtagctctct caacggtgat tggtcggccg    840

atcaagaacc tgctggcgtc tgtgaaaccg ctcaacattc tcaacatcgt gttgagctgt    900

gattggactt tctcaggcat agtcaacgcc ctgatcctcc ttgccgagct ctttgacatc    960

ttctggaccc cccccgatgt caccaactgg atgatctcca tttttggaga gtggcaggcc   1020

gag                                                                 1023
```

<210> SEQ ID NO 31
<211> LENGTH: 341
<212> TYPE: PRT
<213> ORGANISM: Murine norovirus

<400> SEQUENCE: 31

```
Met Arg Met Ala Thr Pro Ser Ser Ala Ser Ser Val Arg Asn Thr Glu
1               5                   10                  15

Lys Arg Lys Asn Lys Lys Thr Ser Ser Lys Leu Ser Val Ser Phe Gly
            20                  25                  30

Ala Pro Gly Ser Leu Ser Ser Glu Ser Glu Asp Glu Val Asn Tyr Met
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Asp Trp Glu Glu Arg Lys Lys Ser Glu Pro Trp
                85                  90                  95

Leu Arg Leu Asp Met Ser Asp Lys Ala Ile Phe Arg Arg Phe Pro His
            100                 105                 110

Leu Arg Pro Lys Glu Asp Lys Ala Asp Ala Pro Ser His Ala Glu Asp
        115                 120                 125

Ala Met Asp Ala Arg Glu Pro Val Val Gly Ser Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Gly Val Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 32
<211> LENGTH: 1023
<212> TYPE: DNA
<213> ORGANISM: Murine norovirus

<400> SEQUENCE: 32

```
atgaggatgg caacgccatc ttctgcgccc tctgtgcgca acacagagaa acgcaaaagc      60

aaaaaggctt catctaaggc tagcgtctcc tttggagcac ctagctctct cttttcagag     120
```

```
agtgaagatg aagccgacta cgcgacccct cctgagcagg aagctcagcc cggtgccctt    180

gcggcccttc acgcagatgg gccgcttgcc gggctccctg tgacgcgaag tgatgcacgc    240

gtgctgatct tcaatgattg ggaggagagg aagaagtccg cgccgtggct acggctggac    300

atgtctgaca aggccatctt ccgtcgcttt ccccatctgc gacctaagga agacaaggcc    360

gatgcaccct cccacgcgga ggatgccatg gatgcaaggg agcccgtggt gggatccatc    420

cttgagcagg atgaccataa gttctaccac tactctgtct acatcggcaa cggccaggtg    480

atgggtgtca acaaccccgg tgccgctgtc tgccaagctg tgattgatgt ggagaagctc    540

cacctatggt ggaggccagt ctgggagccc cgccaacccc tcgacccggc tgagttgagg    600

aagtgcgtcg gcatgactgt tccttatgtg gcaaccactg tcaactgcta ccaggtttgc    660

tgctggattg ttgggatcaa ggacacctgg ctgaagaggg cgaagatctc gagggattcg    720

ccttttata gccctgtcca ggactggaac accgatcccc aggagccctt catcccttcc    780

aagctcagga tggtctctga tggcatttta gtggcccttt caacggtgat tggtcggccg    840

atcaagaacc ttctggcatc tgtgaagccg ctcaacatcc ttaacatcgt gttgagctgt    900

gattggactt tttctggcat agtcaatgcc ctaatttttc ttgctgagct ctttgacatc    960

ttctggaccc cccccgatgt caccaactgg atgatttcca tcttcgggga gtggcaagcc   1020

gag                                                                 1023
```

<210> SEQ ID NO 33
<211> LENGTH: 341
<212> TYPE: PRT
<213> ORGANISM: Murine norovirus

<400> SEQUENCE: 33

```
Met Arg Met Ala Thr Pro Ser Ser Ala Pro Ser Val Arg Asn Thr Glu
1               5                   10                  15

Lys Arg Lys Ser Lys Lys Ala Ser Ser Lys Ala Ser Val Ser Phe Gly
            20                  25                  30

Ala Pro Ser Ser Leu Phe Ser Glu Ser Glu Asp Glu Ala Asp Tyr Ala
        35                  40                  45

Thr Pro Pro Glu Gln Glu Ala Gln Pro Gly Ala Leu Ala Ala Leu His
    50                  55                  60

Ala Asp Gly Pro Leu Ala Gly Leu Pro Val Thr Arg Ser Asp Ala Arg
65                  70                  75                  80

Val Leu Ile Phe Asn Asp Trp Glu Glu Arg Lys Lys Ser Ala Pro Trp
                85                  90                  95

Leu Arg Leu Asp Met Ser Asp Lys Ala Ile Phe Arg Arg Phe Pro His
            100                 105                 110

Leu Arg Pro Lys Glu Asp Lys Ala Asp Ala Pro Ser His Ala Glu Asp
        115                 120                 125

Ala Met Asp Ala Arg Glu Pro Val Val Gly Ser Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205
```

```
Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Thr Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Phe Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 34
<211> LENGTH: 1023
<212> TYPE: DNA
<213> ORGANISM: Murine norovirus

<400> SEQUENCE: 34

```
atgaggatgg caacgccatc ttctgcgccc tctgtgcgca acacagagaa acgcaaaaat      60

aagaaggctt cgtctaaagc tagtgtctcc ttcggagcac ctagccttct ctcttcggag     120

agcgaagacg aagctaatta catgacccct cctgagcagg aagctcagcc cggcgccctt     180

gcggcccttc atgcggaagg gccgcttgcc gggctccccg tgacacgtag tgatgcacgc     240

gtgctgatct tcaatgagtg ggaggagagg aagaagtctg agccgtggct acggctggac     300

atgtctgaca gggctatctt ccgccgctac ccccatctgc ggcctaagga ggataagcct     360

gacgcgccct cccatgcgga ggacgctatg gatgccaggg agcctgcgat cggctctatt     420

ttggagcagg atgaccataa gttctaccat tactctgtct atgtcggcaa tggtcaggtg     480

atgggcgtca acaaccctgg agccgccatt tgccaggctg tgattgacgt ggagaagctc     540

cacctatggt ggagaccagt ctgggagccc catcagcccc tcgacccggc tgagttgaag     600

aagtgtgtcg gcatgacagt cccttatgtg gcaaccactg tcaactgcta ccaggtctgc     660

tgctggattg ttgggattaa ggacacctgg ctgaaaaggg cgaagatttc cagagactcg     720

cccttctaca gtcccgttca ggattggaac attgaccccc aggagccttt cattccgtcc     780

aagctcagga tggtctctga tggtatcctg gtggctctct caacggtgat tggtcggccg     840

atcaaaaacc tgctggcatc tgtgaagccg ctcaacattc tcaacatcgt gttgagctgt     900

gactggactt tctcgggcat agtcaatgcc ctgattcttc ttgctgagct atttgatgtt     960

ttctggactc cccctgatgt caccaattgg atgatctcca tctttggaga gtggcaggct    1020

gaa                                                                  1023
```

<210> SEQ ID NO 35
<211> LENGTH: 341
<212> TYPE: PRT
<213> ORGANISM: Murine norovirus

<400> SEQUENCE: 35

```
Met Arg Met Ala Thr Pro Ser Ser Ala Pro Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Ala Asn Tyr Met
        35                  40                  45

Thr Pro Pro Glu Gln Glu Ala Gln Pro Gly Ala Leu Ala Ala Leu His
    50                  55                  60

Ala Glu Gly Pro Leu Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Arg Ala Ile Phe Arg Arg Tyr Pro His
            100                 105                 110

Leu Arg Pro Lys Glu Asp Lys Pro Asp Ala Pro Ser His Ala Glu Asp
        115                 120                 125

Ala Met Asp Ala Arg Glu Pro Ala Ile Gly Ser Ile Leu Glu Gln Asp
    130                 135                 140

Asp His Lys Phe Tyr His Tyr Ser Val Tyr Val Gly Asn Gly Gln Val
145                 150                 155                 160

Met Gly Val Asn Asn Pro Gly Ala Ala Ile Cys Gln Ala Val Ile Asp
                165                 170                 175

Val Glu Lys Leu His Leu Trp Trp Arg Pro Val Trp Glu Pro His Gln
            180                 185                 190

Pro Leu Asp Pro Ala Glu Leu Lys Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Ile Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Val
305                 310                 315                 320

Phe Trp Thr Pro Pro Asp Val Thr Asn Trp Met Ile Ser Ile Phe Gly
                325                 330                 335

Glu Trp Gln Ala Glu
            340


<210> SEQ ID NO 36
<211> LENGTH: 1023
<212> TYPE: DNA
<213> ORGANISM: Murine norovirus

<400> SEQUENCE: 36

atgaggatgg caacgccatc ttctgcgccc tctgtgcgca acacagagaa acgcaaaaat      60

aagaaggctt cgtctaaagc tagtgtctcc ttcggagcac ctagccttct ctcttcggag     120
```

-continued

```
agcgaagacg aagctaatta catgacccct cctgagcagg aagctcagcc cggcgccctt    180

gcggcccttc atgcggaagg gccgcttgcc gggctccccg tgacacgtag tgatgcacgc    240

gtgctgatct tcaatgagtg ggaggagagg aagaagtctg agccgtggct acggctggac    300

atgtctgaca gggctatctt ccgccgctac ccccatctgc ggcctaagga ggataagcct    360

gacgcgccct cccatgcgga ggacgctatg gatgccaggg agcctgcgat cggctctatt    420

ttggagcagg atgaccataa gttctaccat tactctgtct atgtcggcaa tggtcaggtg    480

atgggcgtca acaaccctgg agccgccatt tgccaggctg tgattgacgt ggagaagctc    540

cacctatggt ggagaccagt ctgggagccc catcagcccc tcgacccggc tgagttgaag    600

aagtgtgtcg gcatgacagt cccttatgtg gcaaccactg tcaactgcta ccaggtctgc    660

tgctggattg ttgggattaa ggacacctgg ctgaaaaggg cgaagatttc cagagactcg    720

cccttctaca gtcccgttca ggactggaac attgaccccc aggagccttt cattccgtct    780

aagctcagga tggtctctga tggcatcctg gtggctctct caacggtgat tggtcggccg    840

atcaaaaacc tgctggcatc tgtgaagccg ctcaacattc tcaacatcgt gttgagctgt    900

gactggactt tctcgggcat agtcaatgcc ctgattcttc ttgctgaact atttgatgtt    960

ttctggactc cccctgatgt caccaattgg atgatctcca tctttggaga gtggcaggct   1020

gaa                                                                 1023
```

<210> SEQ ID NO 37
<211> LENGTH: 341
<212> TYPE: PRT
<213> ORGANISM: Murine norovirus

<400> SEQUENCE: 37

```
Met Arg Met Ala Thr Pro Ser Ser Ala Pro Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Ala Asn Tyr Met
        35                  40                  45

Thr Pro Pro Glu Gln Glu Ala Gln Pro Gly Ala Leu Ala Ala Leu His
    50                  55                  60

Ala Glu Gly Pro Leu Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Arg Ala Ile Phe Arg Arg Tyr Pro His
            100                 105                 110

Leu Arg Pro Lys Glu Asp Lys Pro Asp Ala Pro Ser His Ala Glu Asp
        115                 120                 125

Ala Met Asp Ala Arg Glu Pro Ala Ile Gly Ser Ile Leu Glu Gln Asp
    130                 135                 140

Asp His Lys Phe Tyr His Tyr Ser Val Tyr Val Gly Asn Gly Gln Val
145                 150                 155                 160

Met Gly Val Asn Asn Pro Gly Ala Ala Ile Cys Gln Ala Val Ile Asp
                165                 170                 175

Val Glu Lys Leu His Leu Trp Trp Arg Pro Val Trp Glu Pro His Gln
            180                 185                 190

Pro Leu Asp Pro Ala Glu Leu Lys Lys Cys Val Gly Met Thr Val Pro
        195                 200                 205
```

```
Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Ile Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Val
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 38
<211> LENGTH: 1023
<212> TYPE: DNA
<213> ORGANISM: Murine norovirus

<400> SEQUENCE: 38

```
atgaggatgg caacgccatc ttctgcgtcc tctgtgcgca acacagagaa acgcaaaaat      60

aagaaggctt cgcctaaagc tagtgtctcc ttcggagcac ctagccttct ctcttcggag     120

agtgaagacg aagctaatta cttgacccct cctgagcagg aagctcagcc cggcgccctt     180

gcggctcttc atgcggaagg gccgcttgcc gggctccccg tgacacgtag tgatgcacgc     240

gtgctgatct tcaatgagtg ggaggagagg aagaagtctg agccgtggct acggctggac     300

atgtctgaca gggctatctt ccgccgctac ccccatctgc ggcctaagga ggataagcct     360

gacgcgccct cccatgcgga ggacgctatg gatgccaggg agcctgcgat cggctctatt     420

ttggagcagg atgaccataa gttctaccat tactctgtct atgtcggcaa tggtcaggtg     480

atgggcgtca acaaccctgg agctgccatt tgccaggctg tgattgacgt ggagaagctc     540

cacctatggt ggagaccagt ctgggagccc catcagcccc tcgacccggc tgagttgaag     600

aagtgtgtcg gcatgacagt cccttatgtg gcaaccactg tcaactgcta ccaggtctgc     660

tgctggattg ttgggattaa ggacacctgg ctgaaaaggg cgaagatttc cagagattcg     720

cccttctaca gtcccgttca ggactggaac attgaccccc aggagccttt cattccgtct     780

aaactcagga tggtctctga tggcatcctg gtggctctct caacggtgat tggtcggccg     840

atcaaaaacc tgctggcatc tgtgaagccg ctcaacattc tcaacatcgt gttgagctgt     900

gactggactt tctcgggcat agtcaatgcc ctgattcttc tcgctgagct atttgatgtt     960

ttctggaccc cccctgatgt caccaattgg atgatctcca tctttggaga gtggcaggct    1020

gaa                                                                 1023
```

<210> SEQ ID NO 39
<211> LENGTH: 341
<212> TYPE: PRT
<213> ORGANISM: Murine norovirus

<400> SEQUENCE: 39

-continued

Met Arg Met Ala Thr Pro Ser Ser Ala Ser Ser Val Arg Asn Thr Glu
1 5 10 15

Lys Arg Lys Asn Lys Lys Ala Ser Pro Lys Ala Ser Val Ser Phe Gly
20 25 30

Ala Pro Ser Leu Leu Ser Ser Glu Ser Glu Asp Glu Ala Asn Tyr Leu
35 40 45

Thr Pro Pro Glu Gln Glu Ala Gln Pro Gly Ala Leu Ala Ala Leu His
50 55 60

Ala Glu Gly Pro Leu Ala Gly Leu Pro Val Thr Arg Ser Asp Ala Arg
65 70 75 80

Val Leu Ile Phe Asn Glu Trp Glu Glu Arg Lys Lys Ser Glu Pro Trp
85 90 95

Leu Arg Leu Asp Met Ser Asp Arg Ala Ile Phe Arg Arg Tyr Pro His
100 105 110

Leu Arg Pro Lys Glu Asp Lys Pro Asp Ala Pro Ser His Ala Glu Asp
115 120 125

Ala Met Asp Ala Arg Glu Pro Ala Ile Gly Ser Ile Leu Glu Gln Asp
130 135 140

Asp His Lys Phe Tyr His Tyr Ser Val Tyr Val Gly Asn Gly Gln Val
145 150 155 160

Met Gly Val Asn Asn Pro Gly Ala Ala Ile Cys Gln Ala Val Ile Asp
165 170 175

Val Glu Lys Leu His Leu Trp Trp Arg Pro Val Trp Glu Pro His Gln
180 185 190

Pro Leu Asp Pro Ala Glu Leu Lys Lys Cys Val Gly Met Thr Val Pro
195 200 205

Tyr Val Ala Thr Thr Val Asn Cys Tyr Gln Val Cys Cys Trp Ile Val
210 215 220

Gly Ile Lys Asp Thr Trp Leu Lys Arg Ala Lys Ile Ser Arg Asp Ser
225 230 235 240

Pro Phe Tyr Ser Pro Val Gln Asp Trp Asn Ile Asp Pro Gln Glu Pro
245 250 255

Phe Ile Pro Ser Lys Leu Arg Met Val Ser Asp Gly Ile Leu Val Ala
260 265 270

Leu Ser Thr Val Ile Gly Arg Pro Ile Lys Asn Leu Leu Ala Ser Val
275 280 285

Lys Pro Leu Asn Ile Leu Asn Ile Val Leu Ser Cys Asp Trp Thr Phe
290 295 300

Ser Gly Ile Val Asn Ala Leu Ile Leu Leu Ala Glu Leu Phe Asp Val
305 310 315 320

Phe Trp Thr Pro Pro Asp Val Thr Asn Trp Met Ile Ser Ile Phe Gly
325 330 335

Glu Trp Gln Ala Glu
340

<210> SEQ ID NO 40
<211> LENGTH: 1023
<212> TYPE: DNA
<213> ORGANISM: Murine norovirus

<400> SEQUENCE: 40
atgaggatgg caacgccatc ttctgcgtcc tctgtgcgca acacagagaa acgcaaaaat 60
aagaaggctt cgtctaaagc tagtgtctcc ttcggagcac ctagccttct ctcttcggag 120
agcgaagacg aagctaatta catgacccct cctgagcagg aagctcagcc cggcgccctt 180
gcggctcttc atgcggaagg gccgcttgcc gggctccccg tgacacgtag tgatgcacgc 240
gtgctgatct tcaatgagtg ggaggagagg aagaagtctg agccgtggct acggctggac 300
atgtctgaca gggctatctt ccgccgctac cccatctgc ggcctaagga ggataagcct 360
gatgcgccct cccatgcgga ggacgctatg gatgccaggg agcctgcgat cggctctatt 420
ttggagcagg atgaccataa gttctaccat tactctgtct atgtcggcaa tggtcaggtg 480
atgggcgtca acaaccctgg agctgccatt tgccaggctg tgattgacgt ggagaagctc 540
cacctatggt ggagaccagt ctgggagccc catcagcccc tcgacccggc tgagttgaag 600
aagtgtgtcg gcatgacagt ccccttatgtg gcaaccactg tcaactgcta ccaggtctgc 660
tgctggattg ttgggattaa ggacacctgg ctgaaaaggg cgaagatttc cagagactcg 720
cccttcttca gtcccgttca ggactggaac attgaccccc aggagccttt cattccgtct 780
aagctcagga tggtctctga tggcattctg gtggctctct caacggtgat tggtcggccg 840
atcaaaaacc tgctggcatc tgtgaagccg ctcaacattc tcaacatcgt gttgagctgc 900
gactggactt tctcgggcat agtcaatgcc ctgattcttc ttgctgagct atttgatgtt 960
ttctggactc cccctgatgt caccaattgg atgatctcca tctttggaga gtggcaggct 1020
gaa 1023

<210> SEQ ID NO 41
<211> LENGTH: 341
<212> TYPE: PRT
<213> ORGANISM: Murine norovirus

<400> SEQUENCE: 41

Met Arg Met Ala Thr Pro Ser Ser Ala Ser Ser Val Arg Asn Thr Glu
1 5 10 15

Lys Arg Lys Asn Lys Lys Ala Ser Ser Lys Ala Ser Val Ser Phe Gly
20 25 30

Ala Pro Ser Leu Leu Ser Ser Glu Ser Glu Asp Glu Ala Asn Tyr Met
35 40 45

Thr Pro Pro Glu Gln Glu Ala Gln Pro Gly Ala Leu Ala Ala Leu His
50 55 60

Ala Glu Gly Pro Leu Ala Gly Leu Pro Val Thr Arg Ser Asp Ala Arg
65 70 75 80

Val Leu Ile Phe Asn Glu Trp Glu Glu Arg Lys Lys Ser Glu Pro Trp
85 90 95

Leu Arg Leu Asp Met Ser Asp Arg Ala Ile Phe Arg Arg Tyr Pro His
100 105 110

Leu Arg Pro Lys Glu Asp Lys Pro Asp Ala Pro Ser His Ala Glu Asp
115 120 125

Ala Met Asp Ala Arg Glu Pro Ala Ile Gly Ser Ile Leu Glu Gln Asp
130 135 140

Asp His Lys Phe Tyr His Tyr Ser Val Tyr Val Gly Asn Gly Gln Val
145 150 155 160

Met Gly Val Asn Asn Pro Gly Ala Ala Ile Cys Gln Ala Val Ile Asp
165 170 175

Val Glu Lys Leu His Leu Trp Trp Arg Pro Val Trp Glu Pro His Gln
180 185 190

Pro Leu Asp Pro Ala Glu Leu Lys Lys Cys Val Gly Met Thr Val Pro
195 200 205

Tyr Val Ala Thr Thr Val Asn Cys Tyr Gln Val Cys Cys Trp Ile Val

```
    210                 215                 220

Gly Ile Lys Asp Thr Trp Leu Lys Arg Ala Lys Ile Ser Arg Asp Ser
225                 230                 235                 240

Pro Phe Phe Ser Pro Val Gln Asp Trp Asn Ile Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Val
305                 310                 315                 320

Phe Trp Thr Pro Pro Asp Val Thr Asn Trp Met Ile Ser Ile Phe Gly
                325                 330                 335

Glu Trp Gln Ala Glu
            340


<210> SEQ ID NO 42
<211> LENGTH: 1023
<212> TYPE: DNA
<213> ORGANISM: Murine norovirus

<400> SEQUENCE: 42

atgaggatgg caacgccatc ttctgcgtcc tctgtgcgca acacagagaa acgcaaaaat      60

aagaaggctt cgtctaaagc tagtgtctcc ttcggagcac ctagccttct ctcttcggag     120

agcgaagacg aagctaatta catgacccct cctgagcagg aagctcagcc cggcgccctt     180

gcggctcttc atgcggaagg gccgcttgcc gggctccccg tgacacgtag tgatgcacgc     240

gtgctgatct tcaatgagtg ggaggagagg aagaagtctg agccgtggct acggctggac     300

atgtctgaca gggctatctt ccgccgctac ccccatctgc ggcctaagga ggataagcct     360

gatgcgccct cccatgcgga ggacgctatg gatgccaggg agcctgcgat tggctctatt     420

ttggagcagg atgaccataa gttctaccat tattctgtct atgtcggcaa tggtcaggtg     480

atgggcgtca acaaccctgg agctgccatt tgccaggctg tgattgacgt ggagaagctc     540

cacctatggt ggagaccagt ctgggagccc catcagcccc tcgacccggc tgagttgaag     600

aagtgtgtcg gcatgacagt cccttatgtg gcaaccactg tcaactgcta ccaggtctgc     660

tgctggattg ttgggattaa ggacacctgg ccgaaaaggg cgaagatttc cagagactcg     720

cccttctaca gtcccgttca ggactggaac attgaccccc aggagccttt cattccgtct     780

aagctcagga tggtctctga tggcattctg gtggctctct caacggtgat tggtcggccg     840

atcaaaaacc tgctggcatc tgtgaagccg ctcaacattc tcaacatcgt gttgagctgc     900

gactggactt tctcgggcat agtcaatgcc ctgattcttc ttgctgagct atttgatgtt     960

ttctggactc cccctgatgt caccaattgg atgatctcca tctttggaga gtggcaggct    1020

gaa                                                                  1023


<210> SEQ ID NO 43
<211> LENGTH: 341
<212> TYPE: PRT
<213> ORGANISM: Murine norovirus

<400> SEQUENCE: 43

Met Arg Met Ala Thr Pro Ser Ser Ala Ser Ser Val Arg Asn Thr Glu
```

-continued

```
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Ala Asn Tyr Met
        35                  40                  45

Thr Pro Pro Glu Gln Glu Ala Gln Pro Gly Ala Leu Ala Ala Leu His
    50                  55                  60

Ala Glu Gly Pro Leu Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Arg Ala Ile Phe Arg Arg Tyr Pro His
            100                 105                 110

Leu Arg Pro Lys Glu Asp Lys Pro Asp Ala Pro Ser His Ala Glu Asp
        115                 120                 125

Ala Met Asp Ala Arg Glu Pro Ala Ile Gly Ser Ile Leu Glu Gln Asp
    130                 135                 140

Asp His Lys Phe Tyr His Tyr Ser Val Tyr Val Gly Asn Gly Gln Val
145                 150                 155                 160

Met Gly Val Asn Asn Pro Gly Ala Ala Ile Cys Gln Ala Val Ile Asp
                165                 170                 175

Val Glu Lys Leu His Leu Trp Trp Arg Pro Val Trp Glu Pro His Gln
            180                 185                 190

Pro Leu Asp Pro Ala Glu Leu Lys Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Pro Lys Arg Ala Lys Ile Ser Arg Asp Ser
225                 230                 235                 240

Pro Phe Tyr Ser Pro Val Gln Asp Trp Asn Ile Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Val
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 44
<211> LENGTH: 1023
<212> TYPE: DNA
<213> ORGANISM: Murine norovirus

<400> SEQUENCE: 44

```
atgaggatgg caacgccatc ttctgcgtcc tctgtgcgca acacagagaa acgcaaaaat      60

aagaaggctt cgtctaaagc tagtgtctcc ttcggagcac ctagccttct ctcttcggag     120

agcgaagatg aagctaatta catgacccct cctgagcagg aagctcagcc cggcgccctt     180
```

-continued

```
gcggcccttc atgcggaagg gccgcttgcc gggctccccg tgacgcgtag tgatgcacgc    240

gtgctgatct tcaatgagtg ggaggagagg aagaagtctg agccgtggct acggctggac    300

atgtctgaca gggctatctt ccgccgctac ccccatctgc ggcctaagga agataagcct    360

gacgcgccct cccatgcgga ggacgctatg gatgccaggg agcctgcgat cggctctatt    420

ttggagcagg atgaccataa gttctaccat tactctgtct atgtcggcaa tggtcaggtg    480

atgggcgtca acaaccctgg agctgccatt tgccaggctg tgattgacgt ggagaagctc    540

cacctctggt ggagaccagt ctgggagccc catcagcccc tcgacccggc tgagttgaag    600

aagtgtgtcg gcatgacagt cccttatgtg gcaaccactg tcaactgcta ccaggtctgc    660

tgctggattg ttgggattaa ggacacctgg ctgaaaaggg cgaagatttc cagagactcg    720

cccttcttca gtcccgttca ggactggaac attgaccccc aggagccttt cattccgtct    780

aagctcagga tggtctctga tggcatcctg gtggttctct caacggtgat tggtcggccg    840

atcaaaaacc tgctggcatc tgtgaagccg ctcaacattc tcaacatcgt gttgagctgt    900

gactggactt tctcgggcat agtcaatgcc ctgatccttc ttgctgagct atttgatgtt    960

ttctggactc cccctgatgt caccaattgg atgatctcca tctttggaga gtggcaggct   1020

gaa                                                                 1023


<210> SEQ ID NO 45
<211> LENGTH: 341
<212> TYPE: PRT
<213> ORGANISM: Murine norovirus

<400> SEQUENCE: 45

Met Arg Met Ala Thr Pro Ser Ser Ala Ser Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Ala Asn Tyr Met
        35                  40                  45

Thr Pro Pro Glu Gln Glu Ala Gln Pro Gly Ala Leu Ala Ala Leu His
    50                  55                  60

Ala Glu Gly Pro Leu Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Arg Ala Ile Phe Arg Arg Tyr Pro His
            100                 105                 110

Leu Arg Pro Lys Glu Asp Lys Pro Asp Ala Pro Ser His Ala Glu Asp
        115                 120                 125

Ala Met Asp Ala Arg Glu Pro Ala Ile Gly Ser Ile Leu Glu Gln Asp
    130                 135                 140

Asp His Lys Phe Tyr His Tyr Ser Val Tyr Val Gly Asn Gly Gln Val
145                 150                 155                 160

Met Gly Val Asn Asn Pro Gly Ala Ala Ile Cys Gln Ala Val Ile Asp
                165                 170                 175

Val Glu Lys Leu His Leu Trp Trp Arg Pro Val Trp Glu Pro His Gln
            180                 185                 190

Pro Leu Asp Pro Ala Glu Leu Lys Lys Cys Val Gly Met Thr Val Pro
        195                 200                 205

Tyr Val Ala Thr Thr Val Asn Cys Tyr Gln Val Cys Cys Trp Ile Val
    210                 215                 220
```

```
Gly Ile Lys Asp Thr Trp Leu Lys Arg Ala Lys Ile Ser Arg Asp Ser
225                 230                 235                 240

Pro Phe Phe Ser Pro Val Gln Asp Trp Asn Ile Asp Pro Gln Glu Pro
                245                 250                 255

Phe Ile Pro Ser Lys Leu Arg Met Val Ser Asp Gly Ile Leu Val Val
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Val
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 46
<211> LENGTH: 1023
<212> TYPE: DNA
<213> ORGANISM: Murine norovirus

<400> SEQUENCE: 46

```
atgaggatgg caacgccatc ttctgcgtcc tctgtgcgca acacagagaa acgcaaaaat      60

aagaaggctt cgtctaaagc tagtgtctcc ttcggagcac ctagccttct ctcttcggag     120

agcgaagacg aagctaatta catgacccct cctgagcagg aagctcagcc cggcgccctt     180

gcggcccttc atgcggaagg gccgcttgcc gggctccccg tgacgcgtag tgatgcacgc     240

gtgctgatct tcaatgagtg ggaggagagg aagaagtctg agccgtggct acggctggac     300

atgtctgaca gggctatctt ccgccgctac ccccatctgc ggcctaagga agataagcct     360

gacgcgccct cccatgcgga ggacgctatg gatgccaggg agcctgcgat cggctctatt     420

ttggagcagg atgaccataa gttctaccat tactctgtct atgtcggcaa tggtcaggtg     480

atgggcgtta acaaccctgg agctgccatt tgccaggctg tgattgacgt ggagaagctc     540

cacctctggt ggagaccagt ctgggagccc catcagcccc tcgacccggc tgagttgaag     600

aagtgtgtcg gcatgacagt ccccttatgtg gcaaccactg tcaactgcta ccaggtctgc     660

tgctggattg ttgggattaa ggacacctgg ctgaaaaggg cgaagatttc cagagactcg     720

cccttcttca gtcccgttca ggactggaac attgaccccc aggagccttt cattccgtct     780

aagctcagga tggtctctga tggcatcctg gtggctctct caacggtgat tggtcggccg     840

atcaaaaacc tgctggcatc tgtgaagccg ctcaacattc tcaacatcgt gttgagctgt     900

gactggactt tctcgggcat agtcaatgcc ctgattcttc ttgctgagct atttgatgtt     960

ttctggactc cccctgatgt caccaattgg atgatctcca tctttggaga gtggcaggct    1020

gaa                                                                  1023
```

<210> SEQ ID NO 47
<211> LENGTH: 341
<212> TYPE: PRT
<213> ORGANISM: Murine norovirus

<400> SEQUENCE: 47

```
Met Arg Met Ala Thr Pro Ser Ser Ala Ser Ser Val Arg Asn Thr Glu
1               5                   10                  15
```

```
Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Ala Asn Tyr Met
        35                  40                  45

Thr Pro Pro Glu Gln Glu Ala Gln Pro Gly Ala Leu Ala Ala Leu His
    50                  55                  60

Ala Glu Gly Pro Leu Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Arg Ala Ile Phe Arg Arg Tyr Pro His
            100                 105                 110

Leu Arg Pro Lys Glu Asp Lys Pro Asp Ala Pro Ser His Ala Glu Asp
        115                 120                 125

Ala Met Asp Ala Arg Glu Pro Ala Ile Gly Ser Ile Leu Glu Gln Asp
    130                 135                 140

Asp His Lys Phe Tyr His Tyr Ser Val Tyr Val Gly Asn Gly Gln Val
145                 150                 155                 160

Met Gly Val Asn Asn Pro Gly Ala Ala Ile Cys Gln Ala Val Ile Asp
                165                 170                 175

Val Glu Lys Leu His Leu Trp Trp Arg Pro Val Trp Glu Pro His Gln
            180                 185                 190

Pro Leu Asp Pro Ala Glu Leu Lys Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Phe Ser Pro Val Gln Asp Trp Asn Ile Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Val
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 48
<211> LENGTH: 1023
<212> TYPE: DNA
<213> ORGANISM: Murine norovirus

<400> SEQUENCE: 48

```
atgaggatgg caacgccatc ttctgcgtcc tctgtgcgca acacagagaa acgcaaaaat      60

aagaaggctt cgtctaaagc tagtgtctcc ttcggagcac ctagccttct ctcttcggag     120

agcgaagatg aagctaatta catgacccct cctgagcagg aagctcagcc cggcgccctt     180

gcggcccttc atgcggaagg gccgcttgcc gggctccccg tgacgcgtag tgatgcacgc     240
```

```
gtgctgatct tcaatgagtg ggaggagagg aagaagtctg agccgtggct acggctggac    300

atgtctgaca gggctatctt ccgccgctac ccccatctgc ggcctaagga agataagcct    360

gacgcgccct cccatgcgga ggacgctatg gatgccaggg agcctgcgat cggctctatt    420

ttggagcagg atgaccataa gttctaccat tactctgtct atgtcggcaa tggtcaggtg    480

atgggcgtca acaaccctgg agctgccatt tgccaggctg tgattgacgt ggagaagctc    540

cacctctggt ggagaccagt ctgggagccc catcagcccc tcgacccggc tgagttgaag    600

aagtgtgtcg gcatgacagt cccttatgtg gcaaccactg tcaactgcta ccaggtctgc    660

tgctggattg ttgggattaa ggacacctgg ctgaaaaggg cgaagatttc cagagactcg    720

cccttcttca gtcccgttca ggactggaac attgaccccc aggagccttt cattccgtct    780

aagctcagga tggtctctga tggcatcctg gtggctctct caacggtgat tggtcggccg    840

atcaaaaacc tgctggcatc tgtgaagccg ctcaacattc tcaacatcgt gttgagctgt    900

gactggactt tctcgggcat agtcaatgcc ctgattcttc ttgctgagct atttgatgtt    960

ttctggactc cccctgatgt caccaattgg atgatctcca tctttggaga gtggcaggct   1020

gaa                                                                 1023


<210> SEQ ID NO 49
<211> LENGTH: 341
<212> TYPE: PRT
<213> ORGANISM: Murine norovirus

<400> SEQUENCE: 49

Met Arg Met Ala Thr Pro Ser Ser Ala Ser Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Ala Asn Tyr Met
        35                  40                  45

Thr Pro Pro Glu Gln Glu Ala Gln Pro Gly Ala Leu Ala Ala Leu His
    50                  55                  60

Ala Glu Gly Pro Leu Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Arg Ala Ile Phe Arg Arg Tyr Pro His
            100                 105                 110

Leu Arg Pro Lys Glu Asp Lys Pro Asp Ala Pro Ser His Ala Glu Asp
        115                 120                 125

Ala Met Asp Ala Arg Glu Pro Ala Ile Gly Ser Ile Leu Glu Gln Asp
    130                 135                 140

Asp His Lys Phe Tyr His Tyr Ser Val Tyr Val Gly Asn Gly Gln Val
145                 150                 155                 160

Met Gly Val Asn Asn Pro Gly Ala Ala Ile Cys Gln Ala Val Ile Asp
                165                 170                 175

Val Glu Lys Leu His Leu Trp Trp Arg Pro Val Trp Glu Pro His Gln
            180                 185                 190

Pro Leu Asp Pro Ala Glu Leu Lys Lys Cys Val Gly Met Thr Val Pro
        195                 200                 205

Tyr Val Ala Thr Thr Val Asn Cys Tyr Gln Val Cys Cys Trp Ile Val
    210                 215                 220
```

-continued

```
Gly Ile Lys Asp Thr Trp Leu Lys Arg Ala Lys Ile Ser Arg Asp Ser
225                 230                 235                 240

Pro Phe Phe Ser Pro Val Gln Asp Trp Asn Ile Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Val
305                 310                 315                 320

Phe Trp Thr Pro Pro Asp Val Thr Asn Trp Met Ile Ser Ile Phe Gly
                325                 330                 335

Glu Trp Gln Ala Glu
            340


<210> SEQ ID NO 50
<211> LENGTH: 1023
<212> TYPE: DNA
<213> ORGANISM: Murine norovirus

<400> SEQUENCE: 50

atgaggatgg caacgccatc ttctgcgtcc tctgtgcgca acacagagaa acgcaaaaac      60

aaaaaggctt catctaaagc tagtgtctcc tttggagcac ctagccttct ctcttcggag     120

agtgaagatg aagctaacta tctgacccct cctgagcagg aagctcagcc cggcaccctt     180

gcggccctcc atgctgatgg gccgcacgcc gggctccccg tgacgcggag tgatgcacgc     240

gtgctgatct tcaatgagtg ggaggagagg aagaagtccg agccgtggct gcggctggac     300

atgtctgaca aggccatctt ccgccgctat ccccacttgc ggcctaagga ggataaggct     360

gacgcgccct cccatgcgga ggacgccatg gaggcgaggg agcccgtggt gggatccatt     420

cttgagcagg atgaccataa gttctaccac tactctgtct acatcggtaa cggcctggtg     480

atgggcgtca acaatcccgg cgccgctgtc tgccaggctg tgattgatgt ggagaagctc     540

cacctgtggt ggaggccagt ctgggaaccc cgccagcccc ttgacccggc tgagttgagg     600

aagtgcgttg gcatgaccgt tccctacgta gcaactaccg tcaactgcta ccaggtctgt     660

tgttggattg ttgggatcaa ggacacctgg ctgaagaggg cgaagatctc cagggactcg     720

cccttctata gccctgtcca ggattggaat gttgatcccc aggagccttt cattccgtct     780

aagcttagga tggtctctga tggcatctta gtggctctct caacggtgat tggtcggccg     840

atcaagaacc tactggcatc tgtcaagccg ctcaacatcc ttaacatcgt gttgagctgt     900

gattggactt tctcgggcat cgtcaacgcc ctgatccttc ttgctgagct ttttgacatt     960

ttctggaccc ctcccgatgt caccaactgg atgatctcca tctttggaga gtggcaggcc    1020

gaa                                                                  1023


<210> SEQ ID NO 51
<211> LENGTH: 341
<212> TYPE: PRT
<213> ORGANISM: Murine norovirus

<400> SEQUENCE: 51

Met Arg Met Ala Thr Pro Ser Ser Ala Ser Ser Val Arg Asn Thr Glu
1               5                   10                  15
```

-continued

```
Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Ala Asn Tyr Leu
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Ala Asp Ala Pro Ser His Ala Glu Asp
        115                 120                 125

Ala Met Glu Ala Arg Glu Pro Val Val Gly Ser Ile Leu Glu Gln Asp
    130                 135                 140

Asp His Lys Phe Tyr His Tyr Ser Val Tyr Ile Gly Asn Gly Leu Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 52
<211> LENGTH: 1023
<212> TYPE: DNA
<213> ORGANISM: Murine norovirus

<400> SEQUENCE: 52

```
atgaggatgg caacgccatc ttctgcgtcc tctgtgcgca acacagagaa acgcaaaaac      60

aaaaaggctt cgtctaaggc tagtgtctcc tttggagcac ctagcttact ctcttcggag     120

agcgaagatg aagctaacta catgacccct cctgagcaag aagctcagcc tggcaccctt     180

gcggccctcc atgctgatgg gccgcacgcc gggctccccg tgacgcggag tgatgcacgc     240
```

```
gtgctgatct tcaatgagtg ggaggagagg aagaagtccg agccgtggct acggctggac    300

atgtctgaca aggctatctt ccgccgctac ccccacctgc ggcctaagga agataagcct    360

gacgcgcccc cccatgcgga gggcgccatg gatgcaaagg agcctgtggt ggggtccatt    420

ctcgagcagg atgaccataa gttctatcat tactctgtat acattggcaa cggcatggtg    480

atgggtgtca acaacccagg tgctgccgtg tgtcaggctg tgattgatgt ggagaaactc    540

cacctctggt ggagaccagt ttgggagcct cgtcaacccc tcgacccggc tgagttgagg    600

aagtgtgttg gcatgactgt cccttacgtg gcaaccactg tcaactgcta ccaggtttgc    660

tgctggattg ttgggatcaa ggacacctgg ctgaagaggg cgaagatctc cagggactcg    720

cccttctaca gccctgtgca agactggaat gttgaccccc aggaaccctt tatcccatcc    780

aagctcagga tggtgtctga tggcattctg gtggctctct caacggtgat tggtcggccg    840

atcaagaacc tactggcatc cgtcaagccg ctcaacattc tcaacatcgt gttgagctgt    900

gattggactt tctcgggcat agtcaacgcc ctgattctcc ttgccgagct cttcgacgtc    960

ttctggactc ctcctgatgt taccaactgg atgatttcca tctttggaga gtggcaggct   1020

gag                                                                 1023
```

```
<210> SEQ ID NO 53
<211> LENGTH: 341
<212> TYPE: PRT
<213> ORGANISM: Murine norovirus

<400> SEQUENCE: 53

Met Arg Met Ala Thr Pro Ser Ser Ala Ser Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Ala Asn Tyr Met
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Pro Asp Ala Pro Pro His Ala Glu Gly
        115                 120                 125

Ala Met Asp Ala Lys Glu Pro Val Val Gly Ser Ile Leu Glu Gln Asp
    130                 135                 140

Asp His Lys Phe Tyr His Tyr Ser Val Tyr Ile Gly Asn Gly Met Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
```

-continued

```
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Val
305                 310                 315                 320

Phe Trp Thr Pro Pro Asp Val Thr Asn Trp Met Ile Ser Ile Phe Gly
                325                 330                 335

Glu Trp Gln Ala Glu
            340


<210> SEQ ID NO 54
<211> LENGTH: 1023
<212> TYPE: DNA
<213> ORGANISM: Murine norovirus

<400> SEQUENCE: 54

atgaggatgg caacgccatc ttctgcgtcc tctgtgcgca acacagagaa acgcaaaaac     60

aaaaaggctt catctaaggc tagtgtctcc tttggagcac ctagcttact ctcttcggag    120

agtgaagatg aagttaacta tatgacccct cctgagcagg aagctcagcc cggcaccctc    180

gcggctctcc acgcggatgg gccgcacgcc gggctccccg taacccgaag tgacgcacgc    240

gtgctgatct tcaacgaatg ggaggagagg aagaagtctg agccgtggct acggctggac    300

atgtctgaca aggctatctt ccgccgctac ccccacctgc ggcccaaaga ggataagcct    360

gatgcgcccc cccacgcgga ggacgccatg gatgcaaaag agcctgtggt gggatccatt    420

ctcgagcaag atgaccacaa gttctaccat tactctgtct acattggcaa cggtcaggtg    480

atgggtgtca acaatcctgg cgccgccgtg tgccaggctg tgattgatgt ggagaagctc    540

catctctggt ggagaccagt ctgggagccc cgccagcccc tcgacccggc tgagttgagg    600

aagtgtgttg gcatgaccgt cccttatgcg gcaaccacta tcaactgtta ccaggtttgc    660

tgctggattg ttgggatcaa ggatacctgg ctcaagaggg agaagatctc tagaggctcg    720

cccttctaca gccctgtcca ggattggaat atcgaccccc aggagccctt cattccttcc    780

aagcttagga tggactctga tggcattctg gtggctcttt caacggtgat tggtcggccg    840

atcaagaacc tactggcatc cgtgaagccg ctcaacatcc ttaacatcgt gttgagctgt    900

gactggacct tctcgggcat agtcaacgcc ctgatcctcc ttgctgagct ctttgatatc    960

ttttggactc cccccgatgt caccaactgg atgatttcca tcttcgggga gtggcaggcc   1020

gag                                                                 1023


<210> SEQ ID NO 55
<211> LENGTH: 341
<212> TYPE: PRT
<213> ORGANISM: Murine norovirus

<400> SEQUENCE: 55

Met Arg Met Ala Thr Pro Ser Ser Ala Ser Ser Val Arg Asn Thr Glu
1               5                   10                  15

Lys Arg Lys Asn Lys Lys Ala Ser Ser Lys Ala Ser Val Ser Phe Gly
```

-continued

```
            20                  25                  30

Ala Pro Ser Leu Leu Ser Ser Glu Ser Glu Asp Glu Val Asn Tyr Met
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Pro Asp Ala Pro Pro His Ala Glu Asp
        115                 120                 125

Ala Met Asp Ala Lys Glu Pro Val Val Gly Ser Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Ala Ala Thr Thr Ile Asn Cys Tyr Gln Val Cys Cys Trp Ile Val
    210                 215                 220

Gly Ile Lys Asp Thr Trp Leu Lys Arg Glu Lys Ile Ser Arg Gly Ser
225                 230                 235                 240

Pro Phe Tyr Ser Pro Val Gln Asp Trp Asn Ile Asp Pro Gln Glu Pro
                245                 250                 255

Phe Ile Pro Ser Lys Leu Arg Met Asp Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340


<210> SEQ ID NO 56
<211> LENGTH: 1023
<212> TYPE: DNA
<213> ORGANISM: Murine norovirus

<400> SEQUENCE: 56

atgaggatgg caacgccatc ttctgcgccc tctgtgcgca acacagagaa acgcaaaaac      60

aagaaggctt cgtctaaagc tagtgtctcc tttggagcac ctagcccccct ctcttcggag    120

agcgaagacg aaattaatta catgacccct cctgagcagg aagctcagcc cggcgccctt    180

gcggcccttc atgcggaagg gccgcttgcc gggctccccg tgacgcgtag tgatgcacgc    240

gtgctgatct tcaatgagtg ggaggagagg aagaagtctg atccgtggct acggctggac    300
```

-continued

```
atgtctgata aggctatctt ccgccgttac ccccatctgc ggcctaagga ggataggcct    360

gacgcgccct cccatgcgga ggacgctatg gatgccaagg agcctgtgat cggctctatc    420

ttggagcagg atgatcacaa gttttaccat tactctgtct acatcggtgg cggccttgtg    480

atgggggtca acaaccccag tgctgcggtc tgccaggcaa cgattgatgt ggagaagcta    540

cacctctggt ggcggcctgt ctgggagccc cgccawcccc ttgactcggc tgagttgagg    600

aagtgcgtgg gcatgactgt cccctacgtg gccaccaccg tcaactgtta tcaggtctgc    660

tgctggattg ttggcatcaa ggacacctgg ctgaagaggg cgaagatctc tagagatctg    720

cccttctaca gccccgtcca ggactggaac gtcgaccccc aggagccctt cattccatcc    780

aagctcagga tggtctcgga tggcatcctg gtggccttgt cggcagtgat tggccggcca    840

attaagaacc tactggcctc agttaagccg ctcaacattc tcaacatcgt gctgagctgt    900

gattggacct tttcgggcat tgtcaatgcc ctgatcttgc ttgctgagct ctttgacatc    960

ttttggaccc cccctgatgt raccaactgg atgatctcta tcttcgggga atggcaggcc   1020

gaa                                                                 1023
```

```
<210> SEQ ID NO 57
<211> LENGTH: 341
<212> TYPE: PRT
<213> ORGANISM: Murine norovirus
<220> FEATURE:
<221> NAME/KEY: MOD_RES
<222> LOCATION: (192)..(192)
<223> OTHER INFORMATION: Any amino acid

<400> SEQUENCE: 57

Met Arg Met Ala Thr Pro Ser Ser Ala Pro Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Pro Leu Ser Ser Glu Ser Glu Asp Glu Ile Asn Tyr Met
        35                  40                  45

Thr Pro Pro Glu Gln Glu Ala Gln Pro Gly Ala Leu Ala Ala Leu His
    50                  55                  60

Ala Glu Gly Pro Leu Ala Gly Leu Pro Val Thr Arg Ser Asp Ala Arg
65                  70                  75                  80

Val Leu Ile Phe Asn Glu Trp Glu Glu Arg Lys Lys Ser Asp Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Arg Pro Asp Ala Pro Ser His Ala Glu Asp
        115                 120                 125

Ala Met Asp Ala Lys Glu Pro Val Ile Gly Ser Ile Leu Glu Gln Asp
    130                 135                 140

Asp His Lys Phe Tyr His Tyr Ser Val Tyr Ile Gly Gly Gly Leu Val
145                 150                 155                 160

Met Gly Val Asn Asn Pro Ser Ala Ala Val Cys Gln Ala Thr Ile Asp
                165                 170                 175

Val Glu Lys Leu His Leu Trp Trp Arg Pro Val Trp Glu Pro Arg Xaa
            180                 185                 190

Pro Leu Asp Ser Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
```

```
    210                 215                 220

Gly Ile Lys Asp Thr Trp Leu Lys Arg Ala Lys Ile Ser Arg Asp Leu
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Ala Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340


<210> SEQ ID NO 58
<211> LENGTH: 1023
<212> TYPE: DNA
<213> ORGANISM: Murine norovirus

<400> SEQUENCE: 58

atgaggatgg caacgccatc ttctgcgccc tctgtgcgca acacagagaa acgcaaaaac      60

aagaaggctt cgtctaaagc tagtgtctcc tttggagcac ctagccccct ctcttcggag     120

agcgaagacg aaattaatta catgacccct cctgagcagg aagctcagcc cggcgccctt     180

gcggcccttc atgcggaagg gccgcttgcc gggctccccg tgacgcgtag tgatgcacgc     240

gtgctgatct tcaatgagtg ggaggagagg aagaagtctg atccgtggct acggctggac     300

atgtctgata aggctatctt ccgccgttac ccccatctgc ggcctaagga ggataggcct     360

gacgcgccct cccatgcgga ggacgctatg gatgccaagg agcctgtgat cggctctatc     420

ttggagcagg atgatcacaa gttttaccat tactctgtct acatcggtgg cggccttgtg     480

atgggggtca acaaccccag tgctgcggtc tgccaggcaa cgattgatgt ggagaagcta     540

cacctctggt ggcggcctgt ctgggagccc cgccatcccc ttgactcggc tgagttgagg     600

aagtgcgtgg gcatgactgt cccctacgtg gccaccaccg tcaactgtta tcaggtctgc     660

tgctggattg ttggcatcaa ggacacctgg ctgaagaggg cgaagatctc tagagatctg     720

cccttctaca gccccgtcca ggactggaac gtcgaccccc aggagccctt cattccatcc     780

aagctcagga tggtctcgga tggcatcctg gtggccttgt cggcagtgat tggccggcca     840

attaagaacc tactggcctc agttaagccg ctcaacattc tcaacatcgt gctgagctgt     900

gattggacct tttcgggcat tgtcaatgcc ctgatcttgc ttgctgagct ctttgacatc     960

ttttggaccc cccctgatgt gaccaactgg atgatctcta tcttcgggga atggcaggcc    1020

gaa                                                                  1023


<210> SEQ ID NO 59
<211> LENGTH: 341
<212> TYPE: PRT
<213> ORGANISM: Murine norovirus

<400> SEQUENCE: 59

Met Arg Met Ala Thr Pro Ser Ser Ala Pro Ser Val Arg Asn Thr Glu
```

-continued

```
1               5                   10                  15

Lys Arg Lys Asn Lys Lys Ala Ser Ser Lys Ala Ser Val Ser Phe Gly
            20                  25                  30

Ala Pro Ser Pro Leu Ser Ser Glu Ser Glu Asp Glu Ile Asn Tyr Met
        35                  40                  45

Thr Pro Pro Glu Gln Glu Ala Gln Pro Gly Ala Leu Ala Ala Leu His
    50                  55                  60

Ala Glu Gly Pro Leu Ala Gly Leu Pro Val Thr Arg Ser Asp Ala Arg
65                  70                  75                  80

Val Leu Ile Phe Asn Glu Trp Glu Glu Arg Lys Lys Ser Asp Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Arg Pro Asp Ala Pro Ser His Ala Glu Asp
        115                 120                 125

Ala Met Asp Ala Lys Glu Pro Val Ile Gly Ser Ile Leu Glu Gln Asp
    130                 135                 140

Asp His Lys Phe Tyr His Tyr Ser Val Tyr Ile Gly Gly Gly Leu Val
145                 150                 155                 160

Met Gly Val Asn Asn Pro Ser Ala Ala Val Cys Gln Ala Thr Ile Asp
                165                 170                 175

Val Glu Lys Leu His Leu Trp Trp Arg Pro Val Trp Glu Pro Arg His
            180                 185                 190

Pro Leu Asp Ser Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Leu
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Ala Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340


<210> SEQ ID NO 60
<211> LENGTH: 1023
<212> TYPE: DNA
<213> ORGANISM: Murine norovirus

<400> SEQUENCE: 60

atgaggatgg caacgccatc ttctgcgtcc tctgtgcgca acacagagaa acgcaaaaac      60

aaaaagactt catctaaagc tggtgtctcc tttggagcac ctagccttct ctcttcggag     120

agtgaagatg aagttaatta tatgacccct cctgagcaag aagctcagcc cggcacactt     180
```

-continued

```
gcggcccttc atgctgacgg gccgcacgct gggctccccg tgacgcgaag tgatgcacgc    240

gtgctaatct tcaatgagtg ggaggagagg aagaagtctg agccgtggct acggctagac    300

atgtctgaca aggctatctt tcgtcgcttt ccccatctgc ggcccaagga agataagcct    360

gatgcgccct cccatgcaga ggacgccatg gatgcaaagg agcctgtggt ggggaccatc    420

cttgagcaag atgaccacaa gttctatcac tactctgtct acatcggcaa tggccaggtg    480

atgggcgtca ataatcccgg cgccgccgtc tgccaggccg tgattgatgt ggagaaactc    540

catctgtggt ggagaccagt ctgggagccc cgccagcccc tcgacccggc tgagttgagg    600

aagtgtgttg gcatgaccgt gccctatgtg gcgaccaccg tcaactgcta ccaggtctgc    660

tgctggatcg ttgggatcaa ggacacttgg ctgaagcggg cgaagatttc tagggactcg    720

cccttctaca gccccgttca ggactggaat gttgaccccc aggagccctt catcccatcc    780

aagcttagga tggtctctga tggcatcctg gtggccctct caacggtgat tggtcggccg    840

atcaagaacc tgctggcatc tgtgaagcca ctcaacattc ttaacatcgt gttgagttgt    900

gactggacat tctcgggcat agttaatgcc ctgatcctcc ttgctgagct ctttgatgta    960

ttctggacac cccccgatgt cactaactgg atgatctcca tctttgggga atggcaggcc   1020

gag                                                                  1023


<210> SEQ ID NO 61
<211> LENGTH: 341
<212> TYPE: PRT
<213> ORGANISM: Murine norovirus

<400> SEQUENCE: 61

Met Arg Met Ala Thr Pro Ser Ser Ala Ser Ser Val Arg Asn Thr Glu
1               5                   10                  15

Lys Arg Lys Asn Lys Lys Thr Ser Ser Lys Ala Gly Val Ser Phe Gly
            20                  25                  30

Ala Pro Ser Leu Leu Ser Ser Glu Ser Glu Asp Glu Val Asn Tyr Met
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Phe Pro His
            100                 105                 110

Leu Arg Pro Lys Glu Asp Lys Pro Asp Ala Pro Ser His Ala Glu Asp
        115                 120                 125

Ala Met Asp Ala Lys Glu Pro Val Val Gly Thr Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220
```

```
Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Val
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 62
<211> LENGTH: 1023
<212> TYPE: DNA
<213> ORGANISM: Murine norovirus

<400> SEQUENCE: 62

```
atgaggatgg caacgccatc ttctgcgtcc tctgtgcgca acacagagaa acgcaaaaac      60

aaaaaggctc cgtctaaggc tagcgtctcc tttggagcac ctagccttct ctcttcggag     120

agtgaagacg aagctaacta catgacccct cctgagcagg aagctcagcc cggcgccctc     180

gcggcccttc acgctgaagg gtcgcttgcc gggctccccg tgacgcggag tgatgcacgc     240

gtgctgatct tcaatgagtg ggaggagagg aagaagtccg agccgtggat acggctggac     300

atgtctgaca gggctatctt ccgccgctac ccccatctgc ggcccaggga ggacaagcct     360

gatgcgccct cccacgcgga ggacgccatg gatgctagag agcccgtgat cggctctatc     420

ctggagcagg acgaccacaa gttctaccac tactccgttt acatcggtaa tggccttgtg     480

atgggtgtca acaaccctgg tgctgcggtc tgccaggcaa caattgatgt ggaaaagcta     540

cacctctggt ggagacccgt ctgggagccc cgccagcccc tcgacccggc tgagttgggg     600

aaatgcgttg gcatgactgt tccctatgtg gctaccactg tcaactgcta tcaggtgtgc     660

tgctggattg ttggtattaa ggatacctgg ctgaagaggg cgaagatctc aagggattcg     720

cccttctaca gccctgtcca ggattggaat gttgatcccc aggagccatt catcccatcc     780

aagctcagga tggtgtcgga tggtatcctg gtggccctgt caacggtgat tggtcggccg     840

atcaagaacc tgttggcttc agtcaagccg ctcaacatcc tcaacatcgt gttgagctgt     900

gattggacct tttcgggcat tgtcaacgcc ctgatcctcc tagcggagct ctttgatatc     960

ttttggaccc cccccgatgt gaccaactgg atgatctcca tcttcgggga atggcaggcc    1020

gaa                                                                  1023
```

<210> SEQ ID NO 63
<211> LENGTH: 341
<212> TYPE: PRT
<213> ORGANISM: Murine norovirus

<400> SEQUENCE: 63

```
Met Arg Met Ala Thr Pro Ser Ser Ala Ser Ser Val Arg Asn Thr Glu
1               5                   10                  15
```

```
Lys Arg Lys Asn Lys Lys Ala Pro Ser Lys Ala Ser Val Ser Phe Gly
            20                  25                  30

Ala Pro Ser Leu Leu Ser Ser Glu Ser Glu Asp Glu Ala Asn Tyr Met
        35                  40                  45

Thr Pro Pro Glu Gln Glu Ala Gln Pro Gly Ala Leu Ala Ala Leu His
    50                  55                  60

Ala Glu Gly Ser Leu Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Ile Arg Leu Asp Met Ser Asp Arg Ala Ile Phe Arg Arg Tyr Pro His
            100                 105                 110

Leu Arg Pro Arg Glu Asp Lys Pro Asp Ala Pro Ser His Ala Glu Asp
        115                 120                 125

Ala Met Asp Ala Arg Glu Pro Val Ile Gly Ser Ile Leu Glu Gln Asp
    130                 135                 140

Asp His Lys Phe Tyr His Tyr Ser Val Tyr Ile Gly Asn Gly Leu Val
145                 150                 155                 160

Met Gly Val Asn Asn Pro Gly Ala Ala Val Cys Gln Ala Thr Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Gly Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 64
<211> LENGTH: 1023
<212> TYPE: DNA
<213> ORGANISM: Murine norovirus

<400> SEQUENCE: 64

```
atgaggatgg caacgccatc ttctgcgtcc tctgtgcgca acacagagaa acgcaaaaac      60

aaaaagactt catctaaagc tagtgtctcc tttggagcac ctagccttct ctcttcggag     120

agtgaagatg aagtcaacta catgacccct cctgagcagg aagctcagcc cggcgcgctt     180

gcggcccttc atgccgacgg gccgcacgcc gggctccccg tgacacgaag cgatgcacgc     240
```

```
gtgctgatct tcaacgagtg ggaggagagg aagaagtctg agccgtggct acggttggac    300

atgtctgaca aggccatctt ccgtcgcttt ccccatctgc gacctaagga agataggcct    360

gacgcgccct cccacgcgga ggacgccatg gatgcaagag agcctgtcgt gggaaccatc    420

cttgagcaag atgaccataa gttctaccac tattctgtct acatcggcaa tggtcaggtg    480

atgggcgtca acaaccccgg cgccgccgtc tgccaggccg tgattgatgt ggagaagctc    540

cacctgtggt ggagaccagt ctgggagccc cgccagcccc tcgacccggc tgagttgagg    600

aagtgtgttg gcatgaccgt gccctatgtg gcgactactg tcaactgcta ccaggtctgc    660

tgctggattg tagggatcaa ggatacttgg ctgaagcggg cgaagatctc tagagattcg    720

cccttctaca gccccgtcca ggattggaat gttgatcccc aggagccctt cattccgtct    780

aaactcagga tggtatcaga cggcatcctg gtggctctct caacggtgat tggtcggccg    840

atcaagaacc tgttggcatc tgtgaagcca cttaacatcc tcaacattgt gttgagctgt    900

gactggactt tttcgggcat agtcaacgcc ctgattctcc ttgctgagct ctttgatgtt    960

ttctggactc cccccgatgt caccaactgg atgatttcca tcttcggaga gtggcaggcc   1020

gag                                                                 1023
```

<210> SEQ ID NO 65
<211> LENGTH: 341
<212> TYPE: PRT
<213> ORGANISM: Murine norovirus

<400> SEQUENCE: 65

```
Met Arg Met Ala Thr Pro Ser Ser Ala Ser Ser Val Arg Asn Thr Glu
1               5                   10                  15

Lys Arg Lys Asn Lys Lys Thr Ser Ser Lys Ala Ser Val Ser Phe Gly
            20                  25                  30

Ala Pro Ser Leu Leu Ser Ser Glu Ser Glu Asp Glu Val Asn Tyr Met
        35                  40                  45

Thr Pro Pro Glu Gln Glu Ala Gln Pro Gly Ala Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Phe Pro His
            100                 105                 110

Leu Arg Pro Lys Glu Asp Arg Pro Asp Ala Pro Ser His Ala Glu Asp
        115                 120                 125

Ala Met Asp Ala Arg Glu Pro Val Val Gly Thr Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220
```

```
Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Val
305                 310                 315                 320

Phe Trp Thr Pro Pro Asp Val Thr Asn Trp Met Ile Ser Ile Phe Gly
                325                 330                 335

Glu Trp Gln Ala Glu
            340


<210> SEQ ID NO 66
<211> LENGTH: 1023
<212> TYPE: DNA
<213> ORGANISM: Murine norovirus

<400> SEQUENCE: 66

atgaggatgg caacgccatc ttctgcgtcc tctgtgcgca acacagagaa acgcaaaaac     60

aaaaaggctt cacctaaggc tagcgtctcc tttggagcgc ctagtctact ctcttcggag    120

agtgaggatg aagccaacta catgacccct cctgagcagg aagctcagcc cggtgccctc    180

gcggcccttc acgcggacgg gccgcatgcc gggctccctg tgacccgaag tgatgcacgc    240

gtgctgatct tcaatgattg ggaggagagg aagaagtccg agccgtggct acggctggac    300

atgtctgaca aggccatctt ccgccgcttc ccccatctgc ggcctaggga ggataaaact    360

gatgcaccct cccatgtgga ggacgctatg gatgcaaaag agcctgtggt ggggtccatc    420

ctcgagcagg atgaccacaa gttctaccac tactctgtct acatcggtgg cggccaggtg    480

atgggtgtca acaaccccgg cgccgccgtc tgccaggctg tgattgatgt agagaagctt    540

catctgtggt ggaggccagt ctgggaacca cgccaacccc ttgacccggc tgagttgagg    600

aagtgtgttg gcatgaccgt tccctacgtg gcaaccaccg ttaactgcta ccaagtctgc    660

tgctggattg ttgggatcaa ggacacctgg ctgaagaggg cgaagatttc cagagactcg    720

cctttcttca gccctgttca ggattggaac gtcgaccccc aggagccttt cattccctcc    780

aagctcagga tggtctccga tggtatcctg gtggctctct cgacagtgat tggtcggccg    840

atcaagaacc tgctggcatc tgtcaagcca ctcaacattc ttaacatcgt gttgggctgc    900

gactggactt tttcgggcat agtcaacgcc ctgattcttc ttgctgagct ctttgacatt    960

ttctggaccc cccctgatgt tactaattgg atgatctcta tttttggaga gtggcaggcc   1020

gaa                                                                 1023


<210> SEQ ID NO 67
<211> LENGTH: 341
<212> TYPE: PRT
<213> ORGANISM: Murine norovirus

<400> SEQUENCE: 67

Met Arg Met Ala Thr Pro Ser Ser Ala Ser Ser Val Arg Asn Thr Glu
1               5                   10                  15
```

-continued

```
Lys Arg Lys Asn Lys Lys Ala Ser Pro Lys Ala Ser Val Ser Phe Gly
            20                  25                  30

Ala Pro Ser Leu Leu Ser Ser Glu Ser Glu Asp Glu Ala Asn Tyr Met
        35                  40                  45

Thr Pro Pro Glu Gln Glu Ala Gln Pro Gly Ala Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Asp Trp Glu Glu Arg Lys Lys Ser Glu Pro Trp
                85                  90                  95

Leu Arg Leu Asp Met Ser Asp Lys Ala Ile Phe Arg Arg Phe Pro His
            100                 105                 110

Leu Arg Pro Arg Glu Asp Lys Thr Asp Ala Pro Ser His Val Glu Asp
        115                 120                 125

Ala Met Asp Ala Lys Glu Pro Val Val Gly Ser Ile Leu Glu Gln Asp
    130                 135                 140

Asp His Lys Phe Tyr His Tyr Ser Val Tyr Ile Gly Gly Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Phe Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Gly Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 68
<211> LENGTH: 1023
<212> TYPE: DNA
<213> ORGANISM: Murine norovirus

<400> SEQUENCE: 68

```
atgaggatgg caacgccatc ttctgcgtcc tctgtgcgca acacagagaa acgcaaaaac      60

aaaaaggctt cacctaaggc tagcgtctcc tttggagcgc ctagtctact ctcttcggag     120

agtgaggatg aagctaacta catgacccct cctgagcagg aagctcagcc cggtaccctt     180

gcggcccttc acgcggacgg gccgcatgcc gggctccctg tgacccgaag tgatgcacgc     240
```

-continued

```
gtgctgatct tcaatgattg ggaggagagg aagaagtccg agccgtggct gcggctggac    300

atgtctgaca aggccatctt ccgccgcttc ccccatctgc ggcctaagga ggataagact    360

ggtgcaccct cctgcgcgga ggacgccatg gatgcaaaag agcctgtggt ggggtctatc    420

ctcgagcagg atgaccacaa gttctaccac tactctgtct acatcggtgg cggccaggtg    480

atgggtgtca acaaccccgg cgccgccgtc tgccaggctg tgattgatgt ggagaagctc    540

catctgtggt ggaggccagt ctgggaacca cgtcaacccc ttgacccggc tgagttgagg    600

aagtgtgttg gcatgaccgt tccctatgtg gcaaccaccg ttaactgcta ccaagtttgc    660

tgctggattg ttgggatcaa ggacacctgg ctgaagaggg cgaagatctc tagagactcg    720

cctttcttca gccctgttca ggattggaac gtcgaccccc aggagccttt cattccctcc    780

aagctcagga tggtctctga tggtatcctg gtggctcttt cgacagtgat tggtcggccg    840

atcaagaacc tgctggcatc tgtcaagccg ctcaacattc tcaacatcgt gttgggctgc    900

gactggactt tttcgggcat agtcaacgcc ctaattcttc ttgctgaact ctttgacgtt    960

ttctggaccc cccctgatgt tactaactgg atgatctcta tttttggaga gtggcaggcc   1020

gaa                                                                 1023
```

<210> SEQ ID NO 69
<211> LENGTH: 341
<212> TYPE: PRT
<213> ORGANISM: Murine norovirus

<400> SEQUENCE: 69

```
Met Arg Met Ala Thr Pro Ser Ser Ala Ser Ser Val Arg Asn Thr Glu
1               5                   10                  15

Lys Arg Lys Asn Lys Lys Ala Ser Pro Lys Ala Ser Val Ser Phe Gly
            20                  25                  30

Ala Pro Ser Leu Leu Ser Ser Glu Ser Glu Asp Glu Ala Asn Tyr Met
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Asp Trp Glu Glu Arg Lys Lys Ser Glu Pro Trp
                85                  90                  95

Leu Arg Leu Asp Met Ser Asp Lys Ala Ile Phe Arg Arg Phe Pro His
            100                 105                 110

Leu Arg Pro Lys Glu Asp Lys Thr Gly Ala Pro Ser Cys Ala Glu Asp
        115                 120                 125

Ala Met Asp Ala Lys Glu Pro Val Val Gly Ser Ile Leu Glu Gln Asp
    130                 135                 140

Asp His Lys Phe Tyr His Tyr Ser Val Tyr Ile Gly Gly Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
```

-continued

```
225                 230                 235                 240

Pro Phe Phe Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Gly Cys Asp Trp Thr Phe
    290                 295                 300

Ser Gly Ile Val Asn Ala Leu Ile Leu Leu Ala Glu Leu Phe Asp Val
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 70
<211> LENGTH: 1023
<212> TYPE: DNA
<213> ORGANISM: Murine norovirus

<400> SEQUENCE: 70

```
atgaggatgg caacgccatc ttctgcgccc tctgtgcgca acacagagaa acgcaaaaac     60

aaaaaggctt catctaagac tagcgtctcc tttggagcgc ctagccttct ctcttcggag    120

agtgaagatg aagctgacta tttgacccct cctgagcagg aagctcagcc cggcaccctc    180

gcggcccttc acgccgacgg gccgcacgtc gggctccctg tgacacgaag tgatgcacgc    240

gtgctgatct tcaatgattg ggaggagagg aagaagtccg agccgtggct acggctggac    300

atgtctgata aggccatctt ccgccgcttt ccccacctgc ggcctaagga ggacaaggct    360

gacgcgccct cccatgcgga ggacgccatg gaagcaagag agcctgtggt gggatccatt    420

cttgagcagg atgaccacaa attctaccac tactctgtct acgttgggaa tggcatggtg    480

atgggcgtca acaaccctgg cgccgccgtc tgccaggccg tgatcgatgt agagaaactc    540

catttgtggt ggagaccagt ctgggaaccc cgccagcccc tcgacccggc tgagttgagg    600

aaatgtgtag gcatgactgt tccctacgtg gcaaccaccg tcaactgcta ccaagtctgc    660

tgctggattg ttggaatcaa ggacacttgg ctgaagaggg ccaagatctc tagggactcg    720

cccttctaca gccccgtcca ggactggaat gttgaccccc aggagccctt cattccatcc    780

aagctcagga tggtttctga tgccatcctg gttgccctct caacggtgat tggtcggccg    840

atcaagaacc tgctggcatc tgtgaagccc ctcaacattc tcaatattgt gttgagctgt    900

gactggactt tctcgggcat agtcaatgcc ctgatccttc ttgctgaact ctttgacatc    960

ttctggaccc cccccgatgt caccaactgg atgatctcca tctttgggga atggcaggcc   1020

gaa                                                                 1023
```

<210> SEQ ID NO 71
<211> LENGTH: 341
<212> TYPE: PRT
<213> ORGANISM: Murine norovirus

<400> SEQUENCE: 71

```
Met Arg Met Ala Thr Pro Ser Ser Ala Pro Ser Val Arg Asn Thr Glu
1               5                   10                  15

Lys Arg Lys Asn Lys Lys Ala Ser Ser Lys Thr Ser Val Ser Phe Gly
```

-continued

```
            20                  25                  30

Ala Pro Ser Leu Leu Ser Ser Glu Ser Glu Asp Glu Ala Asp Tyr Leu
        35                  40                  45

Thr Pro Pro Glu Gln Glu Ala Gln Pro Gly Thr Leu Ala Ala Leu His
    50                  55                  60

Ala Asp Gly Pro His Val Gly Leu Pro Val Thr Arg Ser Asp Ala Arg
65                  70                  75                  80

Val Leu Ile Phe Asn Asp Trp Glu Glu Arg Lys Lys Ser Glu Pro Trp
                85                  90                  95

Leu Arg Leu Asp Met Ser Asp Lys Ala Ile Phe Arg Arg Phe Pro His
            100                 105                 110

Leu Arg Pro Lys Glu Asp Lys Ala Asp Ala Pro Ser His Ala Glu Asp
        115                 120                 125

Ala Met Glu Ala Arg Glu Pro Val Val Gly Ser Ile Leu Glu Gln Asp
    130                 135                 140

Asp His Lys Phe Tyr His Tyr Ser Val Tyr Val Gly Asn Gly Met Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Ala Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340


<210> SEQ ID NO 72
<211> LENGTH: 1023
<212> TYPE: DNA
<213> ORGANISM: Murine norovirus

<400> SEQUENCE: 72

atgaggatgg caacgccatc ttctgcgccc tctgtgcgca acacagagaa acgcaaaaac      60

aaaaaggctt catctaagac tagcgtctcc tttggagcgc ctagccttct ctcttcggag     120

agtgaagatg aagctaacta tttgacccct cctgagcagg aagctcagcc cggcaccctt     180

gcggcccttc atgccgacgg gccgcacgcc gggctccctg tgacacgaag tgatgcacgc     240

gtgctgatct tcaatgattg ggaggagagg aagaagtccg agccgtggct acggctggac     300
```

```
atgtctgata aggccatctt ccgccgcttt ccccatctgc ggcctaagga agacaaggct    360

gacgcgccct cccatgcgga ggacgccatg gaagcaagag agcctgtggt gggatccatt    420

cttgagcagg atgaccacaa attctaccac tactctgtct acgttgggaa tggcatggtg    480

atgggcgtca acaaccctgg cgccgccgtc tgccaggccg tgatcgatgt agagaaactt    540

catctgtggt ggagaccagt ctgggaaccc cgccagcccc tcgacccggc tgagctgagg    600

aaatgtgtag gcatgactgt tccctacgtg gcaaccaccg tcaactgtta ccaagtctgc    660

tgctggattg ttggaatcaa ggacacctgg ctgaagaggg ccaagatctc tagggactcg    720

cccttctaca gccccgtcca ggactggaat gttgaccccc aggagccctt cattccatcc    780

aagctcagga tggtttctga tgccatcctg gttgccctct caacggtgat tggtcggccg    840

atcaagaacc tgctggcatc tgtgaagccc ctcaacattc tcaatatcgt gttgagctgt    900

gactggactt tctcgggcat agtcaatgcc ctgatccttc ttgctgaact ctttgacatc    960

ttctggaccc cccccgatgt caccaactgg atggtctcca tctttgggga atggcaggcc   1020

gaa                                                                 1023
```

<210> SEQ ID NO 73
<211> LENGTH: 341
<212> TYPE: PRT
<213> ORGANISM: Murine norovirus

<400> SEQUENCE: 73

```
Met Arg Met Ala Thr Pro Ser Ser Ala Pro Ser Val Arg Asn Thr Glu
1               5                   10                  15

Lys Arg Lys Asn Lys Lys Ala Ser Ser Lys Thr Ser Val Ser Phe Gly
            20                  25                  30

Ala Pro Ser Leu Leu Ser Ser Glu Ser Glu Asp Glu Ala Asn Tyr Leu
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Asp Trp Glu Glu Arg Lys Lys Ser Glu Pro Trp
                85                  90                  95

Leu Arg Leu Asp Met Ser Asp Lys Ala Ile Phe Arg Arg Phe Pro His
            100                 105                 110

Leu Arg Pro Lys Glu Asp Lys Ala Asp Ala Pro Ser His Ala Glu Asp
        115                 120                 125

Ala Met Glu Ala Arg Glu Pro Val Val Gly Ser Ile Leu Glu Gln Asp
    130                 135                 140

Asp His Lys Phe Tyr His Tyr Ser Val Tyr Val Gly Asn Gly Met Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240
```

-continued

```
Pro Phe Tyr Ser Pro Val Gln Asp Trp Asn Val Asp Pro Gln Glu Pro
                245                 250                 255

Phe Ile Pro Ser Lys Leu Arg Met Val Ser Asp Ala Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Val Ser Ile Phe Gly
                325                 330                 335

Glu Trp Gln Ala Glu
            340


<210> SEQ ID NO 74
<211> LENGTH: 1023
<212> TYPE: DNA
<213> ORGANISM: Murine norovirus

<400> SEQUENCE: 74

atgaggatgg caacgccatc ttctgcgccc tctgtgcgca acacagagaa acgcaaaaac      60

aaaaaggctt catctaaggc taacgtctcc tttggagcgc ctagccttct ctcttcggag     120

agtgaagatg aagctaacta tttgacccct cctgagcagg aagctcagcc cggcaccctt     180

gcggcccttc atgctgacgg gccgcacgcc gggctccctg tgacacgaag tgacgcacgc     240

gtgctgatct tcaatgattg ggaggagagg aagaagtccg agccgtggct acggctggac     300

atgtctgata aggccatctt ccgccgcttt ccccacctgc ggcctaagga agacaaggct     360

gacgcgccct cccatgcgga ggacgccatg gatgcaagag agcctgtggt gggatccatt     420

cttgaacagg atgatcacaa gttctaycac tactctgtct acattgggaa tggcatggtg     480

atgggcgtca acaaccctgg cgccgccgtc tgccaggccg tgatcgatgt agagaaactc     540

catttgtggt ggagaccagt ctgggaaccc ccccagcccc tcgacccggc tgagttgagg     600

aaatgtgtag gcatgactgt tccctacgtg gcaaccaccg tcaactgcta ccaagtttgc     660

tgctggattg ttgggatcaa ggacacctgg ctgaagaggg ccaagatctc taggaacttg     720

cccttctaca gccccgtcca ggattggaat gttgaccccc aggagccctt cattccatcc     780

aagctcagga tggtttctga tgccatcctg gttgccctct caacggtgat tggtcggccg     840

atcaagaacc tgctggcatc tgtgaagccc ctcaacattc tcaatatcgt gttgagctgt     900

gactggactt tctcgggtat agtcaatgcc ctgatccttc ttgctgagct ctttgacatc     960

ttctggaccc cccccgatgt caccaactgg atgatctcca tctttgggga atggcaggcc    1020

gaa                                                                  1023


<210> SEQ ID NO 75
<211> LENGTH: 341
<212> TYPE: PRT
<213> ORGANISM: Murine norovirus

<400> SEQUENCE: 75

Met Arg Met Ala Thr Pro Ser Ser Ala Pro Ser Val Arg Asn Thr Glu
1               5                   10                  15

Lys Arg Lys Asn Lys Lys Ala Ser Ser Lys Ala Asn Val Ser Phe Gly
            20                  25                  30
```

```
Ala Pro Ser Leu Leu Ser Ser Glu Ser Glu Asp Glu Ala Asn Tyr Leu
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Asp Trp Glu Glu Arg Lys Lys Ser Glu Pro Trp
                85                  90                  95

Leu Arg Leu Asp Met Ser Asp Lys Ala Ile Phe Arg Arg Phe Pro His
            100                 105                 110

Leu Arg Pro Lys Glu Asp Lys Ala Asp Ala Pro Ser His Ala Glu Asp
        115                 120                 125

Ala Met Asp Ala Arg Glu Pro Val Val Gly Ser Ile Leu Glu Gln Asp
    130                 135                 140

Asp His Lys Phe Tyr His Tyr Ser Val Tyr Ile Gly Asn Gly Met Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Pro Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asn Leu
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Ala Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340


<210> SEQ ID NO 76
<211> LENGTH: 1023
<212> TYPE: DNA
<213> ORGANISM: Murine norovirus

<400> SEQUENCE: 76

atgaggatgg caacgccatc ttctgcgtcc tctgtgcgca acacagagaa acgcaaaaac      60

aaaaaggctt catccagggc tagtgtctcc tttggagcac ctagccttct ctcttcggag     120

agtgaggatg aaaccaacta cttgacccct cctgagcagg aagctcagcc cggcaccctt     180

gcggcccttc acgcggatgg gccgcatgcc gggctccccg tgacccggag tgatgcacgc     240

gtgctgatct tcaatgagtg ggaggagagg aagaagtctg agccgtggct acggctagac     300
```

-continued

```
atgtctgaca aggccatctt tcgccgctat ccccacctgc aaccgaagga ggataaggcc    360

gacgcaccct ctcacgcgga ggatgccatg gatgcgaggg agcctgtggt ggggtccatc    420

ctcgagcagg atgaccataa gttctaccac tactctgtct acattggcaa tggccaggtg    480

atgggcgtca acaaccccgg cgccgcagtc tgccaggctg tgattgatgt ggagaagctc    540

cacctctggt ggaggccagt ctgggagccc cgccagcccc tcgatccggc tgagctgagg    600

aagtgcgtcg gcatgactgt cccgtacgtg gcgaccactg tcaactgtta tcaggtctgc    660

tgctggattg ttgggatcaa agacacttgg ctgaagaggg cgaagatcgc tagggactcg    720

cccttcttca gccctgtcca ggactggaac atcgatcccc aggagccctt cattccctct    780

aaacttagga tggtctctga tggcatcttg gtggctctcg caacggtgat tggtcggccg    840

atcaagaacc tgctggcatc cgtgaagccg ctcaacatct tgaacatcgt gttgggctgc    900

gactggactt tctcgggcat tgtcaacgcc ctgattctcc ttgctgagct ctttgacatc    960

ttctggacgc cccctgatgt cactaattgg atgatctcca tctttggaga gtggcaggct   1020

gag                                                                 1023
```

<210> SEQ ID NO 77
<211> LENGTH: 341
<212> TYPE: PRT
<213> ORGANISM: Murine norovirus

<400> SEQUENCE: 77

```
Met Arg Met Ala Thr Pro Ser Ser Ala Ser Ser Val Arg Asn Thr Glu
1               5                   10                  15

Lys Arg Lys Asn Lys Lys Ala Ser Ser Arg Ala Ser Val Ser Phe Gly
            20                  25                  30

Ala Pro Ser Leu Leu Ser Ser Glu Ser Glu Asp Glu Thr Asn Tyr Leu
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Gln Pro Lys Glu Asp Lys Ala Asp Ala Pro Ser His Ala Glu Asp
        115                 120                 125

Ala Met Asp Ala Arg Glu Pro Val Val Gly Ser Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ala Arg Asp Ser
225                 230                 235                 240
```

```
Pro Phe Phe Ser Pro Val Gln Asp Trp Asn Ile Asp Pro Gln Glu Pro
                245                 250                 255

Phe Ile Pro Ser Lys Leu Arg Met Val Ser Asp Gly Ile Leu Val Ala
            260                 265                 270

Leu Ala Thr Val Ile Gly Arg Pro Ile Lys Asn Leu Leu Ala Ser Val
        275                 280                 285

Lys Pro Leu Asn Ile Leu Asn Ile Val Leu Gly Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 78
<211> LENGTH: 1023
<212> TYPE: DNA
<213> ORGANISM: Murine norovirus

<400> SEQUENCE: 78

```
atgaggatgg caacgccatc ttctgcgccc tctgtgcgca acacagagaa acgcaaaaac      60

aagaaggctt cgtctaaggc tagtgtctcc tttggagcac ctagccctct ctcttcggag     120

agtgaagacg aagttaacta catgacccct cctgagcagg aagctcagcc cggcgccctt     180

gcggcccttc atgcggaagg gccgcttgcc gggctccccg tgacgcgtag tgatgcacgc     240

gtgctgatct tcaatgagtg ggaggagagg aagaagtccg agccgtggct acggctggac     300

atgtctgaca aggctatctt ccgccgctat ccccatctgc gacctaagga ggataagcct     360

gacgcgccct cccatgcgga ggacgctatg gatgccaagg agcccgtgat cggctctatt     420

ttggagcagg atgaccacaa gttctaccac tactctgtct acatcggtgg tggccttgtg     480

atgggagtca acaaccccgg tgctgcggtc tgccaggcaa cgatcgacgt ggagaagctg     540

cacctctggt ggcggcctgt ctgggagccc cgccaacccc ttgactcggc tgagttgagg     600

aagtgtgtgg gcatgaccgt cccctatgtg gccaccaccg tcaactgcta tcaagtttgt     660

tgctggattg ttggcatcaa ggatacttgg ctgaagaggg cgaagatctc tagagacctg     720

cccttctaca gccctgtcca ggactggaat gtcgaccccc aggagccctt tattccatcc     780

aagctcagga tggtgtcaga tggcatcctg gtggccttgt cgacagtgat tggccggcca     840

attaagaacc tgctggcctc ggtcaagccg ctcaacattc tcaacatcgt gctgagttgt     900

gattggacct tttcgggcat tgtcaacgcc ctgatcttgc tcgctgagct tttgacatc      960

ttttggaccc cccctgatgt gaccaactgg atgatctctg tctttgggga gtggcaggcc    1020

gaa                                                                  1023
```

<210> SEQ ID NO 79
<211> LENGTH: 341
<212> TYPE: PRT
<213> ORGANISM: Murine norovirus

<400> SEQUENCE: 79

```
Met Arg Met Ala Thr Pro Ser Ser Ala Pro Ser Val Arg Asn Thr Glu
1               5                   10                  15

Lys Arg Lys Asn Lys Lys Ala Ser Ser Lys Ala Ser Val Ser Phe Gly
            20                  25                  30
```

-continued

```
Ala Pro Ser Pro Leu Ser Ser Glu Ser Glu Asp Glu Val Asn Tyr Met
        35                  40                  45

Thr Pro Pro Glu Gln Glu Ala Gln Pro Gly Ala Leu Ala Ala Leu His
    50                  55                  60

Ala Glu Gly Pro Leu Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Pro Asp Ala Pro Ser His Ala Glu Asp
        115                 120                 125

Ala Met Asp Ala Lys Glu Pro Val Ile Gly Ser Ile Leu Glu Gln Asp
    130                 135                 140

Asp His Lys Phe Tyr His Tyr Ser Val Tyr Ile Gly Gly Gly Leu Val
145                 150                 155                 160

Met Gly Val Asn Asn Pro Gly Ala Ala Val Cys Gln Ala Thr Ile Asp
                165                 170                 175

Val Glu Lys Leu His Leu Trp Trp Arg Pro Val Trp Glu Pro Arg Gln
            180                 185                 190

Pro Leu Asp Ser Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Leu
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Val Phe Gly
                325                 330                 335

Glu Trp Gln Ala Glu
            340
```

<210> SEQ ID NO 80
<211> LENGTH: 1023
<212> TYPE: DNA
<213> ORGANISM: Murine norovirus

<400> SEQUENCE: 80

```
atgaggatgg caacgccatc ttctgcgccc tctgtgcgca acacagagaa acgcaaaaac      60

aaaaaggctt catctaaggt tggtgtctcc tttggagcgc ctagccctct cttttcagag     120

agtgaagatg aagctaacta tttgacccct cctgagcagg aagctcagcc cggcaccctc     180

gcggcccttc acgcagatgg gccgcatgcc gggctccccg tgacgcgaag tgatgcacgc     240

gtgctgatct tcaatgattg ggaggagagg aagaagtccg agccgtggct gcggctggac     300

atgtctgaca aggccatctt ccgccgcttt ccccatctgc ggcccaagga agacaaggcc     360
```

```
gacgcaccct cccatacgga ggatgccatg gatgcaaggg agcccgtggt gggatccatc    420

cttgagcaag acgaccataa gttttaccac tactctgtct acatcggcaa cggccaggtg    480

atgggtgtta acaaccccgg cgccgccgtc tgtcaggctg tgattgatgt ggagaaactc    540

cacctatggt ggaggccagt ctgggaaccc cgccaacccc tcgactcggc tgagttgagg    600

aagtgtattg gcatgaccgt tccttacgtg gcaaccactg tcaattgcta ccaggtctgc    660

tgctggattg tggggatcaa ggacacctgg ctgaagaggg cgaaaatctc gagggattcg    720

cccttttata gccccgtcca ggactggaac atcgatcccc aggaaccctt catcccctcc    780

aagctcagga tggtctctga tggcatccta gtggcccttt caacggtgat tggtcggccg    840

atcaagaacc ttctggcatc tgtgaagccg ctcaacatcc tcaacatcgt gttgagctgt    900

gattggactt tttctggcat agtcaatgcc ctaattcttc ttgctgagct ctttgacatc    960

ttttggaccc cccccgatgt caccaactgg atgatttcta tctttgggga gtggcaagcc   1020

gag                                                                 1023
```

<210> SEQ ID NO 81
<211> LENGTH: 341
<212> TYPE: PRT
<213> ORGANISM: Murine norovirus

<400> SEQUENCE: 81

```
Met Arg Met Ala Thr Pro Ser Ser Ala Pro Ser Val Arg Asn Thr Glu
1               5                   10                  15

Lys Arg Lys Asn Lys Lys Ala Ser Ser Lys Val Gly Val Ser Phe Gly
            20                  25                  30

Ala Pro Ser Pro Leu Phe Ser Glu Ser Glu Asp Glu Ala Asn Tyr Leu
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Asp Trp Glu Glu Arg Lys Lys Ser Glu Pro Trp
                85                  90                  95

Leu Arg Leu Asp Met Ser Asp Lys Ala Ile Phe Arg Arg Phe Pro His
            100                 105                 110

Leu Arg Pro Lys Glu Asp Lys Ala Asp Ala Pro Ser His Thr Glu Asp
        115                 120                 125

Ala Met Asp Ala Arg Glu Pro Val Val Gly Ser Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Ser Ala Glu Leu Arg Lys Cys Ile Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Ile Asp Pro Gln Glu Pro
```

-continued

```
            245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
            325                 330                 335

Glu Trp Gln Ala Glu
            340
```

<210> SEQ ID NO 82
<211> LENGTH: 1023
<212> TYPE: DNA
<213> ORGANISM: Murine norovirus

<400> SEQUENCE: 82

```
atgaggatgg caacgccatc ttctgcgtcc tctgtgcgca acacagagaa acgcaaaaac     60

aaaaagactt catctaaagc tagtgtctcc tttggagcac ctagccttct ctcttcggag    120

agtgaagatg aagttaacta catgacccct cctgagcagg aagctcagcc cggcaccctt    180

gcggcccttc acgccgatgg gccgcatgct gggctccccg tgacgcgaag tgatgcacgc    240

gtgctgatct tcaatgagtg ggaggagagg aagaagtccg agccgtggct acggctggac    300

atgtctgaca aggctatctt ccgccgctat ccccatctgc ggcccaagga ggataagccc    360

gacgcgccct cccatgcgga ggacgccatg gatgcaaggg agcctatggt ggggtccatt    420

cttgagcagg atgaccataa attctatcac tactctgtct acattggcaa tggccaggtg    480

atgggcgtca acaaccccgg cgccgccgtc tgccaggccg tgattgatgt ggagaagctc    540

cacctgtggt ggaggccagt ctgggaaccc cgccaacccc tcgactcggc tgagttaagg    600

aagtgtgttg gtatgactgt tccttacgtg gcgaccactg tcaactgcta tcaggtctgc    660

tgctggattg ttgggatcaa ggatacctgg ctgaagaggg cgaagatctc tagggactcg    720

cccttctaca gccctgtcca ggattggaac atcgaccccc aggagccttt catcccatcc    780

aagctcagga tggtctctga cggcatcttg gtggccctct caacggtgat tggtcggccg    840

atcaagaacc tgttggcgtc tgtgaagcca ctcaatattc tcaacatcgt attgagttgt    900

gactggactt tctcgggcat agtcaacgcc ctgattctcc ttgctgagct ctttgacatc    960

ttttggaccc ctcccgatgt caccaactgg atgatctcca tctttgggga atggcaggcc   1020

gaa                                                                 1023
```

<210> SEQ ID NO 83
<211> LENGTH: 341
<212> TYPE: PRT
<213> ORGANISM: Murine norovirus

<400> SEQUENCE: 83

```
Met Arg Met Ala Thr Pro Ser Ser Ala Ser Ser Val Arg Asn Thr Glu
1               5                   10                  15

Lys Arg Lys Asn Lys Lys Thr Ser Ser Lys Ala Ser Val Ser Phe Gly
            20                  25                  30

Ala Pro Ser Leu Leu Ser Ser Glu Ser Glu Asp Glu Val Asn Tyr Met
```

```
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Pro Asp Ala Pro Ser His Ala Glu Asp
        115                 120                 125

Ala Met Asp Ala Arg Glu Pro Met Val Gly Ser Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Ser Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Ile Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340


<210> SEQ ID NO 84
<211> LENGTH: 1023
<212> TYPE: DNA
<213> ORGANISM: Murine norovirus

<400> SEQUENCE: 84

atgaggatgg caacgccatc ttctgcgccc tctgtgcgca acacagagaa acgcaaaaac      60

aagaaggctt cgtctaaggc tagtgtctcc tttggagcac ctagccctct ctcttcggag     120

agtgaagacg aagttaacta catgacccct cctgagcagg aagctcagcc cggcgccctt     180

gcggcccttc atgcggaagg gccgcttgcc gggctccccg tgacgcgtag tgatgcacgc     240

gtgctgatct tcaatgagtg ggaggagagg aagaagtccg agccgtggct acggctggac     300

atgtctgaca aggctatctt ccgccgctat ccccatctgc gacctaagga ggataagcct     360
```

```
gacgcgccct cccatgcgga ggacgctatg gatgccaagg agcccgtgat cggctctatt    420

ttggagcagg atgaccacaa gttctaccac tactctgtct acatcggtgg tggccttgtg    480

atgggagtca acaaccccgg tgctgcggtc tgccaggcaa cgatcgacgt ggagaagctg    540

cacctctggt ggcggcctgt ctgggagccc cgccaacccc ttgactcggc tgagttgagg    600

aagtgtgtgg gcatgaccgt cccctatgtg gccaccaccg tcaactgcta tcaagtttgt    660

tgctggattg ttggcatcaa ggatacttgg ctgaagaggg cgaagatctc tagagacctg    720

cccttctaca gccctgtcca ggactggaat gtcgaccccc aggagccctt tattccatcc    780

aagctcagga tggtgtcaga tggcatcctg gtggccttgt cgacagtgat tggccggcca    840

attaagaacc tgctggcctc ggtcaagccg ctcaacattc tcaacatcgt gctgagttgt    900

gattggacct tttcgggcat tgtcaacgcc ctgatcttgc tcgctgagct tttgacatc    960

ttttggaccc cccctgatgt gaccaactgg atgatctctg tctttgggga gtggcaggcc   1020

gaa                                                                 1023
```

```
<210> SEQ ID NO 85
<211> LENGTH: 341
<212> TYPE: PRT
<213> ORGANISM: Murine norovirus

<400> SEQUENCE: 85

Met Arg Met Ala Thr Pro Ser Ser Ala Pro Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Pro Leu Ser Ser Glu Ser Glu Asp Glu Val Asn Tyr Met
        35                  40                  45

Thr Pro Pro Glu Gln Glu Ala Gln Pro Gly Ala Leu Ala Ala Leu His
    50                  55                  60

Ala Glu Gly Pro Leu Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Pro Asp Ala Pro Ser His Ala Glu Asp
        115                 120                 125

Ala Met Asp Ala Lys Glu Pro Val Ile Gly Ser Ile Leu Glu Gln Asp
    130                 135                 140

Asp His Lys Phe Tyr His Tyr Ser Val Tyr Ile Gly Gly Gly Leu Val
145                 150                 155                 160

Met Gly Val Asn Asn Pro Gly Ala Ala Val Cys Gln Ala Thr Ile Asp
                165                 170                 175

Val Glu Lys Leu His Leu Trp Trp Arg Pro Val Trp Glu Pro Arg Gln
            180                 185                 190

Pro Leu Asp Ser Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Leu
225                 230                 235                 240

Pro Phe Tyr Ser Pro Val Gln Asp Trp Asn Val Asp Pro Gln Glu Pro
                245                 250                 255
```

```
Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Val Phe Gly
                325                 330                 335

Glu Trp Gln Ala Glu
            340


<210> SEQ ID NO 86
<211> LENGTH: 1023
<212> TYPE: DNA
<213> ORGANISM: Murine norovirus

<400> SEQUENCE: 86

atgaggatgg caacgccatc ttctgcgtcc tctgtgcgca acacagagaa acgcaagaac      60

aaaaaggctt catccaaggc tagtgtctcc tttggagcac ctagccttct ctcttcggag     120

agtgaagatg aagttaacta catgacccct cctgagcagg aagctcagcc cggcacccctt    180

gcggcccttc acgctgatgg gccgcacacc gggctccccg tgacgcgaag tgatgcacgc     240

gtgctgatct tcaacgagtg ggaggagagg aagaagtccg agccgtggct acggctggac     300

atgtctgata aggccatctt ccgtcgctat ccccatctgc gacccaagga agataaggct     360

gacgcgccct cccacgcgga ggacgctatg gatgcaagag agcccgtagt gggatccatt     420

cttgaacagg atgaccataa attctaccac tactctgtct atatcggcaa cggcatggtg     480

atgggtgtta ataatcctgg tgccgccgtc tgccaggctg taattgatgt ggagaagctc     540

cacctgtggt ggaggccagt ttgggaacct cgccaacccc tcgacccggc tgagttgagg     600

aagtgtgttg gcatgaccgt cccttacgtg gcgaccactg tcaattgcta ccaggtctgc     660

tgctggattg ttgggattaa agatacctgg ctgaagagag cgaagatctc tagggactcg     720

cccttctaca gccctgtcca ggattggaat gtcgatcccc aggagccctt catcccgtcc     780

aagcttagga tggtttctga tggcatctta gtggctctct caacggtgat tggtcggcca     840

atcaaaaacc tattggcatc tgtgaagccg ctcaacattc tgaacatcgt cttgagctgt     900

gactggactt tttcgggcat agttaatgcc ctgatccttc ttgctgagct gtttgatatc     960

ttctggactc cccctgatgt caccaattgg atgatctcca tttttggaga atggcaggcc    1020

gaa                                                                  1023


<210> SEQ ID NO 87
<211> LENGTH: 341
<212> TYPE: PRT
<213> ORGANISM: Murine norovirus

<400> SEQUENCE: 87

Met Arg Met Ala Thr Pro Ser Ser Ala Ser Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Val Asn Tyr Met
        35                  40                  45
```

```
Thr Pro Pro Glu Gln Glu Ala Gln Pro Gly Thr Leu Ala Ala Leu His
    50                  55                  60

Ala Asp Gly Pro His Thr Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Ala Asp Ala Pro Ser His Ala Glu Asp
        115                 120                 125

Ala Met Asp Ala Arg Glu Pro Val Val Gly Ser Ile Leu Glu Gln Asp
    130                 135                 140

Asp His Lys Phe Tyr His Tyr Ser Val Tyr Ile Gly Asn Gly Met Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 88
<211> LENGTH: 1023
<212> TYPE: DNA
<213> ORGANISM: Murine norovirus

<400> SEQUENCE: 88

```
atgaggatgg caacgccatc ttctgcgtcc tctgtgcgca acacagagaa acgcaaaaat      60

aaaaaggctt catctaaagc tagtgtctcc tttggagcac ctagcattct ctcttcggag     120

agtgaagatg aagttaacta tttgacccct cctgagcagg aagctcagcc cggcaccctt     180

gcggcccttc acgctgatgg gccgcacgcc gggctccccg tgacgcgaag tgacgcacgc     240

gtgctgatct tcaatgagtg ggaggagagg aagaagtccg agccgtggct acggctggac     300

atgtctgata aggccatctt ccgtcgctac ccccacctgc gacccaagga agataagact     360

gacgcgccct cccatgcgga ggacgccatg gatgcaaagg agcctgcagt ggggtccatt     420
```

```
cttgagcagg atgaccacaa gttctaccat tactctgtct acatcggcaa cggcatggtg    480

atgggtgtca acaatcctgg cgccgccgtc tgccaggctg tgattgatgt ggagaagctc    540

cacctatggt ggaggccagt ttgggaacct cgccaacctc tcgacccggc tgagttgagg    600

aagtgtgttg gcatgaccgt cccttacgtg gcaactactg tcaattgcta ccaagtctgc    660

tgctggattg ttgggattaa agacacttgg ctgaagaggg cgaagatctc tagggactcg    720

cccttctaca gccccgtcca ggattggaac gttgatcccc aggagccctt cattccatcc    780

aagctcagga tggtttctga tggcatctta gttgctctct caacggtgat tggtcggccg    840

atcaagaacc tattggcatc tgtgaaaccg ctcaacattc tgaacatcgt gttgagctgt    900

gactggacct tctcgggcat agttaatgcc ctgatccttc ttgctgagct gtttgatatc    960

ttctggaccc ctcctgacgt caccaactgg atgatctcca tctttggaga gtggcaggcc   1020

gaa                                                                 1023
```

<210> SEQ ID NO 89
<211> LENGTH: 341
<212> TYPE: PRT
<213> ORGANISM: Murine norovirus

<400> SEQUENCE: 89

```
Met Arg Met Ala Thr Pro Ser Ser Ala Ser Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Ile Leu Ser Ser Glu Ser Glu Asp Glu Val Asn Tyr Leu
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Thr Asp Ala Pro Ser His Ala Glu Asp
        115                 120                 125

Ala Met Asp Ala Lys Glu Pro Ala Val Gly Ser Ile Leu Glu Gln Asp
    130                 135                 140

Asp His Lys Phe Tyr His Tyr Ser Val Tyr Ile Gly Asn Gly Met Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Val Asp Pro Gln Glu Pro
                245                 250                 255
```

```
Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340


<210> SEQ ID NO 90
<211> LENGTH: 1023
<212> TYPE: DNA
<213> ORGANISM: Murine norovirus

<400> SEQUENCE: 90

atgaggatgg caacgccatc ttctgcgtcc tctgtgcgca acacagagaa acgcaaaagt      60

aaaaaggctt catctaaagc tagtgtctcc tttggagcac ctagccctct ctcttcggag     120

agtgaagatg aagttaacta tttgacccct cctgagcagg aagctcagcc cggcaccctt     180

gcggcccttc atgctgatgg gccgcacgcc gggctccccg tgacgcgagg tgatgcacgc     240

gtgctgatct tcaatgaatg ggaggagagg aagaagtccg agccgtggct acggctggac     300

atgtctgata aggccatctt ccgtcgctac ccccacctgc gacccaagga agataaggct     360

gatgcgccct ctcatgcgga ggacgccatg gatgcaaagg agcccgcagt ggggtccatt     420

cttgaacagg atgaccacaa gttctaccac tactctgtct acatcggcaa cggcatggtg     480

atgggtgtca acaatcctgg cgccgccgtc tgccaggctg tgattgatgt ggagaagctc     540

cacctatggt ggaggccagt ttgggaacct cgccaacctc tcgacccggc tgagttgagg     600

aagtgtgttg gcatgactgt cccttacgtg gcgactaccg tcaattgcta ccaagtctgc     660

tgctggattg ttgggattaa agacacttgg ccgaagaggg cgaagatctc tagggactcg     720

cccttctaca gccccgccca ggattggaac gttgaccccc aagagccctt cattccgtcc     780

aagctcagga tggtttctga tggcatcttg gtggctctct caacggtgat tggtcggccg     840

atcaagaacc tattggcatc tgtgaaaccg cttaacattc tgaacatcgt gttgagctgt     900

gactggacct tctcgggcat agtcaatgcc ctgatccttc ttgctgagct gtttgatatc     960

ttctggaccc ctcctgacgt caccaactgg atgatctcca tctttggaga gtggcaggcc    1020

gaa                                                                  1023


<210> SEQ ID NO 91
<211> LENGTH: 341
<212> TYPE: PRT
<213> ORGANISM: Murine norovirus

<400> SEQUENCE: 91

Met Arg Met Ala Thr Pro Ser Ser Ala Ser Ser Val Arg Asn Thr Glu
1               5                   10                  15

Lys Arg Lys Ser Lys Lys Ala Ser Ser Lys Ala Ser Val Ser Phe Gly
            20                  25                  30

Ala Pro Ser Pro Leu Ser Ser Glu Ser Glu Asp Glu Val Asn Tyr Leu
        35                  40                  45
```

```
Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Gly Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Ala Asp Ala Pro Ser His Ala Glu Asp
        115                 120                 125

Ala Met Asp Ala Lys Glu Pro Ala Val Gly Ser Ile Leu Glu Gln Asp
    130                 135                 140

Asp His Lys Phe Tyr His Tyr Ser Val Tyr Ile Gly Asn Gly Met Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Pro Lys Arg Ala Lys Ile Ser Arg Asp Ser
225                 230                 235                 240

Pro Phe Tyr Ser Pro Ala Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 92
<211> LENGTH: 1023
<212> TYPE: DNA
<213> ORGANISM: Murine norovirus

<400> SEQUENCE: 92

```
atgaggatgg caacgccatc ttctgcgtcc tctgtgcgca acacagagaa acgcaaaaat     60

aaaaaggctt catctaaagc tagtgtctcc tttggagcac ctagccttct ctcttcggag    120

agtgaagatg aagttaacta tttgacccct cctgagcagg aagctcagcc cggcaccctt    180

gcggcccttc acgctgatgg gccgcacgcc gggctccccg tgacgcgagg tgatgcacgc    240

gtgctgatct tcaatgaatg ggaggagagg aagaagtccg agccgtggct acggctggac    300

atgtctgata aggccatctt ccgtcgctac ccccacctgc gacccaagga agataaggct    360

gacgcgccct ctcatgcgga ggacgccatg gatgtaaagg agcccgcagt ggggtccatt    420
```

```
cttgaacagg atgaccacaa gttctaccat tactctgtct acatcggcaa cggcatggtg    480

atgggtgtca ataatcctgg cgccgccgtc tgccaggctg tgattgatgt ggagaagctt    540

cacctatggt ggaggccagt ttgggaacct cgccaacctc tcgacccggc tgagttgagg    600

aagtgtgttg gcatgaccgt cccttacgtg gcgactactg tcaactgcta ccaagtctgc    660

tgctggattg ttgggattaa agacacttgg ctgaagaggg cgaagatctc tagggactcg    720

cccttctaca gccccgtcca ggattggaac gttgaccccc aagagccctt cattccgtcc    780

aagctcagga tggtttctga tggcatctta gtggttctct caacggtgat tggtcggccg    840

atcaagaacc tattggcatc tgtgaaaccg ctcaacattc tgaacatcgt gttgagctgt    900

gactggacct tctcgggcat agtcaatgcc ctgatccttc ttgctgagct gtttgatatc    960

ttctggaccc ctcctgacgt caccaactgg atgatctcca tctttggaga gtggcaggcc   1020

gaa                                                                 1023
```

```
<210> SEQ ID NO 93
<211> LENGTH: 341
<212> TYPE: PRT
<213> ORGANISM: Murine norovirus

<400> SEQUENCE: 93

Met Arg Met Ala Thr Pro Ser Ser Ala Ser Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Val Asn Tyr Leu
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Gly Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Ala Asp Ala Pro Ser His Ala Glu Asp
        115                 120                 125

Ala Met Asp Val Lys Glu Pro Ala Val Gly Ser Ile Leu Glu Gln Asp
    130                 135                 140

Asp His Lys Phe Tyr His Tyr Ser Val Tyr Ile Gly Asn Gly Met Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Val
```

```
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 94
<211> LENGTH: 1023
<212> TYPE: DNA
<213> ORGANISM: Murine norovirus

<400> SEQUENCE: 94

```
atgaggatgg caacgccatc ttctgcgtcc tctgtgcgca acacagagaa acgcaaaagt      60

aaaaaggctt catctaaagc tagtgtctcc tttggagcac ctagccttct ctcttcggag     120

agtgaagatg aagttaacta tttgacccct cctgagcagg aagctcagcc cggcaccctt     180

gcggcccttc acgctgatgg gccgcacgcc gggctccccg tgacgcgagg tgatgcacgc     240

gtgctgatct tcaatgaatg ggaggagagg aagaagtccg agccgtggct acggctggac     300

atgtctgata aggccatctt ccgtcgctac ccccacctgc gacccaagga agataaggct     360

gatgcgccct ctcatgcgga ggacgccatg gatgcaaagg agcccacagt ggggtccatt     420

cttgaacagg atgaccacaa gttctaccat tactctgtct acatcggcaa cggcatggtg     480

atgggtgtca acaatcctgg cgccgccgtc tgccaggctg tgattgatgt ggagaagctc     540

cacctatggt ggaggccagt ttgggaacct cgccaacctc tcgacccggc tgagttgagg     600

aagtgtgttg gcatgactgt cccttacgtg gcgactaccg tcaattgcta ccaagtctgc     660

tgctggattg ttgggattaa agacacttgg ccgaagaggg cgaagatctc tagggacttg     720

cccttctaca gccccgccca ggattggaac gttgaccccc aagagccctt cattccgtcc     780

aagctcagga tggtttctga tggcatcttg gtggctctct caacggtgat tggtcggccg     840

atcaagaacc tattggcatc tgtgaaaccg cttaacattc tgaacatcgt gttgagctgt     900

gactggacct tctcgggcat agtcaatgcc ctgatccttc ttgctgagct gtttgatatc     960

ttctggaccc ctcctgacgt caccaactgg atgatctcca tctttggaga gtggcaggcc    1020

gaa                                                                  1023
```

<210> SEQ ID NO 95
<211> LENGTH: 341
<212> TYPE: PRT
<213> ORGANISM: Murine norovirus

<400> SEQUENCE: 95

```
Met Arg Met Ala Thr Pro Ser Ser Ala Ser Ser Val Arg Asn Thr Glu
1               5                   10                  15

Lys Arg Lys Ser Lys Lys Ala Ser Ser Lys Ala Ser Val Ser Phe Gly
            20                  25                  30

Ala Pro Ser Leu Leu Ser Ser Glu Ser Glu Asp Glu Val Asn Tyr Leu
        35                  40                  45

Thr Pro Pro Glu Gln Glu Ala Gln Pro Gly Thr Leu Ala Ala Leu His
```

```
    50                  55                  60

Ala Asp Gly Pro His Ala Gly Leu Pro Val Thr Arg Gly Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Ala Asp Ala Pro Ser His Ala Glu Asp
        115                 120                 125

Ala Met Asp Ala Lys Glu Pro Thr Val Gly Ser Ile Leu Glu Gln Asp
    130                 135                 140

Asp His Lys Phe Tyr His Tyr Ser Val Tyr Ile Gly Asn Gly Met Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Pro Lys Arg Ala Lys Ile Ser Arg Asp Leu
225                 230                 235                 240

Pro Phe Tyr Ser Pro Ala Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340


<210> SEQ ID NO 96
<211> LENGTH: 1023
<212> TYPE: DNA
<213> ORGANISM: Murine norovirus

<400> SEQUENCE: 96

atgaggatgg caacgccatc ttctgcgtcc tctgtgcgca atacagagaa acgcaaaagt     60

aaaaaggctt catctaaagc tagtgtctcc tttggagcac ctagccttct ctcttcggag    120

agtgaagatg aagttaacta tttgacccct cctgagcagg aagctcagcc cggcgccctt    180

gcggcccttc acgctgatgg gccgcacgcc gggctccccg tgacgcgagg tgatgcacgc    240

gtgctgatct tcaatgaatg ggaggagagg aagaagtccg agccgtggct acggctggac    300

atgtctgata aggccatctt ccgtcgctac ccccacctgc gacccaagga agataaggct    360

gatgcgccct ctcatgcgga ggacgccatg gatgcaaagg agcccgtagt ggggtccatt    420

cttgaacagg atgaccacaa gttctaccat tactctgtct acatcggcaa cggcatggtg    480
```

```
atgggtgtca acaatcctgg cgccgccgtc tgccaggctg tgattgatgt ggagaagctc    540

cacctatggt ggaggccagt ttgggaacct cgccaacctc tcgacccggc tgagttgagg    600

aagtgtgttg gcatgactgt cccttacgtg gcgactaccg tcaattgcta ccaagtctgc    660

tgctggattg ttgggattaa agacacttgg ctgaagaggg cgaagatctc tagggactcg    720

cccttctaca gccccgccca ggattggaac gttgaccccc aagagccctt cattccgtcc    780

aagctcagga tggtttctga tggcatcttg gtggctctct caacggtgat tggtcggccg    840

atcaagaacc tattggcatc tgtgaaaccg cttaacattc tgaacatcgt gttgagctgt    900

gactggacct tctcgggcat agtcaatgcc ctgatccttc ttgctgagct gtttgatatc    960

ttctggaccc ctcctgacgt caccaactgg atgatctcca tctttggaga gtggcaggcc   1020

gaa                                                                 1023
```

```
<210> SEQ ID NO 97
<211> LENGTH: 341
<212> TYPE: PRT
<213> ORGANISM: Murine norovirus

<400> SEQUENCE: 97

Met Arg Met Ala Thr Pro Ser Ser Ala Ser Ser Val Arg Asn Thr Glu
1               5                   10                  15

Lys Arg Lys Ser Lys Lys Ala Ser Ser Lys Ala Ser Val Ser Phe Gly
            20                  25                  30

Ala Pro Ser Leu Leu Ser Ser Glu Ser Glu Asp Glu Val Asn Tyr Leu
        35                  40                  45

Thr Pro Pro Glu Gln Glu Ala Gln Pro Gly Ala Leu Ala Ala Leu His
    50                  55                  60

Ala Asp Gly Pro His Ala Gly Leu Pro Val Thr Arg Gly Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Ala Asp Ala Pro Ser His Ala Glu Asp
        115                 120                 125

Ala Met Asp Ala Lys Glu Pro Val Val Gly Ser Ile Leu Glu Gln Asp
    130                 135                 140

Asp His Lys Phe Tyr His Tyr Ser Val Tyr Ile Gly Asn Gly Met Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Ala Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270
```

```
Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 98
<211> LENGTH: 1023
<212> TYPE: DNA
<213> ORGANISM: Murine norovirus

<400> SEQUENCE: 98

```
atgaggatgg caacgccatc ttctgcgtcc tctgtgcgca acacagagaa acgcaaaagc      60

aaaaaggctt catctaaaac tagtgtctcc tttggagcac ctagccttct ctcttcggag     120

agtgaagatg aagttaacta tttgacccct cctgagcagg aagctcagcc cggcaccctt     180

gcggcccttc acgctgatgg gccgcacgcc gggctccccg tgacgcgagg tgatgcacgc     240

gtgctgatct tcaatgaatg ggaggagagg aagaagtccg agccgtggct acggctggac     300

atgtctgata aggccatctt ccgtcgctac ccccacctgc gacccaagga agataaggct     360

gatgcgccct ctcatgcgga ggacgccatg gatgcaaagg agcccgtagt ggggtccatt     420

cttgaacagg atgaccacaa gttctaccat tactctgtct acatcggcaa cggcatggtg     480

atgggtgtca acaatcctgg cgccgccgtc tgccaggctg tgattgatgt ggagaagctc     540

cacctatggt ggaggccagt ttgggaacct cgccaacctc tcgacccggc tgagttgagg     600

aagtgcgttg gcatgactgt ccccttacgtg gcgactaccg tcaattgcta ccaagtctgc     660

tgctggattg ttgggattaa agacacttgg ctgaagaggg cgaagatctc tagggactcg     720

cccttctaca gccccgccca ggattggaac gttgaccccc aagagccctt cattccgtcc     780

aagctcagga tggtttctga tggcatcttg gtggctctct caacggtgat tggtcggccg     840

atcaagaacc tattggcatc tgtgaaaccg cttaacattc tgaacatcgt gttgagctgt     900

gactggacct tctcgggcat agtcaatgcc ctgatccttc ttgctgagct gtttgatatc     960

ttctggaccc ctcctgacgt caccaactgg atgatctcca tctttggaga gtggcaggcc    1020

gaa                                                                  1023
```

<210> SEQ ID NO 99
<211> LENGTH: 341
<212> TYPE: PRT
<213> ORGANISM: Murine norovirus

<400> SEQUENCE: 99

```
Met Arg Met Ala Thr Pro Ser Ser Ala Ser Ser Val Arg Asn Thr Glu
1               5                   10                  15

Lys Arg Lys Ser Lys Lys Ala Ser Ser Lys Thr Ser Val Ser Phe Gly
            20                  25                  30

Ala Pro Ser Leu Leu Ser Ser Glu Ser Glu Asp Glu Val Asn Tyr Leu
        35                  40                  45

Thr Pro Pro Glu Gln Glu Ala Gln Pro Gly Thr Leu Ala Ala Leu His
    50                  55                  60
```

-continued

```
Ala Asp Gly Pro His Ala Gly Leu Pro Val Thr Arg Gly Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Ala Asp Ala Pro Ser His Ala Glu Asp
        115                 120                 125

Ala Met Asp Ala Lys Glu Pro Val Val Gly Ser Ile Leu Glu Gln Asp
    130                 135                 140

Asp His Lys Phe Tyr His Tyr Ser Val Tyr Ile Gly Asn Gly Met Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Ala Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 100
<211> LENGTH: 1023
<212> TYPE: DNA
<213> ORGANISM: Murine norovirus

<400> SEQUENCE: 100

```
atgaggatgg caacgccatc ttctgcgtcc tctgtgcgca acacagagaa acgcaagaac      60

aaaaaggctt catctaaggc tagtgtctcc tttggagcac ctagccttct ctcttcggag     120

agtgaagatg aagttaatta catgacccct cctgagcagg aagctcagcc cggcaccctt     180

gcggcccttc atgctgatgg gccgcacgcc gggctccccg tgacgcgaag tgatgcacgc     240

gtgctgatct tcaatgagtg ggaggagagg aagaaatccg agccgtggct acggctggac     300

atgtctgata aggctatctt ccgtcgctac ccccacctgc gacccaggga agacaaggct     360

gacgcgcccc cccatgcgga ggacgctatg gatgcaaggg agcccgtagt gggatccatt     420

cttgaacagg atgaccataa gttctaccac tactctgtct atatcggcaa cggcatggtg     480
```

```
atgggtgtta ataatcctgg tgccgccgtc tgccaggctg taattgatgt ggagaagctc    540

cacctatggt ggaggccagt ctgggaacct cgccaacccc tcgacccggc tgatttgaga    600

aagtgtgttg gcatgaccgt cccttacgtg gcgaccactg tcaattgcta ccaggtctgc    660

tgctggattg ttgggattaa agacacctgg ctgaagaggg cgaagatctc tagggactcg    720

cccttctaca gccctgtcca ggactggaat gttgaccccc aggagccctt catcccgtcc    780

aagcttagga tggtttccga tggcatctta gtggctctct caacggtgat tggtcggccg    840

atcaagaacc tactggcatc tgtgaaaccg ctcaacattt tgaacatcgt gttgagctgt    900

gactggactt tttcgggcat agttaatgcc ctgatccttc ttgctgagct gtttgatatc    960

ttctggactc cccctgatgt caccaactgg atgatctcca tttttggaga atggcaggcc   1020

gaa                                                                 1023
```

```
<210> SEQ ID NO 101
<211> LENGTH: 341
<212> TYPE: PRT
<213> ORGANISM: Murine norovirus

<400> SEQUENCE: 101

Met Arg Met Ala Thr Pro Ser Ser Ala Ser Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Val Asn Tyr Met
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Arg Glu Asp Lys Ala Asp Ala Pro Pro His Ala Glu Asp
        115                 120                 125

Ala Met Asp Ala Arg Glu Pro Val Val Gly Ser Ile Leu Glu Gln Asp
    130                 135                 140

Asp His Lys Phe Tyr His Tyr Ser Val Tyr Ile Gly Asn Gly Met Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Asp Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270
```

```
Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340


<210> SEQ ID NO 102
<211> LENGTH: 1023
<212> TYPE: DNA
<213> ORGANISM: Murine norovirus

<400> SEQUENCE: 102

atgaggatgg caacgccatc ttctgcgtcc cctgtgcgca acacagagaa acgcaaaaat      60

aagaaaaaga cttcatctaa agctagtgtc tcctttggag cacctagcct tccctcttcg     120

gagagtgaag atgaagttaa ctatttgacc cctcctgagc aggaagctca gcccggcacc     180

cttgcggccc ttcacgctga tggccgcac gccgggctcc ccgtgacgcg aggtgatgca      240

cgcgtgctga tcttcaatga atgggaggag aggaaggagt ccgagccgtg gctacggctg     300

gacatgtctg ataaggccat cttccgtcgc tatccccacc tgcgacccaa ggaagacaag     360

gctgacgcgc cctctcatgc ggaggacgcc atggatgcaa aggagcccgt agtggggtcc     420

attcttgaac aggatgacca caagttctac cactactctg tctacatcgg caacggcatg     480

gtgatgggtg tcaataatcc tggcgccgcc gtctgccagg ctgtgattga tgtggagaag     540

ctccacctat ggtggaggcc agtttgggaa cctcgccaac ccctcgaccc ggctgagttg     600

aggaagtgtg ttggcatgac cgtcccttac gtggcaacta ctgtcaattg ctaccaagtc     660

tgctgctgga ttgttgggat taaagacact tggctgaaga gggcgaagat ctctagggac     720

tcgcccttct acagccccgt ccaggattgg aacgttgacc cccaggagcc cttcattccg     780

tccaagctta ggatggtttc tgatggcatc ttagtggctc tctcaatggt gattggtcgg     840

ccgatcaaga acctattggc atctgtgaaa ccgctcaaca ttctgaacat cgtgttgagc     900

tgtgactgga ctttctcggg catagtcaat gccctgatcc ttctcgctga gctgtttgat     960

atcttctgga cccctcctga cgtcaccaac tggatgatct ccatctttgg agagtggcag    1020

gcc                                                                  1023


<210> SEQ ID NO 103
<211> LENGTH: 341
<212> TYPE: PRT
<213> ORGANISM: Murine norovirus

<400> SEQUENCE: 103

Met Arg Met Ala Thr Pro Ser Ser Ala Ser Pro Val Arg Asn Thr Glu
1               5                   10                  15

Lys Arg Lys Asn Lys Lys Lys Thr Ser Ser Lys Ala Ser Val Ser Phe
            20                  25                  30

Gly Ala Pro Ser Leu Pro Ser Ser Glu Ser Glu Asp Glu Val Asn Tyr
        35                  40                  45

Leu Thr Pro Pro Glu Gln Glu Ala Gln Pro Gly Thr Leu Ala Ala Leu
    50                  55                  60
```

-continued

```
His Ala Asp Gly Pro His Ala Gly Leu Pro Val Thr Arg Gly Asp Ala
65                  70                  75                  80

Arg Val Leu Ile Phe Asn Glu Trp Glu Glu Arg Lys Glu Ser Glu Pro
                85                  90                  95

Trp Leu Arg Leu Asp Met Ser Asp Lys Ala Ile Phe Arg Arg Tyr Pro
            100                 105                 110

His Leu Arg Pro Lys Glu Asp Lys Ala Asp Ala Pro Ser His Ala Glu
        115                 120                 125

Asp Ala Met Asp Ala Lys Glu Pro Val Val Gly Ser Ile Leu Glu Gln
    130                 135                 140

Asp Asp His Lys Phe Tyr His Tyr Ser Val Tyr Ile Gly Asn Gly Met
145                 150                 155                 160

Val Met Gly Val Asn Asn Pro Gly Ala Ala Val Cys Gln Ala Val Ile
                165                 170                 175

Asp Val Glu Lys Leu His Leu Trp Trp Arg Pro Val Trp Glu Pro Arg
            180                 185                 190

Gln Pro Leu Asp Pro Ala Glu Leu Arg Lys Cys Val Gly Met Thr Val
        195                 200                 205

Pro Tyr Val Ala Thr Thr Val Asn Cys Tyr Gln Val Cys Cys Trp Ile
    210                 215                 220

Val Gly Ile Lys Asp Thr Trp Leu Lys Arg Ala Lys Ile Ser Arg Asp
225                 230                 235                 240

Ser Pro Phe Tyr Ser Pro Val Gln Asp Trp Asn Val Asp Pro Gln Glu
                245                 250                 255

Pro Phe Ile Pro Ser Lys Leu Arg Met Val Ser Asp Gly Ile Leu Val
            260                 265                 270

Ala Leu Ser Met Val Ile Gly Arg Pro Ile Lys Asn Leu Leu Ala Ser
        275                 280                 285

Val Lys Pro Leu Asn Ile Leu Asn Ile Val Leu Ser Cys Asp Trp Thr
    290                 295                 300

Phe Ser Gly Ile Val Asn Ala Leu Ile Leu Leu Ala Glu Leu Phe Asp
305                 310                 315                 320

Ile Phe Trp Thr Pro Pro Asp Val Thr Asn Trp Met Ile Ser Ile Phe
                325                 330                 335

Gly Glu Trp Gln Ala
            340
```

<210> SEQ ID NO 104
<211> LENGTH: 1023
<212> TYPE: DNA
<213> ORGANISM: Murine norovirus

<400> SEQUENCE: 104

```
atgaggatgg caacgccatc ttctgcgtcc tctgtgcgca acacagagaa acgcaaaaac      60

aaaaagactt catctaaggc tagtgtctcc tttggagcac ctagcttact ctcttcggag     120

agtgaagatg aagttaacta catgacccct cctgagcagg aagctcagcc cggtaccctt     180

gcggcccttc acgccgacgg gccgcacgcc gggctccccg tgacgcggag tgatgcacgc     240

gtgctgatct tcaatgagtg ggaggagagg aagaagtccg agccgtggct acggctggac     300

atgtctgata aggccatctt ccgccgctac ccccatctgc ggcctaagga agacaagccc     360

gatgcgccct cccatgcgga ggacgccatg gatgcaaggg agcccgtggt gggatccatt     420

cttgagcagg atgaccataa gttctaccac tactctgtct acatcggcaa cggtatggtg     480

atgggtgtca acaacccggg tgccgccgtg tgtcaggccg tgattgatgt ggagaaactc     540
```

```
cacctctggt ggaggccagt ctgggagcct cgtcaacccc tcgactcggc tgagttgagg    600

aagtgcatcg gcatgaccgt cccctacgtg gcgaccactg tcaactgcta ccaggtctgc    660

tgctggattg ttgggatcaa ggatacctgg ctgaagaggg cgaagatctc cagggactcg    720

cctttctaca gccctgtgca agactggaat gttgaccccc aggagccctt tatcccatcc    780

aagcttagga tggtgtctga tggcattctg gtggctctat caacggtgat tggtcggccg    840

atcaagaacc tactggcatc tgtcaagccg ctcaacattc ttaacatcgt gttgagctgt    900

gactggactt tttcgggcat agtcaacgcc ctgattctac ttgctgagct ctttgacatc    960

ttctggaccc ctcccgatgt caccaactgg atgatttcca tctttggaga gtggcaggcc   1020

gaa                                                                 1023
```

<210> SEQ ID NO 105
<211> LENGTH: 341
<212> TYPE: PRT
<213> ORGANISM: Murine norovirus

<400> SEQUENCE: 105

```
Met Arg Met Ala Thr Pro Ser Ser Ala Ser Ser Val Arg Asn Thr Glu
1               5                   10                  15

Lys Arg Lys Asn Lys Lys Thr Ser Ser Lys Ala Ser Val Ser Phe Gly
            20                  25                  30

Ala Pro Ser Leu Leu Ser Ser Glu Ser Glu Asp Glu Val Asn Tyr Met
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Glu Trp Glu Glu Arg Lys Lys Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Pro Asp Ala Pro Ser His Ala Glu Asp
        115                 120                 125

Ala Met Asp Ala Arg Glu Pro Val Val Gly Ser Ile Leu Glu Gln Asp
    130                 135                 140

Asp His Lys Phe Tyr His Tyr Ser Val Tyr Ile Gly Asn Gly Met Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Ser Ala Glu Leu Arg Lys Cys Ile Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
```

```
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Ile
305                 310                 315                 320

Phe Trp Thr Pro Pro Asp Val Thr Asn Trp Met Ile Ser Ile Phe Gly
                325                 330                 335

Glu Trp Gln Ala Glu
            340
```

```
<210> SEQ ID NO 106
<211> LENGTH: 1023
<212> TYPE: DNA
<213> ORGANISM: Murine norovirus

<400> SEQUENCE: 106

atgaggatgg caacgccatc ttctgcgtcc tctgtgcgca acacagagaa acgcaaaaac      60

aaaaagactt catctaaagc tagtgtctcc tttggagcac ctagccttct ctcttcggag     120

agtgaagatg aagttaatta tatgacccct cctgagcagg aagctcagcc cggcacgctt     180

gcggcccttc atgctgatgg gccgcacgcc gggctccccg tgacgcgaag tgatgcacgt     240

gtgctgatct tcaatgattg ggaggagagg aagaagtctg agccgtggct acggctggac     300

atgtctgaca aggctatctt ccgtcgcttc ccccatctgc gacccaagga agataagcct     360

gatgcgccct cccacgtgga ggacgccatg gatgcaaagg agcctgtggt ggggaccatc     420

cttgagcaag atgaccataa gttctaccac tactctgtct acattggtaa tggtcaggtg     480

atgggcgtca acaatcctgg cgccgccgtc tgccaggccg tgattgatgt ggagaagctc     540

cacctgtggt ggaggccagt ctgggagccc cgtcagcccc tcgacccggc tgagttgagg     600

aagtgcgttg gcatgactgt gtcctacgtg gcgaccaccg ttaactgcta ccaagtctgc     660

tgctggattg ttgggatcaa ggatacttgg ctgaagcgtg cgaagatctc cagggactcg     720

cccttctaca gccccgttca ggactggaat gttgatcccc aggagccctt catcccatcc     780

aagcttagga tggtgtctga tggcatcctg gtggccctct caacggtgat tggtcggccg     840

atcaagaacc tgctggcatc tgtgaaacca ctcaacattc ttaacatcgt gttgagctgt     900

gattggacct tctcgggcat agtcaacgcc ctgatcctcc ttgctgagct ctttgatgtc     960

ttctggacgc cccccgatgt caccaactgg atgatctcca tctttgggga gtggcaggcc    1020

gag                                                                  1023
```

```
<210> SEQ ID NO 107
<211> LENGTH: 341
<212> TYPE: PRT
<213> ORGANISM: Murine norovirus

<400> SEQUENCE: 107

Met Arg Met Ala Thr Pro Ser Ser Ala Ser Ser Val Arg Asn Thr Glu
1               5                   10                  15

Lys Arg Lys Asn Lys Lys Thr Ser Ser Lys Ala Ser Val Ser Phe Gly
            20                  25                  30

Ala Pro Ser Leu Leu Ser Ser Glu Ser Glu Asp Glu Val Asn Tyr Met
        35                  40                  45

Thr Pro Pro Glu Gln Glu Ala Gln Pro Gly Thr Leu Ala Ala Leu His
    50                  55                  60

Ala Asp Gly Pro His Ala Gly Leu Pro Val Thr Arg Ser Asp Ala Arg
```

```
65                  70                  75                  80

Val Leu Ile Phe Asn Asp Trp Glu Glu Arg Lys Lys Ser Glu Pro Trp
                85                  90                  95

Leu Arg Leu Asp Met Ser Asp Lys Ala Ile Phe Arg Arg Phe Pro His
            100                 105                 110

Leu Arg Pro Lys Glu Asp Lys Pro Asp Ala Pro Ser His Val Glu Asp
        115                 120                 125

Ala Met Asp Ala Lys Glu Pro Val Val Gly Thr Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Ser
        195                 200                 205

Tyr Val Ala Thr Thr Val Asn Cys Tyr Gln Val Cys Cys Trp Ile Val
    210                 215                 220

Gly Ile Lys Asp Thr Trp Leu Lys Arg Ala Lys Ile Ser Arg Asp Ser
225                 230                 235                 240

Pro Phe Tyr Ser Pro Val Gln Asp Trp Asn Val Asp Pro Gln Glu Pro
                245                 250                 255

Phe Ile Pro Ser Lys Leu Arg Met Val Ser Asp Gly Ile Leu Val Ala
            260                 265                 270

Leu Ser Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
    290                 295                 300

Ser Gly Ile Val Asn Ala Leu Ile Leu Leu Ala Glu Leu Phe Asp Val
305                 310                 315                 320

Phe Trp Thr Pro Pro Asp Val Thr Asn Trp Met Ile Ser Ile Phe Gly
                325                 330                 335

Glu Trp Gln Ala Glu
            340
```

<210> SEQ ID NO 108
<211> LENGTH: 1018
<212> TYPE: DNA
<213> ORGANISM: Murine norovirus

<400> SEQUENCE: 108

```
atgaggatgg caacgccatc ttctgcgtcc tctgtgcgca acacagagaa acgcaaaaat      60
aaaaaggctt catctaaggc tagtgtctcc tttggagcac ctagcttact ctcttcggag     120
agtgaagatg aagttaatta catgacccct cctgagcagg aagctcagcc cggcgccctc     180
gcggccctcc atgcggacgg gccgcatgcc gggctccctg tgacccgaag tgatgcacgc     240
gtgctgatct tcaatgattg ggaggagagg aagaggtccg agccgtggct acggctggac     300
atgtctgaca aggctatctt ccgccgctac ccccacctgc ggcctaagga agataaagcc     360
gatgcgccct cccatgcgga ggacgccatg gatgcaaggg agcccataat tgggtccatt     420
cttgagcagg atgatcataa gttctaccat tactctgtct acattggtaa cggccaggtg     480
atgggcgtca acaatcccgg cgccgcggtt tgccaggctg tgattgatgt ggagaagctc     540
```

```
cacctgtggt ggaggccagt gtgggagccc cgtcaacccc tcgacccggc tgagttgagg    600

aagtgcgttg gcatgaccgt tccctatgtg gcgaccaccg tcaattgcta ccaggtctgc    660

tgctggattg ttgggattaa ggacacctgg ccgaagaggg cgaagatctc tagggattcg    720

cccttctaca gtcctgtcca ggactggaac atcgaccccc aggatccttt catcccttcc    780

aagctcagga tggtttctga tggcatcttg gtggctcttg caacggtgat tggtcggccg    840

atcaagaacc tgctggcatc tgtgaagcct ctcaacatcc ttaacatcgt gttgagctgt    900

gactggactt tctcgggcat tgtcaacgcc ctgattctcc ttgctgaact cttcgacatc    960

ttctggaccc cccctgatgt taccaattgg atgatctcca tctttggaga gtggcagg     1018


<210> SEQ ID NO 109
<211> LENGTH: 339
<212> TYPE: PRT
<213> ORGANISM: Murine norovirus

<400> SEQUENCE: 109

Met Arg Met Ala Thr Pro Ser Ser Ala Ser Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Val Asn Tyr Met
        35                  40                  45

Thr Pro Pro Glu Gln Glu Ala Gln Pro Gly Ala Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Asp Trp Glu Glu Arg Lys Arg Ser Glu Pro Trp
                85                  90                  95

Leu Arg Leu Asp Met Ser Asp Lys Ala Ile Phe Arg Arg Tyr Pro His
            100                 105                 110

Leu Arg Pro Lys Glu Asp Lys Ala Asp Ala Pro Ser His Ala Glu Asp
        115                 120                 125

Ala Met Asp Ala Arg Glu Pro Ile Ile Gly Ser Ile Leu Glu Gln Asp
    130                 135                 140

Asp His Lys Phe Tyr His Tyr Ser Val Tyr Ile Gly Asn Gly Gln Val
145                 150                 155                 160

Met Gly Val Asn Asn Pro Gly Ala Ala Val Cys Gln Ala Val Ile Asp
                165                 170                 175

Val Glu Lys Leu His Leu Trp Trp Arg Pro Val Trp Glu Pro Arg Gln
            180                 185                 190

Pro Leu Asp Pro Ala Glu Leu Arg Lys Cys Val Gly Met Thr Val Pro
        195                 200                 205

Tyr Val Ala Thr Thr Val Asn Cys Tyr Gln Val Cys Cys Trp Ile Val
    210                 215                 220

Gly Ile Lys Asp Thr Trp Pro Lys Arg Ala Lys Ile Ser Arg Asp Ser
225                 230                 235                 240

Pro Phe Tyr Ser Pro Val Gln Asp Trp Asn Ile Asp Pro Gln Asp Pro
                245                 250                 255

Phe Ile Pro Ser Lys Leu Arg Met Val Ser Asp Gly Ile Leu Val Ala
            260                 265                 270

Leu Ala Thr Val Ile Gly Arg Pro Ile Lys Asn Leu Leu Ala Ser Val
        275                 280                 285

Lys Pro Leu Asn Ile Leu Asn Ile Val Leu Ser Cys Asp Trp Thr Phe
```

290 295 300

Ser Gly Ile Val Asn Ala Leu Ile Leu Leu Ala Glu Leu Phe Asp Ile
305 310 315 320

Phe Trp Thr Pro Pro Asp Val Thr Asn Trp Met Ile Ser Ile Phe Gly
325 330 335

Glu Trp Gln

<210> SEQ ID NO 110
<211> LENGTH: 1023
<212> TYPE: DNA
<213> ORGANISM: Murine norovirus

<400> SEQUENCE: 110
gtgaaatgag gatggcaacg ccatcttctg cgccctctgt gcgcaacaca gagaaacgca 60
aaaacaagaa ggcttcgtct aaagctagtg tctcctttgg agcacctagc cccctctctt 120
cggagagcga agacgaaatt aattacatga cccctcctga gcaggaagct cagcccggcg 180
cccttgcggc ccttcatgcg gaagggccgc ttgccgggct ccccgtgacg cgtagtgatg 240
cacgcgtgct gatcttcaat gagtgggagg agaggaagaa gtctgatccg tggctacggc 300
tggacatgtc tgataaggct atcttccgcc gttacccccca tctgcggcct aaggaggata 360
ggcctgacgc gccctcccat gcggaggacg ctatggatgc caaggagcct gtgatcggct 420
ctatcttgga gcaggatgat cacaagtttt accattactc tgtctacatc ggtggcggcc 480
ttgtgatggg ggtcaacaac cccagtgctg cggtctgcca ggcaacgatt gatgtggaga 540
agctacacct ctggtggcgg cctgtctggg agccccgcca tccccttgac tcggctgagt 600
tgaggaagtg cgtgggcatg actgtcccct acgtggccac caccgtcaac tgttatcagg 660
tctgctgctg gattgttggc atcaaggaca cctggctgaa gagggcgaag atctctagag 720
atctgccctt ctacagcccc gtccaggact ggaacgtcga cccccaggag cccttcattc 780
catccaagct caggatggtc tcggatggca tcctggtggc cttgtcggca gtgattggcc 840
ggccaattaa gaacctactg gcctcagtta agccgctcaa cattctcaac atcgtgctga 900
gctgtgattg gacctttttcg ggcattgtca atgccctgat cttgcttgct gagctctttg 960
acatcttttg gacccccct gatgtgacca actggatgat ctctatcttc ggggaatggc 1020
agg 1023

<210> SEQ ID NO 111
<211> LENGTH: 8150
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 111
gtgaaatgag gatggcaacg ccatcttctg cgccctctgt gcgcaacaca gagaaacgca 60
aaaacaagaa ggcttcgtct aaagctagtg tctcctttgg agcacctagc cccctctctt 120
cggagagcga agacgaaatt aattacatga cccctcctga gcaggaagct cagcccggcg 180
cccttgcggc ccttcatgcg gaagggccgc ttgccgggct ccccgtgacg cgtagtgatg 240
cacgcgtgct gatcttcaat gagtgggagg agaggaagaa gtctgatccg tggctacggc 300
tggacatgtc tgataaggct atcttccgcc gttaccccca tctgcggcct aaggaggata 360
ggcctgacgc gccctcccat gcggaggacg ctatggatgc caaggagcct gtgatcggct 420

-continued

```
ctatcttgga gcaggatgat cacaagtttt accattactc tgtctacatc ggtggcggcc    480
ttgtgatggg ggtcaacaac cccagtgctg cggtctgcca ggcaacgatt gatgtggaga    540
agctacacct ctggtggcgg cctgtctggg agccccgcca tccccttgac tcggctgagt    600
tgaggaagtg cgtgggcatg actgtcccct acgtggccac caccgtcaac tgttatcagg    660
tctgctgctg gattgttggc atcaaggaca cctggctgaa gagggcgaag atctctagag    720
atctgccctt ctacagcccc gtccaggact ggaacgtcga cccccaggag cccttcattc    780
catccaagct caggatggtc tcggatggca tcctggtggc cttgtcggca gtgattggcc    840
ggccaattaa gaacctactg gcctcagtta agccgctcaa cattctcaac atcgtgctga    900
gctgtgattg gaccttttcg ggcattgtca atgccctgat cttgcttgct gagctctttg    960
acatcttttg gacccccccct gatgtgacca actggatgat ctctatcttc ggggaatggc   1020
aggctgaggg tccctttgac ctcgccctgg atgtcgtgcc cactcttctt ggtgggattg   1080
gcatggcatt tggcctgaca tctgagacca ttgggcgtaa gctcgcctcc accaactcgg   1140
ccctcaaggc cgcccaggag atgggaaagt ttgcaattga ggtcttcaag caaatcatgg   1200
catggatttg gccctccgaa gaccctgttc ctgccctgct ctccaacatg gagcaagctg   1260
tcatcaagaa tgagtgccaa cttgagaatc aactcacggc catgctgcgg gatcgcaacg   1320
ctggagctga gttcctgaaa gcacttgatg aagaagagca ggaggtccgc aagattgctg   1380
ccaagtgcgg gaactctgcc accacgggca cgaccaacgc tctgctagct aggatcagca   1440
tggcgcgcgc agccttcgag aaggcccgcg ctgagcagac atctcgggtt cgacccgtcg   1500
tgatcatggt ctctggcagg cccgggatcg ggaaaacttg tttttgccag aacctggcaa   1560
agaggattgc tgcctccctt ggggatgaga cctcagtcgg catcataccg cgtgccgatg   1620
tggaccactg ggacgcctac aagggcgcca gagttgttct ttgggacgac tttggcatgg   1680
acaatgtggt gaaggatgca ctgcggctgc agatgctcgc tgacacctgc cccgtcacgc   1740
tcaactgtga cagaattgag aacaagggaa agatgtttga ctctcaagtc atcatcatca   1800
ctaccaatca gcaaacccca gtaccccctgg actatgttaa cttggaggca gtttgccgcc   1860
gcatagactt cttggtttat gctgagagcc ctgtggttga cgccgctcga gccagatcac   1920
ccggcgacgt gaccgccgtc aaggccgcca tgaggccaga ctacagccat atcaatttta   1980
ttctggcacc gcagggtggc tttgatcggc agggcaacac cccctacggc aagggcgtca   2040
ctaagatcat tggcgccacc gcgctctgcg caagggcagt cgcccttgtc cacgagcgcc   2100
atgatgactt cggcctccaa agcaagacct atgactttga tgctggtaaa gtgactgcct   2160
tcaaggctat ggcagctgat gctggaatcc cctggtacaa gatggcagcg attggctgta   2220
aggccatgag ctgcacctgt gtggaggaag ccatgaactt gctcaagggc tatgaggtgg   2280
ccccgtgcca ggtggtctac aatggagcca cctacaatgt cagctgcatc aagggtgctc   2340
ccatggtcga gagggtcaag gagcccgagc tacccaaaac actagtcaat tgtgttagga   2400
ggatcaagga ggctcgcctc cgctgctact gcagaatggc cacagatgtc atcacctcca   2460
tcctgcaggc ggctgggaca gctttctcca tctaccatca gattgagaag aaaactcggc   2520
cctccttcta ctgggaccac ggttacacct accgagacgg cccgggtgcc ttcgatctct   2580
ttgaggatga caacgacgga tggtaccact ctgaaggcaa gaaaggcagg aacaagagag   2640
gccgtgggcg gcccggagtt ttcaagtccc gtgggctcac ggacgaggaa tatgatgaat   2700
tcaagaaacg ccgcgagtcc aagggcggca agtactccat tgatgattac ctcgctgacc   2760
gtgagcgaga agaggagctc caggagcgtg atgaagagga ggccatcttt ggggacggtt   2820
```

```
ttggtctgaa ggccacacgc cgttcccgta aagcggagag ggccaagctt agcctagtct   2880
cggggggtga catccgcgcc cgaagaccaa ttgactggaa tgtggtcggc ccctcttggg   2940
ctgacgatga ccgccaggtc gactatggtg agaagatcaa ctttgaggct ccagtctcaa   3000
tctggacccg tgttgtgcaa tttggcacgg ggtggggctt ctgggtcagc ggccacgtct   3060
tcatcactgc caagcatgtg gccccaccca agggcacaga ggtgtttggg cgcaagcctg   3120
gagacttcac cgtcacttcc agtggagact tcctaaaata tcattttacc aatgctgtta   3180
ggcctgacat ccccgccatg gtcttggaaa acggctgcca ggagggcgtc gtcgcctcag   3240
tcctcgtcaa gagggcctcc ggtgagatgc tcgctttggc agtcaggatg ggctcgcaag   3300
ctgccatcaa gatcggcagc gctgtggtgc acgggcagac cggtatgctc ttaaccggtt   3360
ccaatgctaa ggcccaagat ctcgggacca tcccgggtga ttgtggttgc ccctatgtct   3420
acaagaaggg gaacacctgg gtggtgattg gagtgcacgt ggcggccacc aggtctggta   3480
acacagttat cgccgccacc catggagagc ccacacttga ggccctggag tttcagggtc   3540
cccccatgct ccctcgccct tctggcacct atgcaggcct tcctatcgcc gactacggcg   3600
acgccccccc tttgagcacc aagaccatgt tctggcgcac ctcaccagag aagcttcctc   3660
ctggagcttg ggagcctgcc tacctcggct ctaaggacga gagagtcgac gggccttctc   3720
tgcagcaggt tatgcgggat cagcttaaac cctattcaga gtcacgcggc ttgctgcccc   3780
ctcaggagat cttggacgcg gtttgtgatg ccatcgagaa ccgccttgag aacacccttg   3840
agccacaaaa gccctggacg ttcaagaagg cctgtgagag cctggataag aacaccagca   3900
gtgggtaccc ctaccataag cagaaaagca aggattggac agggaccgcc ttcgtcggtg   3960
agcttggtga ccaggccacc catgccaaca acatgtatga gatgggcaag tccatgcggc   4020
ccgtctacac agctgccctc aaggatgagc tagtcaagcc agataagatc tacaagaaga   4080
taaagaagag gctcctttgg ggttctgacc tcggcaccat gatccgtgcc gcccgtgctt   4140
ttggcccctt ttgtgaagct ttgaaggaga cttgcatttt taatcccatc agagtgggca   4200
tgtcaatgaa tgaggatgga cccttcatct tcgcgaggca tgccaatttc aggtaccaca   4260
tggatgcaga ctataccaga tgggactcca cccagcaaag ggccattctg aagcgcgctg   4320
gtgatatcat ggtgcgcctc tcccctgagc cagagctggc tcgggtggtg atggatgatc   4380
tcttggcccc ttcattgcta gatgtcggcg actacaagat cgtcgtcgag gagggactcc   4440
cgtctggttg cccttgcacc acacagctaa atagtatggc ccattggatt ttgaccctct   4500
gcgcgatggt ggaggtgacc cggattgacc ctgacatcgt gatgcaagag tctgaatttt   4560
ccttctatgg tgatgatgag gtggtctcaa ccaaccttga attggacatg accaagtaca   4620
ccatggccct gaagcggtat ggtcttctcc cgacgcgtgc ggacaaggag gagggacccc   4680
tggagcgccg tcagacgctg cagggcatct ccttcttgcg ccgtgcgata atcggtgatc   4740
agtttggctg gtatggccgt cttgaccgtg ccagcattga ccgtcagctt ctttggacta   4800
aaggacccaa ccatcagaat ccctttgaga ctctcccagg acatgctcag agaccctccc   4860
aattgatggc cctgctcggt gaggctgcca tgcatggtga aaagtattac aggactgtgg   4920
cttcccgggt ctccaaggag gccgcccata gtgggataga aatggtggtc ccacgccacc   4980
gatctgttct gcgctgggtg cgctttggaa caatggatgc tgagaccccg caggaacgct   5040
cagcagtctt tgtgaatgag gatgagtgat ggcgcagcgc caaaagccaa cggctctgaa   5100
gccagcggcc aagatcttgt tcctaccgcc gttgaacagg ccgtccccat tcagcccgtg   5160
```

-continued

```
gctggtgcgg ctcttgccgc ccccgccgcc gggcaaatca accaaattga cccctggatc   5220
ttccaaaatt ttgtccaatg ccccccttggt gagttttcca tttcgcctcg aaacacccca   5280
ggtgaaatac tctttgattt ggccctcggg ccagggctca acccctacct tgcccacctc   5340
tcagccatgt acaccggctg ggttgggaac atggaggttc agctggtcct cgccggcaat   5400
gcctttactg ctggcaaggt ggttgttgcc cttgtaccac cctatttccc caaagggtca   5460
ctcaccaccg cccagatcac atgcttccca cacgtcatgt gtgatgtgcg taccctggag   5520
cccattcaac tgcctcttct tgacgtgcgt cgagttcttt ggcatgctac ccaggatcag   5580
gaggaatcta tgcgcctggt ctgcatgctg tacacgccac tccgcacaaa cagcccgggt   5640
gatgagtctt ttgtggtctc tggccgcctt ctttctaagc cggcacctga tttcaacttt   5700
gtatacctga ccccccctat cgagagaact atttaccgga tggttgactt gcccgtgttg   5760
cagccgcggc tgtgcacgca cgctcgttgg ccggccccgg tctatggcct cttggtagac   5820
ccatccctcc catccaatcc ccagtggcag aatggtagag tgcaagttga tgggactctt   5880
cttggtacaa cgcctgtgtc tggttcatgg gtttcctgct ttgcagctga ggctgcctac   5940
gagttccaag ctgggactgg tgaggtggtg accttcacca tgattgagca ggacggatcc   6000
gcctatgtcc ccggtgacag ggcggccccc cttgggtacc ccgacttctc tgggcaactg   6060
gagatcgagg tgcagactga gaccaccaaa acaggcgaca agctcagggt gaccaccttc   6120
gagatgatcc ttggccccac caccaacgtg gaccaggccc cctaccaggg cagagcgtac   6180
gcgagcttaa cagctgcagc ctcgcttgac ctggtggatg ggagagttag ggcggtccca   6240
cgctccatct attctttcca ggatgagctc ccagagtata atgatggtgt tttggttccc   6300
cttgccccac ccctaggccc ctttcttcct ggtgaggttt tgttgaggtt tcgtacctac   6360
atgcgccagc ttgacaccgc tgacgccgca gcgcagccga tcgactgtgc cttgccccag   6420
gagtttatct cctggtttgc aagcaacaac ttcacggtcc agtcggacgc gctcctggtt   6480
aggtaccgga ataccttgac tggccagctc ctgtttgagg ctaagcttta tagtgaaggc   6540
tacattgctg tgtcttactc agggtctggc cccctcactt tccccactga cggcttcttt   6600
gaggttgtca gctgggtccc ccgcctcttt caattggcct ccgtgggaag cttggtaaca   6660
ggccgaacac tcaaacaata atggctggcg cactctttgg tgcgattgga ggtggcctga   6720
tgggcataat tggcaattcc atctcaacag tccagaatct tcaggcaaat aaacaattgg   6780
ctgcacagca atttggctat aattcctctc tgcttgcaac gcaaattcag gcccagaagg   6840
atctcacact gatggggcag cagttcaacc agcagctcca agccaactct ttcaagcatg   6900
accttgagat gcttggcgcc caggtgcaag cccaggcgca ggcccaggag aacgctatca   6960
acatcaggtc ggcgcagctc caggccgcag gcttttcaaa gtccgacgcc attcgcttgg   7020
cctcggggca gcaaccgacg agggccgttg actggtctgg gacgcggtat tacgccgcta   7080
accagccggt tacgggcttc tcgggtggct tcaccccaag ttacactcca ggtaggcaaa   7140
tggcagtccg ccctgtggac acatcccctc taccggtctc gggtggacgc atgccgtccc   7200
ttcgtggagg ttcctggtct ccgcgtgatt acacgccgca gacccaaggc acctacacga   7260
acgggcggtt tgtgtccttc ccaaagatcg ggagtagcag ggcataggtt ggaagagaaa   7320
cctttctgtg aaaatgattt ctgcttactg ctcttttctt ttggtagtat ttagatgcat   7380
tttaaaaaaa aaaaaaaaaa aaaaaaaaaa aaaaggccgg catggtccca gcctcctcgc   7440
tggcgccggc tgggcaacat tccgagggga ccgtcccctc ggtaatggcg aatgggacgg   7500
aattctagcg gccgctagaa ttcactcctc atcaggtgca ggctgcctat cagaaggtgg   7560
```

tggctggtgt ggccaatgcc ctggctcaca aataccactg agatcgatct ttttccctct 7620
gccaaaaatt atggggacat catgaagccc cttgagcatc tgacttctgg ctaataaagg 7680
aaatttattt tcattgcaat agtgtgttgg aattttttgt gtctctcact cggaaggaca 7740
tatgggaggg caaatcattt aaaacatcag aatgagtatt tggtttagag tttggcaaca 7800
tatgcccata tgctggctgc catgaacaaa ggttggctat aaagaggtca tcagtatatg 7860
aaacagcccc ctgctgtcca ttccttattc catagaaaag ccttgacttg aggttagatt 7920 tttttatat tttgttttgt gttatttttt tctttaacat ccctaaaatt ttccttacat 7980
gttttactag ccagattttt cctcctctcc tgactactcc cagtcatagc tgtccctctt 8040
ctcttatgaa gatccctcga cctgcagccc aagcttgcat gcctgcaggt cgactctaga 8100
ggatccccgg gtaccgagct cgaattcatc gatgatatca gatctggttc 8150

<210> SEQ ID NO 112
<211> LENGTH: 7382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112
gtgaaatgag gatggcaacg ccatcttctg cgtcctctgt gcgcaacaca gagaaacgca 60
aaaataaaaa ggcttcatct aaggctagtg tctcctttgg agcacctagc ttactctctt 120
cggagagtga agatgaagtt aattacatga cccctcctga gcaggaagct cagcccggcg 180
ccctcgcggc cctccatgcg gacgggccgc atgccgggct ccctgtgacc cgaagtgatg 240
cacgcgtgct gatcttcaat gattgggagg agaggaagag gtccgagccg tggctacggc 300
tggacatgtc tgacaaggct atcttccgcc gctacccccca cctgcggcct aaggaagata 360
aagccgatgc gccctcccat gcggaggacg ccatggatgc aagggagccc ataattgggt 420
ccattcttga gcaggatgat cataagttct accattactc tgtctacatt ggtaacggcc 480
aggtgatggg cgtcaacaat cccggcgccg cggtttgcca ggctgtgatt gatgtggaga 540
agctccacct gtggtggagg ccagtgtggg agccccgtca acccctcgac ccggctgagt 600
tgaggaagtg cgttggcatg accgttccct atgtggcgac caccgtcaat tgctaccagg 660
tctgctgctg gattgttggg attaaggaca cctggccgaa gagggcgaag atctctaggg 720
attcgccctt ctacagtcct gtccaggact ggaacatcga cccccaggat cctttcatcc 780
cttccaagct caggatggtt tctgatggca tcttggtggc tcttgcaacg gtgattggtc 840
ggccgatcaa gaacctgctg gcatctgtga agcctctcaa catccttaac atcgtgttga 900
gctgtgactg gactttctcg ggcattgtca acgccctgat tctccttgct gaactcttcg 960
acatcttctg gacccccccct gatgttacca attggatgat ctccatcttt ggagagtggc 1020
aggccgaagg gcccttcgac cttgctcttg acatggtgcc caccctgttg ggcgggatcg 1080
ggatggcttt tggcctcacc tctgagacca tcgggcgcaa gctcgcttcc accaactcgg 1140
ctctcaaggc cgcccaagag atgggcaagt tcgccataga ggtcttcaag caaattatgg 1200
cctggatctg gccctctgag gacccagtgc cagccctctt atccaacatg gagcaggcca 1260
tcattaagaa tgagtgtcaa ctggagaacc aactcacggc catgttgcgg gatcgcaacg 1320
caggggctga attcctaagg tcccttgatg aggaggagca ggaagtccgc aagatcgcag 1380
ctaagtgcgg caactcggcc accactggaa ccaccaacgc tctgctggcc aggatcagca 1440

-continued

```
tggcccgcgc ggcctttgag aaagctcgcg ctgaacagac ctcccgagtc cgccctgtgg   1500
tgatcatggt ctcaggcagg cccgggatcg ggaaaacctg cttttgccaa aacctagcca   1560
agaggattgc tgcgtccctg ggtgatgaga cctctgttgg catcatacca cgcgctgatg   1620
tcgaccactg ggatgcttac aagggagcca gagtggttct ctgggatgat ttcggcatgg   1680
acaacgtggt gaaggatgca ctgaggcttc agatgcttgc cgacacgtgc ccagtgacac   1740
tcaattgtga caggattgag aacaagggaa agatgtttga ctctcaggtc attatcatca   1800
ccacaaatca acaaaccccc gtgcccctgg actatgtcaa cctggaggcg gtctgccgcc   1860
gcatagattt cctggtttat gctgagagcc ctgttgttga tgatgctcgg gccagagccc   1920
ctggcgatgt gaatgcagtg aaagctgcca tgaggcccga ttacagccac atcaatttca   1980
tcttggcacc gcagggcggc tttgaccgtc agggaaacac cccctacggt aagggcgtca   2040
ccaagatcat tggcgccact gctctttgcg cgagagcggt tgctcttgtc catgagcgcc   2100
atgatgattt cggcctccag aacaaggtct atgactttga tgccggcaag gtcaccgcct   2160
tcaaagccat ggcggctgac gccggcattc catggtacaa aatggcagct attgggtgca   2220
aagcaatggg gtgcacctgt gtagaggagg ccatgcattt acttaaggat tatgaggtgg   2280
ctccctgtca ggtgatctac aatggtgcca cctataatgt gagctgcatc aagggtgccc   2340
caatggttga aaaggtcaag gagcctgaat tgcccaaaac acttgtcaac tgtgtcagaa   2400
ggataaagga ggcccgcctc cgctgctact gtaggatggc tgctgacgtc atcacgtcca   2460
ttctgcaggc ggccggcacg gccttctcta tttaccacca gattgagaag aggtctagac   2520
catcctttta ttgggatcat ggatacacct accgtgacgg acctggatcc tttgacatct   2580
ttgaggatga cgatgatggg tggtaccact ctgagggaaa gaagggcaag aacaagaagg   2640
gccgggggcg acccggagtc ttcagaaccc gtgggctcac ggatgaggag tacgatgaat   2700
tcaagaagcg ccgcgagtct agggggcggca agtactccat tgatgattac ctcgctgacc   2760
gcgagcgaga agaagaactc ctggagcggg acgaggagga ggctatcttc ggggatggct   2820
tcgggttgaa ggccacccgc cgttcccgca aggcagagag agccaaactg ggcctggttt   2880
ctggtggcga catccgcgcc cgcaagccga tcgactggaa tgtggttggc ccctcctggg   2940
ctgacgatga ccgccaggtc gactacggcg agaagatcaa ctttgaggcc ccagtctcca   3000
tctggtcccg tgttgtgcag ttcggcacgg ggtggggctt ttgggtgagc ggccacgtct   3060
tcatcaccgc caagcatgtg gcgcccccca agggcacgga gatctttggg cgcaagcccg   3120
gggacttcac tgtcacttcc agcggggact tcttgaagta ctacttcacc agcgccgtca   3180
ggcctgacat tcccgccatg gtcctggaga atgggtgcca ggagggcgtc gtcgcctcgg   3240
tccttgtcaa gagagcctcc ggcgagatgc ttgccctggc tgtcaggatg ggttcacagg   3300
ccgccatcaa gattggtagt gccgttgtgc atgggcaaac tggcatgctc ctgactggct   3360
ctaatgccaa ggcccaggac ctcgggacca tcccgggcga ctgtggctgt ccctatgttt   3420
ataagaaggg taacacctgg gttgtgattg gggtgcacgt ggcggccact aggtctggta   3480
acacagtcat tgccgccact cacggagaac ccacacttga ggctctggag ttccagggac   3540
cccccatgct tccccgcccc tcaggcacct atgcaggcct ccccatcgcc gattacggcg   3600
acgctccccc cttgagcacc aagaccatgt tctggcgtac ctcgccagag aagcttcccc   3660
ctggggcttg ggagccagcc tatctcggct ctaaagatga gagggtggac ggtccttccc   3720
ttcagcaggt catgcgagat cagcttaagc cctattcaga accacgcggt ctgcttcccc   3780
```

-continued ctcaagaaat ccttgatgca gtctgcgatg ccattgagaa ccgccttgag aacacccttg 3840
aaccacagaa gccctggaca tttaagaagg cttgtgagag cttggacaag aacaccagta 3900
gcgggtatcc ctatcacaag cagaagagca aggactggac ggggagcgct tttattggcg 3960
atcttggtga ccaggccacc cacgccaaca acatgtatga gatgggtaaa tccatgcgac 4020
ccatttatac agctgccctc aaggatgaac tggttaagcc agacaagatc tacgggaaga 4080
taaagaagag gcttctctgg ggctctgacc ttggcaccat gattcgcgct gcccgtgctt 4140
ttggcccttt ctgtgatgct ctgaaagaaa cctgcatttt caaccccatc agagtgggca 4200
tgtcgatgaa cgaagatggc cccttcatct tcgcaagaca cgccaatttc aggtaccaca 4260
tggatgctga ctataccagg tgggactcca cccaacagag agccatccta aagcgcgctg 4320
gcgacatcat ggtgcgcctc tcccctgagc cagacttggc tcgggttgtc atggatgatc 4380
tcctggcccc ctcgctgttg gacgtcggcg actataagat cgttgtcgag gaggggctcc 4440
catccggctg cccttgcacc acacagctga atagtttggc tcactggatt ttgacccttt 4500
gtgcaatggt tgaggtaacc cgagttgacc ctgacattgt gatgcaagaa tctgagttct 4560
ccttctatgg tgatgacgag gtggtttcga ccaacctcga gttggatatg gttaagtaca 4620
ccatggcttt gaggcggtac ggtctcctcc cgactcgcgc ggacaaggag gagggacctc 4680
tggagcgtcg ccagacgctg cagggcatct ccttcctgcg ccgtgcgata gttggtgacc 4740
agtttgggtg gtacggtcgt cttgatcgtg ccagcatcga ccgccagctc ctctggacta 4800
aaggacctaa ccaccagaac ccctttgaga ctctccctgg acatgctcag agaccctccc 4860
aactaatggc cctgctcggt gaggctgcca tgcatggtga aaagtattac aggactgtgg 4920
cttcccgtgt ctccaaggag gccgcccaaa gtgggataga aatggtagtc ccacgccacc 4980
gatctgttct gcgctgggtg cgctttggaa caatggatgc tgagaccccg caggaacgct 5040
cagcagtctt tgtgaatgag gatgagtgat ggcgcagcgc caaaagccaa tggctctgag 5100
gccagcggcc aggatcttgt tcctgccgcc gttgaacagg ccgtccccat tcaacccgtg 5160
gctggcgcgg ctcttgccgc ccccgccgcc gggcaaatta accaaattga cccctggatc 5220
ttccaaaatt ttgtccagtg ccccccttggt gagttttcca tttcgcctcg aaacacccca 5280
ggtgaaatac tgtttgattt ggccctcggg ccagggctta acccctacct tgcccacctc 5340
tcagccatgt acaccggctg ggttgggaac atggaggttc agctggtcct cgccggcaat 5400
gcctttactg ctggcaaggt ggttgttgcc cttgtaccac cctattttcc caaggggtca 5460
ctcaccactg cccagatcac atgcttccca catgtcatgt gtgatgtgcg caccctggag 5520
cccattcaac tccctcttct tgatgtgcgt cgagtccttt ggcatgctac ccaggatcaa 5580
gaggaatcta tgcgcctggt ttgcatgctg tacacgccac tccgcacaaa cagcccgggt 5640
gatgagtctt ttgtggtctc tggccgcctt ctttctaagc cggcggctga tttcaatttt 5700
gtctacctaa ctcccccat agagagaacc atctaccgga tggtcgactt gcccgtgata 5760
cagccgcggc tgtgcacgca cgcacgttgg cctgccccgg tctatggtct cttggtggac 5820
ccatccctcc cctcaaatcc ccagtggcag aatggaaggg tgcacgttga tgggaccctg 5880
cttggtacca ccccaatctc cggttcatgg gtgtcctgct ttgcggcgga ggctgcctat 5940
aagttccaat cgggcaccgg tgaggtggcg acattcaccc tgattgagca ggatggatct 6000
gcctacgtcc ccggtgacag ggcagcacca ctcggttacc ccgatttctc tgggcaactg 6060
gagatcgagg tccagaccga gaccaccaag actggagaca agctcaaggt caccactttt 6120
gagatgattc ttggcccaac gaccaacgcg gaccaggccc cctaccaggg cagggtgttc 6180
gccagcgtca ctgctgcggc ctctcttgac ttggtggatg gcagggttcg tgcggtccca 6240
agatccatct acggttttca ggacaccatc cctgaataca acgatgggct actggttccc 6300
cttgcccccc caattggtcc ctttctcccc ggcgaggtcc tcctgaggtt ccggacctac 6360
atgcgtcaga tcgacaccgc tgacgccgca gcagaggcga tagactgtgc actcccccag 6420
gagtttgtct cctggttcgc gtctaacgcg ttcaccgtgc agtccgaggc cctgctcctt 6480
agatacagga acaccctgac tgggcaactg ctgttcgagt gcaagctcta caacgaaggt 6540
tacatcgcct tgtcttattc cggctcagga cccctcacct tcccgaccga tggcatcttt 6600
gaggtcgtca gttgggttcc tcgcctttac caattggcct ctgtgggaag tttggcaaca 6660
ggccgaatgc tcaaacaata atggctggtg ctctttttgg agcgattgga ggtggcctga 6720
tgggcataat tggcaattcc atctcaaatg ttcaaaacct tcaggcaaac aaacaattgg 6780
cagctcagca atttggttat aattcttccc tgcttgcaac gcaaattcaa gcccagaagg 6840
atctcactct gatggggcag caattcaacc agcagctcca aaccaactct ttcaagcacg 6900
acttggaaat gcttggcgct caggtgcaag cccaggcgca ggcccaggag aacgccatca 6960
atatcaaaac ggcgcagctc caggccgcag gcttttcaaa gacggatgcc gcacgccttg 7020
ccttggggca gcagcccacg agggccgtgg attggtctgg gacgcggtac tacaccgcta 7080
accagccagt cacgggcttc tcgggtggct ttaccccaac ctacactcca ggtaggcaag 7140
tgacatcccg ccctgtggac acatcccctc taccgatctc gggtggacgc ttgccctccc 7200
ttcgtggagg ttcctggtcc ccgcgcgacc atacgccggc gactcaaggc acctacacga 7260
acggacggtt cgtgtctctc cctaagatcg ggagtagcag ggcataggtt ggaagagaaa 7320
ccttttgtga aaatgatttc tgcttactgc tttcttttct ttgtggtagt tagatgcatt 7380
tt 7382

<210> SEQ ID NO 113
<211> LENGTH: 8150
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 113
gtgaaatgag gatggcaacg ccatcttctg cgtcctctgt gcgcaacaca gagaaacgca 60
aaaataaaaa ggcttcatct aaggctagtg tctcctttgg agcacctagc ttactctctt 120
cggagagtga agatgaagtt aattacatga cccctcctga gcaggaagct cagcccggcg 180
ccctcgcggc cctccatgcg gacgggccgc atgccgggct ccctgtgacc cgaagtgatg 240
cacgcgtgct gatcttcaat gattgggagg agaggaagag gtccgagccg tggctacggc 300
tggacatgtc tgacaaggct atcttccgcc gctaccccca cctgcggcct aaggaagata 360
aagccgatgc gccctcccat gcggaggacg ccatggatgc aagggagccc ataattgggt 420
ccattcttga gcaggatgat cataagttct accattactc tgtctacatt ggtaacggcc 480
aggtgatggg cgtcaacaat cccggcgccg cggtttgcca ggctgtgatt gatgtggaga 540
agctccacct gtggtggagg ccagtgtggg agccccgtca acccctcgac ccggctgagt 600
tgaggaagtg cgttggcatg accgttccct atgtggcgac caccgtcaat tgctaccagg 660
tctgctgctg gattgttggg attaaggaca cctggccgaa gagggcgaag atctctaggg 720
attcgccctt ctacagtcct gtccaggact ggaacatcga cccccaggat cctttcatcc 780

-continued

```
cttccaagct caggatggtt tctgatggca tcttggtggc tcttgcaacg gtgattggtc    840
ggccgatcaa gaacctgctg gcatctgtga agcctctcaa catccttaac atcgtgttga    900
gctgtgactg gactttctcg ggcattgtca acgccctgat tctccttgct gaactcttcg    960
acatcttctg gacccccct gatgttacca attggatgat ctccatcttt ggagagtggc   1020
aggctgaggg tccctttgac ctcgccctgg atgtcgtgcc cactcttctt ggtgggattg   1080
gcatggcatt tggcctgaca tctgagacca ttgggcgtaa gctcgcctcc accaactcgg   1140
ccctcaaggc cgcccaggag atgggaaagt ttgcaattga ggtcttcaag caaatcatgg   1200
catggatttg gccctccgaa gaccctgttc ctgccctgct ctccaacatg gagcaagctg   1260
tcatcaagaa tgagtgccaa cttgagaatc aactcacggc catgctgcgg gatcgcaacg   1320
ctggagctga gttcctgaaa gcacttgatg aagaagagca ggaggtccgc aagattgctg   1380
ccaagtgcgg gaactctgcc accacgggca cgaccaacgc tctgctagct aggatcagca   1440
tggcgcgcgc agccttcgag aaggcccgcg ctgagcagac atctcgggtt cgacccgtcg   1500
tgatcatggt ctctggcagg cccgggatcg ggaaaacttg tttttgccag aacctggcaa   1560
agaggattgc tgcctccctt ggggatgaga cctcagtcgg catcataccg cgtgccgatg   1620
tggaccactg ggacgcctac aagggcgcca gagttgttct ttgggacgac tttggcatgg   1680
acaatgtggt gaaggatgca ctgcggctgc agatgctcgc tgacacctgc cccgtcacgc   1740
tcaactgtga cagaattgag aacaagggaa agatgtttga ctctcaagtc atcatcatca   1800
ctaccaatca gcaaacccca gtacccctgg actatgttaa cttggaggca gtttgccgcc   1860
gcatagactt cttggtttat gctgagagcc ctgtggttga cgccgctcga gccagatcac   1920
ccggcgacgt gaccgccgtc aaggccgcca tgaggccaga ctacagccat atcaatttta   1980
ttctggcacc gcagggtggc tttgatcggc agggcaacac cccctacggc aagggcgtca   2040
ctaagatcat tggcgccacc gcgctctgcg caagggcagt cgcccttgtc cacgagcgcc   2100
atgatgactt cggcctccaa agcaagacct atgactttga tgctggtaaa gtgactgcct   2160
tcaaggctat ggcagctgat gctggaatcc cctggtacaa gatggcagcg attggctgta   2220
aggccatgag ctgcacctgt gtggaggaag ccatgaactt gctcaagggc tatgaggtgg   2280
ccccgtgcca ggtggtctac aatggagcca cctacaatgt cagctgcatc aagggtgctc   2340
ccatggtcga gagggtcaag gagcccgagc tacccaaaac actagtcaat tgtgttagga   2400
ggatcaagga ggctcgcctc cgctgctact gcagaatggc cacagatgtc atcacctcca   2460
tcctgcaggc ggctgggaca gctttctcca tctaccatca gattgagaag aaaactcggc   2520
cctccttcta ctgggaccac ggttacacct accgagacgg cccgggtgcc ttcgatctct   2580
ttgaggatga caacgacgga tggtaccact ctgaaggcaa gaaaggcagg aacaagagag   2640
gccgtgggcg gcccggagtt ttcaagtccc gtgggctcac ggacgaggaa tatgatgaat   2700
tcaagaaacg ccgcgagtcc aagggcggca agtactccat tgatgattac ctcgctgacc   2760
gtgagcgaga agaggagctc caggagcgtg atgaagagga ggccatcttt ggggacggtt   2820
ttggtctgaa ggccacacgc cgttcccgta aagcggagag ggccaagctt agcctagtct   2880
cggggggtga catccgcgcc cgaagaccaa ttgactggaa tgtggtcggc ccctcttggg   2940
ctgacgatga ccgccaggtc gactatggtg agaagatcaa ctttgaggct ccagtctcaa   3000
tctggacccg tgttgtgcaa tttggcacgg ggtggggctt ctgggtcagc ggccacgtct   3060
tcatcactgc caagcatgtg gccccaccca agggcacaga ggtgtttggg cgcaagcctg   3120
```

gagacttcac cgtcacttcc agtggagact tcctaaaata tcattttacc aatgctgtta 3180
ggcctgacat ccccgccatg gtcttggaaa acggctgcca ggagggcgtc gtcgcctcag 3240
tcctcgtcaa gagggcctcc ggtgagatgc tcgctttggc agtcaggatg ggctcgcaag 3300
ctgccatcaa gatcggcagc gctgtggtgc acgggcagac cggtatgctc ttaaccggtt 3360
ccaatgctaa ggcccaagat ctcgggacca tcccgggtga ttgtggttgc ccctatgtct 3420
acaagaaggg gaacacctgg gtggtgattg gagtgcacgt ggcggccacc aggtctggta 3480
acacagttat cgccgccacc catggagagc ccacacttga ggccctggag tttcagggtc 3540
cccccatgct ccctcgccct tctggcacct atgcaggcct tcctatcgcc gactacggcg 3600
acgccccccc tttgagcacc aagaccatgt tctggcgcac ctcaccagag aagcttcctc 3660
ctggagcttg ggagcctgcc tacctcggct ctaaggacga gagagtcgac gggccttctc 3720
tgcagcaggt tatgcgggat cagcttaaac cctattcaga gtcacgcggc ttgctgcccc 3780
ctcaggagat cttggacgcg gtttgtgatg ccatcgagaa ccgccttgag aacacccttg 3840
agccacaaaa gccctggacg ttcaagaagg cctgtgagag cctggataag aacaccagca 3900
gtgggtaccc ctaccataag cagaaaagca aggattggac agggaccgcc ttcgtcggtg 3960
agcttggtga ccaggccacc catgccaaca acatgtatga gatgggcaag tccatgcggc 4020
ccgtctacac agctgccctc aaggatgagc tagtcaagcc agataagatc tacaagaaga 4080
taaagaagag gctcctttgg ggttctgacc tcggcaccat gatccgtgcc gcccgtgctt 4140
ttggcccctt ttgtgaagct ttgaaggaga cttgcatttt taatcccatc agagtgggca 4200
tgtcaatgaa tgaggatgga cccttcatct tcgcgaggca tgccaatttc aggtaccaca 4260
tggatgcaga ctataccaga tggactcca cccagcaaag ggccattctg aagcgcgctg 4320
gtgatatcat ggtgcgcctc tcccctgagc cagagctggc tcgggtggtg atggatgatc 4380
tcttggcccc ttcattgcta gatgtcggcg actacaagat cgtcgtcgag gagggactcc 4440
cgtctggttg cccttgcacc acacagctaa atagtatggc ccattggatt ttgaccctct 4500
gcgcgatggt ggaggtgacc cggattgacc ctgacatcgt gatgcaagag tctgaatttt 4560
ccttctatgg tgatgatgag gtggtctcaa ccaaccttga attggacatg accaagtaca 4620
ccatggccct gaagcggtat ggtcttctcc cgacgcgtgc ggacaaggag gagggacccc 4680
tggagcgccg tcagacgctg cagggcatct ccttcttgcg ccgtgcgata atcggtgatc 4740
agtttggctg gtatggccgt cttgaccgtg ccagcattga ccgtcagctt ctttggacta 4800
aaggacccaa ccatcagaat ccctttgaga ctctcccagg acatgctcag agaccctccc 4860
aattgatggc cctgctcggt gaggctgcca tgcatggtga aaagtattac aggactgtgg 4920
cttcccgggt ctccaaggag gccgcccata gtgggataga aatggtggtc ccacgccacc 4980
gatctgttct gcgctgggtg cgctttggaa caatggatgc tgagaccccg caggaacgct 5040
cagcagtctt tgtgaatgag gatgagtgat ggcgcagcgc caaaagccaa tggctctgag 5100
gccagcggcc aggatcttgt tcctgccgcc gttgaacagg ccgtccccat tcaacccgtg 5160
gctggcgcgg ctcttgccgc ccccgccgcc gggcaaatta accaaattga cccctggatc 5220
ttccaaaatt ttgtccagtg ccccccttggt gagttttcca tttcgcctcg aaacacccca 5280
ggtgaaatac tgtttgattt ggccctcggg ccagggctta acccctacct tgcccacctc 5340
tcagccatgt acaccggctg ggttgggaac atggaggttc agctggtcct cgccggcaat 5400
gcctttactg ctggcaaggt ggttgttgcc cttgtaccac cctattttcc caaggggtca 5460
ctcaccactg cccagatcac atgcttccca catgtcatgt gtgatgtgcg caccctggag 5520

```
cccattcaac tccctcttct tgatgtgcgt cgagtccttt ggcatgctac ccaggatcaa   5580
gaggaatcta tgcgcctggt ttgcatgctg tacacgccac tccgcacaaa cagcccgggt   5640
gatgagtctt ttgtggtctc tggccgcctt ctttctaagc cggcggctga tttcaatttt   5700
gtctacctaa ctccccccat agagagaacc atctaccgga tggtcgactt gcccgtgata   5760
cagccgcggc tgtgcacgca cgcacgttgg cctgccccgg tctatggtct cttggtggac   5820
ccatccctcc cctcaaatcc ccagtggcag aatggaaggg tgcacgttga tgggaccctg   5880
cttggtacca ccccaatctc cggttcatgg gtgtcctgct ttgcggcgga ggctgcctat   5940
aagttccaat cgggcaccgg tgaggtggcg acattcaccc tgattgagca ggatggatct   6000
gcctacgtcc ccggtgacag ggcagcacca ctcggttacc ccgatttctc tgggcaactg   6060
gagatcgagg tccagaccga gaccaccaag actggagaca agctcaaggt caccactttt   6120
gagatgattc ttggcccaac gaccaacgcg gaccaggccc cctaccaggg cagggtgttc   6180
gccagcgtca ctgctgcggc ctctcttgac ttggtggatg gcagggttcg tgcggtccca   6240
agatccatct acggttttca ggacaccatc cctgaataca acgatgggct actggttccc   6300
cttgccccccc caattggtcc ctttctcccc ggcgaggtcc tcctgaggtt ccggacctac   6360
atgcgtcaga tcgacaccgc tgacgccgca gcagaggcga tagactgtgc actcccccag   6420
gagtttgtct cctggttcgc gtctaacgcg ttcaccgtgc agtccgaggc cctgctcctt   6480
agatacagga acaccctgac tgggcaactg ctgttcgagt gcaagctcta caacgaaggt   6540
tacatcgcct tgtcttattc cggctcagga cccctcacct tcccgaccga tggcatcttt   6600
gaggtcgtca gttgggttcc tcgcctttac caattggcct ctgtgggaag tttggcaaca   6660
ggccgaatgc tcaaacaata atggctggcg cactctttgg tgcgattgga ggtggcctga   6720
tgggcataat tggcaattcc atctcaacag tccagaatct tcaggcaaat aaacaattgg   6780
ctgcacagca atttggctat aattcctctc tgcttgcaac gcaaattcag gcccagaagg   6840
atctcacact gatggggcag cagttcaacc agcagctcca agccaactct ttcaagcatg   6900
accttgagat gcttggcgcc caggtgcaag cccaggcgca ggcccaggag aacgctatca   6960
acatcaggtc ggcgcagctc caggccgcag gcttttcaaa gtccgacgcc attcgcttgg   7020
cctcggggca gcaaccgacg agggccgttg actggtctgg gacgcggtat tacgccgcta   7080
accagccggt tacgggcttc tcgggtggct tcaccccaag ttacactcca ggtaggcaaa   7140
tggcagtccg ccctgtggac acatcccctc taccggtctc gggtggacgc atgccgtccc   7200
ttcgtggagg ttcctggtct ccgcgtgatt acacgccgca gacccaaggc acctacacga   7260
acgggcggtt tgtgtccttc ccaaagatcg ggagtagcag ggcataggtt ggaagagaaa   7320
cctttctgtg aaaatgattt ctgcttactg ctcttttctt ttggtagtat ttagatgcat   7380
tttaaaaaaa aaaaaaaaaa aaaaaaaaaa aaaaggccgg catggtccca gcctcctcgc   7440
tggcgccggc tgggcaacat tccgagggga ccgtcccctc ggtaatggcg aatgggacgg   7500
aattctagcg gccgctagaa ttcactcctc atcaggtgca ggctgcctat cagaaggtgg   7560
tggctggtgt ggccaatgcc ctggctcaca aataccactg agatcgatct tttccctct    7620
gccaaaaatt atggggacat catgaagccc cttgagcatc tgacttctgg ctaataaagg   7680
aaatttattt tcattgcaat agtgtgttgg aattttttgt gtctctcact cggaaggaca   7740
tatgggaggg caaatcattt aaaacatcag aatgagtatt tggtttagag tttggcaaca   7800
tatgcccata tgctggctgc catgaacaaa ggttggctat aaagaggtca tcagtatatg   7860
```

-continued aaacagcccc ctgctgtcca ttccttattc catagaaaag ccttgacttg aggttagatt 7920 tttttatat tttgttttgt gttatttttt tctttaacat ccctaaaatt ttccttacat 7980
gttttactag ccagattttt cctcctctcc tgactactcc cagtcatagc tgtccctctt 8040
ctcttatgaa gatccctcga cctgcagccc aagcttgcat gcctgcaggt cgactctaga 8100
ggatccccgg gtaccgagct cgaattcatc gatgatatca gatctggttc 8150

<210> SEQ ID NO 114
<211> LENGTH: 7382
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 114
gtgaaatgag gatggcaacg ccatcttctg cgccctctgt gcgcaacaca gagaaacgca 60
aaaacaagaa ggcttcgtct aaagctagtg tctcctttgg agcacctagc cccctctctt 120
cggagagcga agacgaaatt aattacatga cccctcctga gcaggaagct cagcccggcg 180
cccttgcggc ccttcatgcg gaagggccgc ttgccgggct ccccgtgacg cgtagtgatg 240
cacgcgtgct gatcttcaat gagtgggagg agaggaagaa gtctgatccg tggctacggc 300
tggacatgtc tgataaggct atcttccgcc gttacccccca tctgcggcct aaggaggata 360
ggcctgacgc gccctcccat gcggaggacg ctatggatgc caaggagcct gtgatcggct 420
ctatcttgga gcaggatgat cacaagtttt accattactc tgtctacatc ggtggcggcc 480
ttgtgatggg ggtcaacaac cccagtgctg cggtctgcca ggcaacgatt gatgtggaga 540
agctacacct ctggtggcgg cctgtctggg agccccgcca tccccttgac tcggctgagt 600
tgaggaagtg cgtgggcatg actgtcccct acgtggccac caccgtcaac tgttatcagg 660
tctgctgctg gattgttggc atcaaggaca cctggctgaa gagggcgaag atctctagag 720
atctgccctt ctacagcccc gtccaggact ggaacgtcga cccccaggag cccttcattc 780
catccaagct caggatggtc tcggatggca tcctggtggc cttgtcggca gtgattggcc 840
ggccaattaa gaacctactg gcctcagtta agccgctcaa cattctcaac atcgtgctga 900
gctgtgattg gaccttttcg ggcattgtca atgccctgat cttgcttgct gagctctttg 960
acatcttttg gacccccccct gatgtgacca actggatgat ctctatcttc ggggaatggc 1020
aggccgaagg gcccttcgac cttgctcttg acatggtgcc caccctgttg ggcgggatcg 1080
ggatggcttt tggcctcacc tctgagacca tcgggcgcaa gctcgcttcc accaactcgg 1140
ctctcaaggc cgcccaagag atgggcaagt tcgccataga ggtcttcaag caaattatgg 1200
cctggatctg gccctctgag gacccagtgc cagccctctt atccaacatg gagcaggcca 1260
tcattaagaa tgagtgtcaa ctggagaacc aactcacggc catgttgcgg gatcgcaacg 1320
caggggctga attcctaagg tcccttgatg aggaggagca ggaagtccgc aagatcgcag 1380
ctaagtgcgg caactcggcc accactggaa ccaccaacgc tctgctggcc aggatcagca 1440
tggcccgcgc ggcctttgag aaagctcgcg ctgaacagac ctcccgagtc cgccctgtgg 1500
tgatcatggt ctcaggcagg cccgggatcg ggaaaacctg cttttgccaa aacctagcca 1560
agaggattgc tgcgtccctg ggtgatgaga cctctgttgg catcatacca cgcgctgatg 1620
tcgaccactg ggatgcttac aagggagcca gagtggttct ctgggatgat ttcggcatgg 1680
acaacgtggt gaaggatgca ctgaggcttc agatgcttgc cgacacgtgc ccagtgacac 1740

-continued

```
tcaattgtga caggattgag aacaagggaa agatgtttga ctctcaggtc attatcatca   1800
ccacaaatca acaaaccccc gtgcccctgg actatgtcaa cctggaggcg gtctgccgcc   1860
gcatagattt cctggtttat gctgagagcc ctgttgttga tgatgctcgg gccagagccc   1920
ctggcgatgt gaatgcagtg aaagctgcca tgaggcccga ttacagccac atcaatttca   1980
tcttggcacc gcagggcggc tttgaccgtc agggaaacac cccctacggt aagggcgtca   2040
ccaagatcat tggcgccact gctctttgcg cgagagcggt tgctcttgtc catgagcgcc   2100
atgatgattt cggcctccag aacaaggtct atgactttga tgccggcaag gtcaccgcct   2160
tcaaagccat ggcggctgac gccggcattc catggtacaa aatggcagct attgggtgca   2220
aagcaatggg gtgcacctgt gtagaggagg ccatgcattt acttaaggat tatgaggtgg   2280
ctccctgtca ggtgatctac aatggtgcca cctataatgt gagctgcatc aagggtgccc   2340
caatggttga aaaggtcaag gagcctgaat tgcccaaaac acttgtcaac tgtgtcagaa   2400
ggataaagga ggcccgcctc cgctgctact gtaggatggc tgctgacgtc atcacgtcca   2460
ttctgcaggc ggccggcacg gccttctcta tttaccacca gattgagaag aggtctagac   2520
catcctttta ttgggatcat ggatacacct accgtgacgg acctggatcc tttgacatct   2580
ttgaggatga cgatgatggg tggtaccact ctgagggaaa gaagggcaag aacaagaagg   2640
gccgggggcg acccggagtc ttcagaaccc gtgggctcac ggatgaggag tacgatgaat   2700
tcaagaagcg ccgcgagtct aggggcggca agtactccat tgatgattac ctcgctgacc   2760
gcgagcgaga agaagaactc ctggagcggg acgaggagga ggctatcttc ggggatggct   2820
tcgggttgaa ggccacccgc cgttcccgca aggcagagag agccaaactg ggcctggttt   2880
ctggtggcga catccgcgcc cgcaagccga tcgactggaa tgtggttggc cctcctggg    2940
ctgacgatga ccgccaggtc gactacggcg agaagatcaa ctttgaggcc ccagtctcca   3000
tctggtcccg tgttgtgcag ttcggcacgg ggtggggctt ttgggtgagc ggccacgtct   3060
tcatcaccgc caagcatgtg gcgccccca agggcacgga gatctttggg cgcaagcccg    3120
gggacttcac tgtcacttcc agcggggact tcttgaagta ctacttcacc agcgccgtca   3180
ggcctgacat tcccgccatg gtcctggaga atgggtgcca ggagggcgtc gtcgcctcgg   3240
tccttgtcaa gagagcctcc ggcgagatgc ttgccctggc tgtcaggatg ggttcacagg   3300
ccgccatcaa gattggtagt gccgttgtgc atgggcaaac tggcatgctc ctgactggct   3360
ctaatgccaa ggcccaggac ctcgggacca tcccgggcga ctgtggctgt ccctatgttt   3420
ataagaaggg taacacctgg gttgtgattg gggtgcacgt ggcggccact aggtctggta   3480
acacagtcat tgccgccact cacggagaac ccacacttga ggctctggag ttccagggac   3540
cccccatgct tccccgcccc tcaggcacct atgcaggcct ccccatcgcc gattacggcg   3600
acgctccccc cttgagcacc aagaccatgt tctggcgtac ctcgccagag aagcttcccc   3660
ctggggcttg ggagccagcc tatctcggct ctaaagatga gagggtggac ggtccttccc   3720
ttcagcaggt catgcgagat cagcttaagc cctattcaga accacgcggt ctgcttcccc   3780
ctcaagaaat ccttgatgca gtctgcgatg ccattgagaa ccgccttgag aacacccttg   3840
aaccacagaa gccctggaca tttaagaagg cttgtgagag cttggacaag aacaccagta   3900
gcgggtatcc ctatcacaag cagaagagca aggactggac ggggagcgct tttattggcg   3960
atcttggtga ccaggccacc cacgccaaca acatgtatga gatgggtaaa tccatgcgac   4020
ccatttatac agctgccctc aaggatgaac tggttaagcc agacaagatc tacgggaaga   4080
taaagaagag gcttctctgg ggctctgacc ttggcaccat gattcgcgct gcccgtgctt   4140
```

-continued

```
ttggcccttt ctgtgatgct ctgaaagaaa cctgcatttt caaccccatc agagtgggca   4200
tgtcgatgaa cgaagatggc cccttcatct tcgcaagaca cgccaatttc aggtaccaca   4260
tggatgctga ctataccagg tgggactcca cccaacagag agccatccta aagcgcgctg   4320
gcgacatcat ggtgcgcctc tcccctgagc cagacttggc tcgggttgtc atggatgatc   4380
tcctggcccc ctcgctgttg gacgtcggcg actataagat cgttgtcgag gaggggctcc   4440
catccggctg cccttgcacc acacagctga atagtttggc tcactggatt ttgacccttt   4500
gtgcaatggt tgaggtaacc cgagttgacc ctgacattgt gatgcaagaa tctgagttct   4560
ccttctatgg tgatgacgag gtggtttcga ccaacctcga gttggatatg gttaagtaca   4620
ccatggcttt gaggcggtac ggtctcctcc cgactcgcgc ggacaaggag gagggacctc   4680
tggagcgtcg ccagacgctg cagggcatct ccttcctgcg ccgtgcgata gttggtgacc   4740
agtttgggtg gtacggtcgt cttgatcgtg ccagcatcga ccgccagctc ctctggacta   4800
aaggacctaa ccaccagaac ccctttgaga ctctccctgg acatgctcag agaccctccc   4860
aactaatggc cctgctcggt gaggctgcca tgcatggtga aaagtattac aggactgtgg   4920
cttcccgtgt ctccaaggag gccgcccaaa gtgggataga aatggtagtc ccacgccacc   4980
gatctgttct gcgctgggtg cgctttggaa caatggatgc tgagaccccg caggaacgct   5040
cagcagtctt tgtgaatgag gatgagtgat ggcgcagcgc caaaagccaa cggctctgaa   5100
gccagcggcc aagatcttgt tcctaccgcc gttgaacagg ccgtccccat tcagcccgtg   5160
gctggtgcgg ctcttgccgc ccccgccgcc gggcaaatca accaaattga cccctggatc   5220
ttccaaaatt ttgtccaatg ccccccttggt gagttttcca tttcgcctcg aaacacccca   5280
ggtgaaatac tctttgattt ggccctcggg ccagggctca acccctacct tgcccacctc   5340
tcagccatgt acaccggctg ggttgggaac atggaggttc agctggtcct cgccggcaat   5400
gcctttactg ctggcaaggt ggttgttgcc cttgtaccac cctatttccc caaagggtca   5460
ctcaccaccg cccagatcac atgcttccca cacgtcatgt gtgatgtgcg taccctggag   5520
cccattcaac tgcctcttct tgacgtgcgt cgagttcttt ggcatgctac ccaggatcag   5580
gaggaatcta tgcgcctggt ctgcatgctg tacacgccac tccgcacaaa cagcccgggt   5640
gatgagtctt ttgtggtctc tggccgcctt ctttctaagc cggcacctga tttcaacttt   5700
gtatacctga cccccccctat cgagagaact atttaccgga tggttgactt gcccgtgttg   5760
cagccgcggc tgtgcacgca cgctcgttgg ccggccccgg tctatggcct cttggtagac   5820
ccatccctcc catccaatcc ccagtggcag aatggtagag tgcaagttga tgggactctt   5880
cttggtacaa cgcctgtgtc tggttcatgg gtttcctgct ttgcagctga ggctgcctac   5940
gagttccaag ctgggactgg tgaggtggtg accttcacca tgattgagca ggacggatcc   6000
gcctatgtcc ccggtgacag ggcggccccc cttgggtacc ccgacttctc tgggcaactg   6060
gagatcgagg tgcagactga gaccaccaaa acaggcgaca agctcagggt gaccaccttc   6120
gagatgatcc ttggccccac caccaacgtg gaccaggccc cctaccaggg cagagcgtac   6180
gcgagcttaa cagctgcagc ctcgcttgac ctggtggatg ggagagttag ggcggtccca   6240
cgctccatct attctttcca ggatgagctc ccagagtata atgatggtgt tttggttccc   6300
cttgccccac ccctaggccc ctttcttcct ggtgaggttt tgttgaggtt tcgtacctac   6360
atgcgccagc ttgacaccgc tgacgccgca gcgcagccga tcgactgtgc cttgccccag   6420
gagtttatct cctggtttgc aagcaacaac ttcacggtcc agtcggacgc gctcctggtt   6480
```

-continued

```
aggtaccgga ataccttgac tggccagctc ctgtttgagg ctaagcttta tagtgaaggc   6540

tacattgctg tgtcttactc agggtctggc cccctcactt tccccactga cggcttcttt   6600

gaggttgtca gctgggtccc ccgcctcttt caattggcct ccgtgggaag cttggtaaca   6660

ggccgaacac tcaaacaata atggctggtg ctctttttgg agcgattgga ggtggcctga   6720

tgggcataat tggcaattcc atctcaaatg ttcaaaacct tcaggcaaac aaacaattgg   6780

cagctcagca atttggttat aattcttccc tgcttgcaac gcaaattcaa gcccagaagg   6840

atctcactct gatggggcag caattcaacc agcagctcca aaccaactct ttcaagcacg   6900

acttggaaat gcttggcgct caggtgcaag cccaggcgca ggcccaggag aacgccatca   6960

atatcaaaac ggcgcagctc caggccgcag gcttttcaaa gacggatgcc gcacgccttg   7020

ccttggggca gcagcccacg agggccgtgg attggtctgg gacgcggtac tacaccgcta   7080

accagccagt cacgggcttc tcgggtggct ttaccccaac ctacactcca ggtaggcaag   7140

tgacatcccg ccctgtggac acatcccctc taccgatctc gggtggacgc ttgccctccc   7200

ttcgtggagg ttcctggtcc ccgcgcgacc atacgccggc gactcaaggc acctacacga   7260

acggacggtt cgtgtctctc cctaagatcg ggagtagcag ggcataggtt ggaagagaaa   7320

ccttttgtga aaatgatttc tgcttactgc tttcttttct ttgtggtagt tagatgcatt   7380

tt                                                                  7382
```

<210> SEQ ID NO 115
<211> LENGTH: 363
<212> TYPE: DNA
<213> ORGANISM: Murine norovirus

<400> SEQUENCE: 115

```
atgaggatgg caacgccatc ttctgcgtcc tctgtgcgca acacagagaa acgcaaaaat     60

aaaaaggctt catctaaggc tagtgtctcc tttggagcac ctagcttact ctcttcggag    120

agtgaagatg aagttaatta catgacccct cctgagcagg aagctcagcc cggcgccctc    180

gcggccctcc atgcggacgg gccgcatgcc gggctccctg tgacccgaag tgatgcacgc    240

gtgctgatct tcaatgattg ggaggagagg aagaggtccg agccgtggct acggctggac    300

atgtctgaca aggctatctt ccgccgctac ccccacctgc ggcctaagga agataaagcc    360

gat                                                                  363
```

<210> SEQ ID NO 116
<211> LENGTH: 121
<212> TYPE: PRT
<213> ORGANISM: Murine norovirus

<400> SEQUENCE: 116

```
Met Arg Met Ala Thr Pro Ser Ser Ala Ser Ser Val Arg Asn Thr Glu
1               5                   10                  15

Lys Arg Lys Asn Lys Lys Ala Ser Ser Lys Ala Ser Val Ser Phe Gly
            20                  25                  30

Ala Pro Ser Leu Leu Ser Ser Glu Ser Glu Asp Glu Val Asn Tyr Met
        35                  40                  45

Thr Pro Pro Glu Gln Glu Ala Gln Pro Gly Ala Leu Ala Ala Leu His
    50                  55                  60

Ala Asp Gly Pro His Ala Gly Leu Pro Val Thr Arg Ser Asp Ala Arg
65                  70                  75                  80

Val Leu Ile Phe Asn Asp Trp Glu Glu Arg Lys Arg Ser Glu Pro Trp
                85                  90                  95
```

-continued

```
Leu Arg Leu Asp Met Ser Asp Lys Ala Ile Phe Arg Arg Tyr Pro His
        100                 105                 110

Leu Arg Pro Lys Glu Asp Lys Ala Asp
    115                 120
```